US006969730B2

(12) United States Patent
Cowart et al.

(10) Patent No.: US 6,969,730 B2
(45) Date of Patent: Nov. 29, 2005

(54) AMINES AS HISTAMINE-3 RECEPTOR LIGANDS AND THEIR THERAPEUTIC APPLICATIONS

(75) Inventors: Marlon D. Cowart, Round Lake Beach, IL (US); Youssef L. Bennani, Shaker Heights, OH (US); Ramin Faghih, Lake Forest, IL (US); Gregory A. Gfesser, Waukegan, IL (US); Lawrence A. Black, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 177 days.

(21) Appl. No.: 10/081,207

(22) Filed: Feb. 25, 2002

(65) Prior Publication Data

US 2002/0169188 A1 Nov. 14, 2002

Related U.S. Application Data

(60) Provisional application No. 60/276,793, filed on Mar. 16, 2001.

(51) Int. Cl.$^7$ .................... C07D 307/78; C07D 413/12; A61K 31/343; A61K 31/44; A61K 31/47
(52) U.S. Cl. ................ 514/469; 514/470; 514/212.01; 514/227.8; 514/231.5; 514/252.13; 514/256; 514/317; 514/336; 514/422; 549/463; 549/467; 549/469; 544/62; 544/111; 544/333; 544/359; 546/192; 546/268.1; 540/596; 548/517
(58) Field of Search ................................ 549/462, 467, 549/469; 514/470, 212.01, 231.5, 252.13, 469; 540/596; 544/62, 111, 333, 359; 546/192, 268.1

(56) References Cited

U.S. PATENT DOCUMENTS

| 3,903,092 A | 9/1975 | Chapman et al. ........... 260/293 |
| 3,910,955 A | 10/1975 | Chapman et al. ........... 260/330 |
| 4,237,144 A | 12/1980 | Cragoe et al. .............. 424/270 |
| 4,297,369 A | 10/1981 | Takizawa et al. ........... 424/285 |
| 4,447,620 A | 5/1984 | Sih et al. .................... 548/336 |
| 4,452,986 A | 6/1984 | Johnson et al. ............. 548/336 |
| 4,495,357 A | 1/1985 | Johnson ...................... 546/269 |
| 5,436,246 A | 7/1995 | Bernotas et al. ............ 514/255 |
| 5,648,372 A | 7/1997 | Naito et al. ................. 514/383 |
| 5,747,508 A | 5/1998 | Richter et al. .............. 514/320 |
| 5,858,995 A | 1/1999 | Kawai et al. ............... 514/100 |
| 6,302,837 B1 | 10/2001 | De Nanteuil et al. ....... 574/337 |

FOREIGN PATENT DOCUMENTS

| EP | 0 169 012 A1 | 1/1986 |
| EP | 0 512 570 | 10/1995 |
| EP | 0 978 512 A1 | 2/2000 |
| EP | 0 982 300 | 3/2000 |
| WO | 94/26738 | 11/1994 |
| WO | 95/04052 | 2/1995 |
| WO | 95/29907 | 11/1995 |
| WO | 96/11192 | 4/1996 |
| WO | 98/38188 | 9/1998 |
| WO | 98/52946 | 11/1998 |
| WO | 99/61435 | 12/1999 |
| WO | 00/06254 | 2/2000 |
| WO | 01/23380 | 4/2001 |
| WO | 02/10156 | 2/2002 |

OTHER PUBLICATIONS

Repka–Ramirez Curr. Allergy. Asthma Rep. 3(3): 227–31, 2003.*
Barocelli et al. Pharmacol. Res. 47(4): 299–304, 2003.*
Leurs, R., et al. "Therapeutic potential of histamine $H_3$ receptor agonists", Trends in Pharmacological Sciences 1998, vol. 19 (5), pp.177–183 (May 1998).
Haas, H., et al. "Subcortical modulation of synaptic plasticity in the hippocampus", Behavioural Brain Research, Germany, vol. 66, pp. 41–44 (Jan. 1995).
Schwartz, J., et al. "Histaminergic transmission in the mammalian brain", Physiological Reviews, France, vol. 71, No. 1, pp. 1–51 (Jan. 1991).
Descamps et al., "Benzofurans. XLII. Synthesis of 2–benzofurylmethylamines and amides of coumarilic acids," Chimica therapeutica 5(3):169–184 (1970).
JP 07173158 Abstracts.
Bjenning et al., "Peripherally Administered Ciproxifan Elevates Hypothalamic Histamine Levels And Potently Reduces Food Intake in the Sprague Dawley Rat," Histamine Research In The New Mellennium, Proceedings Of The International Sendai Histamine Symposium Held In Sendai, Japan, Nov. 22–25, 2000, p. 449–450.
De Almeida et al., "Memory Facilitation by Histamine," Arch. Int. Pharmacodyn., 283:193–198 (1986).
Delaunois et al., "Modulation Of Acetylcholine, Capsaicin and Substance P Effects by Histamine $H_3$ Receptors in ISolated Perfused Rabbit Lungs," European Journal Of Pharmacology, 277:243–250 (1995).
Dimitriadou et al., "Functional Relationship Between Mast Cells and C–Sensitive Nerve Fibres Evidenced by Histamine $H_3$–Receptor Modulation in Rat Lung and Spleen," Clinical Science, 87:151–163 (1994).

(Continued)

*Primary Examiner*—Venkataraman Balasubramanian
(74) *Attorney, Agent, or Firm*—Portia Chen

(57) ABSTRACT

Compounds of formula (I)

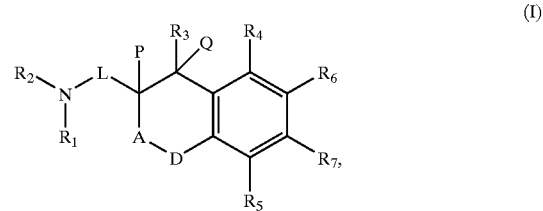

or a pharmaceutically acceptable salts or prodrug thereof which are useful for the modulation of the histamine-3 receptors in mammals and which are useful for the treatment of disorders ameliorated by histamine-3 receptor ligands.

102 Claims, No Drawings

OTHER PUBLICATIONS

Duméry et al., "Development of Amygdaloid Cholinergic Mediation of Passive Avoidance Learning in the Rat," Exp. Brain Res., 67:61–69 (1987).

Ellingboe et al., "Antihyperglycemic Activity of Novel Naphthalenyl 3H–1,2,3,5–Oxathiadiazole 2–Oxides," J. Med. Chem. 36:2485–2493 (1993).

Fitzsimons et al., "Histamine Receptors Signalling in Epidermal Tumor Cell Lines with H–ras Gene Alterations," Inflamm. Res., 47, Supplement I , S50–S51 (1998).

Haas et al., Subcortical Modulation of Synaptic Plasticity in the Hippocampus, Behavioural Brain Research, 66:41–44 (1995).

Hatta et al., "Activation of Histamine $H_3$ Receptors Inhibits Carrier–Mediated Norepinephrine Release in a Human Model of Protracted Myocardial Ischemia$^{1,2}$," The Journal of Pharmacology And Experiemental Therapeutics, 283(2):494–500 (19997).

Imamura et al., "Activation Of Histamine $H_3$–Receptors Inhibits Carrier–Mediated Norepinephrine Release During Protracted Myocardial Ischemia," Circulation Research, 78(3):475–481 (1996).

Imamura et al., "Histamine $H_3$–Receptor–Mediated Inhibition Of Calcitonin Gene–Related Peptide Release From Cardiac C Fiber," Circulation Research, 78(5):863–869 (1996).

Kamei et al., "Participation Of Histamine In The Step–Through Active Avoidance Response And Its Inhibition By $H_1$–Blockers," Japan J. Pharmacol., 57:473–482 (1991).

Leurs et al., "The Histamine $H_3$–Receptor: A Target For Developing New Drugs," Progress In Drug Reseach, 39:127–165 (1992).

Leurs et al., "The Medicinal Chemistry And Therapeutic Potentials Of Ligands Of The Histamine $H_3$ Receptor," Progress In Drug Research, 45:107–165 (1995).

Leurs et al., "Therapeutic Potential Of Histamine $H_3$ Receptor Agonists And Antagonists," Trends In Pharm. Sci, 19:177–183 (1998).

Levi et al., "Histamine $H_3$–Receptors: A New Frontier In Myocardial Ischemia," The Journal Of Pharmacology And Experimental Therapeutics, 292(3):825–830 (2000).

Lin et al., "Involvement Of Histaminergic Neurons In Arousal Mechanisms Demonstrated With $H_3$–Receptor Ligands In The Cat," Brain Research, 523:325–330 (1990).

Matsubara et al., "UK–14,304, R(–)α–Methyl–Histamine And SMS 201–995 Block Plasma Protein Leakage Within Dura Mater By Prejunctional Mechanisms," European Journal Of Pharmacology, 224:145–150 (1992).

Mazurkewicz–Kwilecki et al., "Changes In The Regional Brain Histamine And Histidine Levels In Postmortem Brains Of Alzheimer Patients," Can. J. Physiol. Pharmacol. 67:75–78 (1989).

McLeod et al., "Histamine $H_3$ Antagonists," Progress In Resp. Research 31:133–134 (2001).

Monti et al., "Effects Of Selective Activation Or Blockade Of The Histamine $H_3$ Receptor On Sleep and Wakefulness," European Journal Of Pharmacolgy, 205:283–287 (1991).

Monti et al., "Sleep and Waking During Acute Histamine $H_3$ Agonist BP2.94 Of $H_3$ Antagonist Carboperamide (MR 16155) Administration In Rats," Neuropsychopharmacology, 15(1):31–35 (1996).

Murakami et al., "AQ–0145, A Newly Developed Histamine $H_3$ Antagonist, Decreased Seizure Susceptibility OF Electrically Induced Convulsions In Mice," Meth. Find. Exp. Clin. Pharmacol. 17(C):70–73 (1995).

Onodera et al., "Neuropharmacology Of The Histaminergic Neuron System In The Brain And Its Relationship With Behavioral Disorders," Progress In Neurobiology 42:685–702 (1994).

Panula et al., "Histamine Neurons in Human Hypothalamus: Anatomy in Normal and Alzheimer Diseased Brains, " Neuroscience 44(2):465–481 (1991).

Panula et al., "Neuronal Histamine Deficit in Alzheimer's Disease," Neuroscience 82(4):993–997 (1998).

Perez–Garcia et al., "Effects Of Histamine $H_3$ Receptor Ligands in Experimental Models Of Anxiety And Depression," Psychopharmacology 142:215–220 (1999).

Philips et al., "Recent Advances In Histamine $H_3$ Receptor Agents," Annual Reports In Medicinal Chemistry, 33:31–40 (1998).

Rouleau, "Bioavailability, Antinociceptive And Antiinflammatory Properties Of BP 2–94, A Histamine $H_3$ Receptor Agonist Prodrug," The Journal Of Pharmacology And Experimental Therapeutics, 281(3):1085–1094 (1997).

Sakai et al., "Effects Of Thioperamide, A Histamine $H_3$ Receptor Antagonist, On Locomotor Activity And Brain Histamine Content In Mast Cell–Deficient $W/W^v$ Mice," Life Sciences, 48:2397–2404 (1991).

Schwartz et al., "Histaminergic Transmission in the Mammalian Brain," Physiological Reviews 71(1):1–51 (1991).

Schwartz et al., "Histamine," Psychopharmacology: The Fourth Generation Of Progress, 397–405 (1995).

Shaywitz et al., "Dopaminergic But Not Noradrenergic Mediation Of Hyperactivity And Performance Deficits In The Developing Rat Pup," Psychopharmacology, 82:73–77 (1984).

Szelag, "Role Of Histamine $H_3$–Receptors In The Proliferation Of Neoplastic Cells In Vitro," Med. Sci. Monit., 4(5):747–755 (1998).

Tedford et al., "Cognition And Locomotor Activity In The Developing Rat: Comparisons Of Histamine $H_3$ Receptor Antagonists And ADHD Therapeutics," Society For Neuroscience Abstr., 22:22 (1996).

Tedford et al., "Pharmacological Characterization Of GT–2016, A Non–Thiourea–Containing Histamine $H_3$ Antagonist: In Vitro And In Vivo Studies," The Journal Of Pharmacology And Experimental Therapeutics, 275(2):598–604 (1995).

Wada et al., "Is The Histaminergic Neuron System A Regulatory Center For Whole–Brain Activity?,"Trends In Neurosciences, 14(9):415–418 (1991).

Yates et al., "Effects Of A Novel Histamine $H_3$ Receptor Antagonist, GT–2394, On Food Intake ANd Weight Gain In Sprague–Dawley Rats," Abstracts, Society For Neuroscience, 102:10:219 (Nov. 2000).

Yokoyama et al., "Effect Of Thioperamide, A Histamine $H_3$ Receptor Antagonist, On Electrically Induced Convulsions In Mice," Journal Of Pharmacology, 234 :129–133 (1993).

Yokoyama et al., "Histamine And Seizures Implications For The Treatment Of Epilepsy," CNS Drugs,5(5):321–330 (1996).

* cited by examiner

AMINES AS HISTAMINE-3 RECEPTOR LIGANDS AND THEIR THERAPEUTIC APPLICATIONS

This application claims benefit of U.S. Provisional Application No. 60/276,793 filed Mar. 16, 2001.

TECHNICAL FIELD

This invention relates to compounds useful for treating diseases or conditions caused by or exacerbated by histamine-3 receptor activity, pharmaceutical compositions containing such compounds and methods of treatment using such compounds.

BACKGROUND OF THE INVENTION

Histamine is a well-known mediator in hypersensitive reactions (e.g. allergies, hay fever, and asthma) which are commonly treated with antagonists of histamine or "antihistamines." It has also been established that histamine receptors exist in at least two distinct types, referred to as $H_1$ and $H_2$ receptors.

A third histamine receptor ($H_3$ receptor) is believed to play a role in neurotransmission in the central nervous system, where the $H_3$ receptor is thought to be disposed presynaptically on histaminergic nerve endings (Nature, 302, 832–837 (1983)). The existence of the $H_3$ receptor has been confirmed by the development of selective $H_3$ receptor agonists and antagonists (Nature, 327, 117–123 (1987)) and has subsequently been shown to regulate the release of other neurotransmitters in both the central nervous system and peripheral organs, particularly the lungs, cardiovascular system and gastrointestinal tract.

A number of diseases or conditions may be treated with histamine-3 receptor ligands wherein the $H_3$ ligand may be an antagonist, agonist or partial agonist. Such diseases or conditions include cardiovascular disorders such as acute myocardial infarction; memory processes, dementia and cognition disorders such as Alzheimer's disease and attention-deficit hyperactivity disorder; neurological disorders such as Parkinson's disease, schizophrenia, depression, epilepsy, and seizures or convulsions; cancer such as cutaneous carcinoma, medullary thyroid carcinoma and melanoma; allergic rhinitis; respiratory disorders such as asthma; sleep disorders such as narcolepsy; vestibular dysfunction such as Meniere's disease; gastrointestinal disorders, inflammation, migraine, motion sickness, obesity, pain, and septic shock.

SUMMARY OF INVENTION

In its principle embodiment, the present invention is directed to compounds of formula (I):

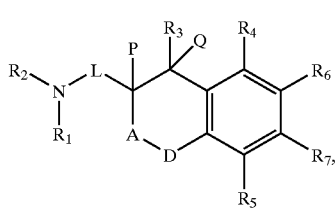

(I)

or a pharmaceutically acceptable salt, ester, amide, or prodrug thereof, wherein A is selected from carbonyl or a covalent bond;

D is selected from O or S;

L is selected from lower alkylene, fluoroalkylene, or hydroxyalkylene;

P and Q taken together form a covalent bond or are both hydrogen;

$R_1$ and $R_2$ are each independently selected from hydrogen, alkyl, aryl, arylalkyl, cycloalkyl, cycloalkylalkyl, heterocycle, heterocyclealkyl, hydroxyalkyl, alkenyl, or alkynyl; or $R_1$ and $R_2$ taken together with the nitrogen atom to which they are attached, together form a heterocycle;

$R_3$ is selected from hydrogen, alkoxy, alkoxycarbonyl, alkyl, alkylcarbonyl, alkylcarbonyloxy, alkylsulfinyl, alkylsulfonyl, alkylthio, aryl, carboxy, carboxyalkyl, cyano, cyanoalkyl, formyl, halogen, haloalkoxy, haloalkyl, heterocycle, hydroxy, hydroxyalkyl, mercapto, nitro, —$NR_AR_B$, ($NR_AR_B$)alkyl, ($NR_AR_B$)carbonyl, or ($NR_AR_B$)sulfonyl;

$R_4$, $R_5$, $R_6$ and $R_7$ are each independently selected from hydrogen, alkoxy, alkoxycarbonyl, alkyl, alkylcarbonyl, alkylcarbonyloxy, alkylsulfinyl, alkylsulfonyl, alkylthio, aryl, carboxy, carboxyalkyl, cyano, cyanoalkyl, cycloalkyl, formyl, halogen, haloalkoxy, haloalkyl, heterocycle, hydroxy, hydroxyalkyl, mercapto, nitro, —$NR_AR_B$, ($NR_AR_B$)alkyl, ($NR_AR_B$)carbonyl, ($NR_AR_B$)sulfonyl, —$L_2R_{20}$, or —$R_{20}L_3R_{22}$;

$L_2$ is selected from alkylene, alkenylene, O, S, S(O), $S(O)_2$, C(=O), C=(NOR$_{21}$), or N($R_A$);

$L_3$ is selected from a covalent bond, alkylene, alkenylene, O, S, C(=O), N(=OR$_{21}$), or N($R_A$);

$R_{20}$ is selected from aryl, heterocycle, or cycloalkyl;

$R_{21}$ is selected from hydrogen or alkyl;

$R_{22}$ is selected from aryl, heterocycle, or cycloalkyl;

$R_A$ and $R_B$ are each independently selected from hydrogen, alkyl, alkylcarbonyl or formyl;

provided that at least one of $R_4$, $R_5$, $R_6$, or $R_7$ is aryl, heterocycle, cycloalkyl, —$L_2R_{20}$ or —$R_{20}L_3R_{22}$.

The compounds can be incorporated into pharmaceutical compositions and can be useful in methods for treating or preventing disorders related to histamine-3 receptor modulation. The compounds, compositions comprising the compounds, and methods for treating or preventing disorders by administering the compounds are further described herein.

DETAILED DESCRIPTION OF THE INVENTION

The present invention discloses compounds and compositions thereof which are useful for selectively modulating the effects of the histamine-3 receptors in a mammal. The compounds of the invention can be used for treating and preventing disorders modulated by the histamine-3 receptor. Typically, the disorders are those that are ameliorated by selectively modulating the histamine-3 receptors in a mammal. One method of the invention provides for treating a disorder selected from acute myocardial infarction, asthma, bipolar disorder, cognitive enhancement, cognitive deficits in psychiatric disorders, cutaneous carcinoma, drug abuse, depression, gastrointestinal disorders, inflammation, jet lag, medullary thyroid carcinoma, melanoma, allergic rhinitis, Meniere's disease, migraine, mood and attention alteration, motion sickness, neurogenic inflammation, obsessive compulsive disorder, pain, Parkinson's disease, schizophrenia, seizures, septic shock, Tourette's syndrome, vertigo, or wakefulness. The method can be particularly useful for treating Alzheimer's disease, attention-deficit hyperactivity disorder, epilepsy, narcolepsy, and cognitive and memory-related disorders, for example, mild cognitive impairment, deficits of memory, and deficits of learning and dementia.

Definition of Terms

As used for the present invention, the following terms have the meanings ascribed.

The term "alkenyl," as used herein, refers to a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of from 2 to 10 carbon atoms containing at least one double bond. Representative examples of alkenylene include, but are not limited to, $-CH=CH-$, $-C(=CH_2)-$ $-CH=CH_2CH_2-$, $-CH_2CH_2C(=CH_2)CH_2-$, $-CH_2CH_2C(=CHCH_3)CH_2-$, and $-CH=C(CH_3)CH_2-$.

The term "alkoxy," as used herein, refers to an alkyl group, as defined herein, appended to the parent molecular moiety through an oxy moiety, as defined herein. Representative examples of alkoxy include, but are not limited to, methoxy, ethoxy, propoxy, 2-propoxy, butoxy, tert-butoxy, pentyloxy, and hexyloxy.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl and methoxymethyl.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl and tert-butoxycarbonyl.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl and n-decyl.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl and 1-oxopentyl.

The term "alkylcarbonyloxy," as used herein, refers to an alkylcarbonyl group, as defined herein, appended to the parent molecular moiety through an oxy moiety, as defined herein. Representative examples of alkylcarbonyloxy include, but are not limited to, acetyloxy, ethylcarbonyloxy and tert-butylcarbonyloxy.

The term "alkylene" means a divalent group derived from a straight or branched chain hydrocarbon of from 1 to 10 carbon atoms. Representative examples of alkylene include, but are not limited to, $-CH_2-$, $-CH_2CH_2-$, $-CH_2CH_2CH_2-$, $-CH_2CH_2CH_2CH_2-$, and $-CH_2CH(CH_3)CH_2-$.

The term "alkylsulfinyl," as used herein, refers to an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfonyl," as used herein, refers to an alkyl group, as defined herein, appended to the parent molecular moiety through a sulfonyl group, as defined herein. Representative examples of alkylsulfonyl include, but are not limited to, ethylsulfonyl, isopropylsulfonyl and methylsulfonyl.

The term "alkylthio," as used herein, refers to an alkyl group, as defined herein, appended to the parent molecular moiety through a sufur atom, as defined herein. Representative examples of alkylthio include, but are not limited to, Methylsulfanyl, ethylsulfinyl, tert-butylsulfinyl and hexylsulfonyl.

The term "aryl," as used herein, refers to a monocyclic-ring system, or a bicyclic- or a tricyclic-fused ring system wherein one or more of the fused rings are aromatic. Representative examples of aryl include, but are not limited to, anthracene, azulenyl, fluorenyl, indanyl, indenyl, naphthyl, phenyl, and tetrahydronaphthyl.

The aryl groups of this invention are substituted with 0, 1, 2, 3, 4 or 5 substituents independently selected from alkenyl, alkoxy, alkoxyalkoxy, alkoxyalkyl, alkoxycarbonyl, alkyl, alkylcarbonyl, alkylcarbonyloxy, alkylsulfinyl, alkylsulfonyl, alkylthio, alkynyl, carboxy, carboxyalkyl, cyano, cyanoalkyl, formyl, halogen, haloalkoxy, haloalkyl, hydroxy, hydroxyalkyl, mercapto, nitro, oximyl, $-NR_AR_B$, $(NR_AR_B)$alkyl, $(NR_AR_B)$carbonyl, and $(NR_AR_B)$sulfonyl.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylcarbonyl," as used herein, refers to an aryl group, as defined herein, appended to the parent molecular moiety through a carbonyl group, as defined herein. Representative examples of arylcarbonyl include, but are not limited to, benzoyl, phenylacetyl, 3-chlorophenylacetyl, 3-methoxyphenylacetyl, 4-fluoro-3-methylphenylacetyl, 3-phenylpropionyl, and 2-naphthylacetyl.

The term "carbonyl," as used herein, refers to a $-C(O)-$ group.

The term "carboxy," as used herein, refers to a $-CO_2H$ group.

The term "carboxyalkyl," as used herein, refers to a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano," as used herein, refers to a $-CN$ group.

The term "cyanoalkyl," as used herein, refers to a cyano group, as defined herein, appended to the parent molecular moiety through an alkyl group, as defined herein. Representative examples of cyanoalkyl include, but are not limited to, cyanomethyl, 2-cyanoethyl and 3-cyanopropyl.

The term "cycloalkyl," as used herein, refers to a saturated cyclic hydrocarbon group containing from 3 to 8 carbons. Examples of cycloalkyl include cyclopropyl, cyclobutyl, cyclopentyl, cyclohexyl, cycloheptyl and cyclooctyl.

The term "cycloalkylalkyl," as used herein, refers to cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl and 4-cycloheptylbutyl.

The term "fluoroalkylene" means an alkylene, as defined herein, containing 1 or fluorine atoms. Representative examples of fluoroalkylene include, but are not limited to, —CH$_2$CH(F)—, —CH$_2$C(F)$_2$—, —CH$_2$C(F)$_2$CH$_2$—, and —CH$_2$CH$_2$C(F)$_2$—.

The term "formyl," as used herein, refers to a —C(O)H group.

The term "halo" or "halogen," as used herein, refers to —Cl, —Br, —I or —F.

The term "haloalkoxy," as used herein, refers to at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl," as used herein, refers to at least one halogen, as defined herein, appended to the parent molecular moiety through an alkyl group, as defined herein. Representative examples of haloalkyl include, but are not limited to, chloromethyl, fluoromethyl, 2-fluoroethyl, trifluoromethyl, pentafluoroethyl, and 2-chloro-3-fluoropentyl.

The term "heterocycle" or "heterocyclic," as used herein, refers to a monocyclic or bicyclic ring system. Monocyclic ring systems are exemplified by any 3- or 4-membered ring containing a heteroatom independently selected from oxygen, nitrogen and sulfur; or a 5-, 6-, or 7-membered ring containing one, two or three heteroatoms wherein the heteroatoms are independently selected from nitrogen, oxygen and sulfur. The 5-membered ring has from 0–2 double bonds and the 6- and 7-membered rings have from 0–3 double bonds. Representative examples of monocyclic ring systems include, but are not limited to, azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridyl, pyrimidinyl, pyridazinyl, 2,5-dihydro-1H-pyrrolyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. More particularly, example of monocyclic ring systems can include, but are not limited to, 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, and 1,4-dioxa-8-azaspiro[4.5]dec-8-yl, 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl. Bicyclic ring systems are exemplified by any of the above monocyclic heterocyclic ring systems fused to an aryl group as defined herein, a cycloalkyl group as defined herein, or another monocyclic heterocyclic ring system. Representative examples of bicyclic ring systems include but are not limited to, benzimidazolyl, benzothiazolyl, benzothienyl, benzoxazolyl, benzofuranyl, benzopyranyl, benzothiopyranyl, benzodioxinyl, 1,3-benzodioxolyl, cinnolinyl, indazolyl, indolyl, indolinyl, indolizinyl, naphthyridinyl, 3H-imidazo[4,5-c]pyridinyl, isobenzofuranyl, isobenzothienyl, isoindolyl, isoindolinyl, isoquinolinyl, phthalazinyl, pyranopyridyl, quinolinyl, quinolizinyl, quinoxalinyl, quinazolinyl, tetrahydroisoquinolinyl, tetrahydroquinolinyl, and thiopyranopyridyl.

The heterocycles of this invention are substituted with 0, 1, 2, or 3 substituents independently selected from alkenyl, alkoxy, alkoxyalkyl, alkoxycarbonyl, alkyl, alkylcarbonyl, alkylcarbonyloxy, alkylsulfinyl, alkylsulfonyl, alkylthio, arylalkyl, carboxy, carboxyalkyl, cyano, cyanoalkyl, formyl, halogen, haloalkoxy, haloalkyl, haloalkylcarbonyl, hydroxy, hydroxyalkyl, mercapto, nitro, oxo, —NR$_A$R$_B$, (NR$_A$R$_B$)alkyl, (NR$_A$R$_B$)carbonyl and (NR$_A$R$_B$)sulfonyl.

The term "heterocyclealkyl," as used herein, refers to a heterocycle, as defined herein, appended to the parent molecular moiety through an alkyl group, as defined herein. Representative examples of heterocyclealkyl include, but are not limited to, pyridin-3-ylmethyl and 2-pyrimidin-2-ylpropyl.

The term "heterocyclecarbonyl," as used herein, refers to a heterocycle, as defined herein, appended to the parent molecular moiety through a carbonyl group, as defined herein. Representative examples of heterocyclecarbonyl include, but are not limited to, 1H-imidazol-1-ylcarbonyl, 4-morpholinylcarbonyl, 1-piperidinylcarbonyl and cyclopentylaminocarbonyl.

The term "hydroxy," as used herein, refers to an —OH group.

The term "hydroxyalkyl," as used herein, refers to one or two hydroxy groups, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypropyl and 2-ethyl-4-hydroxyheptyl.

The term "hydroxyalkylene" means an alkylene, as defined herein, containing 1 or hydroxy groups. Representative examples of hydroxyalkylene include, but are not limited to, —CH$_2$CH(OH)—, —CH$_2$CH(OH)CH$_2$—, —CH$_2$CH$_2$CH(OH)—, and —CH$_2$CH(OH)CH(OH)—.

The term "lower alkylene" as used herein, is a subset of alkylene as defined herein and means a straight or branched chain hydrocarbon group containing from 1 to 6 carbon atoms. Representative examples of lower alkylene are —CH$_2$—, —CH$_2$CH$_2$—, —CH$_2$CH$_2$CH$_2$—, —CH$_2$CH(CH$_3$)CH$_2$—, and —CH$_2$CH$_2$CH$_2$CH$_2$—.

The term "mercapto," as used herein, refers to —SH group.

The term "nitro," as used herein, refers to a —NO$_2$ group.

The term "—NR$_A$R$_B$," as used herein, refers to two groups, R$_A$ and R$_B$, which are appended to the parent molecular moiety through a nitrogen atom. $R_A$ and $R_B$ are each independently selected from hydrogen, alkoxy, alkyl, alkylcarbonyl, and formyl. Representative examples of —$NR_AR_B$ include, but are not limited to, acetylamino, amino, formylamino, dimethylamino, and methylamino.

The term "($NR_AR_B$)alkyl," as used herein, refers to a —$NR_AR_B$ group, as defined herein, appended to the parent molecular moiety through an alkyl group, as defined herein. Representative examples of ($NR_AR_B$)alkyl include, but are not limited to, (amino)methyl, (dimethylamino)methyl and (ethylamino)methyl.

The term "($NR_AR_B$)carbonyl," as used herein, refers to a —$NR_AR_B$ group, as defined herein, appended to the parent molecular moiety through a carbonyl group, as defined herein. Representative examples of ($NR_AR_B$)carbonyl include, but are not limited to, aminocarbonyl, dimethylaminocarbonyl and ethylaminocarbonyl.

The term "($NR_AR_B$)sulfonyl," as used herein, refers to an amino group, as defined herein, appended to the parent molecular moiety through a sulfonyl group, as defined herein. Representative examples of aminosulfonyl include, but are not limited to, aminosulfonyl, dimethylaminosulfonyl and ethylaminosulfonyl.

The term "oximyl" as used herein, refers to a C(=$NOR_{99}$)$R_{100}$ group wherein $R_{99}$ and $R_{100}$ are independently selected from hydrogen and alkyl.

The term "oxo," as used herein, refers to a =O moiety.

The term "oxy," as used herein, refers to a —O— moiety.

The term "sulfinyl," as used herein, refers to a —S(O)— group.

The term "sulfonyl," as used herein, refers to a —$SO_2$— group.

Compounds of the present invention include at least those compounds of formula (I) wherein one substituent represented by $R_4$, $R_5$, $R_6$ or $R_7$ are selected from hydrogen, alkoxy, alkoxycarbonyl, alkyl, alkylcarbonyl, alkylcarbonyloxy, alkylsulfinyl, alkylsulfonyl, alkylthio, aryl, carboxy, carboxyalkyl, cyano, cyanoalkyl, cycloalkyl, formyl, halogen, haloalkoxy, haloalkyl, heterocycle, hydroxy, hydroxyalkyl, mercapto, nitro, —$NR_AR_B$, ($NR_AR_B$)alkyl, ($NR_AR_B$)carbonyl, ($NR_AR_B$)sulfonyl, —$L_2R_{20}$, or —$R_{20}L_3R_{22}$; and the other substituents represented by $R_4$, $R_5$, $R_6$ and $R_7$ is selected from hydrogen or alkyl. Particular groups for the substituents represented by $R_4$, $R_5$, $R_6$ and $R_7$ can be selected from hydrogen, alkyl, heterocycle, —$L_2R_{20}$, and —$R_{20}L_3R_{22}$.

Compounds of the present invention also can have the formula (I) wherein A is a covalent bond; D is O; L is —$CH_2CH_2$—; P and Q taken together form a covalent bond; $R_1$ and $R_2$ taken together with the nitrogen atom to which they are attached form heterocycle; $R_3$, $R_4$, $R_5$, and $R_7$ are hydrogen; and $R_6$ is $L_2R_{20}$.

Heterocycles formed by $R_1$ and $R_2$ can include, but are not limited to, azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl. Particular examples of heterocycles for compounds of the invention are, for example, 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl. The (2R)-2-methyl-1-pyrrolidinyl group may be preferred.

Groups for $R_6$ can include, but are not limited to, a group represented by the formula $L_2R_{20}$, alkylcarbonyl, heterocycle, or a group represented by $R_{20}L_3R_{22}$. Where $R_6$ is $L_2R_{20}$, particular groups for the position can include, but are not limited to, those wherein $L_2$ is C(=O) and $R_{20}$ is aryl; $L_2$ is C(=O) and $R_{20}$ is cycloalkyl; $L_2$ is alkylene or alkenylene and $R_{20}$ is aryl. Specific aryl groups for $R_{20}$ include, but are not limited to, phenyl that is substituted with 0, 1, 2 or 3 substituents selected from hydrogen, alkoxy, alkyl, alkoxycarbonyl, alkylcarbonyl, alkylthio, carboxy, cyano, formyl, haloalkoxy, haloalkyl, halogen, hydroxyalkyl, oximyl, ($NR_AR_B$)carbonyl, or $NR_AR_B$.

Heterocycle groups suitable for $R_6$ are, for example, furyl, imidazolyl, isothiazolyl, isothiazolinyl, isoxazolyl, oxadiazolyl, oxazolyl, pyrazinyl, pyrazolyl, pyridinyl, pyrimidinyl, pyridazinyl, pyrrolyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, indazolyl, indolyl, indolizinyl, naphthyridinyl, isobenzofuranyl, isobenzothienyl, isoindolyl, isoquinolinyl, quinolinyl, quinolizinyl, quinoxalinyl, or quinazolinyl. The heterocycle group for $R_6$ is substituted with 0, 1, 2 or 3 substituents selected from alkenyl, alkoxy, alkoxyalkyl, alkoxycarbonyl, alkyl, alkylcarbonyl, alkylcarbonyloxy, alkylsulfinyl, alkylsulfonyl, alkylthio, arylalkyl, carboxy, carboxyalkyl, cyano, cyanoalkyl, formyl, halogen, haloalkoxy, haloalkyl, haloalkylcarbonyl, hydroxy, hydroxyalkyl, mercapto, nitro, oxo, —$NR_AR_B$, ($NR_AR_B$)alkyl, ($NR_AR_B$)carbonyl and ($NR_AR_B$)sulfonyl; wherein $R_A$ and $R_B$ are as defined in formula (I). Particular heterocycles for $R_6$ are 1,2,4-oxadiazol-3-yl, 3-pyridinyl, 4-isoxazolyl and 1H-imidazol-1-yl, wherein the heterocycle is substituted with 0, 1 or 2 substituents selected from hydrogen, alkyl, haloalkyl, or hydroxyalkyl.

Where $R_6$ is $R_{20}L_3R_{22}$, particular groups for the position can include, but are not limited to, those wherein $R_{20}$ is heterocycle, $L_3$ is a covalent bond or alkylene and $R_{22}$ is aryl; $R_{20}$ is heterocycle, $L_3$ is a covalent bond or alkylene and $R_{22}$ is heterocycle, particularly 2-thienyl; $R_{20}$ is aryl, particularly phenyl, $L_3$ is C(=O) and $R_{22}$ is cycloalkyl; $R_{20}$ is aryl, particularly phenyl, $L_3$ is C(=O) and $R_{22}$ is aryl; and $R_{20}$ is aryl, $L_3$ is a covalent bond or alkylene and $R_{22}$ is heterocycle, particularly 2-thienyl. Phenyl groups are particularly suitable for an aryl group $R_{22}$. Such phenyl groups is substituted with 0, 1, 2 or 3 substituents selected from hydrogen, alkoxy, alkyl, alkoxycarbonyl, alkylcarbonyl, alkylthio, carboxy, cyano, formyl, haloalkoxy, haloalkyl, halogen, hydroxyalkyl, oximyl, ($NR_AR_B$)carbonyl, and $NR_AR_B$.

In one embodiment, compounds of the present invention have formula (I) wherein A is a covalent bond; D is O; L is —$CH_2CH_2$—; P and Q taken together form a covalent bond; $R_1$ and $R_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_3$, $R_4$, $R_5$ and $R_7$ are hydrogen; $R_6$ is $L_2R_{20}$; $L_2$ is C(=O); and $R_{20}$ is aryl.

In another embodiment, compounds of the present invention have formula (I) wherein A is a covalent bond; D is O; L is —CH$_2$CH$_2$—; P and Q taken together form a covalent bond; $R_1$ and $R_2$ taken together with the nitrogen atom to which they are attached, together form a heterocycle selected from 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; $R_3$, $R_4$, $R_5$ and $R_7$ are hydrogen; $R_6$ is $L_2R_{20}$; $L_2$ is C(=O); and $R_{20}$ is aryl.

In another embodiment, compounds of the present invention have formula (I) wherein A is a covalent bond; D is O; L is —CH$_2$CH$_2$—; P and Q taken together form a covalent bond; $R_1$ and $R_2$ taken together with the nitrogen atom to which they are attached, together form a heterocycle (2R)-2-methyl-1-pyrrolidinyl; $R_3$, $R_4$, $R_5$ and $R_7$ are hydrogen; $R_6$ is $L_2R_{20}$; $L_2$ is C(=O); and $R_{20}$ is phenyl substituted with 0, 1, 2 or 3 substitutents selected from hydrogen, alkoxy, alkyl, alkoxycarbonyl, alkylcarbonyl, alkylthio, carboxy, cyano, formyl, haloalkoxy, haloalkyl, halogen, hydroxyalkyl, oximyl, (NR$_A$R$_B$)carbonyl, or —NR$_A$R$_B$.

In another embodiment, compounds of the present invention have formula (I) wherein A is a covalent bond; D is O; L is —CH$_2$CH$_2$—; P and Q taken together form a covalent bond; $R_1$ and $R_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_3$, $R_4$, $R_5$ and $R_7$ are hydrogen; $R_6$ is $L_2R_{20}$; $L_2$ is C(=O); and $R_{20}$ is cycloalkyl.

In another embodiment, compounds of the present invention have formula (I) wherein A is a covalent bond; D is O; L is —CH$_2$CH$_2$—; P and Q taken together form a covalent bond; $R_1$ and $R_2$ taken together with the nitrogen atom to which they are attached, together form a heterocycle selected from 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; $R_3$, $R_4$, $R_5$ and $R_7$ are hydrogen; $R_6$ is $L_2R_{20}$; $L_2$ is C(=O); and $R_{20}$ is cycloalkyl.

In another embodiment, compounds of the present invention have formula (I) wherein A is a covalent bond; D is O; L is —CH$_2$CH$_2$—; P and Q taken together form a covalent bond; $R_1$ and $R_2$ taken together with the nitrogen atom to which they are attached, together form a heterocycle (2R)-2-methyl-1-pyrrolidinyl; $R_3$, $R_4$, $R_5$ and $R_7$ are hydrogen; $R^6$, is $L_2R_{20}$; $L_2$ is C(=O); and $R_{20}$ is cycloalkyl.

In another embodiment, compounds of the present invention have formula (I) wherein A is a covalent bond; D is O; L is —CH$_2$CH$_2$—; P and Q taken together form a covalent bond; $R_1$ and $R_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_3$, $R_4$, $R_5$ and $R_7$ are hydrogen; $R_6$ is $L_2R_{20}$; $L_2$ is selected from alkylene and alkenylene; and $R_{20}$ is aryl.

In another embodiment, compounds of the present invention have formula (I) wherein A is a covalent bond; D is O; L is —CH$_2$CH$_2$—; P and Q taken together form a covalent bond; $R_1$ and $R_2$ taken together with the nitrogen atom to which they are attached, together form a heterocycle selected from 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; $R_3$, $R_4$, $R_5$ and $R_7$ are hydrogen; $R_6$ is $L_2R_{20}$; $L_2$ is selected from alkylene and alkenylene; and $R_{20}$ is aryl.

In another embodiment, compounds of the present invention have formula (I) wherein A is a covalent bond; D is O; L is —CH$_2$CH$_2$—; P and Q taken together form a covalent bond; $R_1$ and $R_2$ taken together with the nitrogen atom to which they are attached, together form a heterocycle (2R)-2-methyl-1-pyrrolidinyl; $R_3$, $R_4$, $R_5$ and $R_7$ are hydrogen; and $R_6$ is $L_2R_{20}$; $L_2$ is selected from alkylene and alkenylene; and $R_{20}$ is phenyl substituted with 0, 1, 2, or 3 substituents selected from hydrogen, alkoxy, alkyl, alkoxycarbonyl, alkylcarbonyl, alkylthio, carboxy, cyano, formyl, haloalkoxy, haloalkyl, halogen, hydroxyalkyl, oximyl, (NR$_A$R$_B$)carbonyl, or —NR$_A$R$_B$.

In another embodiment, compounds of the present invention have formula (I) wherein A is a covalent bond; D is O;

L is —CH$_2$CH$_2$—; P and Q taken together form a covalent bond; R$_1$ and R$_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; R$_3$, R$_4$, R$_5$ and R$_7$ are hydrogen; and R$_6$ is alkylcarbonyl.

In another embodiment, compounds of the present invention have formula (I) wherein A is a covalent bond; D is O; L is —CH$_2$CH$_2$—; P and Q taken together form a covalent bond; R$_1$ and R$_2$ taken together with the nitrogen atom to which they are attached, together form a heterocycle selected from 1-azepanyl, (3S)-3-(dimethylamino) pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl) pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; R$_3$, R$_4$, R$_5$ and R$_7$ are hydrogen; and R$_6$ is alkylcarbonyl.

In another embodiment, compounds of the present invention have formula (I) wherein A is a covalent bond; D is O; L is —CH$_2$CH$_2$—; P and Q taken together form a covalent bond; R$_1$ and R$_2$ taken together with the nitrogen atom to which they are attached, together form a heterocycle (2R)-2-methyl-1-pyrrolidinyl; R$_3$, R$_4$, R$_5$ and R$_7$ are hydrogen; and R$_6$ is alkylcarbonyl.

In another embodiment, compounds of the present invention have formula (I) wherein A is a covalent bond; D is O; L is —CH$_2$CH$_2$—; P and Q taken together form a covalent bond; R$_1$ and R$_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; R$_3$, R$_4$, R$_5$ and R$_7$ are hydrogen; and R$_6$ is heterocycle.

In another embodiment, compounds of the present invention have formula (I) wherein A is a covalent bond; D is O; L is —CH$_2$CH$_2$—; P and Q taken together form a covalent bond; R$_1$ and R$_2$ taken together with the nitrogen atom to which they are attached, together form a heterocycle selected from 1-azepanyl, (3S)-3-(dimethylamino) pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl) pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; R$_3$, R$_4$, R$_5$ and R$_7$ are hydrogen; and R$_6$ is heterocycle.

In another embodiment, compounds of the present invention have formula (I) wherein A is a covalent bond; D is O; L is —CH$_2$CH$_2$—; P and Q taken together form a covalent bond; R$_1$ and R$_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; R$_3$, R$_4$, R$_5$ and R$_7$ are hydrogen; R$_6$ is a heterocycle selected from furyl, imidazolyl, isothiazolyl, isothiazolinyl, isoxazolyl, oxadiazolyl, oxazolyl, pyrazinyl, pyrazolyl, pyridinyl, pyrimidinyl, pyridazinyl, pyrrolyl, tetrazolyl, thiadiazolyl, thiazolyl, thienyl, triazinyl, triazolyl, benzimidazolyl, benzothiazolyl, benzothienyl, benzoxazolyl, benzofuranyl, cinnolinyl, indazolyl, indolyl, indolizinyl, naphthyridinyl, isobenzofuranyl, isobenzothienyl, isoindolyl, isoquinolinyl, quinolinyl, quinolizinyl, quinoxalinyl, or quinazolinyl wherein the heterocycle is substituted with 0, 1, 2, or 3 substituents selected from alkenyl, alkoxy, alkoxyalkyl, alkoxycarbonyl, alkyl, alkylcarbonyl, alkylcarbonyloxy, alkylsulfinyl, alkylsulfonyl, alkylthio, arylalkyl, carboxy, carboxyalkyl, cyano, cyanoalkyl, formyl, halogen, haloalkoxy, haloalkyl, haloalkylcarbonyl, hydroxy, hydroxyalkyl, mercapto, nitro, oxo, —NR$_A$R$_B$, (NR$_A$R$_B$) alkyl, (NR$_A$R$_B$)carbonyl and (NR$_A$R$_B$)sulfonyl; and R$_A$ and R$_B$ are as defined in formula (I).

In another embodiment, compounds of the present invention have formula (I) wherein A is a covalent bond; D is O; L is —CH$_2$CH$_2$—; P and Q taken together form a covalent bond; R$_1$ and R$_2$ taken together with the nitrogen atom to which they are attached, together form a heterocycle (2R)-2-methyl-1-pyrrolidinyl; R$_3$, R$_4$, R$_5$ and R$_7$ are hydrogen; and R$_6$ is a heterocycle selected from 1,2,4-oxadiazol-3-yl, 3-pyridinyl, 4-isoxazolyl, or 1H-imidazol-1-yl wherein the heterocycle is substituted with 0, 1, or 2 substituents selected from hydrogen, alkyl, haloalkyl, or hydroxyalkyl.

In another embodiment, compounds of the present invention have formula (I) wherein A is a covalent bond; D is O; L is —CH$_2$CH$_2$—; P and Q taken together form a covalent bond; R$_1$ and R$_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; R$_3$, R$_4$, R$_5$ and R$_7$ are hydrogen; R$_6$ is —R$_{20}$L$_3$R$_{22}$; R$_{20}$ is heterocycle; L$_3$ is selected from a covalent bond and alkylene; and R$_{22}$ is aryl.

In another embodiment, compounds of the present invention have formula (I) wherein A is a covalent bond; D is O; L is —CH$_2$CH$_2$—; P and Q taken together form a covalent bond; R$_1$ and R$_2$ taken together with the nitrogen atom to which they are attached, together form a heterocycle selected from 1-azepanyl, (3S)-3-(dimethylamino) pyrrolidinyl, (3R)-3-(dimethylamino)pyrrolidinyl, 1H-imidazol-1-yl, (3R)-3-hydroxy-1-pyrrolidinyl, (3S)-3- hydroxy-1-pyrrolidinyl, (2S)-2-(hydroxymethyl) pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; $R_3$, $R_4$, $R_5$ and $R_7$ are hydrogen; $R_6$ is —$R_{20}L_3R_{22}$; $R_{20}$ is heterocycle; $L_3$ is selected from a covalent bond and alkylene; and $R_{22}$ is aryl.

In another embodiment, compounds of the present invention have formula (I) wherein A is a covalent bond; D is O; L is —$CH_2CH_2$—; P and Q taken together form a covalent bond; $R_1$ and $R_2$ taken together with the nitrogen atom to which they are attached, together form a heterocycle (2R)-2-methyl-1-pyrrolidinyl; $R_3$, $R_4$, $R_5$ and $R_7$ are hydrogen; $R_6$ is —$R_{20}L_3R_{22}$; $R_{20}$ is 1,2,4-oxadiazol-3-yl; $L_3$ is selected from a covalent bond and alkylene; and $R_{22}$ is phenyl substituted with 0, 1, 2, or 3 substituents selected from hydrogen, alkoxy, alkyl, alkoxycarbonyl, alkylcarbonyl, alkylthio, carboxy, cyano, formyl, haloalkoxy, haloalkyl, halogen, hydroxyalkyl, oximyl, ($NR_AR_B$)carbonyl, or —$NR_AR_B$.

In another embodiment, compounds of the present invention have formula (I) wherein A is a covalent bond; D is O; L is —$CH_2CH_2$—; P and Q taken together form a covalent bond; $R_1$ and $R_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_3$, $R_4$, $R_5$ and $R_7$ are hydrogen; $R_6$ is —$R_{20}L_3R_{22}$; $R_{20}$ is 1,2,4-oxadiazol-3-yl; $L_3$ is selected from a covalent bond and alkylene; and $R_{22}$ is heterocycle.

In another embodiment, compounds of the present invention have formula (I) wherein A is a covalent bond; D is O; L is —$CH_2CH_2$—; P and Q taken together form a covalent bond; $R_1$ and $R_2$ taken together with the nitrogen atom to which they are attached, together form a heterocycle selected from 1-azepanyl, (3S)-3-(dimethylamino) pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl) pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; $R_3$, $R_4$, $R_5$ and $R_7$ are hydrogen; $R_6$ is —$R_{20}L_3R_{22}$; $R_{20}$ is 1,2,4-oxadiazol-3-yl; $L_3$ is selected from a covalent bond and alkylene; and $R_{22}$ is heterocycle.

In another embodiment, compounds of the present invention have formula (I) wherein A is a covalent bond; D is O; L is —$CH_2CH_2$—; P and Q taken together form a covalent bond; $R_1$ and $R_2$ taken together with the nitrogen atom to which they are attached, together form a heterocycle (2R)-2-methyl-1-pyrrolidinyl; $R_3$, $R_4$, $R_5$ and $R_7$ are hydrogen; $R_6$ is —$R_{20}L_3R_{22}$; $R_{20}$ is 1,2,4-oxadiazol-3-yl; $L_3$ is selected from a covalent bond and alkylene; and $R_{22}$ is 2-thienyl.

In another embodiment, compounds of the present invention have formula (I) wherein A is a covalent bond; D is O; L is —$CH_2CH_2$—; P and Q taken together form a covalent bond; $R_1$ and $R_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_3$, $R_4$, $R_5$ and $R_7$ are hydrogen; $R_6$ is —$R_{20}L_3R_{22}$; $R_{20}$ is aryl; $L_3$ is C(=O); and $R_{22}$ is cycloalkyl.

In another embodiment, compounds of the present invention have formula (I) wherein A is a covalent bond; D is O; L is —$CH_2CH_2$—; P and Q taken together form a covalent bond; $R_1$ and $R_2$ taken together with the nitrogen atom to which they are attached, together form a heterocycle selected from 1-azepanyl, (3S)-3-(dimethylamino) pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl) pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; $R_3$, $R_4$, $R_5$ and $R_7$ are hydrogen; $R_6$ is —$R_{20}L_3R_{22}$; $R_{20}$ is aryl; $L_3$ is C(=O); and $R_{22}$ is cycloalkyl.

In another embodiment, compounds of the present invention have formula (I) wherein A is a covalent bond; D is O; L is —$CH_2CH_2$—; P and Q taken together form a covalent bond; $R_1$ and $R_2$ taken together with the nitrogen atom to which they are attached, together form a heterocycle (2R)-2-methyl-1-pyrrolidinyl; $R_3$, $R_4$, $R_5$ and $R_7$ are hydrogen; $R_6$ is —$R_{20}L_3R_{22}$; $R_{20}$ is phenyl; $L_3$ is C(=O); and $R_{22}$ is cycloalkyl.

In another embodiment, compounds of the present invention have formula (I) wherein A is a covalent bond; D is O; L is —$CH_2CH_2$—; P and Q taken together form a covalent bond; $R_1$ and $R_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_3$, $R_4$, $R_5$ and $R_7$ are hydrogen; $R_6$ is —$R_{20}L_3R_{22}$; $R_{20}$ is aryl; $L_3$ is C(=O); and $R_{22}$ is aryl.

In another embodiment, compounds of the present invention have formula (I) wherein A is a covalent bond; D is O;

L is —CH$_2$CH$_2$—; P and Q taken together form a covalent bond; R$_1$ and R$_2$ taken together with the nitrogen atom to which they are attached, together form a heterocycle selected from 1-azepanyl, (3S)-3-(dimethylamino) pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl) pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1 ]hept-5-yl, or 1,4-dioxa-8-azaspiro[4.5]dec-8-yl; R$_3$, R$_4$, R$_5$ and R$_7$ are hydrogen; R$_6$ is —R$_{20}$L$_3$R$_{22}$; R$_{20}$ is aryl; L$_3$ is C(=O); and R$_{22}$ is aryl.

In another embodiment, compounds of the present invention have formula (I) wherein A is a covalent bond; D is O; L is —CH$_2$CH$_2$—; P and Q taken together form a covalent bond; R$_1$ and R$_2$ taken together with the nitrogen atom to which they are attached, together form a heterocycle (2R)-2-methyl-1-pyrrolidinyl; R$_3$, R$_4$, R$_5$ and R$_7$ are hydrogen; R$_6$ is —R$_{20}$L$_3$R$_{22}$; R$_{20}$ is phenyl; L$_3$ is C(=O); and R$_{22}$ is phenyl substituted with 0, 1, 2, or 3 substituents selected from hydrogen, alkoxy, alkyl, alkoxycarbonyl, alkylcarbonyl, alkylthio, carboxy, cyano, formyl, haloalkoxy, haloalkyl, halogen, hydroxyalkyl, oximyl, (NR$_A$R$_B$)carbonyl, or —NR$_A$R$_B$.

In another embodiment, compounds of the present invention have formula (I) wherein A is a covalent bond; D is O; L is —CH$_2$CH$_2$—; P and Q taken together form a covalent bond; R$_1$ and R$_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; R$_3$, R$_4$, R$_5$ and R$_7$ are hydrogen; R$_6$ is —R$_{20}$L$_3$R$_{22}$; R$_{20}$ is aryl; L$_3$ is C(=O); and R$_{22}$ is heterocycle.

In another embodiment, compounds of the present invention have formula (I) wherein A is a covalent bond; D is O; L is —CH$_2$CH$_2$—; P and Q taken together form a covalent bond; R$_1$ and R$_2$ taken together with the nitrogen atom to which they are attached, together form a heterocycle selected from 1-azepanyl, (3S)-3-(dimethylamino) pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl) pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; R$_3$, R$_4$, R$_5$ and R$_7$ are hydrogen; R$_6$ is —R$_{20}$L$_3$R$_{22}$; R$_{20}$ is aryl; L$_3$ is C(=O); and R$_{22}$ is heterocycle.

In another embodiment, compounds of the present invention have formula (I) wherein A is a covalent bond; D is O; L is —CH$_2$CH$_2$—; P and Q taken together form a covalent bond; R$_1$ and R$_2$ taken together with the nitrogen atom to which they are attached, together form a heterocycle (2R)-2-methyl-1-pyrrolidinyl; R$_3$, R$_4$, R$_5$ and R$_7$ are hydrogen; R$_6$ is —R$_{20}$L$_3$R$_{22}$; R$_{20}$ is phenyl; L$_3$ is C(=O); and R$_{22}$ is 2-thienyl.

According to another embodiment, compounds of the present invention have formula (II)

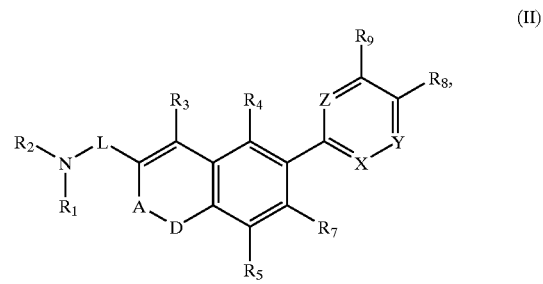

(II)

or a pharmaceutical acceptable salt, ester, amide, or prodrug thereof, wherein

R$_7$ is selected from hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —NR$_A$R$_B$, (NR$_A$R$_B$)alkyl, (NR$_A$R$_B$)carbonyl, or (NR$_A$R$_B$)sulfonyl;

R$_8$ is selected from hydrogen, alkylcarbonyl, arylcarbonyl, cyano, cycloalkylcarbonyl, heterocyclecarbonyl, or (NR$_A$R$_B$)carbonyl;

R$_9$ is selected from hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —NR$_A$R$_B$, (NR$_A$R$_B$)alkyl, (NR$_A$R$_B$)carbonyl, or (NR$_A$R$_B$)sulfonyl;

X is selected from CH, CR$_X$, or N; Y is selected from CH, CR$_Y$, or N;

Z is selected from CH, CR$_Z$, or N;

R$_X$, R$_Y$ and R$_Z$ groups are each independently selected from alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —NR$_A$R$_B$, (NR$_A$R$_B$)alkyl, (NR$_A$R$_B$)carbonyl, or (NR$_A$R$_B$)sulfonyl; and A, D, L, R$_A$, R$_B$, R$_1$, R$_2$, R$_3$, R$_4$, and R$_5$ are as defined in formula (I).

In another embodiment, compounds of the present invention have formula (II) wherein A is a covalent bond; and D, L, R$_A$, R$_B$, R$_1$, R$_2$, R$_3$, R$_4$, R$_5$, R$_7$, R$_8$, R$_9$, X, Y, and Z are as defined in formula (I).

In another embodiment, compounds of the present invention have formula (II) wherein A is a covalent bond, R$_1$ and R$_2$ are each independently selected from hydrogen, alkyl, hydroxyalkyl, alkenyl or alkynyl; R$_8$ is cyano; and D, L, R$_A$, R$_B$, R$_3$, R$_4$, R$_5$, R$_7$ and R$_9$, X, Y, and Z are as defined in formula (I).

In another embodiment, compounds of the present invention have formula (II) wherein L is —CH$_2$CH$_2$—; A is a covalent bond; $R_1$ and $R_2$ are each independently selected from hydrogen, alkyl, hydroxyalkyl, alkenyl or alkynyl; $R_3$, $R_4$, $R_5$, $R_7$ and $R_9$ are hydrogen; $R_8$ is cyano; X is CH; Y is CH; Z is CH; and D, $R_A$, and $R_B$ are as defined in formula (I).

In another embodiment, compounds of the present invention have formula (II) wherein A is a covalent bond; $R_1$ and $R_2$ are each independently selected from hydrogen, alkyl, hydroxyalkyl, alkenyl or alkynyl; $R_8$ is cyano; X is N; Y is CH; Z is CH; and D, L, $R_A$, $R_B$, $R_3$, $R_4$, $R_5$, $R_7$ and $R_9$ are as defined in formula (I).

In another embodiment, compounds of the present invention have formula (II) wherein A is a covalent bond; $R_1$ and $R_2$ are each independently selected from hydrogen, alkyl, hydroxyalkyl, alkenyl or alkynyl; $R_8$ is heterocyclecarbonyl; and D, L, $R_A$, $R_B$, $R_3$, $R_4$, $R_5$, $R_7$, $R_9$, X, Y and Z are as defined in formula (I).

In another embodiment, compounds of the present invention have formula (II) wherein A is a covalent bond; $R_1$ and $R_2$ are each independently selected from hydrogen, alkyl, hydroxyalkyl, alkenyl or alkynyl; $R_8$ is heterocyclecarbonyl wherein the heterocycle is selected from 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl; and D, L, $R_A$, $R_B$, $R_3$, $R_4$, $R_5$, $R_7$, $R_9$, X, Y and Z are as defined in formula (I).

In another embodiment, compounds of the present invention have formula (II) wherein A is a covalent bond; $R_1$ and $R_2$ are each independently selected from hydrogen, alkyl, hydroxyalkyl, alkenyl or alkynyl; $R_8$ is heterocyclecarbonyl wherein the heterocycle is 4-morpholinyl; and D, L, $R_A$, $R_B$, $R_3$, $R_4$, $R_5$, $R_7$, $R_9$, X, Y and Z are as defined in formula (I).

In another embodiment, compounds of the present invention have formula (II) wherein A is a covalent bond; L is —CH$_2$CH$_2$—; $R_1$ and $R_2$ are each independently selected from hydrogen, alkyl, hydroxyalkyl, alkenyl or alkynyl; $R_3$, $R_4$, $R_5$, $R_7$ and $R_9$ are hydrogen; $R_8$ is heterocyclecarbonyl wherein the heterocycle is 4-morpholinyl; X is CH; Y is CH; Z is CH; and D, $R_A$ and $R_B$ are as defined in formula (I).

In another embodiment, compounds of the present invention have formula (II) wherein A is a covalent bond; $R_1$ and $R_2$ are each independently selected from hydrogen, alkyl, hydroxyalkyl, alkenyl or alkynyl; $R_8$ is heterocyclecarbonyl; X is N; Y is CH; Z is CH; and D, L, $R_A$, $R_B$, $R_3$, $R_4$, $R_5$, $R_7$ and $R_9$ are as defined in formula (I).

In another embodiment, compounds of the present invention have formula (II) wherein A is a covalent bond; $R_1$ and $R_2$ are each independently selected from the group consisting of hydrogen, alkyl, hydroxyalkyl, alkenyl and alkynyl; $R_8$ is heterocyclecarbonyl wherein the heterocycle of heterocarbonyl is selected from the group consisting of azetidinyl, morpholinyl, piperazinyl, piperidinyl, pyridinyl, pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl.; X is N; Y is CH; Z is CH; and D, L, $R_A$, $R_B$, $R_3$, $R_4$, $R_5$, $R_7$ and $R_9$ are as defined in formula (I).

In another embodiment, compounds of the present invention have formula (II) wherein A is a covalent bond; $R_1$ and $R_2$ are each independently selected from hydrogen, alkyl, hydroxyalkyl, alkenyl or alkynyl; $R_8$ is heterocyclecarbonyl wherein the heterocycle is selected from 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl; X is N; Y is CH; Z is CH; and D, L, $R_A$, $R_B$, $R_3$, $R_4$, $R_5$, $R_7$ and $R_9$ are as defined in formula (I).

In another embodiment, compounds of the present invention have formula (II) wherein A is a covalent bond; $R_1$ and $R_2$ are each independently selected from hydrogen, alkyl, hydroxyalkyl, alkenyl or alkynyl; $R_8$ is heterocyclecarbonyl wherein the heterocycle is 4-morpholinyl; X is N; Y is CH; Z is CH; and D, L, $R_A$, $R_B$, $R_3$, $R_4$, $R_5$, $R_7$ and $R_9$ are as defined in formula (I).

In another embodiment, compounds of the present invention have formula (II) wherein A is a covalent bond; L is —CH$_2$CH$_2$—; $R_1$ and $R_2$ are each independently selected from hydrogen, alkyl, hydroxyalkyl, alkenyl or alkynyl; $R_3$, $R_4$, $R_5$, $R_7$ and $R_9$ are hydrogen; $R_8$ is heterocyclecarbonyl wherein the heterocycle is 4-morpholinyl; X is N; Y is CH; Z is CH; and D, $R_A$ and $R_B$ are as defined in formula (I).

In another embodiment, compounds of the present invention have formula (II) wherein A is a covalent bond; $R_1$ and $R_2$ taken together with the nitrogen atom to which they are attached, together form a heterocycle and D, L, $R_A$, $R_B$, $R_3$, $R_4$, $R_5$, $R_7$, $R_8$, $R_9$, X, Y and Z are as defined in formula (I).

In another embodiment, compounds of the present invention have formula (II) wherein A is a covalent bond; $R_1$ and $R_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_8$ is cyano; and D, L, $R_A$, $R_B$, $R_3$, $R_4$, $R_5$, $R_7$, $R_9$, X, Y and Z are as defined in formula (I).

In another embodiment, compounds of the present invention have formula (II) wherein A is a covalent bond; $R_1$ and $R_2$ taken together with the nitrogen atom to which they are attached, together form a heterocycle selected from 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; $R_8$ is cyano; and D, L, $R_A$, $R_B$, $R_3$, $R_4$, $R_5$, $R_7$, $R_9$, X, Y and Z are as defined in formula (I).

In another embodiment, compounds of the present invention have formula (II) wherein A is a covalent bond; L is —CH$_2$CH$_2$—; $R_1$ and $R_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_3$, $R_4$, $R_5$, and $R_7$ are independently selected from hydrogen, alkyl, alkylcarbonyl, and halogen; $R_8$ and $R_9$ are independently selected from hydrogen, alkoxy, alkyl, alkoxycarbonyl, alkylcarbonyl, carboxy, cyano, formyl, halogen, haloalkyl, haloalkoxy, hydroxyalkyl, or oximyl; X is selected from CH and CR$_X$; Y is selected from CH and CR$_Y$; Z is selected from CH and CR$_Z$; and R$_X$, R$_Y$, and R$_Z$ are independently selected from alkoxy, alkyl, alkoxycarbonyl, alkylcarbonyl, carboxy, cyano, formyl, halogen, haloalkyl, haloalkoxy, hydroxyalkyl, or oximyl.

In another embodiment, compounds of the present invention have formula (II) wherein A is a covalent bond; L is —CH$_2$CH$_2$—; R$_1$ and R$_2$ taken together with the nitrogen atom to which they are attached, together form a heterocycle selected from 1-azepanyl, (3S)-3-(dimethylamino) pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl) pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; R$_3$, R$_4$, R$_5$, and R$_7$ are independently selected from hydrogen, alkyl, alkylcarbonyl, and halogen; R$_8$ and R$_9$ are independently selected from hydrogen, alkoxy, alkyl, alkoxycarbonyl, alkylcarbonyl, carboxy, cyano, formyl, halogen, haloalkyl, haloalkoxy, hydroxyalkyl, or oximyl; X is selected from CH and CR$_X$; Y is selected from CH and CR$_Y$; Z is selected from CH and CR$_Z$; and R$_X$, R$_Y$, and R$_Z$ are independently selected from alkoxy, alkyl, alkoxycarbonyl, alkylcarbonyl, carboxy, cyano, formyl, halogen, haloalkyl, haloalkoxy, hydroxyalkyl, or oximyl.

In another embodiment, compounds of the present invention have formula (II) wherein A is a covalent bond; L is —CH$_2$CH$_2$—; R$_1$ and R$_2$ taken together with the nitrogen atom to which they are attached, together form a heterocycle substituted with 0, 1 or 2 substituents selected from alkyl; R$_3$, R$_4$, R$_5$, R$_7$, and R$_9$ are hydrogen; R$_8$ is cyano; X is CH; Y is CH; and Z is CH.

In another embodiment, compounds of the present invention have formula (II) wherein L is —CH$_2$CH$_2$—; A is a covalent bond; R$_1$ and R$_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; R$_3$ is heterocycle; R$_4$, R$_5$, R$_7$ and R$_9$ are hydrogen; R$_8$ is cyano; X is CH; Y is CH; and Z is CH.

In another embodiment, compounds of the present invention have formula (II) wherein L is —CH$_2$CH$_2$—; A is a covalent bond; R$_1$ and R$_2$ taken together with the nitrogen atom to which they are attached, together form a heterocycle selected from 1-azepanyl, (3S)-3-(dimethylamino) pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl) pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; R$_3$ is heterocycle; R$_4$, R$_5$, R$_7$ and R$_9$ are hydrogen; R$_8$ is cyano; X is CH; Y is CH; and Z is CH.

In another embodiment, compounds of the present invention have formula (II) wherein L is —CH$_2$CH$_2$—; A is a covalent bond; R$_1$ and R$_2$ taken together with the nitrogen atom to which they are attached, together form a heterocycle (2R)-2-methyl-1-pyrrolidinyl; R$_3$ is heterocycle selected from 2-furyl, 3-pyridinyl, and 2-thienyl wherein the heterocycle is substituted with 0, 1, or 2 substituents selected from hydrogen, alkoxy, alkyl, alkoxycarbonyl, alkylcarbonyl, carboxy, cyano, formyl, halogen, haloalkyl, haloalkoxy, hydroxyalkyl, or oximyl; R$_4$, R$_5$, R$_7$ and R$_9$ are hydrogen; R$_8$ is cyano; X is CH;Y is CH; and Z is CH.

In another embodiment, compounds of the present invention have formula (II) wherein A is a covalent bond; R$_1$ and R$_2$ taken together with the nitrogen atom to which they are attached, together form a heterocycle; R$_8$ is cyano; X is N; Y is CH; Z is CH; and D, L, R$_A$, R$_B$, R$_3$, R$_4$, R$_5$, R$_7$ and R$_8$ are as defined in formula (I).

In another embodiment, compounds of the present invention have formula (II) wherein A is a covalent bond; R$_1$ and R$_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; R$_8$ is cyano; X is N; Y is CH; Z is CH; and D, L, R$_A$, R$_B$, R$_3$, R$_4$, R$_5$, R$_7$ and R$_9$ are as defined in formula (I).

In another embodiment, compounds of the present invention have formula (II) wherein A is a covalent bond; R$_1$ and R$_2$ taken together with the nitrogen atom to which they are attached, together form a heterocycle selected from 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; R$_8$ is cyano; X is N; Y is CH; Z is CH; and D, L, R$_A$, R$_B$, R$_3$, R$_4$, R$_5$, R$_7$ and R$_9$ are as defined in formula (I).

In another embodiment, compounds of the present invention have formula (II) wherein A is a covalent bond; R$_1$ and R$_2$ taken together with the nitrogen atom to which they are attached, together form a heterocycle; R$_8$ is heterocyclecarbonyl; and D, L, R$_A$, R$_B$, R$_3$, R$_4$, R$_5$, R$_7$, R$_9$, X, Y, and Z are as defined in formula (I).

In another embodiment, compounds of the present invention have formula (II) wherein A is a covalent bond; $R_1$ and $R_2$ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_8$ is heterocyclecarbonyl wherein the heterocycle of heterocyclecarbonyl is selected from the group consisting of azetidinyl, morpholinyl, piperazinyl, piperidinyl, pyridinyl, pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; and D, L, $R_A$, $R_B$, $R_3$, $R_4$, $R_5$, $R_7$, $R_9$, X, Y, and Z are as defined in formula (I).

In another embodiment, compounds of the present invention have formula (II) wherein A is a covalent bond; $R_1$ and $R_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_8$ is heterocyclecarbonyl wherein the heterocycle is selected from 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl; and D, L, $R_A$, $R_B$, $R_3$, $R_4$, $R_5$, $R_7$, $R_9$, X, Y, and Z are as defined in formula (I).

In another embodiment, compounds of the present invention have formula (II) wherein A is a covalent bond; $R_1$ and $R_2$ taken together with the nitrogen atom to which they are attached, together form a heterocycle selected from the group consisting of 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2R)-2-methyl-1-pyrrolidinyl, (2S)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, and 1,4-dioxa-8-azaspiro[4.5]dec-8-yl; $R_8$ is heterocyclecarbonyl wherein the heterocycle of heterocyclecarbonyl is selected from the group consisting of azetidinyl, morpholinyl, piperazinyl, piperidinyl, pyridinyl, pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; and D, L, $R_A$, $R_B$, $R_3$, $R_4$, $R_5$, $R_7$, $R_9$, X, Y, and Z are as defined in formula (I).

In another embodiment, compounds of the present invention have formula (II) wherein A is a covalent bond; $R_1$ and $R_2$ taken together with the nitrogen atom to which they are attached, together form a heterocycle selected from 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; $R_8$ is heterocyclecarbonyl wherein the heterocycle is selected from 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl; and D, L, $R_A$, $R_B$, $R_3$, $R_4$, $R_5$, $R_7$, $R_9$, X, Y, and Z are as defined in formula (I).

In another embodiment, compounds of the present invention have formula (II) wherein A is a covalent bond; $R_1$ and $R_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_8$ is heterocyclecarbonyl wherein the heterocycle is 4-morpholinyl; and D, L, $R_A$, $R_B$, $R_3$, $R_4$, $R_5$, $R_7$, $R_9$, X, Y, and Z are as defined in formula (I).

In another embodiment, compounds of the present invention have formula (II) wherein A is a covalent bond; $R_1$ and $R_2$ taken together with the nitrogen atom to which they are attached, together form a heterocycle selected from 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; $R_8$ is heterocyclecarbonyl wherein the heterocycle is 4-morpholinyl; and D, L, $R_A$, $R_B$, $R_3$, $R_4$, $R_5$, $R_7$, $R_9$, X, Y, and Z are as defined in formula (I).

In another embodiment, compounds of the present invention have formula (II) wherein A is a covalent bond; $R_1$ and $R_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_3$, $R_4$, $R_5$, $R_7$ and $R_9$ are hydrogen; $R_8$ is heterocyclecarbonyl wherein the heterocycle is 4-morpholinyl; X is CH; Y is CH; Z is CH; and D, L, $R_A$ and $R_B$ are as defined in formula (I).

In another embodiment, compounds of the present invention have formula (II) wherein A is a covalent bond; $R_1$ and $R_2$ taken together with the nitrogen atom to which they are attached, together form a heterocycle selected from 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; $R_3$, $R_4$, $R_5$, $R_7$ and $R_9$ are hydrogen; $R_8$ is heterocyclecarbonyl wherein the heterocycle is 4-morpholinyl; X is CH; Y is CH; Z is CH; and D, L, $R_A$ and $R_B$ are as defined in formula (I).

In another embodiment, compounds of the present invention have formula (II) wherein A is a covalent bond; $R_1$ and $R_2$ taken together with the nitrogen atom to which they are attached, together form a heterocycle; $R_8$ is heterocyclecarbonyl; X is N; Y is CH; Z is CH; and D, L, $R_A$, $R_B$, $R_3$, $R_4$, $R_5$, $R_7$, and $R_9$ are as defined in formula (I).

In another embodiment, compounds of the present invention have formula (II) wherein A is a covalent bond; L is —$CH_2CH_2$—; $R_1$ and $R_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_8$ is heterocyclecarbonyl wherein the heterocycle is selected from 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl; X is N; Y is CH; Z is CH; and D, L, $R_A$, $R_B$, $R_3$, $R_4$, $R_5$, $R_7$, and $R_9$ are as defined in formula (I).

In another embodiment, compounds of the present invention have formula (II) wherein A is a covalent bond; L is —$CH_2CH_2$—; $R_1$ and $R_2$ taken together with the nitrogen atom to which they are attached, together form a heterocycle selected from 1-azepanyl, (3S)-3-(dimethylamino) pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl) pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; $R_8$ is heterocyclecarbonyl wherein the heterocycle is selected from 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl; X is N; Y is CH; Z is CH; and D, L, $R_A$, $R_B$, $R_3$, $R_4$, $R_5$, $R_7$, and $R_9$ are as defined in formula (I).

In another embodiment, compounds of the present invention have formula (II) wherein A is a covalent bond; L is —$CH_2CH_2$—; $R_1$ and $R_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_8$ is heterocyclecarbonyl wherein the heterocycle is 4-morpholinyl; X is N; Y is CH; Z is CH; and D, L, $R_A$, $R_B$, $R_3$, $R_4$, $R_5$, $R_7$, and $R_9$ are as defined in formula (I).

In another embodiment, compounds of the present invention have formula (II) wherein A is a covalent bond; L is —$CH_2CH_2$—; $R_1$ and $R_2$ taken together with the nitrogen atom to which they are attached, together form a heterocycle selected from 1-azepanyl, (3S)-3-(dimethylamino) pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl) pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; $R_8$ is heterocyclecarbonyl wherein the heterocycle is 4-morpholinyl; X is N; Y is CH; Z is CH; and D, L, $R_A$, $R_B$, $R_3$, $R_4$, $R_5$, $R_7$, and $R_9$ are as defined in formula (I).

In another embodiment, compounds of the present invention have formula (II) wherein A is a covalent bond; L is —$CH_2CH_2$—; $R_1$ and $R_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_3$, $R_4$, $R_5$, $R_7$ and $R_9$ are hydrogen; $R_8$ is heterocyclecarbonyl wherein the heterocycle is 4-morpholinyl; X is N; Y is CH; Z is CH; and D, L, $R_A$, $R_B$, $R_3$, $R_4$, $R_5$, $R_7$, and $R_9$ are as defined in formula (I).

In another embodiment, compounds of the present invention have formula (II) wherein A is a covalent bond; L is —$CH_2CH_2$—; $R_1$ and $R_2$ taken together with the nitrogen atom to which they are attached, together form a heterocycle selected from 1-azepanyl, (3S)-3-(dimethylamino) pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl) pyrrolidinyl, (2R)-2-(hydroxymethyl)pyrrolidinyl, (cis)-2,6- dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; $R_3$, $R_4$, $R_5$, $R_7$ and $R_9$ are hydrogen; $R_8$ is heterocyclecarbonyl wherein the heterocycle is 4-morpholinyl; X is N; Y is CH; Z is CH; and D, L, $R_A$, $R_B$, $R_3$, $R_4$, $R_5$, $R_7$, and $R_9$ are as defined in formula (I).

In another embodiment, compounds of the present invention have formula (II) wherein A is carbonyl; $R_1$ and $R_2$ are each independently selected from the group consisting of hydrogen, alkyl, hydroxyalkyl, alkenyl and alkynyl; and $R_8$ is selected from the group consisting of cyano and heterocyclecarbonyl; and D, L, $R_A$, $R_B$, $R_3$, $R_4$, $R_5$, $R_7$, and $R_9$ are as defined in formula (I).

In another embodiment, compounds of the present invention have formula (II) wherein A is carbonyl; $R_1$ and $R_2$ are each independently selected from the group consisting of hydrogen, alkyl, hydroxyalkyl, alkenyl and alkynyl; and $R_8$ is selected from the group consisting of cyano and heterocyclecarbonyl wherein the heterocycle of heterocyclecarbonyl is selected from the group consisting of azetidinyl, morpholinyl, piperazinyl, piperidinyl, pyridinyl, pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; and D, L, $R_A$, $R_B$, $R_3$, $R_4$, $R_5$, $R_7$, and $R_9$ are as defined in formula (I).

In another embodiment, compounds of the present invention have formula (II) wherein A is carbonyl; $R_1$ and $R_2$ are each independently selected from the group consisting of hydrogen, alkyl, hydroxyalkyl, alkenyl and alkynyl; $R_9$ is selected from the group consisting of cyano and heterocyclecarbonyl wherein the heterocycle of heterocyclecarbonyl is selected from the group consisting of 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl; and D, L, $R_A$, $R_B$, $R_3$, $R_4$, $R_5$, $R_7$, and $R_9$ are as defined in formula (I).

In another embodiment, compounds of the present invention have formula (II) wherein A is carbonyl; $R_1$ and $R_2$ taken together with the nitrogen atom to which they are attached, together form a heterocycle; $R_8$ is selected from cyano or heterocyclecarbonyl; and D, L, $R_A$, $R_B$, $R_3$, $R_4$, $R_5$, $R_7$, $R_9$, X, Y and Z are as defined in formula (I).

In another embodiment, compounds of the present invention have formula (II) wherein A is carbonyl; $R_1$ and $R_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_8$ is selected from cyano or heterocyclecarbonyl wherein the heterocycle is selected from 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl; D, L, $R_A$, $R_B$, $R_3$, $R_4$, $R_5$, $R_7$, $R_9$, X, Y and Z are as defined in formula (I).

In another embodiment, compounds of the present invention have formula (II) wherein A is carbonyl; $R_1$ and $R_2$ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_8$ is selected from the group consisting of cyano and heterocyclecarbonyl wherein the heterocycle of heterocyclecarbonyl is selected from the group consisting of 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl; and D, L, $R_A$, $R_B$, $R_3$, $R_4$, $R_5$, $R_7$, $R_9$, X, Y and Z are as defined in formula (I).

In another embodiment, compounds of the present invention have formula (II) wherein A is carbonyl; $R_1$ and $R_2$ taken together with the nitrogen atom to which they are attached, together form a heterocycle selected from 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; $R_8$ is selected from cyano or heterocyclecarbonyl wherein the heterocycle is selected from 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl; D, L, $R_A$, $R_B$, $R_3$, $R_4$, $R_5$, $R_7$, $R_9$, X, Y and Z are as defined in formula (I).

According to another embodiment, compounds of the present invention have formula (III)

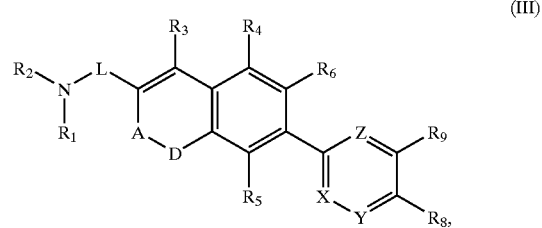

(III)

or a pharmaceutical acceptable salt, ester, amide, or prodrug thereof, wherein $R_6$ is selected from hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —$NR_AR_B$, ($NR_AR_B$)alkyl, ($NR_AR_B$)carbonyl or ($NR_AR_B$)sulfonyl;

$R_8$ is selected from hydrogen, alkylcarbonyl, arylcarbonyl, cyano, cycloalkylcarbonyl, heterocyclecarbonyl or ($NR_AR_B$)carbonyl;

$R_9$ is selected from hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —$NR_AR_B$, ($NR_AR_B$)alkyl, ($NR_AR_B$)carbonyl or ($NR_AR_B$)sulfonyl;

X is selected from CH, $CR_X$ or N;

Y is selected from CH, $CR_Y$ or N;

Z is selected from CH, $CR_Z$ or N;

$R_X$, $R_Y$ and $R_Z$ are each independently selected from alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —$NR_AR_B$, ($NR_AR_B$)alkyl, ($NR_AR_B$)carbonyl or ($NR_AR_B$)sulfonyl; and A, D, L, $R_A$, $R_B$, $R_1$, $R_2$, $R_3$, $R_4$, and $R_5$ are as defined in formula (I).

In another embodiment, compounds of the present invention have formula (III) wherein A is a covalent bond; and D, L, $R_A$, $R_B$, $R_1$, $R_2$, $R_3$, $R_4$, $R_5$, $R_6$, $R_8$, $R_9$, X, Y, and Z are as defined in formula (I).

In another embodiment, compounds of the present invention have formula (III) wherein A is a covalent bond; $R_1$ and $R_2$ are each independently selected from hydrogen, alkyl, hydroxyalkyl, alkenyl or alkynyl; $R_8$ is selected from cyano or heterocyclecarbonyl; and D, L, $R_A$, $R_B$, $R_3$, $R_4$, $R_5$, $R_6$, $R_9$, X, Y, and Z are as defined in formula (I).

In another embodiment, compounds of the present invention have formula (III) wherein A is a covalent bond; $R_1$ and $R_2$ are each independently selected from hydrogen, alkyl, hydroxyalkyl, alkenyl and alkynyl; $R_8$ is selected from cyano or heterocyclecarbonyl wherein the heterocycle is selected from 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl; D, L, $R_A$, $R_B$, $R_3$, $R_4$, $R_5$, $R_6$, $R_9$, X, Y, and Z are as defined in formula (I).

In another embodiment, compounds of the present invention have formula (III) wherein A is a covalent bond; $R_1$ and $R_2$ taken together with the nitrogen atom to which they are attached, together form a heterocycle; $R_8$ is selected from cyano or heterocyclecarbonyl; and D, L, $R_A$, $R_B$, $R_3$, $R_4$, $R_5$, $R_6$, $R_9$, X, Y, and Z are as defined in formula (I).

In another embodiment, compounds of the present invention have formula (III) wherein A is a covalent bond; $R_1$ and $R_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_8$ is selected from cyano or heterocyclecarbonyl wherein the heterocycle is selected from 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl; and D, L, $R_A$, $R_B$, $R_3$, $R_4$, $R_5$, $R_6$, $R_9$, X, Y, and Z are as defined in formula (I).

In another embodiment, compounds of the present invention have formula (III) wherein A is a covalent bond; $R_1$ and $R_2$ taken together with the nitrogen atom to which they are attached, together form a heterocycle selected from 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo [2.2.1]hept-5-yl, or 1,4-dioxa-8-azaspiro[4.5]dec-8-yl; $R_8$ is selected from cyano or heterocyclecarbonyl wherein the heterocycle is selected from 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl; and D, L, $R_A$, $R_B$, $R_3$, $R_4$, $R_5$, $R_6$, $R_9$, X, Y, and Z are as defined in formula (I).

In another embodiment, compounds of the present invention have formula (III) wherein A is carbonyl; and D, L, $R_A$, $R_B$, $R_1$, $R_2$, $R_3$, $R_4$, $R_5$, $R_6$, $R_8$, $R_9$, X, Y, and Z are as defined in formula (I).

In another embodiment, compounds of the present invention have formula (III) wherein A is carbonyl; $R_1$ and $R_2$ are each independently selected from hydrogen, alkyl, hydroxyalkyl, alkenyl or alkynyl; $R_8$ is cyano; and D, L, $R_A$, $R_B$, $R_3$, $R_4$, $R_5$, $R_6$, $R_9$, X, Y, and Z are as defined in formula (I).

In another embodiment, compounds of the present invention have formula (III) wherein L is —$CH_2CH_2$—; A is carbonyl; $R_1$ and $R_2$ are each independently selected from hydrogen, alkyl, hydroxyalkyl, alkenyl or alkynyl; $R_3$ is methyl, $R_4$, $R_5$, $R_6$ and $R_9$ are hydrogen; $R_8$ is cyano; X is CH; Y is CH; Z is CH; and D, $R_A$ and $R_B$ are as defined in formula (I).

In another embodiment, compounds of the present invention have formula (III) wherein A is carbonyl; $R_1$ and $R_2$ are each independently selected from hydrogen, alkyl, hydroxyalkyl, alkenyl or alkynyl; $R_8$ is heterocyclecarbonyl; and D, L, $R_A$, $R_B$, $R_3$, $R_4$, $R_5$, $R_6$, $R_9$, X, Y, and Z are as defined in formula (I).

In another embodiment, compounds of the present invention have formula (III) wherein A is carbonyl; $R_1$ and $R_2$ are each independently selected from hydrogen, alkyl, hydroxyalkyl, alkenyl or alkynyl; $R_8$ is heterocyclecarbonyl wherein the heterocycle is selected from 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl; and D, L, $R_A$, $R_B$, $R_3$, $R_4$, $R_5$, $R_6$, $R_9$, X, Y, and Z are as defined in formula (I).

In another embodiment, compounds of the present invention have formula (III) wherein A is carbonyl; $R_1$ and $R_2$ taken together with the nitrogen atom to which they are attached, together form a heterocycle; $R_9$ is cyano; and D, L, $R_A$, $R_B$, $R_3$, $R_4$, $R_5$, $R_6$, $R_9$, X, Y, and Z are as defined in formula (I).

In another embodiment, compounds of the present invention have formula (III) wherein A is carbonyl; $R_1$ and $R_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1- pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_8$ is cyano; and D, L, $R_A$, $R_B$, $R_3$, $R_4$, $R_5$, $R_6$, $R_9$, X, Y, and Z are as defined in formula (I).

In another embodiment, compounds of the present invention have formula (III) wherein L is —CH$_2$CH$_2$—; A is carbonyl; $R_1$ and $R_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_3$ is methyl; $R_4$, $R_5$, $R_6$ and $R_9$ are hydrogen; $R_8$ is cyano; X is CH; Y is CH; Z is CH; and D, L, $R_A$ and $R_B$ are as defined in formula (I).

In another embodiment, compounds of the present invention have formula (III) wherein L is —CH$_2$CH$_2$—; A is carbonyl; $R_1$ and $R_2$ taken together with the nitrogen atom to which they are attached, together form a heterocycle selected from 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; $R_3$ is methyl; $R_5$, $R_6$ and $R_9$ are hydrogen; $R_8$ is cyano; X is CH; Y is CH; Z is CH; and D, L, $R_A$ and $R_B$ are as defined in formula (I).

In another embodiment, compounds of the present invention have formula (III) wherein A is carbonyl; $R_1$ and $R_2$ taken together with the nitrogen atom to which they are attached, together form a heterocycle; $R_5$ is heterocyclecarbonyl; and D, L, $R_A$, $R_B$, $R_3$, $R_4$, $R_5$, $R_6$, $R_9$, X, Y, and Z are as defined in formula (I).

In another embodiment, compounds of the present invention have formula (III) wherein A is carbonyl; $R_1$ and $R_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_8$ is heterocyclecarbonyl wherein the heterocycle is selected from 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl; and D, L, $R_A$, $R_B$, $R_3$, $R_4$, $R_5$, $R_6$, $R_9$, X, Y, and Z are as defined in formula (I).

In another embodiment, compounds of the present invention have formula (III) wherein A is carbonyl; $R_1$ and $R_2$ taken together with the nitrogen atom to which they are attached, together form a heterocycle selected from 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; $R_8$ is heterocyclecarbonyl wherein the heterocycle is selected from 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl; and D, L, $R_A$, $R_B$, $R_3$, $R_4$, $R_5$, $R_6$, $R_9$, X, Y, and Z are as defined in formula (I).

According to another embodiment, compounds of the present invention have formula (IV)

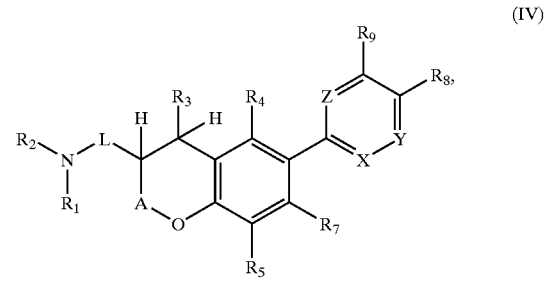

(IV)

or a pharmaceutical acceptable salt, ester, amide, or prodrug thereof, wherein $R_7$ is selected from hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —NR$_A$R$_B$, (NR$_A$R$_B$)alkyl, (NR$_A$R$_B$)carbonyl or (NR$_A$R$_B$)sulfonyl;

$R_8$ is selected from hydrogen, alkylcarbonyl, arylcarbonyl, cyano, cycloalkylcarbonyl, heterocyclecarbonyl or $(NR_AR_B)$carbonyl;

$R_9$ is selected from hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —$NR_AR_B$, $(NR_AR_B)$alkyl, $(NR_AR_B)$carbonyl or $(NR_AR_B)$sulfonyl;

X is selected from CH, $CR_X$ or N;
Y is selected from CH, $CR_Y$ or N;
Z is selected from CH, $CR_Z$ or N;

$R_X$, $R_Y$ and $R_Z$ are each independently selected from alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —$NR_A$, $R_B$, $(NR_AR_B)$alkyl, $(NR_AR_B)$carbonyl or $(NR_AR_B)$sulfonyl; and D, L, $R_A$, $R_B$, $R_1$, $R_2$, $R_3$, $R_4$ and $R_5$ are as defined in formula (I).

In another embodiment, compounds of the present invention have formula (IV) wherein A is a covalent bond; and D, L, $R_A$, $R_B$, $R_1$, $R_2$, $R_3$, $R_4$, $R_5$, $R_7$, $R_8$, $R_9$, X, Y, and Z are as defined in formula (I).

In another embodiment, compounds of the present invention have formula (IV) wherein A is a covalent bond; $R_1$ and $R_2$ are each independently selected from hydrogen, alkyl, hydroxyalkyl, alkenyl or alkynyl; $R_8$ is cyano; and D, L, $R_A$, $R_B$, $R_3$, $R_4$, $R_5$, $R_7$, $R_9$, X, Y, and Z are as defined in formula (I).

In another embodiment, compounds of the present invention have formula (IV) wherein L is —$CH_2CH_2$—; A is a covalent bond; $R_1$ and $R_2$ are each independently selected from hydrogen, alkyl, hydroxyalkyl, alkenyl or alkynyl; $R_3$, $R_4$, $R_5$, $R_7$ and $R_9$ are hydrogen; $R_8$ is cyano; X is CH; Y is CH; Z is CH; and D, $R_A$ and $R_B$ are as defined in formula (I).

In a further embodiment, compounds of the present invention have formula (V)

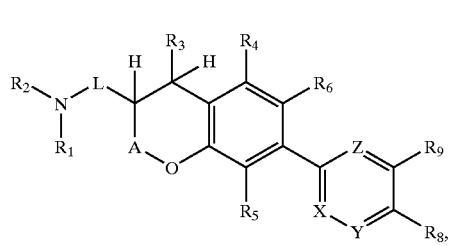

(V)

or a pharmaceutical acceptable salt, ester, amide, or prodrug thereof, wherein $R_6$ is selected from hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —$NR_AR_B$, $(NR_AR_B)$alkyl, $(NR_AR_B)$carbonyl or $(NR_AR_B)$sulfonyl;

$R_8$ is selected from hydrogen, alkylcarbonyl, arylcarbonyl, cyano, cycloalkylcarbonyl, heterocyclecarbonyl or $(NR_AR_B)$carbonyl;

$R_9$ is selected from hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —$NR_AR_B$, $(NR_AR_B)$alkyl, $(NR_AR_B)$carbonyl or $(NR_AR_B)$sulfonyl;

X is selected from CH, $CR_X$ or N;
Y is selected from CH, $CR_Y$ or N;
Z is selected from CH, $CR_Z$ or N;

$R_X$, $R_Y$ and $R_Z$ are each independently selected from alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —$NR_AR_B$, $(NR_AR_B)$alkyl, $(NR_AR_B)$carbonyl or $(NR_AR_B)$sulfonyl; and A, D, L, $R_A$, $R_B$, $R_1$, $R_2$, $R_3$, $R_4$, $R_5$ are as defined in formula (I).

In another embodiment, compounds of the present invention have formula (V) wherein A is a covalent bond; and D, L, $R_A$, $R_B$, $R_1$, $R_2$, $R_3$, $R_4$, $R_5$, $R_6$, $R_8$, $R_9$, X, Y, and Z are as defined in formula (I).

In another embodiment, compounds of the present invention have formula (IV) wherein A is a covalent bond; $R_1$ and $R_2$ are each independently selected from hydrogen, alkyl, hydroxyalkyl, alkenyl or alkynyl; $R_8$ is cyano; and D, L, $R_A$, $R_B$, $R_3$, $R_4$, $R_5$, $R_6$, $R_9$, X, Y, and Z are as defined in formula (I).

In another embodiment, compounds of the present invention have formula (IV) wherein L is —$CH_2CH_2$—; A is a covalent bond; $R_1$ and $R_2$ are each independently selected from hydrogen, alkyl, hydroxyalkyl, alkenyl or alkynyl; $R_3$, $R_4$, $R_5$, $R_6$ and $R_9$ are hydrogen; $R_8$ is cyano; X is CH; Y is CH; Z is CH; and D, $R_A$ and $R_B$ are as defined in formula (I).

In a further embodiment, compounds of the present invention have formula (VI)

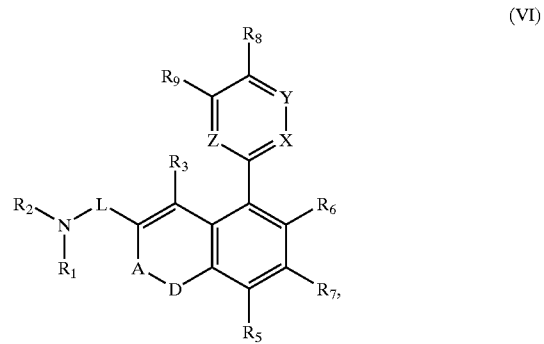

(VI)

or a pharmaceutical acceptable salt, ester, amide, or prodrug thereof, wherein $R_5$, $R_6$, and $R_7$ are selected from hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —$NR_AR_B$, $(NR_AR_B)$alkyl, $(NR_AR_B)$carbonyl or $(NR_AR_B)$sulfonyl;

$R_8$ is selected from hydrogen, alkylcarbonyl, arylcarbonyl, cyano, cycloalkylcarbonyl, heterocyclecarbonyl and $(NR_AR_B)$carbonyl; $R_9$ is selected from hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —$NR_AR_B$, $(NR_AR_B)$alkyl, $(NR_AR_B)$carbonyl or $(NR_AR_B)$sulfonyl;

X is selected from CH, $CR_X$ or N;
Y is selected from CH, $CR_Y$ or N;
Z is selected from CH, $CR_Z$ or N;

$R_X$, $R_Y$ and $R_Z$ are each independently selected from alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —NR$_A$R$_B$, (NR$_A$R$_B$)alkyl, (NR$_A$R$_B$)carbonyl or (NR$_A$R$_B$)sulfonyl; and A, D, L, R$_A$, R$_B$, R$_1$, R$_2$, and R$_3$, are as defined in formula (I).

In another embodiment, compounds of the present invention have formula (VI) wherein A is a covalent bond; R$_1$ and R$_2$ taken together with the nitrogen atom to which they are attached, together form a heterocycle; P, Q, D, L, R$_A$, R$_B$, and R$_3$, are as defined in formula (I) and R$_5$, R$_6$, R$_7$, R$_8$, and R$_9$ are defined as in formula (VI).

In another embodiment, compounds of the present invention have formula (VI) wherein A is a covalent bond; R$_1$ and R$_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; R$_8$ is cyano; and P, Q, D, L, R$_A$, R$_B$, and R$_3$, are as defined in formula (I) and R$_5$, R$_6$, R$_7$, and R$_9$ are defined as in formula (VI).

In another embodiment, compounds of the present invention have formula (VI) wherein A is a covalent bond; R$_1$ and R$_2$ taken together with the nitrogen atom to which they are attached, together form a heterocycle selected from 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; R$_8$ is cyano; and P, Q, D, L, R$_A$, R$_B$, and R$_3$, are as defined in formula (I) and R$_5$, R$_6$, R$_7$, and R$_9$ are defined as in formula (VI).

In another embodiment, compounds of the present invention have formula (VI) wherein L is —CH$_2$CH$_2$—; A is a covalent bond; R$_1$ and R$_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; R$_3$, R$_5$, R$_6$, R$_7$ and R$_9$ are hydrogen; R$_8$ is cyano; X is CH; Y is CH; and Z is CH.

In another embodiment, compounds of the present invention have formula (VI) wherein L is —CH$_2$CH$_2$—; A is a covalent bond; R$_1$ and R$_2$ taken together with the nitrogen atom to which they are attached, together form a heterocycle selected from 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; R$_3$, R$_5$, R$_6$, R$_7$ and R$_9$ are hydrogen; R$_8$ is cyano; X is CH; Y is CH; and Z is CH.

In a further embodiment, compounds of the present invention have formula (VII)

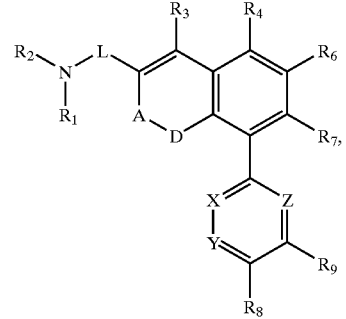

(VII)

or a pharmaceutical acceptable salt, ester, amide, or prodrug thereof, wherein

R$_4$, R$_6$, and R$_7$ are selected from hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —NR$_A$R$_B$, (NR$_A$R$_B$)alkyl, (NR$_A$R$_B$)carbonyl or (NR$_A$R$_B$)sulfonyl;

R$_8$ is selected from hydrogen, alkylcarbonyl, arylcarbonyl, cyano, cycloalkylcarbonyl, heterocyclecarbonyl or (NR$_A$R$_B$)carbonyl;

R$_9$ is selected from hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —NR$_A$R$_B$, (NR$_A$R$_B$)alkyl, (NR$_A$R$_B$)carbonyl or (NR$_A$R$_B$)sulfonyl; X is selected from CH, CR$_X$ or N; Y is selected from CH, CR$_Y$ or N; Z is selected from CH, CR$_Z$ or N; R$_X$, R$_Y$ and R$_Z$ are each independently selected from alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —NR$_A$R$_B$, (NR$_A$R$_B$)alkyl, (NR$_A$R$_B$)carbonyl or (NR$_A$R$_B$)sulfonyl; and L, A, D, R$_1$, R$_2$, R$_3$, R$_A$, and R$_B$ are as defined in formula (I).

In another embodiment, compounds of the present invention have formula (VII) wherein A is a covalent bond; R$_1$ and R$_2$ taken together with the nitrogen atom to which they are attached, together form a heterocycle; P, Q, D, L, R$_A$, R$_B$, and R$_3$, are as defined in formula (I) and R$_4$, R$_6$, R$_7$, R$_8$, and R$_9$ are defined as in formula (VII).

In another embodiment, compounds of the present invention have formula (VII) wherein A is a covalent bond; R$_1$ and $R_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_8$ is cyano; and P, Q, D, L, $R_A$, $R_B$, and $R_3$, are as defined in formula (I) and $R_4$, $R_6$, $R_7$, and $R_9$ are defined as in formula (VII).

In another embodiment, compounds of the present invention have formula (VII) wherein A is a covalent bond; $R_1$ and $R_2$ taken together with the nitrogen atom to which they are attached, together form a heterocycle selected from 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; $R_8$ is cyano; and P, Q, D, L, $R_A$, $R_B$, and $R_3$, are as defined in formula (I) and $R_4$, $R_6$, $R_7$, and $R_9$ are defined as in formula (VII).

In another embodiment, compounds of the present invention have formula (VII) wherein L is —CH$_2$CH$_2$—; A is a covalent bond; $R_1$ and $R_2$ taken together with the nitrogen atom to which they are attached, together form a heterocycle selected from azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; $R_3$, $R_4$, $R_6$, $R_7$ and $R_9$ are hydrogen; $R_8$ is cyano; X is CH; Y is CH; and Z is CH.

In another embodiment, compounds of the present invention have formula (VII) wherein L is —CH$_2$CH$_2$—; A is a covalent bond; $R_1$ and $R_2$ taken together with the nitrogen atom to which they are attached, together form a heterocycle selected from 1-azepanyl, (3S)-3-(dimethylamino) pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl) pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, or 1,4-dioxa-8-azaspiro[4.5]dec-8-yl; $R_3$, $R_4$, $R_6$, $R_7$ and $R_9$ are hydrogen; $R_8$ is cyano; X is CH; Y is CH; and Z is CH.

The present invention also provides, pharmaceutical compositions comprising a therapeutically effective amount of a compound of formula (I–VII) in combination with a pharmaceutically acceptable carrier.

According to another embodiment, the present invention provides a method of selectively modulating the effects of the histamine-3 receptors in a mammal comprising administering an effective amount of a compound of formula (I–VII).

According to another embodiment, the present invention provides a method of treating or preventing a disorder ameliorated by modulating the histamine-3 receptors in a mammal comprising administering an effective amount of a compound of formula (I–VII).

According to still another embodiment, the present invention provides a method of treating a disorder selected from acute myocardial infarction, asthma, bipolar disorder, cognitive enhancement, cognitive deficits in psychiatric disorders, cutaneous carcinoma, drug abuse, depression, gastrointestinal disorders, inflammation, jet lag, medullary thyroid carcinoma, melanoma, allergic rhinitis, Meniere's disease, migraine, mood and attention alteration, motion sickness, neurogenic inflammation, obsessive compulsive disorder, pain, Parkinson's disease, schizophrenia, seizures, septic shock, Tourette's syndrome, vertigo, or wakefulness.

According to another embodiment, the present invention provides a method of treating Alzheimer's disease by administering an effective amount of a compound of formula (I–VII).

According to another embodiment, the present invention provides a method of treating attention-deficit hyperactivity disorder by administering an effective amount of a compound of formula (I–VII).

According to another embodiment, the present invention provides a method of treating epilepsy by administering an effective amount of a compound of formula (I–VII).

According to another embodiment, the present invention provides a method of treating narcolepsy by administering an effective amount of a compound of formula (I–VII).

According to still another embodiment, the present invention provides a method of treating obesity by administering an effective amount of a compound of formula (I–VII).

According to still another embodiment, the present invention provides a method of treating a disorder selected from mild cognitive impairment, deficits of memory, and deficits of learning and dementia by administering an effective amount of a compound of formula (I–VII).

Representative compounds of the invention include, but are not limited to:

4-(2-{2-[(2R)-2-methylpyrrolidinyl]ethyl}-1-benzofuran-5-yl)benzonitrile;

4-{2-[2-(-pyrrolidinyl)ethyl]-1-benzofuran-5-yl}benzonitrile;

4-{2-[2-(2-methyl-1-pyrrolidinyl)ethyl]-1-benzofuran-5-yl}benzonitrile;

4-{2-[2-(1-piperidinyl)ethyl]-1-benzofuran-5-yl}benzonitrile;

4-{2-[2-(diethylamino)ethyl]-1-benzofuran-5-yl}benzonitrile;

4-{2-[2-(2-methyl-1-piperidinyl)ethyl]-1-benzofuran-5-yl}benzonitrile;

4-(2-{2-[(3R)-3-hydroxypyrrolidinyl]ethyl}-1-benzofuran-5-yl)benzonitrile;

4-{2-[2-(1H-imidazol-1-yl)ethyl]-1-benzofuran-5-yl}benzonitrile;

4-(2-{2-[(3S)-3-(dimethylamino)pyrrolidinyl]ethyl}-1-benzofuran-5-yl)benzonitrile;

4-(2-{2-[(2S)-2-(hydroxymethyl)pyrrolidinyl]ethyl}-1-benzofuran-5-yl)benzonitrile;
4-(2-{2-[(2R,6S)-2,6-dimethylpiperidinyl]ethyl}-1-benzofuran-5-yl)benzonitrile;
4-(2-{2-[(2R,5R)-2,5-dimethylpyrrolidinyl]ethyl}-1-benzofuran-5-yl)benzonitrile;
4-{2-[2-(1-azepanyl)ethyl]-1-benzofuran-5-yl}benzonitrile;
4-{2-[2-(4- methyl-1-piperidinyl)ethyl]-1-benzofuran-5-yl}benzonitrile;
4-(2-{2-[(2-pyrrolidine methyl carboxylate)]ethyl}-1-benzofuran-5-yl)benzonitrile;
4-{2-[2-(3,6-dihydro-1(2H)-pyridinyl)ethyl]-1-benzofuran-5-yl}benzonitrile;
4-(2-{2-[(2R)-2-(hydroxymethyl)pyrrolidinyl]ethyl}-1-benzofuran-5-yl)benzonitrile;
4-(2-{2-[tert-butyl(methyl)amino]ethyl}-1-benzofuran-5-yl)benzonitrile;
4-(2-{2-[isopropyl(methyl)amino]ethyl}-1-benzofuran-5-yl)benzonitrile;
4-(2-{2-[isobutyl(methyl)amino]ethyl}-1-benzofuran-5-yl)benzonitrile;
4-(2-{2-[ethyl(isopropyl)amino]ethyl}-1-benzofuran-5-yl)benzonitrile;
4-(2-{2-[ethyl(propyl)amino]ethyl}-1-benzofuran-5-yl)benzonitrile;
4-(4-{2-[2-(2-methyl-1-pyrrolidinyl)ethyl]-1-benzofuran-5-yl}benzoyl)morpholine;
4-(4-{2-[2-(1-piperidinyl)ethyl]-1-benzofuran-5-yl}benzoyl)morpholine;
N,N-diethyl-N-(2-{5-[4-(4-morpholinylcarbonyl)phenyl]-1-benzofuran-2-yl}ethyl)amine;
4-(4-{2-[2-(2-methyl-1-piperidinyl)ethyl]-1-benzofuran-5-yl}benzoyl)morpholine;
(3R)-1-(2-{5-[4-(4-morpholinylcarbonyl)phenyl]-1-benzofuran-2-yl}ethyl)-3-pyrrolidinol;
4-[4-(2-{2-[(2R,5R)-2,5-dimethylpyrrolidinyl]ethyl}-1-benzofuran-5-yl)benzoyl]morpholine;
4-[4-(2-{2-[(2R,6S)-2,6-dimethylpiperidinyl]ethyl}-1-benzofuran-5-yl)benzoyl]morpholine;
4-(4-{2-[2-(azepinyl)ethyl]-1-benzofuran-5-yl}benzoyl)morpholine;
4-(4-{2-[2-(4-methyl-1-piperidinyl)ethyl]-1-benzofuran-5-yl}benzoyl)morpholine;
4-(4-{2-[2-(4-morpholino)ethyl]-1-benzofuran-5-yl}benzoyl)morpholine;
4-(4-{2-[2-(3,6-dihydro-1(2H)-pyridinyl)ethyl]-1-benzofuran-5-yl}benzoyl)morpholine;
4-(4-{2-[2-(2S)pyrrolidinylmethanol)ethyl]-1-benzofuran-5-yl}benzoyl)morpholine;
N-(tert-butyl)-N-methyl-N-(2-{5-[4-(4-morpholinylcarbonyl)phenyl]-1-benzofuran-2-yl}ethyl)amine;
N-isopropyl-N-methyl-N-(2-{5-[4-(4-morpholinylcarbonyl)phenyl]-1-benzofuran-2-yl}ethyl)amine;
N-isobutyl-N-methyl-N-(2-{5-[4-(4-morpholinylcarbonyl)phenyl]-1-benzofuran-2-yl}ethyl)amine;
N-ethyl-N-isopropyl-N-(2-{5-[4-(4-morpholinylcarbonyl)phenyl]-1-benzofuran-2-yl}ethyl)amine;
N,N-dimethyl-N-(2-{5-[4-(4-morpholinylcarbonyl)phenyl]-1-benzofuran-2-yl}ethyl)amine;
N-ethyl-N-(2-{5-[4-(4-morpholinylcarbonyl)phenyl]-1-benzofuran-2-yl}ethyl)-N-propylamine;
4-{4-methyl-2-oxo-3-[2-(1-pyrrolidinyl)ethyl]-2H-chromen-7-yl}benzonitrile;
4-{4-methyl-2-oxo-3-[2-(1-piperidinyl)ethyl]-2H-chromen-7-yl}benzonitrile;
4-{3-[2-(diethylamino)ethyl]-4-methyl-2-oxo-2H-chromen-7-yl}benzonitrile;
4-[(6-{2-[2-(1-pyrrolidinyl)ethyl]-1-benzofuran-5-yl}-3-pyridinyl)carbonyl]morpholine;
4-{[6-(2-{2-[(2R)-methylpyrrolidinyl]ethyl}-1-benzofuran-5-yl)-3-pyridinyl]carbonyl}morpholine;
4-[(6-{2-[2-(1-piperidinyl)ethyl]-1-benzofuran-5-yl}-3-pyridinyl)carbonyl]morpholine;
4-[(6-{2-[2-(N,N-diethyl)ethyl]-1-benzofuran-5-yl}-3-pyridinyl)carbonyl]morpholine;
(3R)-1-(2-{5-[5-(4-morpholinylcarbonyl)-2-pyridinyl]-1-benzofuran-2-yl}ethyl)-3-pyrrolidinol;
4-{[6-(2-{2-[(2S,5S)-2,5-dimethylpyrrolidinyl]ethyl}-1-benzofuran-5-yl)-3-pyridinyl]carbonyl}morpholine;
4-{[6-(2-{2-[(2R,6S)-2,5-dimethylpiperidinyl]ethyl}-1-benzofuran-5-yl)-3-pyridinyl]carbonyl}morpholine;
4-{[6-(2-{2-[1-azepanyl]ethyl}-1-benzofuran-5-yl)-3-pyridinyl]carbonyl}morpholine;
4-[(6-{2-[2-(4-methyl-1-piperidinyl)ethyl]-1-benzofuran-5-yl}-3-pyridinyl)carbonyl]morpholine;
4-[(6-{2-[2-(4-morpholinyl)ethyl]-1-benzofuran-5-yl}-3-pyridinyl)carbonyl]morpholine;
N-(tert-butyl)-N-methyl-N-(2-{5-[5-(4-morpholinylcarbonyl)-2-pyridinyl]-1-benzofuran-2-yl}ethyl)amine;
N-isobutyl-N-methyl-N-(2-{5-[5-(4-morpholinylcarbonyl)-2-pyridinyl]-1-benzofuran-2-yl}ethyl)amine;
N-isopropyl-N-methyl-N-(2-{5-[5-(4-morpholinylcarbonyl)-2-pyridinyl]-1-benzofuran-2-yl}ethyl)amine;
N-ethyl-N-isopropyl-N-(2-{5-[5-(4-morpholinylcarbonyl)-2-pyridinyl]-1-benzofuran-2-yl}ethyl)amine;
N, N-dimethyl-N-(2-{5-[5-(4-morpholinylcarbonyl)-2-pyridinyl]-1-benzofuran-2-yl}ethyl)amine;
N-ethyl-N-propyl-N-(2-{5-[5-(4-morpholinylcarbonyl)-2-pyridinyl]-1-benzofuran-2-yl}ethyl)a
8-(2-{5-[5-(4-morpholinylcarbonyl)-2-pyridinyl]-1-benzofuran-2-yl}ethyl)-1,4-diox8-azaspiro[4.5]decane;
5-(2-{5-[5-(4-morpholinylcarbonyl)-2-pyridinyl]-1-benzofuran-2-yl}ethyl)-2-ox5-azabicyclo[2.2.1]heptane;
(2S)-1-(2-{5-[5-(4-morpholinylcarbonyl)-2-pyridinyl]-1-benzofuran-2-yl}ethyl)-2-pyrrolidinol
N-allyl-N-(2-{5-[5-(4-morpholinylcarbonyl)-2-pyridinyl]-1-benzofuran-2-yl}ethyl)amine;
3-[(2-{5-[5-(4-morpholinylcarbonyl)-2-pyridinyl]-1-benzofuran-2-yl}ethyl)amino]-1-propanol;
N-(2-{5-[5-(4-morpholinylcarbonyl)-2-pyridinyl]-1-benzofuran-2-yl}ethyl)-N-propylamine;
4-(2-{2-[(3R)-3-(dimethylamino)pyrrolidinyl]ethyl}-1-benzofuran-5-yl)benzonitrile;
4-(2-{2-[(2R)-2-methylpyrrolidinyl]ethyl}-2,3-dihydro-1-benzofuran-5-yl)benzonitrile;
(4-fluorophenyl)(2-{2-[(2R)-2-methyl-1-pyrrolidinyl]ethyl}-1-benzofuran-5-yl)methanone;
(3-fluorophenyl)(2-{2-[(2R)-2-methyl-1-pyrrolidinyl]ethyl}-1-benzofuran-5-yl)methanone;
(2-fluorophenyl)(2-{2-[(2R)-2-methyl-1-pyrrolidinyl]ethyl}-1-benzofuran-5-yl)methanone;
(3-chlorophenyl)(2-{2-[(2R)-2-methyl-1-pyrrolidinyl]ethyl}-1-benzofuran-5-yl)methanone;
(4-chlorophenyl)(2-{2-[(2R)-2-methyl-1-pyrrolidinyl]ethyl}-1-benzofuran-5-yl)methanone;
(4-methoxyphenyl)(2-{2-[(2R)-2-methyl-1-pyrrolidinyl]ethyl}-1-benzofuran-5-yl)methanone;

(4-fluoro-3-methylphenyl)(2-{2-[(2R)-2-methyl-1-pyrrolidinyl]ethyl}-1-benzofuran-5-yl)methanone;
cyclopropyl(2-{2-[(2R)-2-methyl-1-pyrrolidinyl]ethyl}-1-benzofuran-5-yl)methanone;
3-ethyl-1-(2-{2-[(2R)-2-methyl-1-pyrrolidinyl]ethyl}-1-benzofuran-5-yl)-1-pentanone;
(4-chloro-3-methylphenyl)(2-{2-[(2R)-2-methyl-1-pyrrolidinyl]ethyl}-1-benzofuran-5-yl)methanone;
(2-{2-[(2R)-2-methyl-1-pyrrolidinyl]ethyl}-1-benzofuran-5-yl)[4-(methylthio)phenyl]methanone;
[4-(dimethylamino)phenyl](2-{2-[(2R)-2-methyl-1-pyrrolidinyl]ethyl}-1-benzofuran-5-yl)methanone;
(4-methylphenyl)(2-{2-[(2R)-2-methyl-1-pyrrolidinyl]ethyl}-1-benzofuran-5-yl)methanone;
(3,5-difluorophenyl)(2-{2-[(2R)-2-methyl-1-pyrrolidinyl]ethyl}-1-benzofuran-5-yl)methanone;
(2-methoxyphenyl)(2-{2-[(2R)-2-methyl-1-pyrrolidinyl]ethyl}-1-benzofuran-5-yl)methanone;
(3-methoxyphenyl)(2-{2-[(2R)-2-methyl-1-pyrrolidinyl]ethyl}-1-benzofuran-5-yl)methanone;
(2-{2-[(2R)-2-methyl-1-pyrrolidinyl]ethyl}-1-benzofuran-5-yl)(phenyl)methanone;
4-(2-{2-[(2R)-2-methyl-1-pyrrolidinyl]ethyl}-1-benzofuran-4-yl)benzonitrile;
2-{2-[(2R)-2-methylpyrrolidin-1-yl]ethyl}-1-benzofuran-6-carbonitrile;
3-(2-{2-[(2R)-2-methylpyrrolidin-1-yl]ethyl}-11benzofuran-5-yl)-5-(thien-2-ylmethyl)-1,2,4-oxadiazole;
4-[3-(2-{2-[(2R)-2-methylpyrrolidin-1-yl]ethyl}-1-benzofuran-5-yl)-1,2,4-oxadiazol-5-yl]benzonitrile;
5-(4-chlorophenyl)-3-(2-{2-[(2R)-2-methylpyrrolidin-1-yl]ethyl}-1-benzofuran-5-yl)-1,2,4-oxadiazole;
5-(2-chlorophenyl)-3-(2-{2-[(2R)-2-methylpyrrolidin-1-yl]ethyl}-1-benzofuran-5-yl)-1,2,4-oxadiazole;
5-(4-fluorobenzyl)-3-(2-{2-[(2R)-2-methylpyrrolidin-1-yl]ethyl}-1-benzofuran-5-yl)-1,2,4-oxadiazole;
5-(4-methoxybenzyl)-3-(2-{2-[(2R)-2-methylpyrrolidin-1-yl]ethyl}-1-benzofuran-5-yl)-1,2,4-oxadiazole;
3-{[3-(2-{2-[(2R)-2-methylpyrrolidin-1-yl]ethyl}-1-benzofuran-5-yl)-1,2,4-oxadiazol-5-yl]methyl}benzonitrile;
3-(2-{2-[(2R)-2-methylpyrrolidin-1-yl]ethyl}-1-benzofuran-5-yl)-5-phenyl-1,2,4-oxadiazole;
5-(4-fluorophenyl)-3-(2-{2-[(2R)-2-methylpyrrolidin-1-yl]ethyl}-1-benzofuran-5-yl)-1,2,4-oxadiazole;
5-(3-chloro-4-fluorophenyl)-3-(2-{2-[(2R)-2-methylpyrrolidin-1-yl]ethyl}-1-benzofuran-5-yl)-1,2,4-oxadiazole;
5-(chloromethyl)-3-(2-{2-[(2R)-2-methylpyrrolidin-1-yl]ethyl}-1-benzofuran-5-yl)-1,2,4-oxadiazole;
3-(2-{2-[(2R)-2-methylpyrrolidin-1-yl]ethyl}-1-benzofuran-5-yl)-5-propyl-1,2,4-oxadiazole;
5-ethyl-3-(2-{2-[(2R)-2-methylpyrrolidin-1-yl]ethyl}-1-benzofuran-5-yl)-1,2,4-oxadiazole;
5-methyl-3-(2-{2-[(2R)-2-methylpyrrolidin-1-yl]ethyl}-1-benzofuran-5-yl)-1,2,4-oxadiazole;
4-(3-bromo-2-{2-[(2R)-2-methylpyrrolidin-1-yl]ethyl}-1-benzofuran-5-yl)benzonitrile;
4-(3-(2-furyl)-2-{2-[(2R)-2-methylpyrrolidin-1-yl]ethyl}-1-benzofuran-5-yl)benzonitrile;
4-[2-{2-[(2R)-2-methyl-1-pyrrolidinyl]ethyl}-3-(3-pyridinyl)-1-benzofuran-5-yl]benzonitrile;
4-[2-{2-[(2R)-2-methyl-1-pyrrolidinyl]ethyl}-3-(3-thienyl)-1-benzofuran-5-yl]benzonitrile;
4-(3-(2-formyl-3-thienyl)-2-{2-[(2R)-2-methyl-1-pyrrolidinyl]ethyl}-1-benzofuran-5-yl)benzonitrile;
2-methyl-4-(2-{2-[(2R)-2-methyl-1-pyrrolidinyl]ethyl}-1-benzofuran-5-yl)benzonitrile;
3-methyl-4-(2-{2-[(2R)-2-methyl-1-pyrrolidinyl]ethyl}-1-benzofuran-5-yl)benzonitrile;
4-(6-methyl-2-{2-[(2R)-2-methyl-1-pyrrolidinyl]ethyl}-1-benzofuran-5-yl)benzonitrile
4-(4-methyl-2-{2-[(2R)-2-methyl-1-pyrrolidinyl]ethyl}-1-benzofuran-5-yl)benzonitrile;
4-(7-methyl-2-{2-[(2R)-2-methyl-1-pyrrolidinyl]ethyl}-1-benzofuran-5-yl)benzonitrile;
4-(7-fluoro-2-{2-[(2R)-2-methyl-1-pyrrolidinyl]ethyl}-1-benzofuran-5-yl)benzonitrile;
2-fluoro-4-(2-{2-[(2R)-2-methyl-1-pyrrolidinyl]ethyl}-1-benzofuran-5-yl)benzonitrile;
3-(2-{2-[(2R)-2-methyl-1-pyrrolidinyl]ethyl}-1-benzofuran-5-yl)benzonitrile;
(2R)-1-{2-[5-(4-fluorophenyl)-1-benzofuran-2-yl]ethyl}-2-methylpyrrolidine;
(2R)-1-{2-[5-(3,4-dichlorophenyl)-1-benzofuran-2-yl]ethyl}-2-methylpyrrolidine;
(2R)-2-methyl-1-{2-[5-(2-methylphenyl)-1-benzofuran-2-yl]ethyl}pyrrolidine;
(2R)-2-methyl-1-{2-[5-(3-methylphenyl)-1-benzofuran-2-yl]ethyl}pyrrolidine;
(2R)-2-methyl-1-{2-[5-(4-methylphenyl)-1-benzofuran-2-yl]ethyl}pyrrolidine;
4-{2-[2-(2-methylpyrrolidin-1-yl)-ethyl]-benzofuran-5-yl}-benzoic acid methyl ester;
(2R)-1-2-[5-(2-methoxyphenyl)-1-benzofuran-2-yl]ethyl}-2-methylpyrrolidine;
(2R)-1-{2-[5-(3-methoxyphenyl)-1-benzofuran-2-yl]ethyl}-2-methylpyrrolidine;
(2R)-1-{2-[5-(4-methoxyphenyl)-1-benzofuran-2-yl]ethyl}-2-methylpyrrolidine;
(2R)-1-{2-[5-(3-fluorophenyl)-1-benzofuran-2-yl]ethyl}-2-methylpyrrolidine;
(2R)-1-{2-[5-(2-chlorophenyl)-1-benzofuran-2-yl]ethyl}-2-methylpyrrolidine;
(2R)-1-{2-[5-(3-chlorophenyl)-1-benzofuran-2-yl]ethyl}-2-methylpyrrolidine;
1-{2-[5-(4-chlorophenyl)-benzofuran-2-yl]-ethyl}-2-methylpyrrolidine;
(2R)-2-methyl-[-(2-{5-[3-(trifluoromethyl)phenyl]-1-benzofuran-2-yl}ethyl)pyrrolidine;
(2R)-2-methyl-1-(2-{5-[4-(trifluoromethyl)phenyl]-1-benzofuran-2-yl}ethyl)pyrrolidine;
(2R)-2-methyl-1-(2-{5-[3-(trifluoromethoxy)phenyl]-1-benzofuran-2-yl}ethyl)pyrrolidine;
(2R)-2-methyl-1-(2-{5-[4-(trifluoromethoxy)phenyl]-1-benzofuran-2-yl}ethyl)pyrrolidine;
(2R)-1-{2-[5-(3,4-dimethylphenyl)-1-benzofuran-2-yl]ethyl}-2-methylpyrrolidine;
(2R)-1-{2-[5-(3,5-dichlorophenyl)-1-benzofuran-2-yl]ethyl}-2-methylpyrrolidine;
(2R)-1-{2-[5-(3,5-dimethylphenyl)-1-benzofuran-2-yl]ethyl}-2-methylpyrrolidine;
[4-(2-{2-[(2R)-2-methyl-1-pyrrolidinyl]ethyl}-1-benzofuran-5-yl)phenyl]methanol;
3-(2-{2-[(2R)-2-methyl-1-pyrrolidinyl]ethyl}-1-benzofuran-5-yl)pyridine;
(2R)-1-(2-{5-[2-(4-fluorophenyl)vinyl]-1-benzofuran-2-yl}ethyl)-2-methylpyrrolidine;
1-[3-(2-{2-[(2R)-2-methyl-1-pyrrolidinyl]ethyl}-1-benzofuran-5-yl)phenyl]ethanone;
1-[3-(2-{2-[(2R)-2-methyl-1-pyrrolidinyl]ethyl}-1-benzofuran-5-yl)phenyl]ethanol;
2-[3-(2-{2-[(2R)-2-methyl-1-pyrrolidinyl]ethyl}-1-benzofuran-5-yl)phenyl]-2-propanol;
1-[3-(2-{2-[(2R)-2-methyl-1-pyrrolidinyl]ethyl}-1-benzofuran-5-yl)phenyl]ethanone oxime;

1-[3-(2-{2-[(2R)-2-methyl-1-pyrrolidinyl]ethyl}-1-benzofuran-5-yl)phenyl]ethanone O-methyloxime;
1-[3-(2-{2-[(2R)-2-methyl-1-pyrrolidinyl]ethyl}-1-benzofuran-5-yl)phenyl]ethanone O-ethyloxime;
1-[3-(2-{2-[(2R)-2-methyl-1-pyrrolidinyl]ethyl}-1-benzofuran-5-yl)phenyl]ethanone O-(tert-butyl)oxime;
ethyl 3-(2-{2-[(2R)-2-methyl-1-pyrrolidinyl]ethyl}-1-benzofuran-5-yl)benzoate;
3-(2-{2-[(2R)-2-methyl-1-pyrrolidinyl]ethyl}-1-benzofuran-5-yl)benzoic acid;
N-methoxy-N-methyl-3-(2-{2-[(2R)-2-methyl-1-pyrrolidinyl]ethyl}-1-benzofuran-5-yl)benzamide;
1-[3-(2-{2-[(2R)-2-methyl-1-pyrrolidinyl]ethyl}-1-benzofuran-5-yl)phenyl]-1-propanone;
cyclopropyl[3-(2-{2-[(2R)-2-methyl-1-pyrrolidinyl]ethyl}-1-benzofuran-5-yl)phenyl]methanone;
3-methyl-1-[3-(2-{2-[(2R)-2-methyl-1-pyrrolidinyl]ethyl}-1-benzofuran-5-yl)phenyl]-1-butanone;
3-(2-{2-[(2R)-2-methyl-1-pyrrolidinyl]ethyl}-1-benzofuran-5-yl)benzaldehyde;
3-(2-{2-[(2R)-2-methyl-1-pyrrolidinyl]ethyl}-1-benzofuran-5-yl)phenyl](2-thienyl)methanone;
(3-fluorophenyl)[3-(2-{2-[(2R)-2-methyl-1-pyrrolidinyl]ethyl}-1-benzofuran-5-yl)phenyl]methanone;
[3-(2-{2-[(2R)-2-methyl-1-pyrrolidinyl]ethyl}-1-benzofuran-5-yl)phenyl]methanol;
(2R)-1-[2-(5-benzyl-1-benzofuran-2-yl)ethyl]-2-methylpyrrolidine;
1-(2-{2-[(2R)-2-methyl-1-pyrrolidinyl]ethyl}-1-benzofuran-5-yl)-1H-imidazole;
4-(3-bromo-2-{2-[(2R)-2-methyl-1-pyrrolidinyl]ethyl}-1-benzofuran-5-yl)-2-methylbenzonitrile;
4-(3-chloro-2-{2-[(2R)-2-methyl-1-pyrrolidinyl]ethyl}-1-benzofuran-5-yl)benzonitrile
4-(3,6-dichloro-2-{2-[(2R)-2-methyl-1-pyrrolidinyl]ethyl}-1-benzofuran-5-yl)benzonitrile;
4-(3-iodo-2-{2-[(2R)-2-methyl-1-pyrrolidinyl]ethyl}-1-benzofuran-5-yl)benzonitrile;
4-(2-{2-[(2R)-2-methyl-5-oxo-1-pyrrolidinyl]ethyl}-1-benzofuran-5-yl)benzonitrile;
4-(3-acetyl-2-{2-[(2R)-2-methyl-1-pyrrolidinyl]ethyl}-1-benzofuran-5-yl)benzonitrile;
cyclopropyl[4-(2-{2-[(2R)-2-methyl-1-pyrrolidinyl]ethyl}-1-benzofuran-5-yl)phenyl]methanone;
3,5-dimethyl-4-(2-{2-[(2R)-2-methyl-1-pyrrolidinyl]ethyl}-1-benzofuran-5-yl)isoxazole;
4-[2-(2-aminoethyl)-1-benzofuran-5-yl]benzonitrile;
4-(2-{2-[(2R)-2-ethyl-1-pyrrolidinyl]ethyl}-1-benzofuran-5-yl)benzonitrile;
4-(2-{2-[(2S)-2-(fluoromethyl)-1-pyrrolidinyl]ethyl}-1-benzofuran-5-yl)benzonitrile;
4-(2-{2-[(2R)-2-methyl-1-pyrrolidinyl]ethyl}-1-benzothien-5-yl)benzonitrile;
4-(2-{2-[(2S)-2-methylpyrrolidinyl]ethyl}-1-benzofuran-5-yl)benzonitrile;
(2R)-2-methyl-1-[2-(5-phenoxy-1-benzofuran-2-yl)ethyl]pyrrolidine;
(2R)-1-(2-{5-[(3-fluorophenyl)thio]-1-benzofuran-2-yl}ethyl)-2-methylpyrrolidine;
3-(2-{3-[(2R)-2-methyl-1-pyrrolidinyl]propyl}-1-benzofuran-5-yl)benzonitrile;
3-(2-{[(2R)-2-methyl-1-pyrrolidinyl]methyl}-1-benzofuran-5-yl)benzonitrile;
3-(2-{4-[(2R)-2-methyl-1-pyrrolidinyl]butyl}-1-benzofuran-5-yl)benzonitrile;
4-(4-{2-[(2S)-methyl-1-pyrrolidinyl)ethyl}-1-benzofuran-5-yl}benzoyl)morpholine;
4-{4-methyl-2-oxo-3-[2-(2S)-methyl-1-pyrrolidinyl ethyl]-2H-chromen-6-yl}benzonitrile;
4-{4-methyl-2-oxo-3-[2-(2R)-methyl-1-pyrrolidinyl ethyl]-2H-chromen-6-yl}benzonitrile;
4-{[6-(2-{2-[(2S)-methylpyrrolidinyl]ethyl}-1-benzofuran-5-yl)-3-pyridinyl]carbonyl}morpholine;
4-(2-{2-[(2R)-2-methylpyrrolidinyl]ethyl}-2,3-dihydro-1-benzofuran-5-yl)benzonitrile;
4-(2-{2-[(2S)-2-methyl-1-pyrrolidinyl]ethyl}-1-benzofuran-4-yl)benzonitrile;
4-{2-[2-(2(S)-methyl-pyrrolidinyl-1-yl)-ethyl]-benzofuran-6-yl}-benzonitrile;
3-(2-{2-[(2S)-2-methyl-1-pyrrolidinyl]ethyl}-1-benzofuran-5-yl)benzonitrile;
4-(2-{2-[(2S)-2-methyl-1-pyrrolidinyl]ethyl}-1-benzofuran-5-yl)benzonitrile;
4-(2-{2-[(2S)-2-ethyl-1-pyrrolidinyl]ethyl}-1-benzofuran-5-yl)benzonitrile;
4-(2-{2-[(2R)-2-ethyl-1-pyrrolidinyl]ethyl}-1-benzofuran-5-yl)benzonitrile;
4-(2-{2-[2-ethyl-1-pyrrolidinyl]ethyl}-1-benzofuran-5-yl)benzonitrile;
4-(2-{2-[(2S,5S)-2,5-dimethylpyrrolidinyl]ethyl}-1-benzofuran-5-yl)benzonitrile;
4-(2-{2-[(trans)-2,5-dimethylpyrrolidinyl]ethyl}-1-benzofuran-5-yl)benzonitrile;
3,5-dimethyl-4-{2-[2-(2R)-methyl-pyrrolidinyl-1-yl)-ethyl]-benzofuran-5-yl}-isoxazole;
5-{2-[2-(2R)-methyl-pyrrolidinyl)-ethyl]-benzofuran-5-yl}-2-phenyl-oxazole;
2-{2-[2-(2R)-methyl-pyrrolidinyl-1-yl)-ethyl]-benzofuran-5-yl}-thiazole;
4-{2-[2-(2R)-methyl-pyrrolidin-1-yl)-ethyl]-benzofuran-5-yl}-1H-pyrazole;
4-{2-[2-(2R)-methyl-pyrrolidin-1-yl)-ethyl]-benzofuran-5-yl}-1-phenyl-1H-pyrazole;
1-methyl-4-{2-[(2R)-(2-methyl-pyrrolidin-1-yl)-ethyl]-benzofuran-5-yl}-1H-imidazole;
4-{2-[2-(2R)-methyl-pyrrolidin-1-yl)-ethyl]-benzofuran-5-yl}-thiazole;
2-{2-[2-(2R)-methyl-pyrrolidin-1-yl)-ethyl]-benzofuran-5-yl}-1H-imidazole;
4-{2-[2-(2R)-methyl-pyrrolidin-1-yl)-ethyl]-benzofuran-5-yl}-1H-benzoimidazole;
3-methyl-6-{(2R)-[2-(2-methyl-pyrrolidin-1-yl)-ethyl]-benzofuran-5-yl}-pyridazine;
2-{2-[2-(2R)-methyl-pyrrolidin-1-yl-ethyl]-benzofuran-5-yl}-pyrazine;
5-{2-[2-(2R)-methyl-pyrrolidin-1-yl-ethyl]-benzofuran-5-yl}-pyrimidine;
5-{2-[2-(2R)-methyl-pyrrolidin-1-yl-ethyl]-benzofuran-5-yl}-pyridazin-4-ylamine;
5-{2-[2-(2R)-methyl-pyrrolidin-1-yl-ethyl]-benzofuran-5-yl}-nicotinonitrile;
4-{2-[2-(2R)-methyl-pyrrolidin-1-yl-ethyl]-benzofuran-5-yl}-1H-indole;
4-{2-[2-(2R)-methyl-pyrrolidin-1-yl-ethyl]-benzofuran-5-yl}-phthalonitrile;
5-{2-[2-(2R)-methyl-pyrrolidin-1-yl-ethyl]-benzofuran-5-yl}-indan-1-one;
1-{2-[5-(5,6-dihydro-2H-pyran-3-yl-benzofuran-2-yl]-ethyl}-(2R)-methyl-pyrrolidine;
1-[2-(5-cyclohept-1-enyl-benzofuran-2-yl)-ethyl]-2R)-methyl-pyrrolidine;
(2R)-methyl-1-(2-{5-[2-(11H-10-thia-dibenzo[a,d] cyclohepten-5-ylidene)-ethyl]-benzofuran-2-yl}-ethyl)-pyrrolidine;

4-{2-[2-(2R)-methyl-pyrrolidin-1-yl)-ethyl]-benzofuran-5-yl}-pyridine;
3,5-dimethyl-4-{2-[2-(2R)-methyl-pyrrolidin-1-yl)-ethyl]-benzofuran-4-yl}-isoxazole;
5-{2-[2-(2R)-methyl-pyrrolidin-1-yl)-ethyl]-benzofuran-4-yl}-2-phenyl-oxazole;
2-{2-[2-(2R)-methyl-pyrrolidin-1-yl)-ethyl]-benzofuran-4-yl}-thiazole;
4-{2-[2-(2R)-methyl-pyrrolidin-1-yl)-ethyl]-benzofuran-4-yl}-1H-pyrazole;
4-{2-[2-(2R)-methyl-pyrrolidin-1-yl)-ethyl]-benzofuran-4-yl}-1-phenyl-1H-pyrazole;
1-methyl-4-{2-[(2R)-(2-methyl-pyrrolidin-1-yl)-ethyl]-benzofuran-4-yl}-1H-imidazole;
4-{2-[2-(2R)-methyl-pyrrolidin-1-yl)-ethyl]-benzofuran-4-yl}-thiazole;
2-{2-[2-(2R)-methyl-pyrrolidin-1-yl)-ethyl]-benzofuran-4-yl}-1H-imidazole;
4-{2-[2-(2R)-methyl-pyrrolidin-1-yl)-ethyl]-benzofuran-4-yl}-1H-benzoimidazole;
3-methyl-6-{(2R)-[2-(2-methyl-pyrrolidin-1-yl)-ethyl]-benzofuran-4-yl}-pyridazine;
2-{2-[2-(2R)-methyl-pyrrolidin-1-yl)-ethyl]-benzofuran-4-yl}-pyrazine;
5-{2-[2-(2R)-methyl-pyrrolidin-1-yl)-ethyl]-benzofuran-4-yl}-pyrimidine;
5-{2-[2-(2R)-methyl-pyrrolidin-1-yl)-ethyl]-benzofuran-4-yl}-pyridazin-4-ylamine;
5-{2-[2-(2R)-methyl-pyrrolidin-1-yl)-ethyl]-benzofuran-4-yl}-nicotinonitrile;
4-{2-[2-(2R)-methyl-pyrrolidin-1-yl)-ethyl]-benzofuran-4-yl}-1H-indole;
4-{2-[2-(2R)-methyl-pyrrolidin-1-yl)-ethyl]-benzofuran-4-yl}-phthalonitrile;
5-{2-[2-(2R)-methyl-pyrrolidin-1-yl)-ethyl]-benzofuran-4-yl}-indan-1-one;
1-{2-[4-(5,6-dihydro-2H-pyran-3-yl)-benzofuran-2-yl]-ethyl}-(2R)-methyl-pyrrolidine;
1-[2-(4-cyclohept-1-enyl-benzofuran-2-yl)-ethyl]-(2R)-methyl-pyrrolidine;
(2R)-methyl-1-(2-{4-[2-(11H-10-thia-dibenzo[a,d]cyclohepten-5-ylidene)-ethyl]-benzofuran-2-yl}-ethyl)-pyrrolidine;
4-{2-[2-(2R)-methyl-pyrrolidin-1-yl)-ethyl]-benzofuran-4-yl}-pyridine;
3,5-dimethyl-4-{2-[2-(2R)-methyl-pyrrolidin-1-yl)-ethyl]-benzofuran-6-yl}-isoxazole;
5-{2-[2-(2R)-methyl-pyrrolidin-1-yl)-ethyl]-benzofuran-6-yl}-2-phenyl-oxazole;
2-{2-[2-(2R)-methyl-pyrrolidin-1-yl)-ethyl]-benzofuran-6-yl}-thiazole;
4-{2-[2-(2R)-methyl-pyrrolidin-1-yl)-ethyl]-benzofuran-6-yl}-1H-pyrazole;
4-{2-[2-(2R)-methyl-pyrrolidin-1-yl)-ethyl]-benzofuran-6-yl}-1-phenyl-1H-pyrazole;
1-methyl-4-{2-[2(R)-(2-methyl-pyrrolidin-1-yl)-ethyl]-benzofuran-6-yl}-1H-imidazole;
4-{2-[2-(2(R)-methyl-pyrrolidin-1-yl)-ethyl]-benzofuran-6-yl}-thiazole;
2-{2-[2-(2(R)-methyl-pyrrolidin-1-yl)-ethyl]-benzofuran-6-yl}-1H-imidazole;
4-{2-[2-(2(R)-methyl-pyrrolidin-1-yl)-ethyl]-benzofuran-6-yl}-1H-benzoimidazole;
3-methyl-6-{(2R)-[2-(2-methyl-pyrrolidin-1-yl)-ethyl]-benzofuran-6-yl}-pyridazine;
2-{2-[2-(2(R)-methyl-pyrrolidin-1-yl)-ethyl]-benzofuran-6-yl}-pyrazine;
5-{2-[2-(2(R)-methyl-pyrrolidin-1-yl)-ethyl]-benzofuran-6-yl}-pyrimidine;
5-{2-[2-(2(R)-methyl-pyrrolidin-1-yl)-ethyl]-benzofuran-6-yl}-pyridazin-4-ylamine;
5-{2-[2-(2(R)-methyl-pyrrolidin-1-yl)-ethyl]-benzofuran-6-yl}-nicotinonitrile;
4-{2-[2-(2(R)-methyl-pyrrolidin-1-yl)-ethyl]-benzofuran-6-yl}-1H-indole;
4-{2-[2-(2(R)-methyl-pyrrolidin-1-yl)-ethyl]-benzofuran-6-yl}-phthalonitrile;
5-{2-[2-(2(R)-methyl-pyrrolidin-1-yl)-ethyl]-benzofuran-6-yl}-indan-1-one;
1-{2-[6-(5,6-dihydro-2H-pyran-3-yl)-benzofuran-2-yl]-ethyl}-2(R)-methyl-pyrrolidine;
1-[2-(6-cyclohept-1-enyl-benzofuran-2-yl)-ethyl]-2(R)-methyl-pyrrolidine;
2(R)-methyl-1-(2-{6-[2-(11H-10-thia-dibenzo[a,d]cyclohepten-5-ylidene)-ethyl]-25 benzofuran-2-yl}-ethyl)-pyrrolidine;
4-{2-[2-(2(R)-methyl-pyrrolidin-1-yl)-ethyl]-benzofuran-6-yl}1-pyridine;
3,5-dimethyl-4-{2-2-[2-(2 pr)-methyl-pyrrolidine-2-yl)-ethyl]-benzofuran-7-yl}-isoxazole;
5-{2-[2-(2(R)-methyl-pyrrolidin-1-y)-ethyl]-benzofuran-7-yl}-2-phenyl-oxazole;
2-{2-[2-(2(R)-methyl-pyrrolidin-1-yl)-ethyl]-benzofuran-7-yl}-thiazole;
4-{2-[2-(2(R)-methyl-pyrrolidin-1-yl)-ethyl]-benzofuran-7-yl}-1H-pyrazole;
4-{2-[2-(2(R)-methyl-pyrrolidin-1-yl)-ethyl]-benzofuran-7-yl}-phenyl-1H-pyrazole;
1-methyl-4-{2-[2(R)-(2-methyl-pyrrolidin-1-yl)-ethyl]-benzofuran-7-yl}-1H-imidazole;
4-{2-[2-(2(R)-methyl-pyrrolidin-1-yl)-ethyl]-benzofuran-7-yl}-thiazole;
2-{2-[2-(2(R)-methyl-pyrrolidin-1-yl)-ethyl]-benzofuran-7-yl}-1H-imidazole;
4-{2-[2-(2(R)-methyl-pyrrolidin-1-yl)-ethyl]-benzofuran-7-yl}-1H-benzoimidazole;
3-methyl-6-{2(R)-[2-(2-methyl-pyrrolidin-1-yl)-ethyl]-benzofuran-7-yl}-pyridazine;
2-{2-[2-(2(R)-methyl-pyrrolidin-1-yl)-ethyl]-benzofuran-7-yl}-pyrazine;
5-{2-[2-(2(R)-methyl-pyrrolidin-1-yl)-ethyl]-benzofuran-7-yl}-pyrimidine;
5-{2-[2-(2(R)-methyl-pyrrolidin-1-yl)-ethyl]-benzofuran-7-yl}-pyridazin-4-ylamine;
5-{2-[2-(2(R)-methyl-pyrrolidin-1-yl)-ethyl]-benzofuran-7-yl}-nicotinonitrile;
4-{2-[2-(2(R)-methyl-pyrrolidin-1-yl)-ethyl]-benzofuran-7-yl}-1H-indole;
4-{2-[2-(2(R)-methyl-pyrrolidin-1-yl)-ethyl]-benzofuran-7-yl}-phthalonitrile;
5-{2-[2-(2(R)-methyl-pyrrolidin-1-yl)-ethyl]-benzofuran-7-yl}-indan-1-one;
1-{2-[7-(5,6-dihydro-2H-pyran-3-yl)-benzofuran-2-yl]-ethyl}-2(R)-methyl-pyrrolidine;
1-[2-(7-cyclohept-1-enyl-benzofuran-2-yl)-ethyl]-2(R)-methyl-pyrrolidine;
2(R)-methyl-1-(2-{7-[2-(11H-10-thia-dibenzo[a,d]cyclohepten-5-ylidene)-ethyl]-benzofuran-2-yl}-ethyl)-pyrrolidine;
4-{2-[2-(2(R)-methyl-pyrrolidin-1-yl)-ethyl]-benzofuran-7-yl}-pyridine;
1-{2-[2-(2(R)-methylpyrrolidin-1-yl)-ethyl]-benzofuran-5-yl}-1H-imidazole-4,5-dicarbonitrile;
4,5-dichloro-1-{-2-[2-(2(R)-methylpyrrolidin-1-yl)-ethyl]-benzofuran-5-yl)}-1H-imidazole;

1-{2-[2-(2(R)-methylpyrrolidin-1-yl)-ethyl]-benzofuran-5-yl}-1H-benzoimidazole;
3-{2-[2-(2(R)-methylpyrrolidin-1-yl)-ethyl]-benzofuran-5-yl}-3H-imidazo[4,5-c]pyridine;
(5-hydroxymethyl-3-{2-[2-(2(R)-methylpyrrolidin-1-yl)-ethyl]-benzofuran-5-yl}-3H-imidazol-4-yl)-methanol;
1-{2-[2-(2(R)-methylpyrrolidin-1-yl)-ethyl]-benzofuran-5-yl}-1H-pyrrole;
1-(1-{2-[2-(2(R)-methylpyrrolidin-1-yl)-ethyl]-benzofuran-5-yl}-1H-pyrrol-3-yl)-ethanone;
3-methyl-1-{2-[2-(2(R)-methylpyrrolidin-1-yl)-ethyl]-benzofuran-5-yl}-1H-pyrrole;
1-{2-[2-(2(R)-methylpyrrolidin-1-yl)-ethyl]-benzofuran-5-yl}-3,4-bis-trifluoromethyl-1H-pyrrole;
1-{2-[2-(2(R)-methylpyrrolidin-1-yl)-ethyl]-benzofuran-5-yl}-1H-pyrazole;
4-methyl-1-{2-[2-(2(R)-methylpyrrolidin-1-yl)-ethyl]-benzofuran-5-yl}-1H-pyrazole;
1-{2-[2-(2(R)-methylpyrrolidin-1-yl)-ethyl]-benzofuran-5-yl}-1H-pyrazole-4-carboxylic acid ethyl ester;
1-{2-[2-(2(R)-methylpyrrolidin-1-yl)-ethyl]-benzofuran-5-yl}-1H-pyrazole-4-carbonitrile;
4-chloro-1-{2-[2-(2(R)-methylpyrrolidin-1-yl)-ethyl]-benzofuran-5-yl}-1H-pyrazole;
3,5-dimethyl-1-{2-[2-(2(R)-methylpyrrolidin-1-yl)-ethyl]-benzofuran-5-yl}-1H-pyrazole;
(4-methoxy-phenyl)-methyl-{2-[2-(2(R)-methyl-pyrrolidin-1-yl)-ethyl]-benzofuran-5-yl}-amine;
benzo[1,3]dioxol-5-yl-methyl-{2-[2-(2-methyl-pyrrolidin-1-yl)-ethyl]-benzofuran-5-yl}-amine;
cyclohexyl-methyl-{2-[2-(2(R)-methyl-pyrrolidin-1-yl)-ethyl]-benzofuran-5-yl}-amine; and
{2-[2-(2(R)-methyl-pyrrolidin-1-yl)-ethyl]-benzofuran-5-yl}-(tetrahydro-pyran-4-yl)-amine.

Determination of Biological Activity

To determine the effectiveness of representative compounds of this invention as histamine-3 receptor ligands ($H_3$ receptor ligands), the following tests were conducted according to methods previously described (European Journal of Pharmacology, 188:219–227 (1990); Journal of Pharmacology and Experimental Therapeutics, 275: 598–604 (1995); Journal of Pharmacology and Experimental Therapeutics, 276:1009–1015 (1996); and Biochemical Pharmacology, 22: 3099–3108 (1973)).

Briefly, male Sprague-Dawley rat brain cortices were homogenized (1 g tissue/10 mL buffer) in 50 mM Tris-HCl/5 mM EDTA containing protease inhibitor cocktail (Calbiochem) using a polytron set at 20,500 rpm. Homogenates were centrifuged for 20 minutes at 40,000×g. The supernatant was decanted, and pellets were weighed. The pellet was resuspended by polytron homogenization in 40 mL 50 mM Tris-HCl/5 mM EDTA with protease inhibitors and centrifuged for 20 minutes at 40,000×g. The membrane pellet was resuspended in 6.25 volumes (per gram wet weight of pellet) of 50 mM Tris-HCl/5 mM EDTA with protease inhibitors and aliquots flash frozen in liquid $N_2$ and stored at −70° C. until used in assays. Rat cortical membranes (12 mg wet weight/tube) were incubated with ($^3$H)-N-α-methylhistamine (~0.6 nM) with or without $H_3$ receptor antagonists in a total incubation volume of 0.5 mL of 50 mM Tris-HCl/5 mM EDTA (pH 7.7). Test compounds were dissolved in DSMO to provide a 20 mM solution, serially diluted and then added to the incubation mixture prior to initiating the incubation assay by addition of the membranes. Thioperamide (3 $\mu$M) was used to determine non-specific binding. Binding incubations were conducted for 30 minutes at 25° C. and terminated by addition of 2 mL of ice cold 50 mM Tris-HCl (pH 7.7) and filtration through 0.3% polyethylenimine-soaked Unifilter plates (Packard). These filters were washed 4 additional times with 2 mL of ice-cold 50 mM Tris-HCl and dried for 1 hour. Radioactivity was determined using liquid scintillation counting techniques. Results were analyzed by Hill transformation and Ki values were determined using the Cheng-Prusoff equation.

TABLE 1

| Example Number | Ki (nM) |
| --- | --- |
| 1 | 4.44 |
| 2 | 46.8 |
| 3 | 7.45 |
| 4 | 58.8 |
| 5 | 49.4 |
| 6 | 44.9 |
| 7 | 94.9 |
| 8 | 1995 |
| 9 | 136 |
| 10 | 22.9 |
| 11 | 19.3 |
| 12 | 38.4 |
| 13 | 78.4 |
| 14 | 25.1 |
| 15 | 1000 |
| 16 | 92.2 |
| 17 | 165 |
| 18 | 60.5 |
| 19 | 77.7 |
| 20 | 180 |
| 21 | 44.4 |
| 22 | 69.2 |
| 23 | 1.97 |
| 24 | 11.7 |
| 25 | 14.4 |
| 26 | 27.2 |
| 27 | 55.4 |
| 28 | 9.24 |
| 29 | 8.46 |
| 30 | 13.7 |
| 31 | 24.6 |
| 32 | 265 |
| 33 | 32.3 |
| 34 | 6.89 |
| 35 | 67.9 |
| 36 | 52.1 |
| 37 | 248 |
| 38 | 26.0 |
| 39 | 148 |
| 40 | 32.2 |
| 41 | 51.5 |
| 42 | 41.8 |
| 43 | 14.6 |
| 44 | 17.2 |
| 45 | 1.61 |
| 46 | 18.5 |
| 47 | 59.8 |
| 48 | 30.8 |
| 49 | 14.4 |
| 50 | 37.1 |
| 51 | 3.07 |
| 52 | 162 |
| 53 | 242 |
| 54 | 197 |
| 55 | 575 |
| 56 | 105 |
| 57 | 115 |
| 58 | 133 |
| 59 | 79.1 |
| 60 | 1000 |
| 61 | 143 |
| 62 | 112 |
| 63 | 1000 |
| 64 | 1000 |
| 65 | 596 |
| 66 | 90.4 |
| 68 | 2.2 |

TABLE 1-continued

| Example Number | Ki (nM) |
|---|---|
| 69 | 0.6 |
| 70 | 2.1 |
| 71 | 2.0 |
| 72 | 2.7 |
| 73 | 2.9 |
| 74 | 3.5 |
| 75 | 9.9 |
| 76 | 4.0 |
| 77 | 6.0 |
| 78 | 8.2 |
| 79 | 3.8 |
| 80 | 1.4 |
| 81 | 1.4 |
| 82 | 1.6 |
| 83 | 1.1 |
| 84 | 2.8 |
| 85 | 42 |
| 86 | 3.5 |
| 87 | 16 |
| 88 | 64 |
| 89 | 12 |
| 90 | 21 |
| 91 | 10 |
| 92 | 15 |
| 93 | 6 |
| 94 | 16 |
| 95 | 12 |
| 96 | 223 |
| 97 | 1.4 |
| 98 | 0.7 |
| 99 | 3.6 |
| 100 | 6 |
| 101 | 3.4 |
| 102 | 18 |
| 103 | 13 |
| 104 | 41 |
| 105 | 6 |
| 106 | 2.3 |
| 107 | 8 |
| 108 | 8 |
| 109 | 10 |
| 110 | 6 |
| 111 | 9 |
| 112 | 3 |
| 113 | 77 |
| 114 | 97 |
| 115 | 33 |
| 116 | 30 |
| 117 | 110 |
| 118 | 42 |
| 119 | 66 |
| 120 | 23 |
| 121 | 51 |
| 122 | 17 |
| 123 | 16 |
| 124 | 34 |
| 125 | 63 |
| 126 | 81 |
| 127 | 120 |
| 128 | 110 |
| 129 | 150 |
| 130 | 60 |
| 131 | 22 |
| 132 | 19 |
| 133 | 6.4 |
| 134 | 3.2 |
| 135 | 31 |
| 136 | 0.4 |
| 137 | 2.8 |
| 138 | 1.2 |
| 139 | 3.1 |
| 140 | 21 |
| 141 | 44 |
| 142 | 29 |
| 148 | 19 |
| 149 | 3.3 |
| 150 | 3.6 |
| 151 | 53 |
| 152 | 2.6 |
| 153 | 32 |
| 154 | 2 |
| 155 | 16 |
| 156A | 3.7 |
| 156B | 9.7 |
| 157 | 8.4 |
| 158 | >1000 |
| 159 | 14 |
| 160 | 7.6 |
| 161 | 1.6 |
| 162 | 581 |
| 163 | 3.7 |
| 164 | 24 |
| 165 | 16.8 |

As shown by the data in Table 1, the compounds of the present invention bind to the histamine-3 receptors and therefore may have utility in the treatment of diseases or conditions ameliorated with histamine-3 receptor ligands.

Compounds of the present invention are histamine-3 receptor ligands that modulate function of the histamine-3 receptor by antagonizing the activity of the receptor. These compounds may be inverse agonists that inhibit the basal activity of the receptor or they may be antagonists that completely block the action of receptor-activating agonists. These compounds may also be partial agonists that partially block or partially activate the histamine-3 receptor receptor or they may be agonists that activate the receptor.

Abbreviations

Abbreviations which have been used in the descriptions of the schemes and the examples that follow are: Ac for acetyl; DCM for dichloromethane; DMF for N,N-dimethylformamide; DMSO for dimethylsulfoxide; EtOAc for ethyl acetate; HPLC for high pressure liquid chromatography; Me for methyl; NMP for 1-methyl-2-pyrrolidinone; i-Pr for isopropyl; TFA for trifluoroacetic acid; TosCl for p-toluenesufonyl chloride; TBDMS for tert-butyldimethylsilyl; TLC for thin layer chromatography; THF for tetrahydrofuran; TMEDA for N, N, N', N'-tetramethylethylenediamine; and p-TSA for para-toluenesulfonic acid.

Preparations of Compounds of the Present Invention

The compounds and processes of the present invention will be better understood in connection with the following synthetic schemes and methods which illustrate a means by which the compounds can be prepared.

The compounds of this invention can be prepared by a variety of synthetic procedures. Representative procedures are shown in, but are not limited to, Schemes 1–12.

Scheme 1

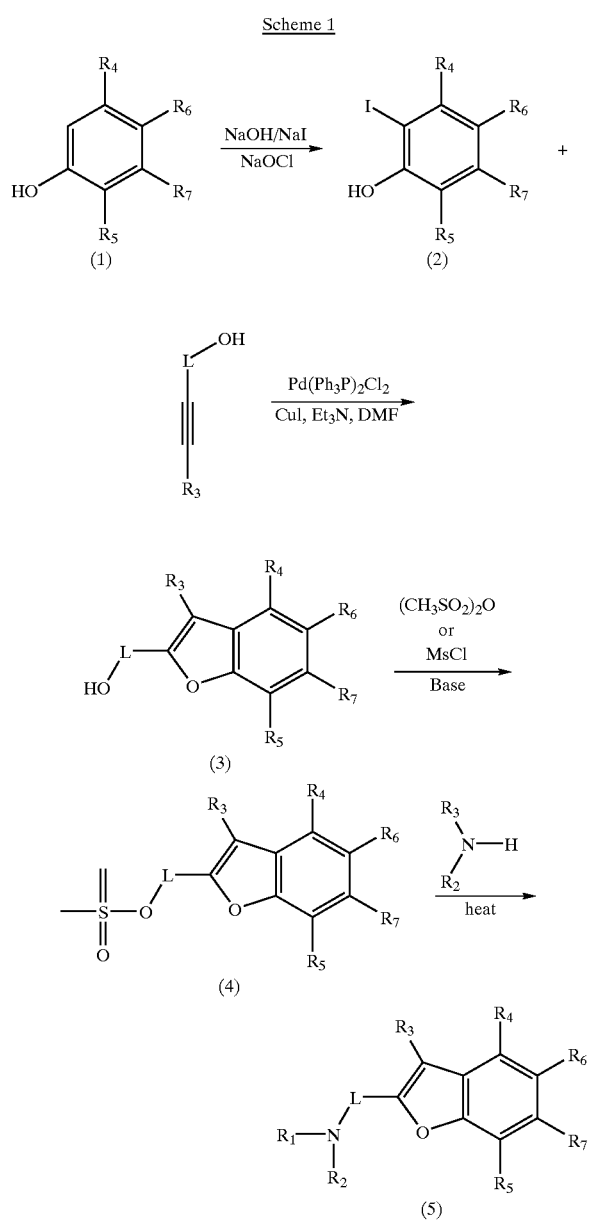

Alternatively mesylates of general formula (4) may be treated with secondary or primary amine hydrochlorides in the presence of a base such as triethylamine, diisopropylethylamine or N-methylmorpholine in a solvent such as DMF or Tiff with heat to provide benzofurans of general formula (5).

Scheme 2

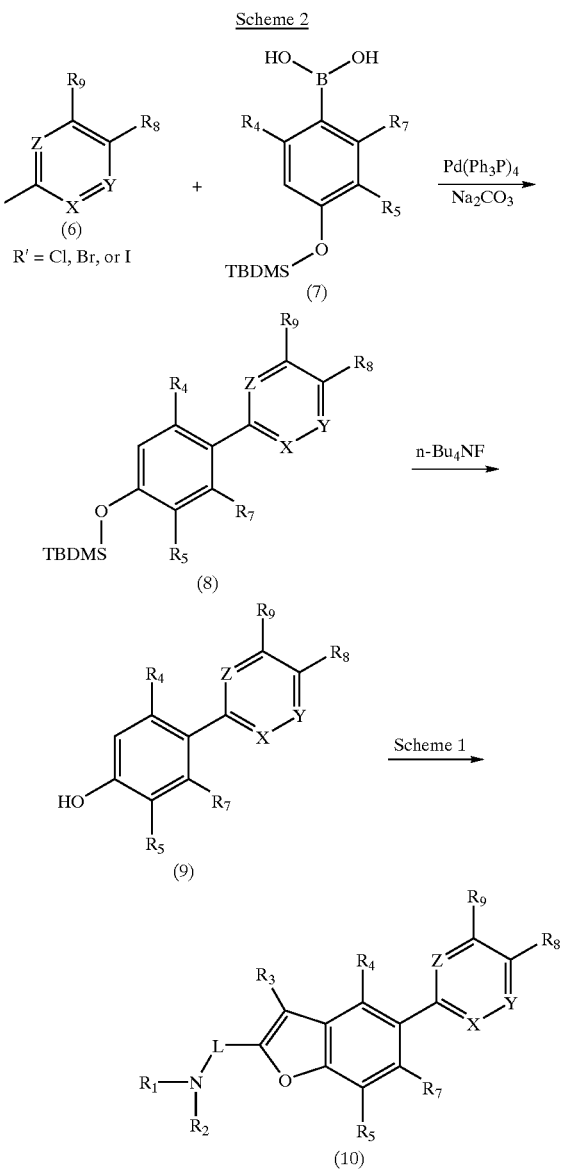

Benzofurans of general formula (5), wherein L, $R_1$, $R_2$, $R_3$, $R_4$, $R_5$, $R_6$ and $R_7$ are as defined in formula (I), may be prepared as described in Scheme I. Phenols of general formula (1) may be treated with sodium hypochlorite, sodium iodide and sodium hydroxide in a solvent such as methanol to provide iodides of general formula (2). Iodides of general formula (2) may be treated with substituted propargyl alcohols, dichlorobis(triphenylphosphine) palladium, copper iodide, a base such as triethylamine in a solvent such as DMF with heat to provide benzofurans of general formula (3). Alcohols of general formula (3) may be treated with methanesulfonyl chloride or methanesulfonyl anhydride, a base such as triethylamine, diisopropylethylamine or N-methylmorpholine in a solvent such as dichloromethane or THF to provide mesylates of general formula (4). Mesylates of general formula (4) may be treated with secondary or primary amines in solvents such as DMF or THF with heat to provide amines of general formula (5).

Benzofurans of general formula (10), wherein L, $R_1$, $R_2$, $R_3$, $R_4$, $R_5$, $R_7$, $R_8$, $R_9$, X, Y and Z are as defined in formula (II), may be prepared as described in Scheme 2. Halides of general formula (6) may be treated with boronic acids of general formula (7), under Suzuki conditions such as tetrakis (triphenylphosphine)palladium, a base such as aqueous sodium carbonate in a solvent such as toluene with heat to provide tert-butyldimethylsilyl protected alcohols of general formula (8). Protected alcohols of general formula (8) may be treated with tetrabutylammonium fluoride in a solvent such as THF to provide phenols of general formula (9). Phenols of general formula (9) may be treated using conditions as described in Scheme 1 to provide benzofurans of general formula (10).

Scheme 3

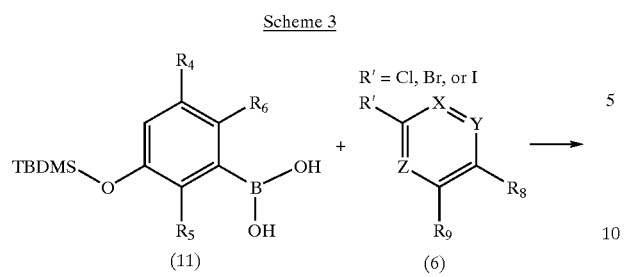

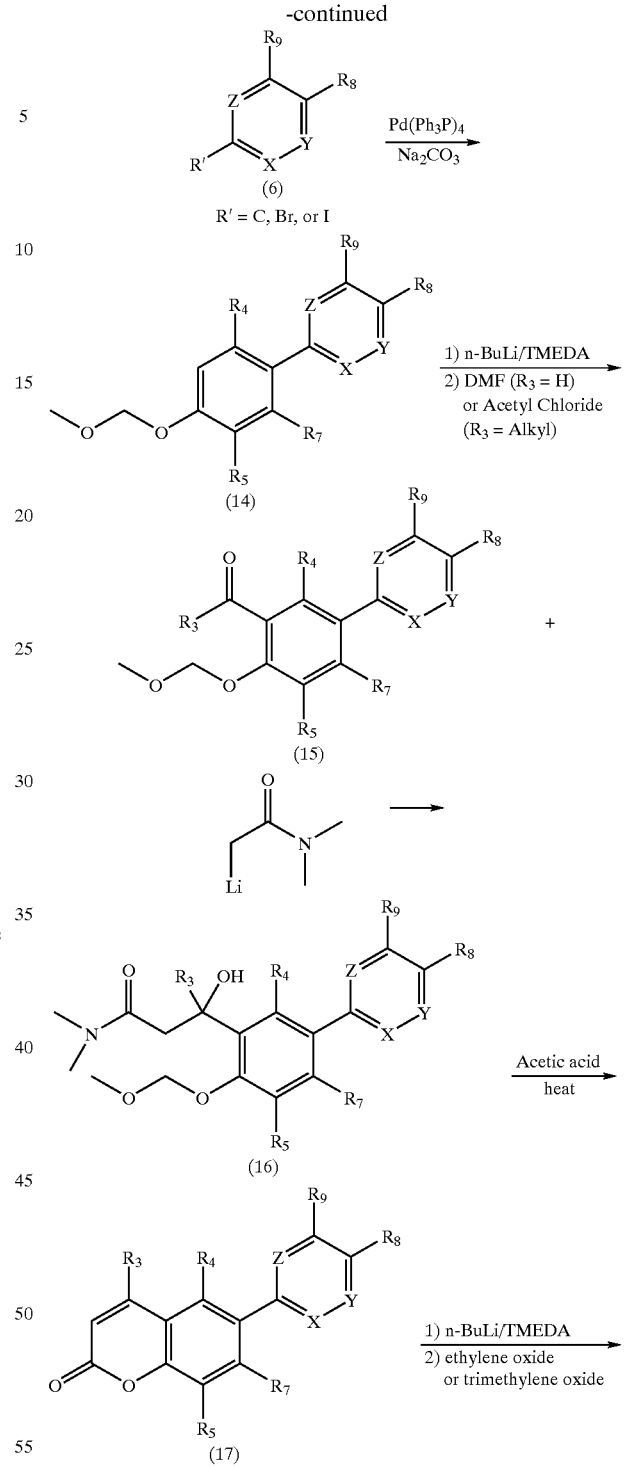

Benzofurans of general formula (12), wherein L, $R_1$, $R_2$, $R_3$, $R_4$, $R_5$, $R_6$, X, Y, Z, $R_8$, and $R_9$ are as defined in formula (III), may be prepared as described in Scheme 3. Boronic acids of general formula (11) may be treated with halides as described in Scheme 2 to provide compounds of general formula (11a). Compounds of general formula (11a) may be treated with tetra-butylammonium fluoride and then as described in Scheme 1 and Scheme 2 to provide benzofurans of general formula (12).

Scheme 4

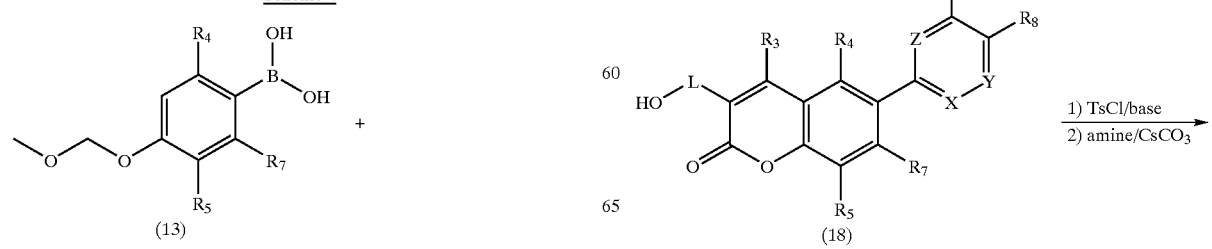

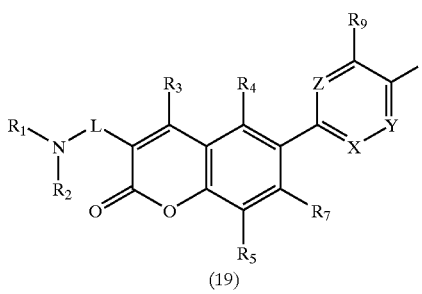

(19)

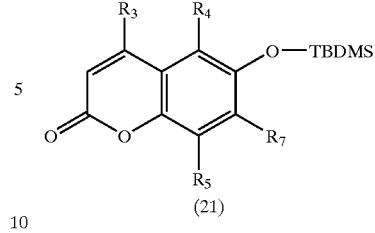

(21)

1) n-BuLi, TMEDA
   ethylene oxide
   or trimethylene oxide
2) CH$_3$SO$_2$Cl, base
3) R$_1$R$_2$NH, heat Chromenes of general formula (19), wherein L, R$_1$, R$_2$, R$_3$, R$_4$, R$_5$, R$_7$, R$_8$, R$_9$, X, Y and Z are as defined by formula (II), may be prepared as described in Scheme 4. Boronic acids of general formula (13) may be treated with halides of general formula (6), tetrakis(triphenylphosphine)palladium, a base such as aqueous sodium carbonate in a solvent such as toluene with heat to provide compounds of general formula (14). Compounds of general formula (14) may be treated with n-butyl lithium, N, N, N', N'-tetramethylethylenediamine followed by DMF or acetyl chloride to provide compounds of general formula (15) which may be treated with [2-(dimethylamino)-2-oxoethyl] lithium in a solvent such as THF to provide compounds of general formula (16). Compounds of general formula (16) may be treated with acetic acid with heat to provide chromenes of general formula (17). Chromenes of general formula (17) may be treated with butyl lithium, N, N, N', N'-tetramethylethylenediamine followed by ethylene oxide or trimethylene oxide to provide alcohols of general formula (18). Alternatively (17) may be treated with butyl lithium, N, N, N', N'-tetramethylethylenediamine and (2-bromoethoxy) tert-butyldimethylsilane followed by tetrabutylammonium fluoride deprotection to provide alcohols of general formula (18). Alcohols of general formula (18) may be converted to the respective mesylate and further reacted with amines as described in scheme 1 to provide chromenes of general formula (19).

Scheme 5

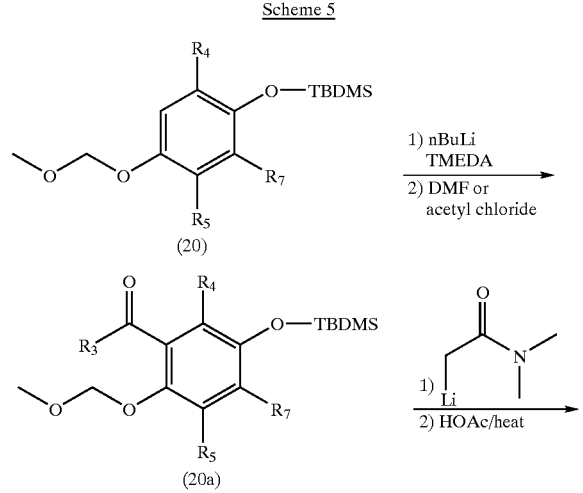

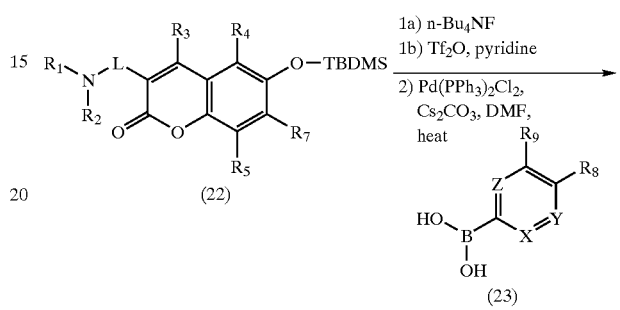

(22)

1a) n-Bu$_4$NF
1b) Tf$_2$O, pyridine
2) Pd(PPh$_3$)$_2$Cl$_2$,
   Cs$_2$CO$_3$, DMF,
   heat (23)

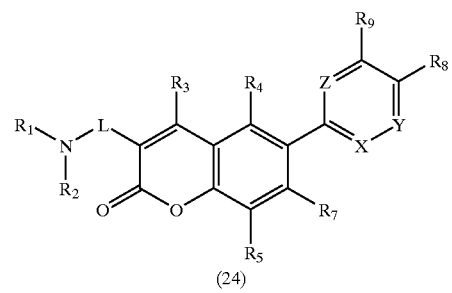

(24)

Alternatively chromenes of general formula (24) wherein L, R$_1$, R$_2$, R$_3$, R$_4$, R$_5$, R$_7$, R$_8$ and R$_9$ are as defined in formula (II), may be prepared as described in scheme 5. Compound of general structure (21) may be prepared from Scheme 4 by substituting compound of general structure (20) for compound of general formula (14). Compound of general formula (20) may be treated with n-butyl lithium followed by DMF or acetyl chloride to provide compounds of general formula (20a). Compounds of general formula (20a) may be treated with [2-(dimethylamino)-2-oxoethyl]lithium followed by acetic acid and heat to provide chromenes of general formula (21). Chromenes of general formula (21) may be treated with n-butyl lithium, N, N, N', N'-tetramethylethylenediamine followed by ethylene oxide or trimethylene oxide to provide alcohols which may be treated with methanesulfonyl chloride, a base such as triethylamine, diisopropylethylamine or N-methylmorpholine in a solvent such as dichloromethane or THF to provide mesylates which may be treated with secondary or primary amines in solvents such as DMF or THF with heat to provide amines of general formula (22). Amines of general formula (22) may be treated with tetrabutylammonium fluoride followed by treatment with triflic anhydride, pyridine and boronic acids of general formula (23), dichlorobis(triphenylphosphine)palladium, cesium carbonate in a solvent such as DMF with heat to provide compound of general formula (24).

Scheme 6

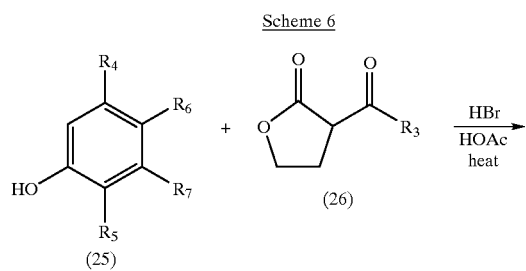

Alternatively chromenes of general structure (28), wherein $R_1$, $R_2$, $R_3$, $R_4$, $R_5$, $R_6$ and $R_7$ are as defined by formula (III), may be prepared as described in Scheme 6. Phenols of general formula (25) may be treated with compounds of general formula (26) and hydrobromic acid in acetic acid with heat to provide compounds of general formula (27), which may be treated with amines as described in Scheme 4 to provide chromenes of general formula (28).

Scheme 7

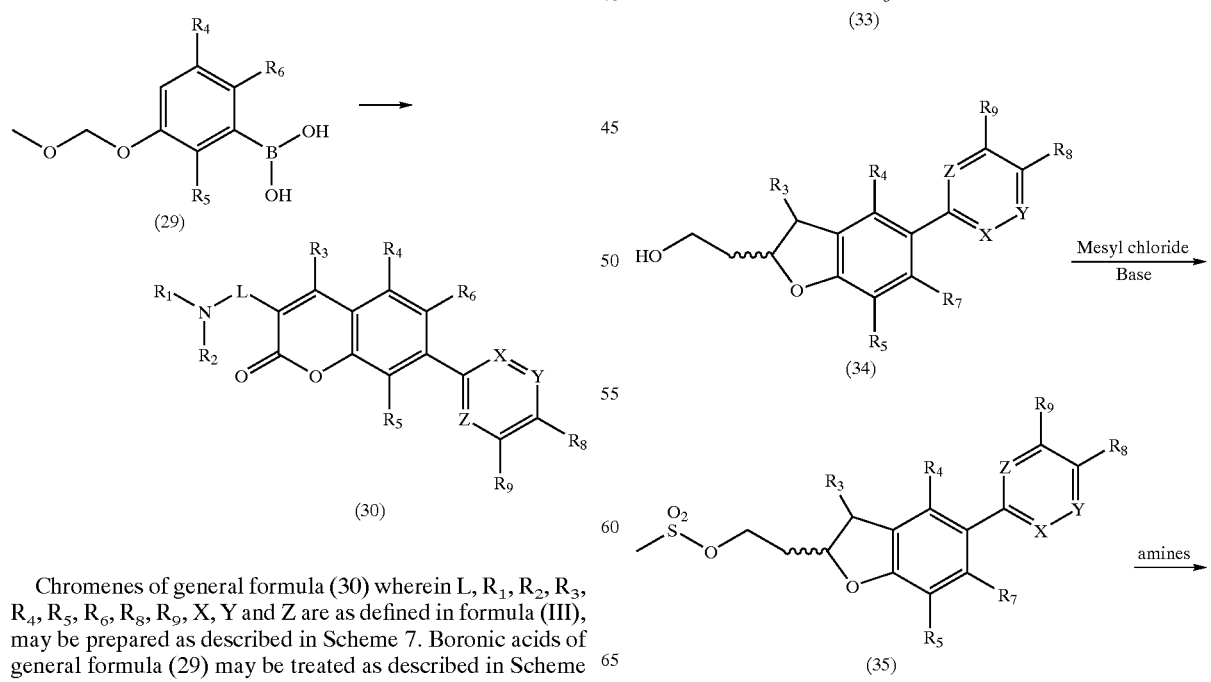

Chromenes of general formula (30) wherein L, $R_1$, $R_2$, $R_3$, $R_4$, $R_5$, $R_6$, $R_8$, $R_9$, X, Y and Z are as defined in formula (III), may be prepared as described in Scheme 7. Boronic acids of general formula (29) may be treated as described in Scheme 4 to provide Chromenes of general formula (30).

Scheme 8

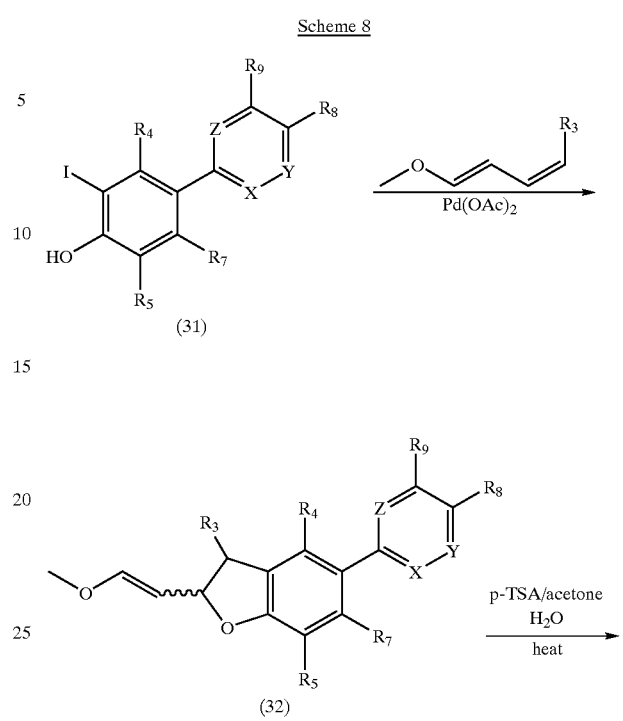

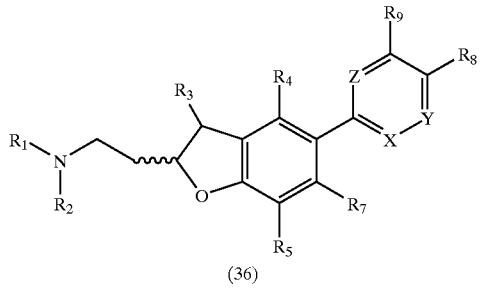

(36)

Compounds of general formula (36) wherein L, $R_1$, $R_2$, $R_3$, $R_4$, $R_5$, $R_7$, $R_8$, $R_9$, X, Y, and Z are as defined in formula (IV), may be prepared as described in Scheme 8. Iodides of general structure (31) may be treated with 5-substituted-1-methoxypentadienes and palladium acetate with heat to provide dihydrofurans of general structure (32), which may be treated with para-toluenesulfonic acid in aqueous acetone with heat to provide compounds of general formula (33). The reduction of compound of general structure (33) using sodium borohydride in solvents such as methanol may provide alcohols of general formula (34). Alcohols of general formula (34) may be treated with methanesulfonyl chloride with bases such as triethylamine, diisopropylethylamine or N-methylmorpholine in solvents such as dichloromethane or THF to provide mesylates of general formula (35). Mesylates of general formula (35) may be treated with secondary or primary amines in a solvent such as DMF or THF with heat to provide amines of general formula (36).

Scheme 9

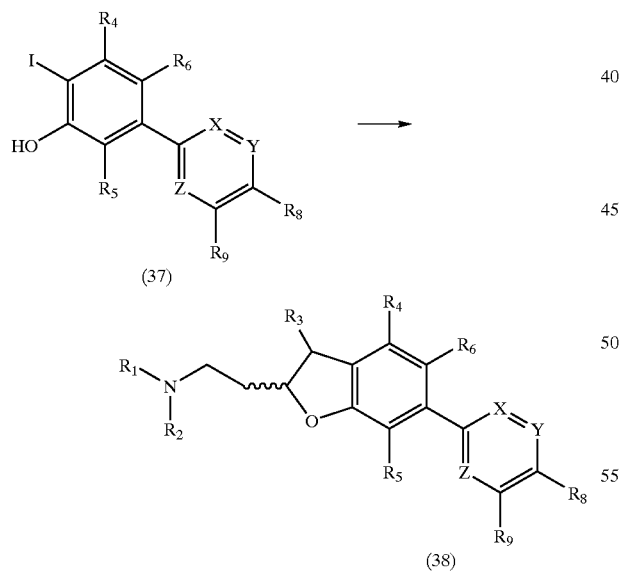

Dihydrofurans of general formula (38) wherein $R_1$, $R_2$, $R_3$, $R_4$, $R_5$, $R_6$, $R_8$, $R_9$, X, Y and Z are as defined in formula (IV), may be prepared as described in Scheme 9. Iodides of general formula (37) may be treated as described in Scheme 8 to provide dihydrofurans of general formula (38).

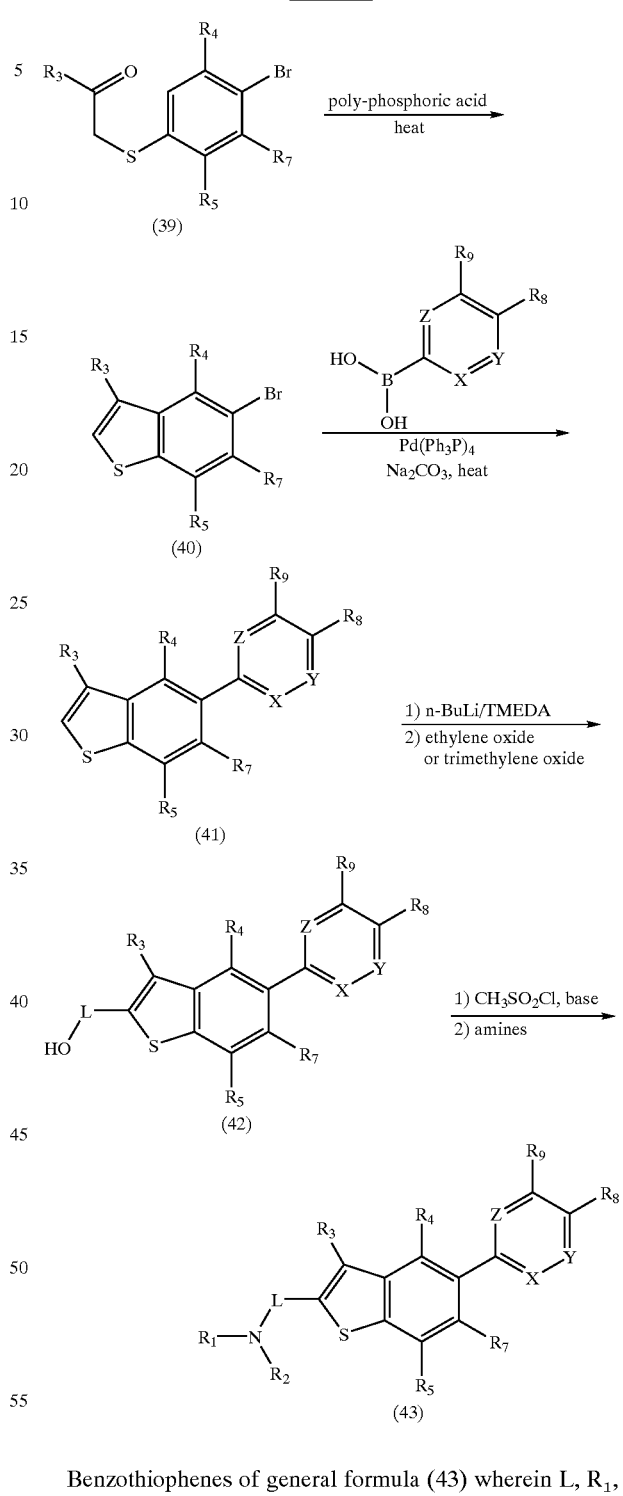

Benzothiophenes of general formula (43) wherein L, $R_1$, $R_2$, $R_3$, $R_4$, $R_5$, $R_7$, $R_8$, $R_9$, X, Y and Z are defined in formula (I), may be prepared as described in Scheme 10. Compounds of general formula (39) may be treated with poly-phosphoric acid with heat to provide benzothiophenes of general formula (40). Benzothiophenes of general formula (40) may be treated with boronic acids, tetrakis(triphenylphosphine) palladium, a base such as aqueous sodium carbonate in a solvent such as toluene with heat to provide compounds of general formula (41). Compounds of general formula (41)

may be treated with n-butyl lithium, N, N, N', N'-tetramethylethylenediamine followed by ethylene oxide to provide alcohols of general formula (42). Alcohols of general formula (42) may be converted to the mesylate and then further treated with amines as described in Scheme 1 to provide benzothiophenes of general formula (43).

Scheme 11

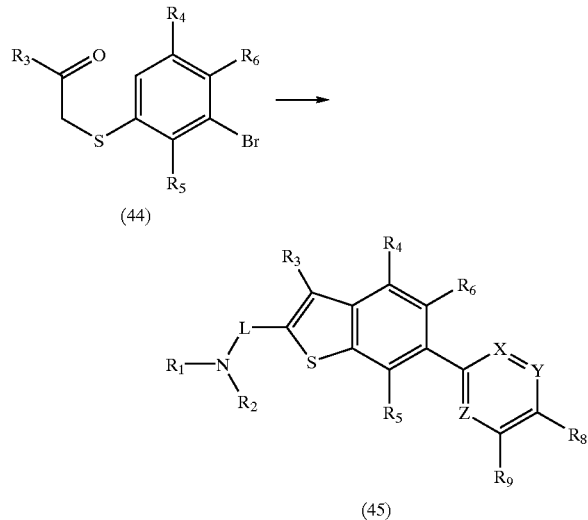

Benzothiophenes of general formula (45) wherein $R_1$, $R_2$, $R_3$, $R_4$, $R_5$, $R_6$, $R_8$, $R_9$ and X, Y and Z are defined in formula (I), may be prepared as described in Scheme 11. Compounds of general formula (44) may be processed as described in Scheme 10 to provide compounds of general formula (45).

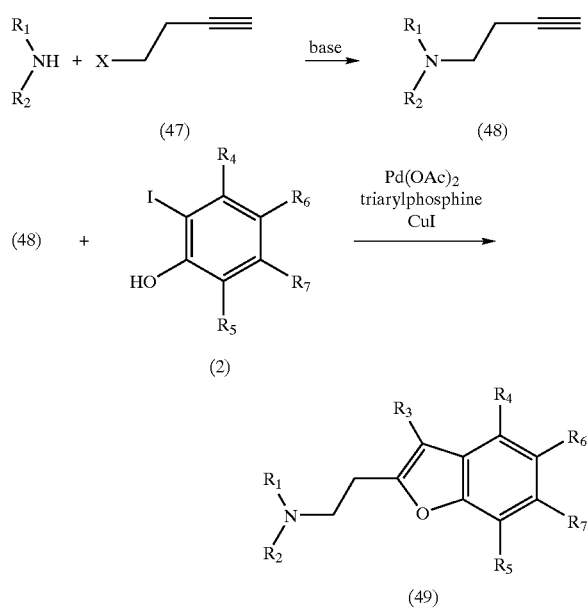

Benzofurans of general formula (49) wherein $R_1$, $R_2$, $R_3$, $R_4$, $R_5$, $R_6$, and $R_7$ are as defined in formula (I), may be prepared as described in Scheme 12. Primary and secondary amines may be treated with a base such as potassium carbonate (325 mesh powdered) and an alkyne of general formula (47) wherein X=Cl, Br, I, $OS(O)_2CH_3$ or OTs to provide alkynes of general formula (48). Alkynes of general formula (48) may be treated with a phenol of general formula (2), a palladium catalyst such as palladium(II) acetate, a triarylphoshine such as triphenylphoshine or tris (2-methylphenyl)phosphine, copper iodide, and a base such as diisopropylamine in a solvent such as acetonitrile followed by heat to provide benzofurans of general formula (49).

The compounds and processes of the present invention will be better understood by reference to the following examples, which are intended as an illustration of and not a limitation upon the scope of the invention.

EXAMPLES

Example 1

4-(2-{2-[(2R)-2-methyl-1-pyrrolidinyl]ethyl}-1-benzofuran-5-yl)benzonitrile

Example 1A

4'-hydroxy-3'-iodo[1,1'-biphenyl]-4-carbonitrile

To a solution of 4-hydroxy-4'-cyanobiphenyl (6.00 g, 30.8 mmol), sodium iodide (4.61 g, 30.8 mmol) and sodium hydroxide (1.23 g, 30.8 mmol) in methanol (90 mL) at 0° C. was added an aqueous solution of sodium hypochlorite (47 mL of 5.25% Clorox™, 2.29 g, 30.8 mmol) over 45 minutes. The mixture was stirred cold for 1 hour, warmed to ambient temperature and diluted with sodium thiosulfate solution (10 mL), water (80 mL) and adjusted to a pH of 7 by addition of sodium dihydrogen phosphate. The mixture was extracted with dichloromethane (2×90 mL). The combined organic extracts were dried ($Na_2SO_4$), filtered and concentrated under reduced pressure to give a white powder. The solid was crystallized from dichloroethane/hexane and chromatographed on silica with dichloromethane to give the titled compound (5.19 g, 53%). MS (DCI) m/z 339[M+$NH_4^+$]+;

Example 1B

4-[2-(2-hydroxyethyl)-1-benzofuran-5-yl]benzonitrile

To a solution of Example 1A (5.19 g, 16.2 mmol), triethylamine (5.60 ML, 40.4 mmol) and 3-butyn-1-ol (1.90 g, 27.2 mmol) in dimethylformamide (13 mL) at 20° C. was added cuprous iodide (0.46 g, 2.4 mmol) and bis-triphenylphosphine palladium dichloride (0.56 g, 0.80 mmol). The mixture was stirred at 65° C. for 12 hours then cooled to ambient temperature and diluted with dichloromethane (20 mL) and hexane (100 mL). Celite (5 g) was added with stirring and the solids were removed by filtration. The filtrate was washed with water (600 mL). The organic layer was separated and the aqueous layer extracted with dichloromethane (3×100 mL). The combined organic solution was dried ($Na_2SO_4$), filtered and concentrated under reduced pressure to give a tan solid. The solid was chromatographed on silica with 3% methanol in dichloromethane to give the titled compound (4.02 g, 95%). MS (DCI) m/z 263 (M+H)+;

Example 1C

2-[5-(4-cyanophenyl)-1-benzofuran-2-yl]ethyl Methanesulfonate

To a solution of Example 1B (0.57 g, 2.2 mmol) and triethylamine (0.9 mL, 6.5 mmol) in dichloromethane (10 mL) at 20° C. was added methane sulfonyl chloride (0.79 g, 4.5 mmol). The mixture was stirred for 30 min., diluted with dichloromethane, washed with water, dried ($Na_2SO_4$), filtered and concentrated under reduced pressure. The residue was chromatographed on silica with dichloromethane to give the titled compound (0.66 g, 89%). MS (DCI) m/z 359 $(M+H)^+$.

Example 1D 4-(2-{2-[(2R)-2-methyl-1-pyrrolidinyl]ethyl}-1-benzofuran-5-yl)benzonitrile A suspension of Example 1C (0.19 g, 0.55 mmol), (2R)-2-methylpyrrolidine hydrobromide (0.17 g, 1.0 mmol) and sodium carbonate (0.23 g, 2.2 mmol) in acetonitrile (0.4 mL) was heated to 50° C. with stirring for 48 hours. The reaction was cooled to ambient temperature, diluted with acetonitrile and centrifuged. The supernatant liquid was removed and the solids washed with acetonitrile. The combined liquids were concentrated under reduced pressure and the residue chromatographed by reverse phase HPLC with aqueous $CF_3CO_2H$/acetonitrile to give the titled compound (0.065 g, 34%). $^1$H NMR (300 MHz, $CD_3OD$) δ7.88 (m, 1H), 7.71 (m, 4H), 7.50 (m, 2H), 6.82 (s, 1H), 3.72–3.9 (m, 2H), 3.58 (m, 1H), 3.25–3.5 (m, 4H), 2.48 (m, 1H), 2.05–2.2 (m, 2H), 1.75 (m, 1H), 1.50 (d, J=6 Hz, 3H); MS (DCI) m/z 331 $(M+H)^+$;

Example 2

4-{2-[2-(1-pyrrolidinyl)ethyl]-1-benzofuran-5-yl}benzonitrile

The product from Example 1C and pyrrolidine were processed as described in Example 1D to provide the titled compound. $^1$H NMR (300 MHz, $CD_3OD$) δ7.7 (m, 5H), 7.50 (d, J=8.7 Hz, 1H), 7.42 (dd, J=8.7, 1.5 Hz, 1H), 6.51 (s, 1H), 3.1 (m 2H), 2.95 (m, 2H), 2.65 (m, 4H), 1.9 (m, 4H); MS (DCI) m/z 317 $(M+H)^+$;

Example 3

4-{2-[2-(2-methyl-1-pyrrolidinyl)ethyl]-1-benzofuran-5-yl}benzonitrile

The product from Example 1C and 2-methyl-pyrrolidine were processed as described in Example 1D to provide the titled compound. $^1$H NMR (300 MHz, $CD_3OD$) δ 7.88 (m, 1H), 7.80 (m, 4H), 7.60 (m, 2H), 6.82 (s, 1H), 3.8–3.9 (m, 2H), 3.58 (m, 1H), 3.25–3.5 (m, 4H), 2.48 (m, 1H), 2.05–2.2 (m, 2H), 1.75 (m, 1H), 1.50 (d, 3H, J=6 Hz); MS (DCI) m/z 331 $(M+H)^+$;

Example 4

4-{2-[2-(1-piperidinyl)ethyl]-1-benzofuran-5-yl}benzonitrile

The product from Example 1C and piperidine were processed as described in Example 1D to provide the titled compound. $^1$H NMR (300 MHz, $CD_3OD$) δ 7.88 (m, 1H), 7.80 (m, 4H), 7.60 (m, 2H), 6.82 (s, 1H), 3.65 (m, 2H), 3.55 (m, 2H), 3.33 (m, 2H), 3.05 (m, 2H), 2.0 (m, 2H), 1.5–1.9 (m, 4H); MS (DCI) m/z 331 $(M+H)^+$;

Example 5

4-{2-[2-(diethylamino)ethyl]-1-benzofuran-5-yl}benzonitrile

The product from Example 1C and diethylamine were processed as described in Example 1D to provide the titled compound. $^1$H NMR (300 MHz, $CD_3OD$) δ 7.75 (m, 1H), 7.80 (m, 4H), 7.60 (m, 2H), 6.85 (s, 1H), 3.6 (t, J=7.5 Hz, 2H), 3.25–3.5 (m, 6H), (t, 6H, J=6.6 Hz); MS (DCI) m/z 319 $(M+H)^+$;

Example 6

4-{2-[2-(2-methyl-1-piperidinyl)ethyl]-1-benzofuran-5-yl}benzonitrile

The product from Example 1C and 2-methylpiperidine were processed as described in Example 1D to provide the titled compound. $^1$H NMR (300 MHz, $CD_3OD$) δ 7.88 (m, 1H), 7.80 (m, 4H), 7.60 (m, 2H), 6.82 (s, 1H), 3.1–3.8 (m, 7H), 1.6–2.1 (m, 6H), 1.45 (d, 3H, J=6 Hz); MS (DCI) m/z 345 $(M+H)^+$;

Example 7

4-(2-{2-[(3R)-3-hydroxypyrrolidinyl]ethyl}-1-benzofuran-5-yl)benzonitrile

The product from Example 1C and 3-(R)-hydroxypyrrolidine were processed as described in Example 1D to provide the titled compound. $^1$H NMR (300 MHz, $CD_3OD$) δ 7.88 (m, 1H), 7.80 (m, 4H), 7.60 (m, 2H), 6.80 (s, 1H), 4.55 (bs, 1H), 3.8–3.9 (m, 4H), 3.25–3.5 (m, 4H), 2.05–2.4 (m, 2H); MS (DCI) m/z 333 $(M+H)^+$;

Example 8

4-{2-[2-(1H-imidazol-1-yl)ethyl]-1-benzofuran-5-yl}benzonitrile

The product from Example 1C and imidazole were processed as described in Example 1D to provide the titled compound. $^1$H NMR (300 MHz, $CD_3OD$) δ 8.88 (s, 1H), 7.88 (m, 1H), 7.80 (m, 5H), 7.60 (m, 4H), 6.75 (s, 1H), 4.7 (t, J=6.3 Hz, 2H), 3.5 (t, J=6.3 Hz, 2H); MS (DCI) m/z 314 $(M+H)^+$;

Example 9

4-(2-{2-[(3S)-3-(dimethylamino)pyrrolidinyl]ethyl}-1-benzofuran-5-yl)benzonitrile The product from Example 1C and 3-(S)-(dimethylamino)pyrrolidine were processed as described in Example 1D to provide the titled compound. $^1$H NMR (300 MHz, $CD_3OD$) 67 7.88 (m, 1H), 7.80 (m, 4H), 7.58 (m, 2H), 6.80 (s, 1H), 4.43 (m, 1H), 3.6–3.9 (m, 4H), 3.35–3.45 (m, 4H), 2.95 (s, 6H), 2.6 (m, 1H), 2.35 (m, 1H); MS (DCI) m/z 360 $(M+H)^+$;

Example 10

4-(2-{2-[(2S)-2-(hydroxymethyl)pyrrolidinyl]ethyl}-1-benzofuran-5-yl)benzonitrile The product from Example 1C and 2-(S)-(hydroxymethyl)pyrrolidine were processed as described in Example 1D to provide the titled compound. MS (DCI) m/z 347 $(M+H)^+$;

Example 11

4-(2-{2-[-2,6-dimethylpiperidinyl]ethyl}-1-benzofuran-5-yl)benzonitrile

The product from Example 1C and dimethylpiperidine were processed as described in Example 1D to provide the titled compound. MS (DCI) m/z 360 $(M+H)^+$;

Example 12

4-(2-{2-[(2R,5R)-2,5-dimethylpyrrolidinyl]ethyl}-1-benzofuran-5-yl)benzonitrile

The product from Example 1C and (2R,5R)-dimethylpyrrolidine were processed as described in Example 1D to provide the titled compound. MS (DCI) m/z 345 (M+H)$^+$;

Example 13

4-{2-[2-(1-azepanyl)ethyl]-1-benzofuran-5-yl}benzonitrile

The product from Example 1C and azepine were processed as described in Example 1D to provide the titled compound. MS (DCI) m/z 345 (M+H)$^+$;

Example 14

4-{2-[2-(4-methyl-1-piperidinyl)ethyl]-1-benzofuran-5-yl}benzonitrile

The product from Example 1C and 4-methylpiperidine were processed as described in Example 1D to provide the titled compound. MS (DCI) m/z 345 (M+H)$^+$;

Example 15

4-(2-{2-[2-pyrrolidine methyl carboxylate]ethyl}-1-benzofuran-5-yl)benzonitrile

The product from Example 1C and (L)-proline methyl ester were processed as described in Example 1D to provide the titled compound. MS (DCI) m/z 375 (M+H)$^+$;

Example 16

4-{2-[2-(3,6-dihydro-1(2H)-pyridinyl)ethyl]-1-benzofuran-5-yl}benzonitrile

The product from Example 1C and 1,2,3,6-tetrahydropyridine were processed as described in Example 1D to provide the titled compound. MS (DCI) m/z 329 (M+H)$^+$;

Example 17

4-(2-{2-[(2R)-2-(hydroxymethyl)pyrrolidinyl]ethyl}-1-benzofuran-5-yl)benzonitrile The product from Example 1C and (D)-prolinol were processed as described in Example 1D to provide the titled compound. $^1$H NMR (300 MHz, CD$_3$OD) δ 7.87 (m, 1H), 7.82 (m, 4H), 7.58 (m, 2H), 6.80 (s, 1H), 3.95 (m, 2H), 3.72 (m, 2H), 3.58 (m, 1H), 3.35–3.4 (m, 4H), 1.95–2.3 (m, 4H); MS (DCI) m/z 347 (M+H)$^+$;

Example 18

4-(2-{2-[tert-butyl(methyl)amino]ethyl}-1-benzofuran-5-yl)benzonitrile

The product from Example 1C and tert-butyl(methyl)amine were processed as described in Example 1D to provide the titled compound. MS (DCI) m/z 333 (M+H)$^+$;

Example 19

4-[2-{2-isopropyl(methyl)amino]ethyl}-1-benzofuran-5-yl]benzonitrile

The product from Example 1C and isopropyl(methyl)amine were processed as described in Example 1D to provide the titled compound. MS (DCI) m/z 319 (M+H)$^+$;

Example 20

4-(2-{2-[isobutyl(methyl)amino]ethyl}-1-benzofuran-5-yl)benzonitrile

The product from Example 1C and isobutyl(methyl)amine were processed as described in Example 1D to provide the titled compound. MS (DCI) m/z 333 (M+H)$^+$;

Example 21

4-(2-{2-[ethyl(isopropyl)amino]ethyl}-1-benzofuran-5-yl)benzonitrile

The product from Example 1C and ethyl(isopropyl)amine were processed as described in Example 1D to provide the titled compound. MS (DCI) m/z 333 (M+H)$^+$;

Example 22

4-(2-{2-[ethyl(propyl)amino]ethyl}-1-benzofuran-5-yl)benzonitrile

The product from Example 1C and ethyl(propyl)amine were processed as described in Example 1D to provide the titled compound. MS (DCI) m/z 333 (M+H)$^+$;

Example 23

4-(4-{2-[2-(2-methyl-1-pyrrolidinyl)ethyl]-1-benzofuran-5-yl}benzoyl)morpholine

Example 23A

4'-(4-morpholinylcarbonyl)[1,1'-biphenyl]-4-ol

To a solution of 4-hydroxy-biphenyl-4'-carboxylic acid (5.35 g, 25.0 mmol), morpholine (2.39 g, 27.5 mmol) and triethylamine (3.5 mL, 25 mmol) in dichloromethane (100 mL) was added 1-[3-(dimethylamino)propyl]-3-ethylcarbodiimide hydrochloride. The mixture was stirred for 16 hours, diluted with aqueous NaH$_2$PO$_4$ and filtered. The solid was washed with 1:2 diethyl ether/water (100 mL) then with water (400 mL). The solid was dried in vacuo to give the titled compound (5.89 g, 83%). MS (DCI) m/z 284 (M+H)$^+$;

Example 23B 3-iodo-4'-(4-morpholinylcarbonyl)[1,1'-biphenyl]-4-ol

The product from Example 23A was processed as described in Example 1A to provide the titled compound. MS (DCI) m/z 410 (M+H)$^+$.

Example 23C

2-{5-[4-(4-morpholinylcarbonyl)phenyl]-1-benzofuran-2-yl}ethanol

The product from Example 23B was processed as described in Example 1B to provide the titled compound. MS (DCI) m/z 352 (M+H)$^+$;

Example 23D

2-{5-[4-(4-morpholinylcarbonyl)phenyl]-1-benzofuran-2-yl}ethyl methanesulfonate

The product from Example 23C was processed as described in Example 1C to provide the titled compound.

Example 23E 4-(4-{2-[2-(2-methyl-1-pyrrolidinyl)ethyl]-1-benzofuran-5-yl}benzoyl)morpholine The product from Example 23D and 2-methyl-pyrrolidine were processed as described in Example 1D to provide the titled compound. $^1$H NMR (300 MHz, d$_4$-methanol) 67 7.83 (m, 1H), 7.74 (d, 3=8.4 Hz, 2H), 7.57 (m, 2H), 7.52 (d, J=8.4 Hz, 2H), 6.80 (s, 1H), 3.2–3.9 (m, 7H), 2.35 (m, 1H), 2.10 (m, 2H), 1.76 (m, 1H), 1.48 (d, J=7.2 Hz, 3H); MS (DCI) m/z 419 (M+H)$^+$;

Example 24

4-(4-{2-[2-(1-piperidinyl)ethyl]-1-benzofuran-5-yl}benzoyl)morpholine

The product from Example 23D and piperidine were processed as described in Example 1D to provide the titled compound. $^1$H NMR (300 MHz, CD$_3$OD) δ 7.82 (m, 1H), 7.73 (d, J=8.1, 2H), 7.54 (m, 2H), 7.51 (d, J=8.1 Hz, 2H), 6.77(s, 1H), 3.32–3.8 (m, 14H), 3.07 (m, 2H), 1.5–2.1 (m, 6H); MS (DCI) m/z 419 (M+H)$^+$;

Example 25

N,N-diethyl-N-(2-{5-[4-(4-morpholinylcarbonyl)phenyl]-1-benzofuran-2-yl}ethyl)amine The product from Example 23D and diethylamine were processed as described in Example 1D to provide the titled compound. $^1$H NMR (300 MHz, CD$_3$OD) δ 7.82 (m, 1H), 7.74 (d, J=8.1, 2H), 7.54 (m, 2H), 7.51 (d, J=8.1 Hz, 2H), 6.80(s, 1H), 3.32–3.8 (m, 16H), 1.38 (t, J=7.5 Hz, 6H); MS (DCI) m/z 407 (M+H)$^+$;

Example 26

4-(4-{2-[2-(2-methyl-1-piperidinyl)ethyl]-1-benzofuran-5-yl}benzoyl)morpholine

The product from Example 23D and 2-methyl-piperidine were processed as described in Example 1D to provide the titled compound. $^1$H NMR (300 MHz, CD$_3$OD) δ 7.82 (m, 1H), 7.74 (d, J=8.1, 2H), 7.56 (m, 2H), 7.52 (d, J=8.1 Hz, 2H), 6.80 (s, 1H), 3.4–3.78 (m, 15H), 1.6–2.1 (m, 6H), 1.46 (d, J=6.3 Hz, 3H); MS (DCI) m/z 433 (M+H)$^+$;

Example 27

(3R)-1-(2-{5-[4-(4-morpholinylcarbonyl)phenyl]-1-benzofuran-2-yl}ethyl)-3-pyrrolidinol The product from Example 23D and 3-(R)-pyrrolidinol were processed as described in Example 1D to provide the titled compound. $^1$H NMR (300 MHz, CD$_3$OD) δ 7.82 (m, 1H), 7.73 (d, J=8.1 Hz, 2H), 7.55 (m, 2H), 7.52 (d, J=8.1 Hz, 2H), 6.78 (s, 1H), 3.35–3.8 (m, 17H), 2.3–2.4 (m, 2H); MS (DCI) m/z 421 (M+H)$^+$;

Example 28

4-[4-(2-{2-[(2R,5R)-2,5-dimethylpyrrolidinyl]ethyl}-1-benzofuran-5-yl)benzoyl]morpholine The product from Example 23D and (2R,5R)-dimethylpyrrolidine were processed as described in Example 1D to provide the titled compound. $^1$H NMR (300 MHz, CD$_3$OD) δ 7.82 (m, 1H), 7.76 (d, J=8.1 Hz, 2H), 7.56 (m, 2H), 7.52 (d, J=8.1 Hz, 2H), 6.81 (s, 1H), 3.3–3.8 (m, 14H), 1.6–2.1 (m, 4H), 1.50 (d, J=6.6 Hz, 3H), 1.38 (d, J=6.6 Hz, 3H); MS (DCI) m/z 433 (M+H)$^+$;

Example 29

4-[4-(2-{2-[-2,6-dimethylpiperidinyl]ethyl}-1-benzofuran-5-yl)benzoyl]morpholine The product from Example 23D and -dimethylpiperidine were processed as described in Example 1D to provide the titled compound. $^1$H NMR (300 MHz, CD$_3$OD) δ 7.82 (m, 1H), 7.74 (d, J=8.1, 2H), 7.56 (m, 2H), 7.52 (d, J=8.1 Hz, 2H), 6.80 (s, 1H), 3.45–3.85 (m, 14H), 1.6–2.1 (m, 6H), 1.48 (d, J=6.3 Hz, 6H); MS (DCI) m/z 446 (M+H)$^+$;

Example 30

4-(4-{2-[2-(azepanyl)ethyl]-1-benzofuran-5-yl}benzoyl)morpholine

The product from Example 23D and azepane were processed as described in Example 1D to provide the titled compound. $^1$H NMR (300 MHz, CD$_3$OD) δ 7.82 (m, 1H), 7.73 (d, J=8.1, 2H), 7.56 (m, 2H), 7.52 (d, J=8.1 Hz, 2H), 6.77(s, 1H), 3.3–3.8 (m, 16H), 1.6–2.1 (m, 8H); MS (DCI) m/z 433 (M+H)$^+$;

Example 31

4-(4-{2-[2-(4-methyl-1-piperidinyl)ethyl]-1-benzofuran-5-yl}benzoyl)morpholine

The product from Example 23D and 4-methyl piperidine were processed as described in Example 1D to provide the titled compound. $^1$H NMR (300 MHz, CD$_3$OD) δ 7.82 (m, 1H), 7.75 (d, J=8.1, 2H), 7.58 (m, 2H), 7.52 (d, J=8.1 Hz, 2H), 6.76 (s, 1H), 3.35–3.8 (m, 14H), 3.05 (m, 2H), 2.00 (m, 2H), 1.75 (m, 1H), 1.49 (m, 2H), 1.05 (d, J=6.6 Hz, 3H); MS (DCI) m/z 433 (M+H)$^+$;

Example 32

4-(4-{2-[2-(4-morpholine)ethyl]-1-benzofuran-5-yl}benzoyl)morpholine

The product from Example 23D and morpholine were processed as described in Example 1D to provide the titled compound. $^1$H NMR (300 MHz, CD$_3$OD) δ 7.82 (m, 1H), 7.75 (d, J=8.1, 2H), 7.58 (m, 2H), 7.52 (d, J=8.1 Hz, 2H), 6.80 (s, 1H), 3.32–3.8 (m, 16H), 3.37 (t, J=7.5 Hz, 4H); MS (DCI) m/z 421 (M+H)$^+$;

Example 33

4-(4-{2-[2-(3,6-dihydro-1(2H)-pyridinyl)ethyl]-1-benzofuran-5-yl}benzoyl)morpholine The product from Example 23D and 1,2,3,6-tetrahydropyridine were processed as described in Example 1D to provide the titled compound. $^1$H NMR (300 MHz, CD$_3$OD) δ 7.83 (m, 1H), 7.74 (d, J=8.1, 2H), 7.58 (m, 2H), 7.51 (d, J=8.1 Hz, 2H), 6.80 (s, 1H), 6.05 (m, 1H), 5.79 (m, 2H), 3.4–3.8 (m, 12H), 3.41 (t, J=7.5 Hz, 4H), 2.5 (m, 2H); MS (DCI) m/z 416 (M+H)$^+$;

Example 34

4-(4-{2-[2-(2S)-pyrrolidinylmethanol)ethyl]-1-benzofuran-5-yl}benzoyl)morpholine The product from Example 23D and 2-(S)-(hydroxymethyl)pyrrolidine were processed as described in Example 1D to provide the titled compound. $^1$H NMR (300 MHz, CD$_3$OD) δ 7.81 (m, 1H), 7.73 (m, 2H), 7.55 (m, 2H), 7.50 (dm 2H, J=8.4 Hz), 6.77 (s, 1H), 3.3–4.0 (m, 17H), 1.9–2.3 (m, 4H); MS (DCI) m/z 434 (M+H)$^+$;

Example 35

N-(tert-butyl)-N-methyl-N-(2-{5-[4-(4-morpholinylcarbonyl)phenyl]-1-benzofuran-2-yl}ethyl)amine The product from Example 23D and tert-butyl(methyl)amine were processed as described in Example 1D to provide the titled compound. $^1$H NMR (300 MHz, CD$_3$OD) δ 7.83 (m, 1H), 7.74 (d, J=8.1, 2H), 7.55 (m, 2H), 7.51 (d, J=8.1 Hz, 2H), 6.81 (s, 1H), 3.3–3.8 (m, 12H), 2.93 (s, 3H), 1.48 (s, 9H); MS (DCI) m/z 421 (M+H)$^+$;

Example 36

N-isopropyl-N-methyl-N-(2-{5-[4-(4-morpholinylcarbonyl)phenyl]-1-benzofuran-2-yl}ethyl)amine The product from Example 23D and isopropyl(methyl)amine were processed as described in Example 1D to provide the titled compound. $^1$H NMR (300 MHz, CD$_3$OD) δ 7.82 (m, 1H), 7.74 (d, J=8.1, 2H), 7.58 (m, 2H), 7.52 (d, J=8.1 Hz, 2H), 6.81 (s, 1H), 3.3–3.8 (m, 13H), 2.97 (s, 3H), 1.42 (d, 6.3 Hz, 3H), 1.37 (d, 6.3 Hz, 3H); MS (DCI) m/z 407 (M+H)$^+$;

Example 37

N-isobutyl-N-methyl-N-(2-{5-[4-(4-morpholinylcarbonyl)phenyl]-1-benzofuran-2-yl}ethyl)amine The product from Example 23D and isobutyl(methyl)amine were processed as described in Example 1D to provide the titled compound. $^1$H NMR (300 MHz, CD$_3$OD) δ 7.82 (m, 1H), 7.74 (d, J=8.1, 2H), 7.58 (m, 2H), 7.51 (d, J=8.1 Hz, 2H), 6.81 (s, 1H), 3.3–3.8 (m, 14H), 2.96 (s, 3H), 2.2 (m, 1H), 1.09 (d, J=6.6 Hz, 6H); MS (DCI) m/z 421 (M+H)$^+$;

Example 38

N-ethyl-N-isopropyl-N-(2-{5-[4-(4-morpholinylcarbonyl)phenyl]-1-benzofuran-2-yl}ethyl)amine The product from Example 23D and isopropyl(ethyl)amine were processed as described in Example 1D to provide the titled compound. $^1$H NMR (300 MHz, CD$_3$OD) δ 7.83 (m, 1H), 7.74 (d, J=8.1, 2H), 7.58 (m, 2H), 7.53 (d, J=8.1 Hz, 2H), 6.80 (s, 1H), 3.3–3.8 (m, 15H), 1.41 (m, 9H); MS (DCI) m/z 421 (M+H)$^+$;

Example 39

N,N-dimethyl-N-(2-{5-[4-(4-morpholinylcarbonyl)phenyl]-1-benzofuran-2-yl}ethyl)amine The product from Example 23D and dimethylamine were processed as described in Example 1D to provide the titled compound. MS (DCI) m/z 378 (M+H)$^+$;

Example 40

N-ethyl-N-(2-{5-[4-(4-morpholinylcarbonyl)phenyl]-1-benzofuran-2-yl}ethyl)-N-propylamine The product from Example 23D and ethyl(propyl)amine were processed as described in Example 1D to provide the titled compound. $^1$H NMR (300 MHz, CD$_3$OD) δ 7.84 (m, 1H), 7.74 (d, J=8.1, 2H), 7.58 (m, 2H), 7.53 (d, J=8.1 Hz, 2H), 6.82(s, 1H), 3.32–3.8 (m, 14H), 3.20 (m, 2H), 1.80 (m, 2H), 1.38 (t, J=7.5 Hz, 3H), 1.05 (t, J=7.5 Hz, 3H); MS (DCI) m/z 421 (M+H)$^+$;

Example 41

4-{4-methyl-2-oxo-3-[2-(1-pyrrolidinyl)ethyl]-2H-chromen-6-yl}benzonitrile

Example 41A 3-(2-bromoethyl)-6-hydroxy-4-methyl-2H-chromen-2-one

To a solution of resorcinol (7.03 g, 64.0 mmol) in a solution consisting of HBr (104 mL, 422 mmol) and glacial acetic acid (10 mL) at 0° C. was slowly added 2-acetylbutyrolactone (5.8 mL, 54 mmol). The mixture was warmed to ambient temperature and then heated to reflux for 2 hours. The mixture was cooled to ambient temperature and diluted with water (350 mL). The mixture was filtered and the solid dried in vacuo overnight to give the titled compound (15.5 g, 85%). $^1$H NMR (300 MHz, CD$_3$OD) δ 10.5 (s, 1H), 7.6 (d, J=8.7 Hz, 1H), 6.8 (dd, J=6.6 Hz, 11.4 Hz, 1H), 6.7 (d, J=2.1 Hz, 1H), 3.6 (t, J=7.5 Hz, 2H), 3.1 (t, J=7.6 Hz, 2H), 2.4 (s, 3H); MS (DCI) m/z 283, 284 (M+H)$^+$;

Example 41B 6-hydroxy-4-methyl-3-[2-(1-pyrrolidinyl)ethyl]-2H-chromen-2-one

A solution of Example 41A (0.20 g, 0.70 mmol) and pyrrolidine (0.50 mL, 6.0 mmol) in DMF (2 mL) was heated to 75° C. for 16 hours, cooled to ambient temperature, diluted with water (20 mL) and extracted with ethyl acetate (3×50 mL). The combined ethyl acetate was dried (MgSO$_4$), filtered, concentrated under reduced pressure and chromatographed on silica with 10% methanol in dichloromethane to give the titled compound (0.48 g, 25%). MS (DCI) m/z 274 (M+H)$^+$;

Example 41C

To a solution of Example 41B (0.105 g, 0.38 mmol), N-phenyltrifluoromethane sulfonimide (0.143 g, 0.38 mmol) in dichloromethane (2 mL) at 0° C. was added triethylamine (0.68 mL, 0.48 mmol). The mixture was stirred at ambient temperature for 12 hours, diluted with diethyl ether (40 mL) and washed sequentially with aqueous NaOH (1N, 2×30 mL), water and brine, dried (MgSO$_4$), filtered and evaporated to provide the triflate. A mixture of the triflate (0.2 g, 0.49 mmol), 4-cyanophenylboronic acid (0.082 g, 0.54 mmol), Pd(PPh$_3$)$_2$Cl$_2$ (0.035 g) and Cs$_2$CO$_3$ (0.96 g, 2.9 mmol) in DMF (5 mL) was stirred for 5 hours, diluted with ethyl acetate and washed sequentially with aqueous NaOH (1N, 3×25 mL), water (3×25 mL) and brine. The organic solution was dried (MgSO$_4$), filtered, evaporated under reduced pressure. The residue was chromatographed on silica with dichloromethane ethyl acetate methanol to give the titled compound. NMR (300 MHz, CDCl$_3$) δ 7.75 (m, 3H) 7.5 (m, 1H), 7.2 (m 2H), 7.1 (m, 1H) 3.1 (m, 2H), 2.9 (m, 4H), 2.5 (s, 3H), 2.0, (m, 4H), 1.6 (m, 2H); MS (DCI) ml/z 359 (M+H)$^+$;

Example 42

4-{4-methyl-2-oxo-3-[2-(1-piperidinyl)ethyl]-2H-chromen-6-yl}benzonitrile

The product from Example 41A and piperidine were processed as described in Examples 41B and 41C to provide the titled compound. NMR (300 MHz, CDCl$_3$) δ7.75 (m, 3H) 7.6 (m, 3H), 7.2 (m, 1H), 2.95 (m, 2H), 2.6 (m, 6H), 2.5 (s, 3H), 1.7 (m, 4H), 1.5 (m, 2H); MS (DCI) m/z 373 (M+H)$^+$.

Example 43

4-{3-[2-(diethylamino)ethyl]-4-methyl-2-oxo-2H-chromen-6-yl}benzonitrile

The product from Example 41A and diethylamine were processed as described in Examples 41B and 41C to provide the titled compound. NMR (300 MHz, CDCl$_3$) δ7.75 (m, 5H), 7.5 (m, 2H), 2.9 (m, 2H), 2.7 (m, 6H), 2.5 (s, 3H), 1.1 (t, J=9 Hz, 6H); MS (DCI) m/z 361 (M+H)$^+$;

Example 44

4-[(6-{2-[2-(1-pyrrolidinyl)ethyl]-1-benzofuran-5-yl}-3-pyridinyl)carbonyl]morpholine

Example 44A

4-[(6-chloro-3-pyridinyl)carbonyl]morpholine

To a solution of chloronicotinoyl chloride (3.52 g, 2.00 mmol) and triethylamine (3.1 mL, 2.22 mmol) in dichloromethane (5 mL) at 0° C. was slowly added morpholine (1.75 mL, 2.00 mmol). The mixture was warmed to ambient temperature, washed with water (2×25 mL), brine (1×25 mL), dried (Na$_2$SO$_4$), filtered and concentrated under reduced pressure. The product was chromatographed on silica with ethyl acetate to give the titled compound (4.0 g, 88%). MS (DCI) m/z 227 (M+H)$^+$;

Example 44B

4-[5-(4-morpholinylcarbonyl)-1,6-dihydro-2-pyridinyl]phenol

A mixture of Example 44A (4.0 g, 17.6 mmol), Pd(Ph$_3$P)$_4$ (1.0 g, 0.86 mmol), 4-O-tert-butyldimethylsilyl-phenylboric acid (4.9 g, 23.6 mmol) in toluene (60 mL) and aqueous sodium carbonate (2.76 g dissolved in 25 mL water) was heated to reflux for 12 hours, then cooled to ambient temperature. The mixture was diluted with ethyl acetate (100 mL), washed with water (1×50 mL), dried (Na$_2$SO$_4$), filtered and concentrated under reduced pressure. The residue was stirred in THF (200 mL) containing tetrabutylammonium fluoride (30 mL, 1.0M, 30.0 mmol) for 16 hours. The mixture was diluted with ethyl acetate (100 mL), washed sequentially with water (1×50 mL), aqueous ammonium chloride (1×50 mL), brine (1×50 mL), dried (Na$_2$SO$_4$), filtered and concentrated under reduced pressure to give a solid. The solid was precipitated from ethyl acetate (75 mL), filtered to provide the titled compound as a tan solid (4.27 g, 70%).

Example 44C 2-iodo-4-[5-(4-morpholinylcarbonyl)-2-pyridinyl] phenol

A mixture of Example 44B (4.25 g, 15.0 mmol) sodium iodide (2.36 g, 15.7 mmol) and sodium hydroxide (0.63 g, 15.7 mmol) was stirred in methanol (90 mL) with heating until a clear solution was obtained. The solution was then cooled to 0° C. and to this was slowly added sodium hypochlorite (22 mL of 5.25%, 1.15 g, 15.5 mmol) (Clorox™) over 45 minutes. While maintaining 0° C., two sequential additions of NaI (0.3 g, 1.5 mmol) and Clorox (2.2 mL, 0.12 g, 1.5 mmol) were made both 2 hours and 4 hours later. The mixture was stirred for 12 hours at ambient temperature, quenched by the sequential addition of aqueous sodium thiosulfate (10 mL), water (800 mL) and sufficient aqueous sodium dihydrogen phosphate (NaH$_2$PO$_4$) to adjust the pH to 7. The mixture was extracted with dichloromethane, and the combined extracts dried (Na$_2$SO$_4$), filtered and concentrated under reduced pressure to give a tan foam. The product was crystallized from ethanol to give the titled compounds as a tan solid (3.78 g, 61%). MS (DCI) m/z 411 (M+H)$^+$;

Example 44D

2-{5-[5-(4-morpholinylcarbonyl)-2-pyridinyl]-1-benzofuran-2-yl}ethanol

To a solution of Example 44C (2.85 g, 6.95 mmol), triethylamine (2.4 mL, 17.4 mmol), and 3-butyn-1-ol (0.73 g, 10.4 mmol) in dimethylformamide (15 mL) at 20° C. was added cuprous iodide (0.2 g, 1.0 mmol) and bis-triphenylphosphine palladium dichloride (0.24 g, 0.35 mmol). The mixture was stirred for one hour, then heated to 65° C. for 16 hours. The reaction was cooled to 23° C., diluted with dichloromethane (200 mL) and water (100 mL). The mixture was stirred with Celite then filtered. The filtrate was washed with water (1×50 mL), the organic phase separated, dried (Na$_2$SO$_4$), filtered and concentrated under reduced pressure to give a tan foam. The residue was chromatographed on silica using 5% methanol in dichloromethane to give the titled compound as a yellow solid (1.83 g, 75%/). MS (DCI) m/z 353 (M+H)$^+$;

Example 44E

2-{5-[5-(4-morpholinylcarbonyl)-2-pyridinyl]-1-benzofuran-2-yl}ethyl methanesulfonate The product from Example 44D was processed as described in Example 1C to provide the titled compound.

Example 44F

4-[(6-{2-[2-(1-pyrrolidinyl)ethyl]-1-benzofuran-5-yl}-3-pyridinyl)carbonyl]morpholine The product from Example 44E and pyrrolidine were processed as described in Example 1D to provide the titled compound. $^1$H NMR (300 MHz, CD$_3$OD) δ8.70 (m, 1H), 8.24 (d, J=1.8 Hz, 1H), 7.98 (m, 3H), 7.60 (d, J=8.7 Hz, 1H), 6.84 (s, 1H), 3.3–3.8 (m, 12H), 3.18 (m, 2H), 2.0–2.25 (m, 6H); MS (DCI) m/z 406 (M+H)$^+$;

Example 45

4-{[6-(2-{2-[(2R)-methylpyrrolidinyl]ethyl}-1-benzofuran-5-yl)-3-pyridinyl]carbonyl}morpholine The product from Example 44E and 2-(R)-methylpyrrolidine were processed as described in Example 1D to provide the titled compound. MS (DCI) m/z 420 (M+H)$^+$;

Example 46

4-[(6-{2-[2-(1-piperidinyl)ethyl]-1-benzofuran-5-yl}-3-pyridinyl)carbonyl]morpholine The product from Example 44E and piperidine were processed as described in Example 1D to provide the titled compound. ¹H NMR (300 MHz, CD₃OD) δ8.70 (m, 1H), 8.22 (d, J=1.8 Hz, 1H), 7.95 (m, 3H), 7.58 (d, J=8.7 Hz, 1H), 6.82 (s, 1H), 3.3–3.8 (m, 12H), 3.05 (m, 2H), 1.5–2.0 (m, 8H); MS (DCI) m/z 420 (M+H)⁺;

Example 47

4-[(6-{2-[2-(N,N-diethyl)ethyl]-1-benzofuran-5-yl}-3-pyridinyl)carbonyl]morpholine The product from Example 44E and diethylamine were processed as described in Example 1D to provide the titled compound. ¹H NMR (300 MHz, CD₃OD) δ8.70 (m, 1H), 8.24 (d, J=1.8 Hz, 1H), 7.95 (m, 3H), 7.58 (d, J=8.7 Hz, 1H), 6.84 (s, 1H), 3.3–3.8 (m, 12H), 1.38 (t, J=7.5 Hz, 6H); MS (DCI) m/z 408 (M+H)⁺;

Example 48

(3R)-1-(2-{5-[5-(4-morpholinylcarbonyl)-2-pyridinyl]-1-benzofuran-2-yl}ethyl)-3-pyrrolidinol The product from Example 44E and 3-(R)-hydroxypyrrolidine were processed as described in Example 1D to provide the titled compound. ¹H NMR (300 MHz, CD₃OD) δ8.70 (m, 1H), 8.24 (d, J=1.8 Hz, 1H), 7.95 (m, 3H), 7.58 (d, J=8.7 Hz, 1H), 6.82 (s, 1H), 4.55 (m, 1H), 3.3–3.8 (m, 16H), 2.0–2.4 (m, 2H); MS (DCI) m/z 422 (M+H)⁺;

Example 49

4-{[6-(2-{2-[(2R,5R)-2,5-dimethylpyrrolidinyl]ethyl}-1-benzofuran-5-yl)-3-pyridinyl]carbonyl}morpholine The product from Example 44E and (2R,5R)-dimethylpyrrolidine were processed as described in Example 1D to provide the titled compound. ¹H NMR (300 MHz, CD₃OD) δ8.70 (m, 1H), 8.24 (d, J=1.8 Hz, 1H), 7.95 (m, 3H), 7.58 (d, J=8.7 Hz, 1H), 6.86 (s, 1H), 3.3–3.8 (m, 12H), 1.2–2.4 (m, 10H); MS (DCI) m/z 434 (M+H)⁺;

Example 50

4-{[6-(2-{2-[-2,6-dimethylpiperidinyl]ethyl}-1-benzofuran-5-yl)-3-pyridinyl]carbonyl}morpholine The product from Example 44E and -dimethylpiperidine were processed as described in Example 1D to provide the titled compound. ¹H NMR (300 MHz, CD₃OD) δ8.70 (m, 1H), 8.24 (d, J=1.8 Hz, 1H), 7.95 (m, 3H), 7.58 (d, J=8.7 Hz, 1H), 6.86 (s, 1H), 3.45–3.85 (m, 12H), 1.6–2.1 (m, 6H), 1.48 (d, J=6.3 Hz, 6H); MS (DCI) m/z 448 (M+H)⁺;

Example 51

4-{[6-(2-{2-[1-azepanyl]ethyl}-1-benzofuran-5-yl)-3-pyridinyl]carbonyl}morpholine The product from Example 44E and azepine were processed as described in Example 1D to provide the titled compound. ¹H NMR (300 MHz, CD₃OD) δ8.70 (m, 1H), 8.24 (d, J=1.8 Hz, 1H), 7.95 (m, 3H), 7.58 (d, J=8.7 Hz, 1H), 6.86 (s, 1H), 3.3–3.8 (m, 16H), 1.95 (m, 4H), 1.75 (m, 4H); MS (DCI) m/z 434 (M+H)⁺;

Example 52

4-[(6-{2-[2-(4-methyl-1-piperidinyl)ethyl]-1-benzofuran-5-yl}-3-pyridinyl)carbonyl]morpholine The product from Example 44E and 4-methylpiperidine were processed as described in Example 1D to provide the titled compound. ¹H NMR (300 MHz, CD₃OD) δ8.70 (m, 1H), 8.22 (d, J=1.8 Hz, 1H), 7.97 (m, 3H), 7.58 (d, J=8.7 Hz, 1H), 6.82 (s, 1H), 3.3–3.8 (m, 14H), 3.05 (m, 2H), 1.95 (m, 2H), 1.75 (m, 1H), 1.5 (m, 2H), 1.05 (d, J=6.6 Hz, 3H); MS (DCI) m/z 434 (M+H)⁺;

Example 53

4-[(6-{2-[2-(4-morpholinyl)ethyl]-1-benzofuran-5-yl}-3-pyridinyl)carbonyl]morpholine The product from Example 44E and morpholine were processed as described in Example 1D to provide the titled compound. ¹H NMR (300 MHz, CD₃OD) δ8.70 (m, 1H), 8.24 (d, J=1.8 Hz, 1H), 7.95 (m, 3H), 7.58 (d, J=8.7 Hz, 1H), 6.82 (s, 1H), 3.3–4.1 (m, 16H), 3.37 (t, J=7.5 Hz, 4H); MS (DCI) m/z 422 (M+H)⁺;

Example 54

N-(tert-butyl)-N-methyl-N-(2-{5-[5-(4-morpholinylcarbonyl)-2-pyridinyl]-1-benzofuran-2-yl}ethyl)amine The product from Example 44E and tert-butyl(methyl)amine were processed as described in Example 1D to provide the titled compound. ¹H NMR (300 MHz, CD₃OD) δ8.70 (m, 1H), 8.24 (d, J=1.8 Hz, 1H), 7.96 (m, 3H), 7.59 (d, J=8.7 Hz, 1H), 6.85 (s, 1H), 3.3–3.8 (m, 12H), 2.93 (s, 3H), 1.48 (s, 9H); MS (DCI) m/z 422 (M+H)⁺;

Example 55

N-isobutyl-N-methyl-N-(2-{5-[5-(4-morpholinylcarbonyl)-2-pyridinyl]-1-benzofuran-2-yl}ethyl)amine The product from Example 44E and isobutyl(methyl)amine were processed as described in Example 1D to provide the titled compound. ¹H NMR (300 MHz, CD₃OD) δ8.70 (m, 1H), 8.23 (d, J=1.8 Hz, 1H), 7.98 (m, 3H), 7.59 (d, J=8.7 Hz, 1H), 6.85 (s, 1H), 3.0–3.8 (m, 14H), 2.98 (s, 3H), 2.2 (m, 1H), 1.09 (d, J=6.6 Hz, 6H); MS (DCI) m/z 422 (M+H)⁺;

Example 56

N-isopropyl-N-methyl-N-(2-{5-[5-(4-morpholinylcarbonyl)-2-pyridinyl]-1-benzofuran-2-yl}ethyl)amine The product from Example 44E and isopropyl(methyl)amine were processed as described in Example 1D to provide the titled compound. ¹H NMR (300 MHz, CD₃OD) δ8.70 (m, 1H), 8.24 (d, J=1.8 Hz, 1H), 7.96 (m, 3H), 7.59 (d, J=8.7 Hz, 1H), 6.85 (s, 1H), 3.3–3.8 (m, 13H), 2.88 (s, 3H), 1.40 (d, 6.3 Hz, 3H), 1.36 (d, 6.3 Hz, 3H); MS (DCI) m/z 408 (M+H)⁺;

Example 57

N-ethyl-N-isopropyl-N-(2-{5-[5-(4-morpholinylcarbonyl)-2-pyridinyl]-1-benzofuran-2-yl}ethyl)amine The product from Example 44E and ethyl(isopropyl)amine were processed as described in Example 1D to provide the titled compound. ¹H NMR (300 MHz, CD₃OD) δ8.70 (m, 1H), 8.25 (d, J=1.8 Hz, 1H), 7.98 (m, 311), 7.59 (d, J=8.7 Hz, 1H), 6.85 (s, 1H), 3.3–3.8 (m, 15H), 1.4 (m, 9H); MS (DCI) m/z 422 (M+H)⁺;

Example 58

N,N-dimethyl-N-(2-{5-[5-(4-morpholinylcarbonyl)-2-pyridinyl]-1-benzofuran-2-yl}ethyl)amine The product from Example 44E and dimethylamine were processed as described in Example 1D to provide the titled compound. $^1$H NMR (300 MHz, CD$_3$OD) δ8.70 (m, 1H), 8.24 (d, J=1.8 Hz, 1H), 7.96 (m, 3H), 7.59 (d, J=8.7 Hz, 1H), 6.84 (s, 1H), 3.35–3.8 (m, 12H), 2.98 (s, 6H); MS (DCI) m/z 380 (M+H)$^+$;

Example 59

N-ethyl-N-propyl-N-(2-{5-[5-(4-morpholinylcarbonyl)-2-pyridinyl]-1-benzofuran-2-yl}ethyl)amine The product from Example 44E and ethyl(propyl)amine were processed as described in Example 1D to provide the titled compound. $^1$H NMR (300 MHz, CD$_3$OD) δ8.70 (m, 1H), 8.23 (d, J=1.8 Hz, 1H), 7.98 (m, 3H), 7.58 (d, J=8.7 Hz, 1H), 6.85 (s, 1H), 3.2–3.8 (m, 14H), 3.20 (m, 2H), 1.80 (m, 2H), 1.38 (t, J=7.5 Hz, 3H), 1.05 (t, J=7.5 Hz, 3H); MS (DCI) m/z 422 (M+H)$^+$;

Example 60

8-(2-{5-[5-(4-morpholinylcarbonyl)-2-pyridinyl]-1-benzofuran-2-yl}ethyl)-1,4-dioxa-8-azaspiro[4.5]decane The product from Example 44E and 1,4-dioxa-8-azaspiro[4.5]decane were processed as described in Example 1D to provide the titled compound. $^1$H NMR (300 MHz, CD$_3$OD) δ8.70 (m, 1H), 8.24 (d, J=1.8 Hz, 1H), 7.95 (m, 3H), 7.58 (d, J=8.7 Hz, 1H), 6.82 (s, 1H), 3.3–4.1 (m, 20H), 2.05 (m, 4H); MS (DCI) m/z 478 (M+H)$^+$;

Example 61

5-(2-{5-[5-(4-morpholinylcarbonyl)-2-pyridinyl]-1-benzofuran-2-yl}ethyl)-2-oxa-5-azabicyclo[2.2.1]heptane The product from Example 44E and 2-oxo-5-azabicyclo[2.2.1]heptane were processed as described in Example 1D to provide the titled compound. $^1$H NMR (300 MHz, CD$_3$OD) δ8.70 (m, 1H), 8.24 (d, J=1.8 Hz, 1H), 7.95 (m, 3H), 7.58 (d, J=8.7 Hz, 1H), 6.82 (s, 1H), 4.7 (m, 1H), 4.55 (m, 1H), 3.3–4.0 (m, 14H), 2.4 (m, 2H), 2.2 (m, 2H); MS (DCI) m/z 434 (M+H)$^+$;

Example 62

(2S)-1-(2-{5-[5-(4-morpholinylcarbonyl)-2-pyridinyl]-1-benzofuran-2-yl}ethyl)-2-pyrrolidinol The product from Example 44E and 2-(R)-hydroxymethylpyrrolidine were processed as described in Example 1D to provide the titled compound. $^1$H NMR (300 MHz, CD$_3$OD) δ8.70 (m, 1H), 8.23 (d, J=1.8 Hz, 1H), 7.98 (m, 3H), 7.57 (d, J=8.7 Hz, 1H), 6.82 (s, 1H), 3.3–4.0 (m, 15H), 1.9–2.3 (m, 6H); MS (DCI) m/z 436 (M+H)$^+$;

Example 63

N-allyl-N-(2-{5-[5-(4-morpholinylcarbonyl)-2-pyridinyl]-1-benzofuran-2-yl}ethyl)amine The product from Example 44E and allylamine were processed as described in Example 1D to provide the titled compound. $^1$H NMR (300 MHz, CD$_3$OD) δ8.70 (m, 1H), 8.24 (d, J=1.8 Hz, 1H), 7.96 (m, 3H), 7.59 (d, J=8.7 Hz, 1H), 6.81 (s, 1H), 5.95 (m, 1H), 5.55 (m, 2H), 3.25–3.8 (m, 14H); MS (DCI) m/z 392 (M+H)$^+$;

Example 64

3-[(2-{5-[5-(4-morpholinylcarbonyl)-2-pyridinyl]-1-benzofuran-2-yl}ethyl)amino]-1-propanol The product from Example 44E and 3-amino-1-propanol were processed as described in Example 1D to provide the titled compound. $^1$H NMR (300 MHz, CD$_3$OD) δ8.70 (m, 1H), 8.23 (d, J=1.8 Hz, 1H), 7.98 (m, 3H), 7.59 (d, J=8.7 Hz, 1H), 6.82 (s, 1H), 3.20–3.8 (m, 16H), 1.92 (m, 2H); MS (DCI) m/z 410 (M+H)$^+$;

Example 65

N-(2-{5-[5-(4-morpholinylcarbonyl)-2-pyridinyl]-1-benzofuran-2-yl}ethyl)-N-propylamine The product from Example 44E and propylamine were processed as described in Example 1D to provide the titled compound. $^1$H NMR (300 MHz, CD$_3$OD) δ8.70 (m, 1H), 8.24 (d, J=1.8 Hz, 1H), 7.98 (m, 3H), 7.58 (d, J=8.7 Hz, 1H), 6.82 (s, 1H), 3.25–3.8 (m, 12H), 3.05 (t, J=7.5 Hz, 2H), 1.74 (m, 2H), 1.05 (t, J=7.5 Hz, 3H); MS (DCI) m/z 394 (M+H)$^+$;

Example 66

4-(2-{2-[(3R)-3-(dimethylamino)pyrrolidinyl]ethyl}-1-benzofuran-5-yl)benzonitrile The product from Example 1C and 3-(R)-(dimethylamino)pyrrolidine were processed as described in Example 1D to provide the titled compound. MS (DCI) m/z 360 (M+H)$^+$;

Example 67

4-(2-{2-[(2R)-2-methylpyrrolidinyl]ethyl}-2,3-dihydro-1-benzofuran-5-yl)benzonitrile

Example 67A

4-{2-[(E)-2-methoxyethenyl]-2,3-dihydro-1-benzofuran-5-yl}benzonitrile

A solution of Example 1A (0.20 g, 0.623 mmol), 1-methoxybutadiene (0.18 g, 2.18 mmol), palladium diacetate (0.007 g, 0.031 mmol), sodium bicarbonate (0.261 g, 3.11 mmol) and tetrabutyl ammonium chloride (0.173 g, 0.623 mmol) was heated at 60° C. in DMF (3 mL) under an atmosphere of nitrogen for 36 hours. The reaction was cooled to 23° C., diluted with CH$_2$Cl$_2$ (50 mL), filtered through Celite. The solution was concentrated under reduce pressure and the residue was purified on silica using CH$_2$Cl$_2$ to give the titled compound (0.95 g, 55%). $^1$H NMR (CDCl$_3$): 3.05 (m, 1H), 3.40 (m, 1H), 3.60 (s, 3H), 5.00 (m, 1H), 5.22 (m, 1H), 6.72 (d, J=14 Hz, 1H), 6.83 (d, J=7 Hz, 1H), 7.38 (m, 2H), 7.65 (m, 4H); MS (DCI): 278 (M+H$^+$), 295 (M+NH$_4^+$).

Example 67B

4-[2-(2-oxoethyl)-2,3-dihydro-1-benzofuran-5-yl]benzonitrile

A solution of Example 67A (0.5 g, 1.8 mmol) in acetone (10 mL) and p-toluenesulfonic acid monohydrate (0.51 g, 2.7 mmol) was stirred for 45 minutes, diluted with CH$_2$Cl$_2$ (150 mL), washed with cold aqueous sodium bicarbonate (2×100 mL, 10% solution), water (2×100 mL), dried (Na$_2$SO$_4$), filtered and concentrated under reduced pressure. The residue was purified on silica using CH$_2$Cl$_2$ to give the titled compound (0.41 g, 87%). $^1$H NMR (CDCl$_3$): 2.95 (m, 2H), 3.65 (m, 3H), 6.82 (d, J=7 Hz, 1H), 7.40 (m, 2H), 7.62 (m, 4H), 9.55(d, J=7 Hz, 1H); MS (DCI) 263 (M$^+$), 281 (M+NH$_4^+$).

Example 67C

4-[2-(2-hydroxyethyl)-2,3-dihydro-1-benzofuran-5-yl]benzonitrile

A solution of Example 67B (0.25 g, 0.95 mmol) and sodium borohydride (0.054 g, 1.42 mmol)in methanol (5 mL) was stirred for 1 hour, cooled on ice and quenched with aqueous NaHCO$_3$ (50 mL). The mixture was extracted with dichloromethane (3×100 mL), the organic extracts combined and washed with water (1×150 mL), brine (1×150 mL), dried (Na$_2$SO$_4$), filtered and concentrated under reduced pressure to provide the titled compound (0.24 g, 95%). $^1$H NMR (CDCl$_3$): 1.90 (m, 2H), 2.90 (m, 2H), 3.46 (m, 2H), 5.40 (m, 1H), 6.85 (d, J=7 Hz, 1H), 7.38 (m, 2H), 7.65 (m, 4H); MS (DCI) 265 (M$^+$), 283 (M+NH$_4^+$).

Example 67D

2-[5-(4-cyanophenyl)-2,3-dihydro-1-benzofuran-2-yl]ethyl methanesulfonate

To a solution of Example 67C (0.23 g, 0.87 mmol) and methanesulfonyl chloride (0.075 mL, 0.96 mmol) in CH$_2$Cl$_2$ (5 mL) at 0° C. was added triethylamine (0.13 mL, 9.4 mmol). The mixture was stirred for 30 minutes, diluted with CH$_2$Cl$_2$ (75 mL), washed with water (3×100 mL), dried (Na$_2$SO$_4$), filtered and concentrated under reduced pressure. The residue was purified on silica using CH$_2$Cl$_2$ to provide the titled compound (0.278 g, 90%). $^1$H NMR (CDCl$_3$): H NMR: 1.95 (m, 2H), 2.93 (m, 2H), 3.00 (s, 3H), 3.46 (m, 2H), 5.00 (m, 1H), 6.81 (d, J=7 Hz, 1H), 7.40 (m, 2H), 7.65 (m, 4H); MS (DCI) 343 (M$^+$), 361 (M+NH$_4^+$).

Example 67E 4-(2-{2-[(2R)-2-methylpyrrolidinyl]ethyl}-2,3-dihydro-1-benzofuran-5-yl)benzonitrile A solution of Example 67D (0.2 g, 0.58 mmol), R-2-methylpyrrolidine-(L)-tartrate 1.45 mmol) and cesium carbonate (0.95 g) in acetonitrile (5 mL) was heated to 60° C. for 48 hours under an atmosphere of nitrogen. The reaction was allowed to come to ambient temperature, diluted with CH$_2$Cl$_2$ (100 mL), washed with aqueous NaHCO$_3$ (2×100 mL), H$_2$O (1×100 mL), brine (100 mL), dried (Na$_2$SO$_4$), filtered and concentrated under reduced pressure. The residue was purified by on silica using CHCl$_3$/CH$_3$OH/NH$_4$OH (95:5:0.5) to provide the titled compound (0.14 g, 72%). $^1$H NMR (CDCl$_3$): 1.10 (d, J=7 Hz, 2H), 1.50 (m, 2H), 1.70 (m, 4H), 1.98 (m, 2H), 2.10 (m, 2H), 2.25 (m, 1H), 3.00 (m, 2H), 4.60 (m, 1H), 6.80 (d, J=7 Hz, 1H), 7.45 (m, 2H), 7.70 (m, 4H); MS(ESI) 333 (M+H$^+$).

Example 68

(4-fluorophenyl)(2-{2-[(2R)-2-methyl-1-pyrrolidinyl]ethyl}-1-benzofuran-5-yl)methanone

Example 68A (4-fluorophenyl)(4-hydroxy-3-iodophenyl)methanone (4-Fluorophenyl)(4-hydroxyphenyl)methanone (20.0 g, 92.5 mmol) in concentrated ammonium hydroxide (770 mL) was allowed to stir at 25° C. for 15 minutes and then treated with potassium iodide (74.79 g, 450.5 mmol) and iodine (23.48 g, 92.5 mmol) in water (185 mL). The reaction mixture was allowed to stir at 25° C. for 18 hours and then filtered. The precipitate was dissolved in ethyl acetate, washed with water and brine, dried, filtered and the filtrate concentrated under reduced pressure to provide the title compound as a pale green solid (23.4 g, 74% yield). $^1$HNMR (300 MHZ, CD$_3$OD) δ 6.91 (d, 1H, J=8.9 Hz), 7.26 (t, 2H), 7.64 (d, 1H, J=8.9 Hz), 7.78 (t, 2H), 8.17 (s, 1H); MS (DCI) m/z 342.9 (M+H)$^+$, 360 (M+NH$_4$)$^+$.

Example 68B (2R)-1-(3-butynyl)-2-methylpyrrolidine (R)-2-methylpyrrolidine (L) tartrate (1.65 g, 7.00 mmol) and 325 mesh powdered K$_2$CO$_3$ (2.03 g, 14.7 mmol) in acetonitrile (60 mL) were heated at 50° C. in a sealed bottle for 24 hours. The mixture was allowed to cool to room temperature and was treated with 3-butynyl 4-methylbenzenesulfonate (1.24 mL, 7.0 mmol). The mixture was stirred for one hour at room temperature and then was heated at 50° C. for 24 hours. The mixture was allowed to cool to room temperature, filtered, and the filter cake washed with acetonitrile. The filtrate was diluted to a total volume of 70 mL with acetonitrile and used as a 0.1M solution in subsequent steps.

Example 68C (4-fluorophenyl)(2-{2-[(2R)-2-methyl-1-pyrrolidinyl]ethyl}-1-benzofuran-5-yl)methanone The product from Example 68A (6.5 g, 18.5 mmol) was sequentially treated with a 0.1M solution of the product from Example 68B in acetonitrile (230 mL, 23.0 mmol), Pd(OAc)$_2$ (0.127 g, 0.566 mmol), tris(4-methylphenyl) phosphine (0.344 g, 1.130 mmol), and copper iodide (1.08 g, 95.72 mmol). After stirring at 25° C. for 10 minutes, the reaction mixture was treated with diisopropyl amine (26.6 mL, 189 mmol) and then heated at 60° C. in an inert atmosphere for 16 hours. The reaction mixture was allowed to cool to room temperature, filtered through celite, and the filtrate concentrated under reduced pressure. The residue was purified on silica gel using 90% DCM, 9.9% MeOH, 0.1% NH$_4$OH to provide the title compound (1.21 g, 18.0% yield). $^1$HNMR (300 MHz, CD$_3$OD) δ 1.09 (d, 3H, J=6.1 Hz), 1.46 (m, 1H), 1.81 (m, 2H), 2.02–2.28 (m, 2H), 2.49 (m, 2H) 3.06 (m, 2H), 3.28 (m, 2H), 6.68 (s, 1H),), 7.27 (t, 2H), 7.58 (d, 1H, J=8.9 Hz), 7.71 (d, 1H, J=8.9 Hz) 7.86 (t, 2H), 7.97 (s, 1H); MS (ESI) m/z 352 (M+H)$^+$.

Example 69

(3-fluorophenyl)(2-{2-[(2R)-2-methyl-1-pyrrolidinyl]ethyl}-1-benzofuran-5-yl)methanone

Example 69A (3-fluorophenyl)(4-hydroxyphenyl)methanone (3-fluorophenyl)(4-methoxyphenyl)methanone (1.0 g, 4.34 mmol) in 50 mL DCM at −78° C. while stirring was treated with 1M boron tribromide (13.03 mL, 13.03 mmol) dropwise over 20 minutes. The mixture was allowed to warm to 25° C. and stir for 18 hours. The mixture was treated with water (1 mL) and stirred for 5 minutes, followed by additional water (2 mL) and stirred for 10 minutes, and finally treated with more water (50 mL) and stirred for 20 minutes. The mixture was then extracted with DCM (50 mL ×2). The organic layers were combined, dried, filtered, and the filtrate evaporated under reduced pressure. The residue was purified by flash chromatography to provide the title compound (0.69 g, 74% yield). $^1$HNMR (300 MHz, $CD_3OD$) δ 6.92 (d, 2H, J=8.9 Hz), 7.26 (m, 1H), 7.41–7.58 (m, 3H), 7.79 (d, 2H, J=8.9 Hz); MS (DCI) m/z 217 (M+H)$^+$, 234 (M+NH$_4$)$^+$.

Example 69B (3-fluorophenyl)(4-hydroxy-3-iodophenyl) methanone

The product from Example 69A, potassium iodide and iodine were processed as described in Example 68A to provide the title compound. $^1$HNMR (300 MHz, $CD_3OD$) δ 6.92 (d, 1H, J=8.9 Hz), 7.31–7.59 (m, 4H), 7.67 (d, 1H, J=8.9 Hz), 8.18 (s, 1H); MS (DCI) m/z 343 (M+H)$^+$, 360 (M+NH$_4$)$^+$.

Example 69C (3-fluorophenyl)(2-{2-[(2R)-2-methyl-1-pyrrolidinyl]ethyl}-1-benzofuran-5-yl)methanone The product from Example 69B and a 0.1 M solution of the product from Example 68B were processed as described in Example 68C to provide the title compound. $^1$HNMR (300 MHz, $CD_3OD$) δ 1.26 (d, 3H, J=6.1 Hz), 1.57 (m, 1H), 1.91 (m, 2H), 2.10–2.63 (m, 2H), 2.87 (m, 2H) 3.18 (m, 2H), 3.42 (m, 2H), 6.76 (s, 1H), 7.37–7.59 (m, 5H), 7.76 (d, 1H, J=8.9 Hz), 7.98 (s, 1H); MS (ESI) m/z 352.1 (M$^+$+1).

Example 70

(2-fluorophenyl)(2-{2-[(2R)-2-methyl-1-pyrrolidinyl]ethyl}-1-benzofuran-5-yl)methanone Example 70A (2-fluorophenyl)(4-hydroxy-3-iodophenyl) methanone (2-Fluorophenyl)(4-hydroxyphenyl)methanone, potassium iodide and iodine were processed as described in Example 68A to provide the title compound. MS (DCI) m/z 343 (M+H)$^+$, 360 (M+NH$_4$)$^+$.

Example 70B (2-fluorophenyl)(2-{2-[(2R)-2-methyl-1-pyrrolidinyl]ethyl}-1-benzofuran-5-yl)methanone The product from Example 70A and a 0.1M solution of the product from Example 68B were processed as described in Example 68C to provide the title compound. $^1$HNMR (300 MHz, $CD_3OD$) δ 1.28 (d, 3H, J=6.1 Hz), 1.59 (m, 1H), 1.93 (m, 2H), 2.10–2.78 (m, 2H), 2.93 (m, 2H), 3.18 (m, 2H), 3.45 (m, 2H), 6.76 (s, 1H), 7.21–7.38 (m, 2H), 7-50–7.67 (m, 3H), 7.79 (d, 1H, J=8.9 Hz), 7.99 (s, 1H); MS (ESI) m/z 352.1 (M+H)$^+$.

Example 71

(3-chlorophenyl)(2-{2-[(2R)-2-methyl-1-pyrrolidinyl]ethyl}-1-benzofuran-5-yl)methanone Example 71A 4-(benzyloxy)benzoyl Chloride 4-Benzyloxybenzoic acid (15.0 g, 65.72 mmol) in dichloromethane (150 mL) and dimethylformamide (0.75 mL) was cooled to 0° C. After 30 minutes, the mixture was treated with neat oxalyl chloride (11.5 mL, 131.44 mmol) dropwise over 25 minutes. The resulting mixture was stirred at room temperature for 120 minutes followed by evaporation of solvent under reduced pressure to provide the title compound as a light yellow solid (18.2 g, 112% yield). $^1$HNMR (300 MHz, $CDCl_3$) δ 7.03 (d, 2H, J=8.9 Hz), 7.23–7.43 (m, 5H), 8.07 (d, 2H, J=8.9 Hz).

Example 71B 4-(benzyloxy)-N-methoxy-N-methylbenzamide

The product from Example 71A (18 g, 72.96 mmol) in DCM at room temperature was treated with N,O-dimethylhydroxylamine hydrochloride (7.83 g, 80.26 mmol) slowly. The mixture was cooled to 0° C., stirred for 30 minutes, and treated with triethylamine (25.47 mL, 182.41 mmol) dropwise. The mixture was allowed to warm to 25° C., stirred for 16 hours, and treated with DCM (150 mL). The mixture was washed with saturated $NaHCO_3$, brine, and water. The organic phase was dried, filtered, and the filtrate evaporated under reduced pressure to provide the title compound as a pale yellow solid (18.65 g, 95% yield). $^1$HNMR (300 MHz, $CDCl_3$) δ 3.36 (s, 3H), 3.56 (s, 3H) 6.98 (d, 2H, J=8.9 Hz), 7.33–7.46 (m, 5H), 7.76 (d, 2H, J=8.9 Hz); MS (ESI) m/z 272 (M+H)$^+$.

Example 71C 4-hydroxy-N-methoxy-N-methylbenzamide

10% Palladium on charcoal (4.5 g) in methanol (10 mL) was treated with the product from Example 71B (18.60 g, 68.55 mmol) in 150 mL methanol. The mixture was placed under hydrogen atmosphere at 67 psi. The reaction mixture was filtered and the filtrate was evaporated under reduced pressure. The residue was purified by flash chromatography to provide the title compound (10.3 g, 83% yield). $^1$HNMR (300 MHz, $CD_3OD$) δ 3.32 (s, 3H), 3.58 (s, 3H), 6.81 (d, 2H, J=8.9 Hz). 7.59 (d, 2H, J=8.9 Hz); MS (DCI) m/z 182 (M+H)$^+$, 199 (M+NH$_4$)$^+$.

Example 71D 4-hydroxy-3-iodo-N-methoxy-N-methylbenzamide

The product from Example 71C (10.3 g, 56.84 mmol) in concentrated ammonium hydroxide (400 mL) was stirred at 25° C. for 15 minutes and then treated with KI (45.96 g, 276.83 mmol) and $I_2$ (14.43 g, 56.84 mmol) in water (65 mL). After stirring at room temperature for 16 hours, the solvent was removed under reduced pressure and the residue was redissolved in DCM (500 mL) and washed with water (350 mL×2). The organic phase was dried, filtered, and the filtrate was concentrated under reduced pressure. The residue was purified by flash chromatography on silica gel using 90% $CH_2Cl_2$, 10% MeOH, to provide the title compound as a white solid (11.6 g, 67% yield). $^1$HNMR (300 MHz, $CD_3OD$) δ 3.32 (s, 3H), 3.59 (s, 3H), 6.83 (d, 1H, J=8.9 Hz). 7.58 (d, 1H, J=8.9 Hz), 8.06 (s, 1H); MS (DCI) m/z 308 (M+H)$^+$, 325 (M+NH$_4$)$^+$.

Example 71E

N-methoxy-N-methyl-2-{2-[(2R)-2-methyl-1-pyrrolidinyl]ethyl}-1-benzofuran-5-carboxamide The product from Example 71D (11.6 g, 37.77 mmol) in acetonitrile (50 mL) was treated sequentially with a 0.12M solution of the product from Example 68B (378 mL, 45.33 mmol), Pd(OAc)$_2$ (0.254 g, 1.13 mmol), tris(4-methylphenyl)phosphine (0.518 g, 1.699 mmol), and diisopropyl amine (39.7 mL, 283.3 mmol). After stirring at 25° C. for 10 minutes, the mixture was treated with copper iodide (2.158 g, 11.33 mmol) and heated at 50° C. in an inert atmosphere for 18 hours. The reaction mixture was allowed to cool to room temperature, filtered through celite, and the filtrate was concentrated under reduced pressure. The residue was purified on silica gel using 95% DCM, 9.9% MeOH, 0.1% NH$_4$OH to provide the title compound (1.22 g, 10.2% yield). $^1$HNMR (300 MHz, CD$_3$OD) δ 1.18 (d, 3H, J=6.1 Hz), 1.47 (m, 1H), 1.78 (m, 2H), 1.91–2.34 (m, 2H), 2.50 (m, 2H) 3.06 (m, 2H), 3.26 (m, 2H), 3.38 (s, 3H), 3.59 (s, 3H), 6.63 (s, 1H), 7.51 (q, 2H), 7.84 (1H); MS (ESI) m/z 317.2 (M+H)$^+$.

Example 71F (3-chlorophenyl)(2-{2-[(2R)-2-methyl-1-pyrrolidinyl]ethyl}-1-benzofuran-5-yl)methanone The product from Example 71E (0.05 g, 0.158 mmol) in 5 mL of anhydrous THF at 0° C. was treated with 3-chlorophenylmagnesium bromide (1.58 mL, 0.79 mmol). The mixture was allowed to slowly warm to 25° C. and stir under nitrogen for 18 hours. The reaction mixture was quenched with saturated ammonium chloride solution and extracted with DCM (50 mL×2). The organic phases were combined, dried, filtered, and the filtrate evaporated under reduced pressure. The residue was purified by preparative HPLC on a Waters Nova-Pak HR C18 column (40 mm×100 mm, 6 μm particle size) using a gradient of 10% to 100% acetonitrile: 0.1% aqueous TFA over 12 minute (15 minute run time) at a flow rate of 70 mL/minute to provide the title compound. $^1$HNMR (300 MHz, CD$_3$OD) δ 1.50 (d, 3H), 1.72 (m, 1H), 2.10 (m, 2H), 2.35 (m, 1H), 3.30 (m, 4H), 3.55 (m, 1H), 3.80 (m, 2H), 6.90 (s, 1H), 7.50–7.80 (m, 6H), 8.02 (d, 1H); MS (ESI) m/z 368 (M+H)$^+$.

Example 72

(4-chlorophenyl)(2-{2-[(2R)-2-methyl-1-pyrrolidinyl]ethyl}-1-benzofuran-5-yl)methanone The product from Example 71E and 4-chlorophenylmagnesium bromide were processed as described in Example 71F to provide the title compound. $^1$HNMR (300 MHz, CD$_3$OD) δ 1.18 (d, 3H, J=6.1 Hz), 1.46 (m, 1H), 1.78 (m, 2H), 2.01–2.36 (m, 2H), 2.50 (m, 2H), 3.03 (m, 2H), 3.23 (m, 2H), 6.67 (s, 1H), 7.57 (m, 3H), 7.78 (m, 3H), 7.97 (s, 1H); MS (ESI) m/z 368.1 (M$^+$+1).

Example 73

(4-methoxyphenyl)(2-{2-[(2R)-2-methyl-1-pyrrolidinyl]ethyl}-1-benzofuran-5-yl)methanone The product from Example 71E and 4-methoxyphenylmagnesium bromide were processed as described in Example 71F to provide the title compound. $^1$HNMR (CD$_3$OD) δ 1.18 (d, 3H, J=6.1 Hz), 1.46 (m, 1H), 2.01–2.32 (m, 2H), 2.50 (m, 2H), 3.06 (m, 2H), 3.24 (m 2H), 3.88 (s, 3H), 6.67 (s, 1H), 7.05 (d, 2H, J=8.9 Hz), 7.54 (d, 2H, J=8.9 Hz), 7.68 (d, 2H, J=8.9 Hz), 7.80 (d, 2H, J=8.9 Hz), 7.92 (s, 1H); MS (ESI) m/z 364.1 (M$^+$+1).

Example 74

(4-fluoro-3-methylphenyl)(2-{2-[(2R)-2-methyl-1-pyrrolidinyl]ethyl}-1-benzofuran-5-yl)methanone The product from Example 71E and (4-fluoro-3-methyl)phenylmagnesium bromide were processed as described in Example 71F to provide the title compound. $^1$HNMR (300 MHz, CD$_3$OD) δ 1.17 (d, 3H), 1.45 (m, 1H), 1.80 (m, 2H), 2.0 (m, 1H), 2.3 (m, 4H), 2.50 (m, 2H), 3.05 (m, 2H), 3.25 (m, 2H), 6.65 (s, 1H), 7.2 (m, 1H), 7.57 (d, 1H), 7.63 (m, 1H), 7.70 (dd, 2H), 7.95 (d, 1H); MS (ESI) m/z 366 (M+H)$^+$.

Example 75 cyclopropyl(2-{2-[(2R)-2-methyl-1-pyrrolidinyl]ethyl}-1-benzofuran-5-yl)methanone The product from Example 71E and cyclopropylmagnesium bromide were processed as described in Example 71F to provide the title compound. $^1$HNMR (300 MHz, CD$_3$OD) δ 1.10 (m, 5H), 1.28 (d, 3H), 1.78 (m, 1H), 2.10 (m, 2H), 2.38 (m, 1H), 2.9 (m, 1H), 3.2–3.8(m, 6H), 6.85 (s, 1H), 7.58 (d, 1H), 8.05 (dd, 1H), 8.33 (d, 1H); MS (ESI) m/z 298 (M+H)$^+$.

Example 76

3-ethyl-1-(2-{2-[(2R)-2-methyl-1-pyrrolidinyl]ethyl}-1-benzofuran-5-yl)-1-pentanone The product from Example 71E and 2-ethylbutylmagnesium bromide were processed as described in Example 71F to provide the title compound. $^1$HNMR (300 MHz, CD$_3$OD) δ 0.9 (m, 6H), 1.23 (m, 1H), 1.20 (m, 6H), 1.75 (m, 1H), 2.1 (m, 2H), 2.35 (m, 1H), 3.05 (m, 1H), 3.2–3.5 (m, 7H), 3.55 (m, 1H), 3.8 (m, 1H), 6.85 (s, 1H), 7.55 (d, 1H) 7.95 (dd, 1H), 8.24 (d, 1H); MS (ESI) m/z 342 (M+H)$^+$.

Example 77

(4-chloro-3-methylphenyl)(2-{2-[(2R)-2-methyl-1-pyrrolidinyl]ethyl}-1-benzofuran-5-yl)methanone The product from Example 71E and 4-chloro-3-methylphenylmagnesium bromide were processed as described in Example 71F to provide the title compound. $^1$HNMR (300 MHz, CD$_3$OD) δ 1.47 (d, 3H), 1.75 (m, 1H), 1.80 (m, 2H), 2.10 (m, 2H), 2.38 (m, 1H), 2.44 (s, 3H), 3.50 (m, 2H), 3.55 (m, 1H), 3.80 (m, 2H), 6.85 (s, 1H), 7.5 (m, 3H), 7.7 (bs, 1H), 7.79 (dd, 1H), 8.01 (d, 1H); MS (ESI) m/z 382 (M+H)$^+$.

Example 78

(2-{2-[(2R)-2-methyl-1-pyrrolidinyl]ethyl}-1-1-benzofuran-5-yl)[4-(methylthio)phenyl]methanone The product from Example 71E and 4-(methylthio)phenylmagnesium bromide were processed as described in Example 71F to provide the title compound. $^1$HNMR (300 MHz, CD$_3$OD) δ 1.45 (d, 3H), 1.75 (m, 1H), 1.80 (m, 2H), 2.30 (m, 2H), 2.38 (m, 1H), 2.54 (s, 3H), 3.50 (m, 2H), 3.55 (m, 1H), 3.80 (m, 2H), 6.85 (s, 1H), 7.4 (dd, 2H), 7.7 (bs, 1H), 7.6 (dd, 1H), 7.75 (m, 3H), 8.0 (d, 1H); MS (ESI) m/z 380 (M+H)$^+$.

Example 79

[4-(dimethylamino)phenyl](2-{2-[(2R)-2-methyl-1-pyrrolidinyl]ethyl}-1-benzofuran-5-yl)methanone The product from Example 71E and 4-(dimethylamino)phenylmagnesium bromide were processed as described in Example 71F to provide the title compound. $^1$HNMR (300 MHz, CD$_3$OD) δ 1.44 (d, 3H), 1.73 (m, 1H), 1.80 (m, 2H), 2.15 (m, 2H), 2.35 (m, 1H), 3.18 (s, 6H), 3.50 (m, 2H), 3.55 (m, 1H), 3.80 (m, 2H), 6.80 (dd, 2H), 6.85 (s, 1H), 7.56 (dd, 1H), 7.65 (dd, 1H), 7.75 (dd, 2H), 7.95 (d, 1H); MS (ESI) m/z 377 (M+H)$^+$.

Example 80

(4-methylphenyl)(2-{2-[(2R)-2-methyl-1-pyrrolidinyl]ethyl}-1-benzofuran-5-yl)methanone The product from Example 71E and 4-methylphenylmagnesium bromide were processed as described in Example 71F to provide the title compound. $^1$HNMR (300 MHz, CD$_3$OD) δ 1.48 (d, 3H), 1.75 (m, 1H), 2.1 (m, 2H), 2.38 (m, 1H), 2.45 (s, 3H), 3.30 (m, 4H), 3.57 (m, 1H), 3.80 (m, 2H), 6.85 (s, 1H), 7.38 (dd, 2H), 7.60 (dd, 1H), 7.70 (dd, 2H), 7.75 (dd, 1H), 8.0 (d, 1H); MS (ESI) m/z 348 (M+H)$^+$.

Example 81

(3,5-difluorophenyl)(2-{2-[(2R)-2-methyl-1-pyrrolidinyl]ethyl}-1-benzofuran-5-yl)methanone The product from Example 71E and 3,5-difluorophenylmagnesium bromide were processed as described in Example 71F to provide the title compound. $^1$HNMR (300 MHz, CD$_3$OD) δ 1.45 (d, 3H), 1.75 (m, 1H), 2.13 (m, 2H), 2.35 (m, 1H), 3.30 (m, 4H), 3.56 (m, 1H), 3.82 (m, 2H), 6.88 (s, 1H), 7.38 (dd, 2H), 7.30 (m, 3H), 7.63 (dd, 1H), 7.80 (dd, 1H), 8.05 (d, 1H); MS (ESI) m/z 370 (M+H)$^+$.

Example 82

(2-methoxyphenyl)(2-{2-[(2R)-2-methyl-1-pyrrolidinyl]ethyl}-1-benzofuran-5-yl)methanone The product from Example 71E and 2-methoxyphenylmagnesium bromide were processed as described in Example 71F to provide the title compound. $^1$HNMR (300 MHz, CD$_3$OD) δ 1.42 (d, 3H), 1.72 (m, 1H), 2.10 (m, 2H), 2.35 (m, 1H), 3.30 (m, 4H), 3.55 (m, 1H), 3.70 (s 3H), 3.80 (m, 2H), 6.80 (s, 1H), 7.1 (m, 2H), 7.30 (dd, 1H), 7.53 (m, 2H), 7.75 (dd, 1H), 7.95 (d, 1H); MS (ESI) m/z 364 (M+H)$^+$.

Example 83

(3-methoxyphenyl)(2-{2-[(2R)-2-methyl-1-pyrrolidinyl]ethyl}-1-benzofuran-5-yl)methanone The product from Example 71E and 3-methoxyphenylmagnesium bromide were processed as described in Example 71F to provide the title compound. $^1$HNMR (300 MHz, CD$_3$OD) δ 1.42 (d, 3H), 1.72 (m, 1H), 2.10 (m, 2H), 2.35 (m, 1H), 3.30 (m, 4H), 3.55 (m, 1H), 3.80 (m, 2H), 3.83 (s, 3H), 6.83 (s, 1H), 7.2 (m, 1H), 7.30 (m, 2H), 7.45 (m, 1H), 7.60 (m, 2H), 7.80 (dd, 1H), 8.02 (d, 1H); MS (ESI) m/z 364 (M+H)$^+$.

Example 84

(2-{2-[(2R)-2-methyl-1-pyrrolidinyl]ethyl}-1-benzofuran-5-yl)(phenyl)methanone

The product from Example 71E and phenylmagnesium bromide were processed as described in Example 71F to provide the title compound. $^1$HNMR (300 MHz, CD$_3$OD) δ 1.15 (d, 3H), 1.45 (m, 1H), 1.80 (m, 2H), 2.00 (m, 1H), 2.30 (m, 1H), 2.50 (m, 2H), 3.30 (m, 4H), 6.63 (s, 1H), 7.55 (m, 3H), 7.65 (m, 1H), 7.80 (m, 3H), 7.98 (d, 1H); MS (ESI) m/z 334 (l+H)$^+$.

Example 85

4-(2-{2-[(2R)-2-methyl-1-pyrrolidinyl]ethyl}-1-benzofuran-4-yl)benzonitrile

Example 85A 2-iodo-1,3-benzenediol

Resorcinol (2.75 g, 25 mmol) in 20 mL of water and ice was treated with iodine (6.7 g, 26.4 mmol) and NaHCO$_3$ (2.3 g, 27.4 mmol) in one portion. After stirring for 1 hour, the precipitate was separated by filtration and the filtrate was extracted twice (2×75 mL) with diethyl ether. The organic phase was dried over sodium sulfate and evaporated under reduced pressure. The solid was triturated with 20 ML of chloroform and left at −18° C. for 24 hours. The solid was separated by filtration to provide the title compound (78% yield). $^1$HNMR (300 MHz, CDCl$_3$) δ 4.85 (s, 1H), 6.30 (m, 2H), 6.95 (m, 1H). MS (CDI) m/z 237 (M+H)$^+$.

Example 85B 2-(2-hydroxyethyl)-1-benzofuran-4-ol

The product from Example 85A (0.2 g, 0.85 mmol) in 5 mL of DMF under nitrogen was treated with palladium bis(triphenylphosphine) dichloride (30 mg, 0.043 mmol), copper iodide (24 mg, 0.13 mmol), triethylamine (0.2 g, 2.12 mmol) and 3-butyn-1-ol (0.11 g, 1.53 mmol). The mixture was heated at 60° C. for 14 hours. After filtration over celite, the mixture was diluted with 150 mL of CH$_2$Cl$_2$ and washed with sodium bicarbonate (100 mL), water (100 mL) and brine (100 mL). The organic phase was dried over sodium sulfate, filtered, and the filtrate was evaporated under reduced pressure. The residue was purified by silica gel chromatography using a mixture of CH$_2$Cl$_2$/MeOH (95:5) to provide the title compound (62% yield). $^1$HNMR (300 MHz, CDCl$_3$) δ 3.05 (m, 2H), 4.0 (m, 2H), 6.60 (m, 2H), 7.03 (m, 2H). MS (CDI) m/z 179 (M+H)$^+$.

Example 85C 2-(2-hydroxyethyl)-1-benzofuran-4-yl trifluoromethanesulfonate

The product from Example 85B (0.1 g, 0.56 mmol) in 10 mL of CH$_2$Cl$_2$ at 0° C. was treated with triethylamine (0.11 g, 1.12 mmol), DMAP (7 mg, 0.056 mmol) and N-phenyl-trifluoromethanesulfonimide (0.22 g, 0.62 mmol). The mixture was stirred at room temperature for 3 hours. The reaction mixture was diluted with 100 mL of CH$_2$Cl$_2$ and washed twice with water (2×100 mL) and brine (100 mL). The organic phase was dried over sodium sulfate, filtered, and the filtrate was evaporated under reduced pressure to provide the title compound (94% yield). $^1$HNMR (300 MHz, CDCl$_3$) δ 3.10 (m, 2H), 4.0 (m, 2H), 6.60 (s, 1H), 7.15 (m, 1H), 7.22 (m, 1H), 7.45(m, 1H). MS (CDI) m/z 311 (M+H)$^+$.

Example 85D

4-[2-(2-hydroxyethyl)-1-benzofuran-4-yl] benzonitrile

The product from Example 85C (0.1 g, 0.32 mmol) in 8 mL of benzene/ethanol (2:1), was treated with 4-cyanophenylboronic acid (0.052 g, 0.35 mmol), palladium diacetate (0.0032 mmol), biphenyl-2-yl-dicyclohexylphosphine (0.0048 mmol) and Na$_2$CO$_3$ (2M, 0.87 mmol) and heated at 75° C. for 14 hours. The mixture was diluted with 100 mL of CH$_2$Cl$_2$ and washed successively with water (100 mL) and brine (100 mL), dried over sodium sulfate, filtered, and the filtrate was evaporated under reduced pressure. The residue was purified by chromatography over silica using CH$_2$Cl$_2$ to provide the title compound (55% yield). $^1$HNMR (300 MHz, CDCl$_3$) δ 3.10 (m, 2H), 4.05 (m, 2H), 6.62 (s, 1H), 6.90 (m, 1H), 7.25 (m, 2H), 7.52 (m, 2H), 7.73(m, 2H). MS (CDI) m/z 264 (M+H)$^+$.

Example 85E

2-[4-(4-cyanophenyl)-1-benzofuran-2-yl]ethyl methanesulfonate

The product from Example 85D (015 g, 0.57 mmol) in CH$_2$Cl$_2$ (10 mL) at 0° C. was treated with triethylamine (64 mg, 0.63 mmol) and methanesulfonyl chloride (68 mg, 0.59 mmol). After 45 minutes at room temperature the reaction was diluted with 50 mL CH$_2$Cl$_2$ and the mixture was washed with water (2×50 mL). The organic phase was dried over sodium sulfate and evaporated to provide the title compound (99% yield). $^1$HNMR (300 MHz, CDCl$_3$) δ 2.70 (m, 2H), 2.94 (s, 3H), 3.90 (m, 2H), 6.60 (s, 1H), 6.90 (m, 1H), 7.35 (m, 3H), 7.69 (m, 4H). MS (CDI) m/z 342 (M+H)$^+$.

Example 85F 4-(2-{2-[(2R)-2-methyl-1-pyrrolidinyl]ethyl}-1-benzofuran-4-yl)benzonitrile The product from Example 85E (0.086 g, 0.25 mmol), (2R)-2-methylpyrrolidine-L-tartaric acid (0.12 g, 0.5 mmol) and cesium carbonate (0.41 g, 1.26 mmol) in 2 mL of MeCN were combined and heated at 45° C. for two days. The mixture was diluted with 100 mL of CH$_2$Cl$_2$ and washed with a saturated solution of sodium bicarbonate (50 mL), water (50 mL) and brine (50 mL). The organic layer was dried, filtered, and the filtrate evaporated. The residue was purified by column chromatography over silica gel using a mixture of CH$_2$Cl$_2$:MeOH:NH$_4$OH (95:5:0.5) to provide the title compound (40% yield). $^1$HNMR (300 MHz, CDCl$_3$) δ 1.20 (d, 3H), 1.58 (m, 4H), 2.20–2.50 (m, 5H), 2.78 (m, 2H), 6.62 (s, 1H), 7.28 (m, 3H), 7.69 (m, 4H). MS (CSI) m/z 331 (M+H)$^+$.

Example 86

4-(2-{2-[(2R)-2-methyl-1-pyrrolidinyl]ethyl}-1-benzofuran-6-yl)benzonitrile

Example 86A 4-iodobenzene-1,3-diol

A solution of iodine monochloride (8.2 g, 50.5 mmol) in dry diethyl ether (100 mL) was added drop-wise over 45 minutes to a cold solution (0° C.) of resorcinol (5.5 g, 49.9 mmol) in dry ether (50 mL). After stirring at room temperature for one hour 100 mL of water and 1.0 g of sodium sulfite was added. The organic phase was separated and the aqueous phase was washed with 100 mL of ether, the combine ether phase was dried over sodium sulfate and evaporated under reduced pressure. The residue was purified using flash chromatography over silica gel using a mixture of CH$_2$Cl$_2$:MeOH (100:1) to provide the title compound in 50% yield. $^1$HNMR (300 MHz, CDCl$_3$) δ 4.95 (s, 1H), 6.23 (m, 1H), 6.55 (m, 1H), 7.43 (m, 1H). MS (CDI) m/z 237 (M+H)$^+$.

Example 86B 2-(2-hydroxyethyl)-1-benzofuran-6-ol

The product from Example 86A was processed as described in Example 85B to provide the title compound. $^1$HNMR (300 MHz, CDCl$_3$) δ 3.00 (m, 2H), 3.98 (m, 2H), 6.40 (s, 1H), 6.73 (m, 1H), 6.90 (d, 1H), 7.30 (m, 1H). MS (CDI) m/z 179 (M+H)$^+$.

Example 86C 2-(2-hydroxyethyl)-1-benzofuran-6-yl trifluoromethanesulfonate

The product from Example 86B was processed as described in Example 85C to provide the title compound. $^1$HNMR (300 MHz, CDCl$_3$) δ 3.00 (m, 2H), 4.2 (m, 2H), 6.65 (s, 1H), 7.20 (m, 1H), 7.22 (m, 1H), 7.35(m, 1H). MS (CDI) m/z 311 (M+H)$^+$.

Example 86D

4-[2-(2-hydroxyethyl)-1-benzofuran-6-yl]benzonitrile

The product from Example 86C was processed as described in Example 85D to provide the title compound. $^1$HNMR (300 MHz, CDCl$_3$) δ 3.15 (m, 2H), 4.00 (m, 2H), 6.52 (s, 1H), 6.95 (m, 1H), 7.35 (m, 2H), 7.52 (m, 2H), 7.70(m, 2H); MS (CDI) m/z 264 (M+H)$^+$.

Example 86E

2-[6-(4-cyanophenyl)-1-benzofuran-2-yl]ethyl methanesulfonate

The product from Example 86D was processed as described in Example 85E to provide the title compound. $^1$HNMR (300 MHz, CDCl$_3$) δ 2.65 (m, 2H), 2.99 (s, 3H), 3.95 (m, 2H), 6.45 (s, 1H), 6.95 (m, 1H), 7.30 (m, 3H), 7.69 (m, 4H); MS (CDI) m/z 342 (M+H)$^+$.

Example 86F 4-(2-{2-[(2R)-2-methyl-1-pyrrolidinyl]ethyl}-1-benzofuran-6-yl)benzonitrile The product from Example 86E was processed as described in Example 85F to provide the title compound. $^1$HNMR (300 MHz, CDCl$_3$) δ 1.20 (d, 3H), 1.58 (m, 4H), 2.20–2.50 (m, 51H), 2.78 (m, 2H), 6.52 (s, 1H), 7.40 (m, 1H), 7.58 (m, 1H), 7.60 (s, 1H), 7.73 (m, 4H); MS (CSI) m/z 331 (M+H)$^+$.

Example 87

3-(2-{2-[(2R)-2-methylpyrrolidin-1-yl]ethyl}-1-benzofuran-5-yl)-5-(thien-2-ylmethyl)-1,2,4-oxadiazole

Example 87A 4-hydroxy-3-iodobenzonitrile

In a 2000 mL round-bottom flask containing 10.0 g (84 mmol) of 4-cyanophenol, 450 mL conc. ammonium hydroxide was added and contents were allowed to stir at 25° C. for 15 min. Next, a solution of 67.9 g (409 mmol) potassium iodide and 21.3 g (84 mmol) iodine chips, dissolved in 100 mL water, was quickly added. The reaction mixture was allowed to stir at 25° C. for 18 h at which time contents were filtered. The filtrate was concentrated under reduced pressure and redissolved in 500 mL dichloromethane. The organic layer was then washed twice with 250 mL water, dried, and concentrated under reduced pressure to provide the title compound as a light yellow solid (14.3 g, 67% yield). ¹HNMR (300 MHz, CDCl₃) δ 7.03 (d, 1H), 7.66 (dd, 1H), 7.98 (s, 1H); MS DCI m/e, 263 (M+NH₄)⁺.

Example 87B

2-{2-[(2R)-2-methylpyrrolidin-1-yl]ethyl}-1-benzofuran-5-carbonitrile

The product from Example 87A (10.0 g, 40.81 mmol) was sequentially treated with 0.1M (2R)-1-(3-butynyl)-2-methylpyrrolidine in acetonitrile (490 mL, 48.9 mmol), Pd(OAc)₂ (0.275 g, 1.22 mmol), Ptol₃ (0.747 g, 2.44 mmol), and copper iodide (1.16 g, 6.122 mmol). After stirring at 25° C. for 10 min, diisopropyl amine (43.0 mL) was added and the reaction mixture was heated at 60° C. in an inert atmosphere for 16 h. The reaction mixture was cooled, filtered through celite, concentrated under reduced pressure, and purified on silica gel using 95% DCM, 9.5% MeOH, 0.1% NH₄OH to provide the title compound as a brown semi-solid (2.56 g, 24.6% yield). ¹HNMR (300 MHz, CD₃OD) δ 1.09 (d, 3H, J=6.1 Hz), 1.46 (m, 1H), 1.81 (m, 2H), 2.02–2.38 (m, 2H), 2.59 (m, 2H) 3.08 (m, 2H), 3.28 (m, 2H), 6.70 (s, 1H), 7.58 (s, 1H), 7.97 (s, 1H); MS (ESI) m/e 255 (M+H)⁺.

Example 87C

N'-hydroxy-2-{2-[(2R)-2-methylpyrrolidin-1-yl]ethyl}-1-benzofuran-5-carboximidamide The product from Example 87B (2.5 g, 9.83 mmol) in EtOH (200 mL) was stirred at 25° C. for 10 minutes. The mixture was treated with hydroxylamine hydrochloride (1.71 g, 24.6 mmol) and potassium carbonate (4.49 g, 32.48 mmol) and the resulting mixture was heated at 95° C. for 16 h with stirring. The reaction mixture was subsequently cooled, filtered through celite, and concentrated under reduced pressure. The crude product was purified with flash chromatography to provide the title compound (1.43 g, 51% yield). MS (ESI) m/e 288 (M+H)⁺.

Example 87D 3-(2-{2-[(2R)-2-methylpyrrolidin-1-yl]ethyl}-1-benzofuran-5-yl)-5-(thien-2-ylmethyl)-1,2,4-oxadiazole The product from Example 87C (0.06 g, 0.209 mmol) in acetone (10 mL) was treated with triethylamine (34.9 μL, 0.25 mmol) and stirred at 25° C. for 10 minutes. The mixture was slowly treated with thien-2-ylacetyl chloride (25.7 μL, 0.25 mmol) and stirred at 25° C. for 18 h. The solvent was evaporated under reduced pressure, redissolved in dichloromethane (DCM) (25 mL), washed twice with water (25 mL), dried, and concentrated. The residue was dissolved in toluene (25 mL) and heated at 110° C. in the presence of 3 Å molecular sieves for 16 h. The solvent was evaporated and crude product was purified on a Waters Nova-Pak HR C18 column (40 mm×100 mm, 6 □m particle size) using a gradient of 10% to 100% acetonitrile: 0.1% aqueous TFA over 12 min (15 min run time) at a flow rate of 70 mL/min to provide the title compound. ¹HNMR (300 MHz, CD₃OD) δ 1.42 (d, 3H, J=6.1 Hz), 1.78 (m, 1H), 2.09 (m, 2H), 2.36 (m, 1H), 3.20–3.59 (m, 5H), 3.78 (m, 2H), 4.59 (s, 2H), 6.82 (s, 1H), 7.01 (t, 1H). 7.09 (s, 1H), 7.38 (dd, 1H), 7.60 (d, 1H), 8.01 (dd, 1H), 8.27 (s, 1H); MS (ESI) m/e 394 (M+H)⁺.

Example 88

4-[3-(2-{2-[(2R)-2-methylpyrrolidin-1-yl]ethyl}-1-benzofuran-5-yl)-1,2,4-oxadiazol-5-yl]benzonitrile 4-Cyanobenzoyl chloride was processed as described in Example 87D to provide the title compound. ¹HNMR (300 MHz, CD₃OD) δ 1.46 (d, 3H, J=6.1 Hz), 1.78 (m, 1H), 2.09 (m, 2H), 2.36 (m, 1H), 3.18–3.79 (m, 7H), 6.82 (s, 1H), 7.18 (m, 2H), 7.65 (d, 1H), 8.03 (d, 2H), 8.16 (dd, 1H), 8.41 (s, 1H); MS (ESI) m/e 399 (M+H)⁺.

Example 89

5-(4-chlorophenyl)-3-(2-{2-[(2R)-2-methylpyrrolidin-1-yl]ethyl}-1-benzofuran-5-yl)-1,2,4-oxadiazole 4-Chlorobenzoyl chloride was processed as described in Example 87D to provide the title compound. MS (ESI) m/e 408 (M+H)⁺.

Example 90

5-(2-chlorophenyl)-3-(2-{2-[(2R)-2-methylpyrrolidin-1-yl]ethyl}-1-benzofuran-5-yl)-1,2,4-oxadiazole 2-Chlorobenzoyl chloride was processed as described in Example 87D to provide the title compound. ¹HNMR (300 MHz, CD₃OD) δ 1.46 (d, 3H, J=6.1 Hz), 1.78 (m, 1H), 2.11 (m, 2H), 2.38 (m, 1H), 3.21–3.90 (m, 7H), 6.88 (s, 1H), 7.56–7.73 (m, 4H), 8.17 (m, 2H), 8.41 (s, 1H); MS (ESI) m/e 408 (M+H)⁺.

Example 91

5-(4-fluorobenzyl)-3-(2-{2-[(2R)-2-methylpyrrolidin-1-yl]ethyl}-1-benzofuran-5-yl)-1,2,4-oxadiazole (4-Fluorophenyl)acetyl chloride was processed as described in Example 87D to provide the title compound. ¹HNMR (300 MHz, CD₃OD) δ 1.46 (d, 3H, J=6.1 Hz), 1.78 (m, 1H), 2.11 (m, 2H), 2.38 (m, 1H), 3.21–3.90 (m, 7H), 4.38 (s, 2H), 6.82 (s, 1H), 7.10 (m, 2H), 7.42 (m, 2H), 7.59 (d, 1H), 7.99 (dd, 1H), 8.26 (s, 1H); MS (ESI) m/e 406 (M+H)⁺.

Example 92

5-(4-methoxybenzyl)-3-(2-{2-[(2R)-2-methylpyrrolidin-1-yl]ethyl}-1-benzofuran-5-yl)-1,2,4-oxadiazole (4-Methoxyphenyl)acetyl chloride was processed as described in Example 87D to provide the title compound. ¹HNMR (300 MHz, CD₃OD) δ 1.46 (d, 3H, J=6.1 Hz), 1.78 (m, 1H), 2.10 (m, 2H), 2.38 (m, 1H), 3.21–3.90 (m, 7H), 3.78 (s, 3H), 4.28 (s, 2H), 6.83 (s, 1H), 6.92 (d, 2H), 7.32 (d, 2H), 7.59 (d, 1H), 7.99 (dd, 1H), 8.26 (s, 1H); MS (ESI) m/e 418 (M+H)⁺.

Example 93

3-{[3-(2-{2-[(2R)-2-methylpyrrolidin-1-yl]ethyl}-1-benzofuran-5-yl)-1,2,4-oxadiazol-5-yl]methyl}benzonitrile 3-Cyanobenzoyl chloride was processed as described in Example 87D to provide the title compound. ¹HNMR (300 MHz, CD₃OD) δ 1.46 (d, 3H, J=6.1 Hz), 1.78 (m, 1H), 2.11 (m, 2H), 2.38 (m, 1H), 3.21–3.91 (m, 7H), 6.86 (s, 1H), 7.56 (m, 2H), 7.62 (d, 1H), 8.09 (dd, 1H), 8.21 (m, 1H), 8.38 (m, 2H); MS (ESI) m/e 399 (M+H)⁺.

Example 94

3-(2-{2-[(2R)-2-methylpyrrolidin-1-yl]ethyl}-1-benzofuran-5-yl)-5-phenyl-1,2,4-oxadiazole Benzoyl chloride was processed as described in Example 87D to provide the title compound. MS (ESI) m/e 374 (M+H)⁺.

Example 95

5-(4-fluorophenyl)-3-(2-{2-[(2R)-2-methylpyrrolidin-1-yl]ethyl}-1-benzofuran-5-yl)-1,2,4-oxadiazole 4-Fluorobenzoyl chloride was processed as described in Example 87D to provide the title compound. MS (ESI) m/e 392 (M+H)$^+$.

Example 96

5-(3-chloro-4-fluorophenyl)-3-(2-{2-[(2R)-2-methylpyrrolidin-1-yl]ethyl}-1-benzofuran-5-yl)-1,2,4-oxadiazole 3-Chloro-4-fluorobenzoyl chloride was processed as described in Example 87D to provide the title compound. MS (ESI) m/e 426 (M+H)$^+$.

Example 97

5-(chloromethyl)-3-(2-{2-[(2R)-2-methylpyrrolidin-1-yl]ethyl}-1-benzofuran-5-yl)-1,2,4-oxadiazole Chloroacetyl chloride was processed as described in Example 87D to provide the title compound. $^1$HNMR(300 MHz, CD$_3$OD) δ 1.46 (d, 3H, J=6.1 Hz), 1.78 (m, 1H), 2.10 (m, 2H), 2.38 (m, 1H), 3.21–3.90 (m, 7H), 4.96 (s, 2H), 6.83 (s, 1H), 7.61 (d, 1H), 8.02 (dd, 1H), 8.29 (s, 1H); MS (ESI) m/e 346 (M+H)$^+$.

Example 98

3-(2-{2-[(2R)-2-methylpyrrolidin-1-yl]ethyl}-1-benzofuran-5-yl)-5-propyl-1,2,4-oxadiazole Butanoyl chloride was processed as described in Example 87D to provide the title compound. $^1$HNMR (300 MHz, CD$_3$OD) δ 1.42–1.48 (m, 10H), 1.78 (m, 1H), 2.10 (m, 2H), 2.38 (m, 1H), 3.21–3.90 (m, 7H), 4.96, 6.83 (s, 1H), 7.59 (d, 1H), 8.01 (dd, 1H), 8.27 (s, 1H); MS (ESI) m/e 340 (M+H)$^+$.

Example 99

5-ethyl-3-(2-{2-[(2R)-2-methylpyrrolidin-1-yl]ethyl}-1-benzofuran-5-yl)-1,2,4-oxadiazole Propanoyl chloride was processed as described in Example 87D to provide the title compound. MS (ESI) m/e 326 (M+H)$^+$.

Example 100

5-methyl-3-(2-{2-[(2R)-2-methylpyrrolidin-1-yl]ethyl}-1-benzofuran-5-yl)-1,2,4-oxadiazole Acetyl chloride was processed as described in Example 87D to provide the title compound. MS (ESI) m/e 312 (M+H)$^+$.

Example 101

4-(3-bromo-2-{2-[(2R)-2-methylpyrrolidin-1-yl]ethyl}-1-benzofuran-5-yl)benzonitrile The product from Example 1D (2.5 g, 5.2 mmol) and trifluoroacetic acid (40 mL) (TFA) were combined and stirred at 25° C. for 10 min. The mixture was slowly treated with a solution of Br$_2$ (450 μL, 7.8 mmol) in TFA (10 mL). The mixture was allowed to stir at 25° C. for 1 h and then treated with saturated aqueous Na$_2$SO$_3$. The mixture was concentrated and redissolved in 50 mL ethyl acetate. The organic phase was washed with 1M NaOH, dried, and concentrated under reduced pressure to provide the title compound (2.1 g, 97% yield). $^1$HNMR (300 MHz, CD$_3$OD) δ 1.16 (d, 3H, J=6.1 Hz), 1.42 (m, 1H), 1.78 (m, 2H), 1.98 (m, 1H), 2.32 (m, 1H), 2.50 (m, 2H), 3.11 (m, 2H), 3.28 (m, 2H), 7.58–7.70 (m, 3H), 7.82 (m, 4H); MS (ESI) m/e 409 (M+H)$^+$.

Example 102

4-(3-(2-furyl)-2-{2-[(2R)-2-methylpyrrolidin-1-yl]ethyl}-1-benzofuran-5-yl)benzonitrile The product from Example 101 (0.100 g, 0.244 mmol) in dimethoxyethane (DME) (10 mL) was treated with Pd(PPh$_3$)$_4$ (0.008 g, 0.0073 mmol), 2-furylboronic acid (0.041 g, 0.317 mmol), and 1M Na$_2$CO$_3$ (1 mL) and the reaction mixture was refluxed in an inert atmosphere for 18 h. The mixture was allowed to cool to room temperature, filtered through celite, and concentrated under reduced pressure. The crude product was purified on a Waters Nova-Pak HR C18 column (40 mm×100 mm, 6 μm particle size) using a gradient of 10% to 100% acetonitrile: 0.1% aqueous TFA over 12 min (15 min run time) at a flow rate of 70 mL/min to provide the title compound. $^1$HNMR (300 MHz, CD$_3$OD) δ 1.46 (d, 3H, J=6.1 Hz), 1.78 (m, 1H), 2.09 (m, 2H), 2.38 (m, 1H), 3.46–3.96 (m, 7H), 6.67 (s, 1H), 6.98 (s, 1H), 7.64–7.77 (m, 3H). 7.81–7.92 (m, 4H), 8.16 (s, 1H); MS (ESI) m/e 397 (M+H)$^+$.

Example 103

4-[2-{2-[(2R)-2-methyl-1-pyrrolidinyl]ethyl}-3-(3-pyridinyl)-1-benzofuran-5-yl]benzonitrile 3-Pyridinylboronic acid was processed as described in Example 102 to provide the title compound. 1HNMR (300 MHz, CD$_3$OD) δ 1.46 (d, 3H, J=6.1 Hz), 1.78 (m, 1H), 2.06 (m, 2H), 2.37 (m, 1H), 3.20–3.96 (m, 7H), 7.73–7.87 (m, 8H). 8.36 (d, 1H), 8.76 (s, 1H), 8.92 (s, 1H); MS (ESI) m/e 408 (M+H)$^+$.

Example 104

4-[2-{2-[(2R)-2-methyl-1-pyrrolidinyl]ethyl}-3-(3-thienyl)-1-benzofuran-5-yl]benzonitrile 3-Thienylboronic acid was processed as described in Example 102 to provide the title compound. $^1$HNMR (300 MHz, CD$_3$OD) δ 1.43 (d, 3H, J=6.1 Hz), 1.76 (m, 1H), 2.03 (m, 2H), 2.35 (m, 1H), 3.18–3.89 (m, 7H), 7.42 (dd, 1H), 7.65–7.72 (m, 4H), 7.78–7.87 (m, 5H); MS (ESI) m/e 413 (M+H)$^+$.

Example 105

4-(3-(2-formyl-3-thienyl)-2-{2-[(2R)-2-methyl-1-pyrrolidinyl]ethyl}-1-benzofuran-5-yl)benzonitrile 2-Formyl-3-thienylboronic acid was processed as described in Example 102 to provide the title compound. MS (ESI) m/e 441 (M+H)$^+$.

Example 106

2-methyl-4-(2-{2-[(2R)-2-methyl-1-pyrrolidinyl]ethyl}-1-benzofuran-5-yl)benzonitrile

Example 106A

4'-methoxy-3-methyl-1,1'-biphenyl-4-carbonitrile

4-Bromo-2-methylbenzonitrile (4.9 g, 25.0 mmol), Pd(PPh$_3$)$_4$ (578 mg) in benzene (50 mL) and 2.0 M aqueous solution of $Na_2CO_3$ (25 mL, 50.0 mmol) was treated with 4-methoxyphenylboronic acid (4.56 g, 30.0 mmol) in ethanol (20 mL) and heated at 75° C. for 17 hours. The mixture was allowed to cool to room temperature and the phases were separated. The aqueous phase was extracted with diethyl ether (3×40 mL). The original benzene layer and the diethyl ether extracts were combined, filtered over celite, dried over sodium sulfate, and filtered. The filtrate was concentrated under reduced pressure and the residue was purified by chromatography over silica using a mixture of hexane/$CH_2Cl_2$ (3:1) to provide the title compound as a white powder (5.73 g, 85% yield). $^1$HNMR (300 MHz, $CDCl_3$) δ 2.35 (3H), 3.70 (s, 3H), 6.80–7.50 (m, 7H); MS (DCI) m/z 224 (M+H)$^+$.

Example 106B

4'-hydroxy-3-methyl-1,1'-biphenyl-4-carbonitrile

The product from Example 106A (5.60 g, 25.4 mmol) in $CH_2Cl_2$ (120 mL) at 78° C. was treated with 1.0 M $BBr_3$ (in $CH_2Cl_2$, 76 mL, 76.0 mmol) dropwise over 1 hour. After stirring for 14 hours at room temperature, the mixture was warmed to 0° C. (ice bath) and treated with water (0.5 mL). After 10 minutes, additional water was added (2.0 mL), ice bath was removed, and 5.0 mL of water was added. The mixture was then treated with another 20 mL of water and allowed to stir for 45 minutes. The mixture was filtered and the filtrate extracted with $CH_2Cl_2$. The $CH_2Cl_2$ layers were combined, dried over sodium sulfate, filtered, and the filtrate concentrated under reduced pressure to provide the title compound as an off-white powder (5.04 g, 94% yield). $^1$HNMR (300 MHz, $CDCl_3$) δ 2.35 (s, 3H), 5.0 (s, 1H), 6.79–7.50 (m, 7H); MS (DCI) m/z 210 (M+H)$^+$.

Example 106C

4'-hydroxy-3'-iodo-3-methyl-1,1'-biphenyl-4-carbonitrile

The product from Example 106B (4.67 g, 22.3 mmol), NaI (3.343 g, 22.3 mmol), and NaOH (892 mg, 22.3 mmol) were combined in methanol (70 mL) at 0° C. and treated with bleach (5.25%, 31.6 g) dropwise over 30 minutes. After being stirred at 0° C. for 80 minutes, the mixture was quenched with 10% aqueous sodium thiosulfate (10 mL). The mixture was acidified with 1M aqueous HCl (25 mL), neutralized with dipotassium hydrogen phosphate, recooled to 0° C., and filtered. The solids were rinsed with water, then mostly dissolved in 50% EtOAc/hexanes and filtered. When this filtrate was mostly concentrated crystals began to form. The solids were slurried with 20% EtOAc/hexanes, collected by filtration, and washed with 10% EtOAc/hexanes followed by hexanes to provide the impure title compound as a light tan powder (52% yield). MS (ESI APCI negative ion detection) m/z 334 (M–H)$^-$; $^1$HNMR (300 MHz, $d_6$-DMSO) δ 2.52 (s, 3H), 6.98 (d, 1 H), 7.58–7.63 (m, 2 H), 7.73 (s, 1 H), 7.78 (d, 1 H), 8.06 (d, 1 H), 10.66 (s, 1 H).

Example 106D 2-methyl-4-(2-{2-[(2R)-2-methyl-1-pyrrolidinyl]ethyl}-1-benzofuran-5-yl)benzonitrile The product from Example 106C (670 mg, 2.00 mmol), palladium (II) acetate (22 mg, 0.10 mmol), tri-o-tolylphosphine (61 mg, 0.20 mmol), copper (I) iodide (114 mg, 0.60 mmol), and diisopropylamine (2.8 mL, 20 mmol) were dissolved into a 0.1M MeCN solution of (R)-1-but-3-ynyl-2-methylpyrrolidine (30 mL, 3.0 mmol) and heated at 55° C. overnight. The mixture was cooled to room temperature, concentrated under reduced pressure, and chromatographed through a short column of silica with a 10 to 100% gradient of EtOAc/$CH_2Cl_2$ to provide the impure title compound as an orange-brown foam (55% yield), a portion of which was purified by HPLC [Waters Nova-Pak HR C18 column (40 mm×100 mm, 6 μm particle size) using a gradient of 10% to 100% MeCN/0.1% aqueous TFA over 12 min (15 min run time) at a flow rate of 70 mL min.]. TFA salt: MS (AP) m/z 345 (M+H)$^+$; $^1$HNMR (300 MHz, $CD_3OD$) δ 1.49 (d, 3 H), 1.68–1.82 (m, 1 H), 1.99–2.23 (m, 2H), 2.30–2.44 (m, 1 H), 2.60 (s, 3 H), 3.22–3.90 (m, 7 H) 6.82 (s, 1 H), 7.55–7.87 (m, 6 H).

Example 107

3-methyl-4-(2-{2-[(2R)-2-methyl-1-pyrrolidinyl]ethyl}-1-benzofuran-5-yl)benzonitrile

Example 107A

4'-hydroxy-3'-iodo-2-methyl-1,1'-biphenyl-4-carbonitrile

4'-Hydroxy-2-methyl-1,1'-biphenyl-4-carbonitrile was processed as described in Example 106C to provide the title compound as a light tan powder (69% yield). MS (ESI APCI negative ion detection) m/z 334 (M–H)$^-$; $^1$HNMR (300 MHz, $d_6$-DMSO) 67 2.27 (s, 3H), 6.96 (d, 1 H), 7.23 (dd, 1 H), 7.37 (d, 1 H), 7.65–7.69 (m, 2 H), 7.77 (d, 1 H), 10.56 (s, 1H).

Example 107B 3-methyl-4-(2-{2-[(2R)-2-methyl-1-pyrrolidinyl]ethyl}-1-benzofuran-5-yl)benzonitrile The product from Example 107A was processed as described in Example 106D to provide the impure title compound as an orange-brown foam (42% yield), a portion of which was purified by HPLC to provide the TFA salt. $^1$HNMR (300 MHz, $CD_3OD$) δ 1.49 (d, 3 H), 1.68–1.83 (m, 1 H), 1.98–2.24 (m, 2 H), 2.29 (s, 3 H), 2.29–2.43 (m, 1 H), 3.18–3.90 (m, 7 H), 6.79 (s, 1 H), 7.24 (dd, 1 H), 7.39 (d, 1 H), 7.50–7.70 (m, 4 H).

Example 108

4-(6-methyl-2-{2-[(2R)-2-methyl-1-pyrrolidinyl]ethyl}-1-benzofuran-5-yl)benzonitrile and 4-(4-methyl-2-{2-[(2R)-2-methyl-1-pyrrolidinyl]ethyl}-1-benzofuran-5-yl)benzonitrile 4'-hydroxy-5'-iodo-2'-methyl-1,1'-biphenyl-4-carbonitrile and 4'-hydroxy-3'-iodo-2'-methyl-1,1,'-biphenyl-4-carbonitrile 4'-Hydroxy-2'-methyl-1,1'-biphenyl-4-carbonitrile was processed as described in Example 106C, except that after neutralization with dipotassium hydrogen phosphate the mixture was extracted with 20% hexanes/EtOAc. The residue was chromatographed through silica with a 25% to 75% gradient of $CH_2Cl_2$/hexanes to provide a 7.6:1 mixture (NMR) of the title compounds as a white microcrystalline solid (67% yield). MS (ESI APCI negative ion detection) m/z 334 (M–H)$^-$; $^1$HNMR (300 MHz, $CDCl_3$) δ 2.18 (s, 3 H), 5.29 (s, 1 H), 6.93 (s, 1 H), 7.38 (d, 2 H), 7.48 (s, 1 H), 7.69 (d, 2 H).

Example 108B 4-(6-methyl-2-{2-[(2R)-2-methyl-1-pyrrolidinyl]
ethyl}-1-benzofuran-5-yl)benzonitrile and 4-(4-methyl-2-{2-[(2R)-2-methyl-1-pyrrolidinyl]
ethyl}-1-benzofuran-5-yl)benzonitrile The 7.6:1 mixture of Example 108A was processed as described Example 106D, except that after concentration the residue was partitioned between $CH_2Cl_2$ and 10% aqueous ammonia. The residue was chromatographed through a short column of silica with a 0% to 2% gradient of $MeOH/CH_2Cl_2$ and then purified by HPLC [Waters Nova-Pak HR C18 column (40 mm×100 mm, 6 □m particle size) using a gradient of 10% to 100% MeCN/0.1% aqueous TFA over 12 min (15 min run time) at a flow rate of 70 mL/min.] to provide the TFA salt of the title compounds as a brown-orange gum (23% yield). MS (ESI APCI) m/z 345 (M+H)$^+$; $^1$HNMR (300 MHz, $CD_3OD$) δ 1.48 (d, 3 H), 1.67–1.83 (m, 1 H), 1.98–2.23 (m, 2 H), 2.3–2.42 (m, 1 H), 2.31 (s, 3 H), 3.19–3.61 (m, 5 H), 3.70–3.88 (m, 2 H), 6.53 (s, 1H), 7.32 (s, 1 H), 7.36 (s, 1 H), 7.52 (d, 2 H), 7.79 (d, 2 H).

Example 109

4-(7-methyl-2-{2-[(2R)-2-methyl-1-pyrrolidinyl]
ethyl}-1-benzofuran-5-yl)benzonitrile

Example 109A

4'-hydroxy-5'-iodo-3'-methyl-1,1'-biphenyl-4-carbonitrile

4'-hydroxy-3'-methyl-1,1'-biphenyl-4-carbonitrile (875 mg, 4.18 mmol) was dissolved into DMF (20 mL) and treated with N-iodosuccinimide (1.012 g, 4.5 mmol). The solution was stirred at room temperature for four days. Then the mixture was stirred with tetramethylguanidine (1 mL) for ten minutes, poured into an aqueous mixture of $Na_2SO_3$ and $Na_2CO_3$, adjusted to pH 9 with aqueous potassium dihydrogen phosphate, and diluted with ether. The gum which separated from the biphasic mixture was dissolved into EtOAc and added to a rapidly stirred mixture of the aqueous phase and ether. The organic phase was separated, filtered, combined with the original ethereal phase, concentrated, and chromatographed through silica with a 50% to 100% gradient of $CH_2Cl_2$/hexanes to provide the title compound as an off-white powder (17% yield). MS (ESI APCI negative ion detection) m/z 334 (M−H)$^-$; $^1$HNMR (300 MHz, $CDCl_3$) δ 2.38 (s, 3 H), 7.26 (s, 1 H), 7.33 (d, 1 H), 7.60 (d, 2 H), 7.66–7.74 (m, 3 H).

Example 109B 4-(7-methyl-2-{2-[(2R)-2-methyl-1-pyrrolidinyl]
ethyl}-1-benzofuran-5-yl)benzonitrile The product from Example 109A was processed as described for Example 106D to provide the title compound as a brown-orange gum (44% yield), a portion of which was purified by HPLC [Waters Nova-Pak HR C18 column (40 mm×100 mm, 6 μm particle size) using a gradient of 10% to 100% MeCN/0.1% aqueous TFA over 12 min (15 min run time) at a flow rate of 70 mL/min.] to provide the TFA salt. MS (ESI APCI) m/z 345 (M+H)$^+$; $^1$HNMR (300 MHz, $CD_3OD$) δ 1.49 (s, 3 H), 1.68–1.83 (m, 1 H), 1.99–2.23 (m, 2 H), 2.30–2.43 (m, 1 H), 2.57 (s, 3 H), 3.21–3.64 (m, 5 H), 3.71–3.91 (m, 2 H), 6.79 (s, 1 H), 7.41 (m, 1H), 7.68 (d, 1 H), 7.75–7.84 (m, 4 H).

Example 110

4-(7-fluoro-2-{2-[(2R)-2-methyl-1-pyrrolidinyl]
ethyl}-1-benzofuran-5-yl)benzonitrile

Example 110A

3'-fluoro-4'-hydroxy-5'-iodo-1,1'-biphenyl-4-carbonitrile

3'-Fluoro-4'-hydroxy-1,1'-biphenyl-4-carbonitrile (320 mg, 1.50 mmol) was dissolved into DMF (7 mL) and treated with N-iodosuccinimide (360 mg, 1.60 mmol). The solution was stirred at room temperature overnight. Then the mixture was poured into an aqueous mixture of $Na_2SO_3$ and $Na_2CO_3$, adjusted to pH 9 with aqueous potassium dihydrogen phosphate, and extracted with ether. The combined organic phases were dried ($Na_2SO_4$) and concentrated to provide the title compound as a pinkish solid (100% yield). MS (ESI APCI negative ion detection) m/z 338 (M−H)$^-$.

Example 110B 4-(7-fluoro-2-{2-[(2R)-2-methyl-1-pyrrolidinyl]
ethyl}-1-benzofuran-5-yl)benzonitrile The product from Example 110A was processed as described for Example 106D, except that after the solution was heated overnight, it was heated for an additional eight hours at 80° C. The reaction mixture was cooled to room temperature and chromatographed through a short column of silica with 1:8 hexanes/$CH_2Cl_2$, followed by a 0 to 2% gradient of $MeOH/CH_2Cl_2$. The appropriate fractions were concentrated and purified by HPLC [Waters Nova-Pak HR C18 column (25 mm×100 mm, 6 μm particle size) using a gradient of 10% to 100% MeCN 10.1% aqueous TFA over 8 min (10 min run time) at a flow rate of 40 mL/min.] to provide the title compound (2% yield). MS (ESI) m/z 349 (M+H)$^+$; $^1$HNMR (300 MHz, $CD_3OD$) δ 1.18 (d, 3 H), 1.39–1.53 (m, 1 H), 1.74–1.86 (m, 2 H), 1.95–2.09 (m, 1 H), 2.26–2.38 (m, 1 H), 2.44–2.63 (m, 2 H), 2.98–3.36 (m, 4 H), 6.72 (d, 1 H), 7.37 (dd, 1 H), 7.65 (d, 1 H), 7.77–7.87 (m, 4 H).

Example 111

2-fluoro-4-(2-{2-[(2R)-2-methyl-1-pyrrolidinyl]
ethyl}-1-benzofuran-5-yl)benzonitrile

Example 111A 3-fluoro-4'-methoxy-1,1'-biphenyl-4-carbonitrile

A mixture of 4-methoxyphenylboronic acid (4.56 g, 30.0 mmol) in ethanol (20 mL) was added to a solution of 4-bromo-2-fluorobenzonitrile (5.00 g, 25.0 mmol) and tetrakis(triphenylphosphine)palladium (578 mg, 0.50 mmol) in benzene (50 mL). The resulting mixture was treated with a 2.0 M aqueous solution of $Na_2CO_3$ (25 mL, 50 mmol) and heated briefly at reflux, then at 65° C. overnight. The mixture was cooled to room temperature and treated with 6.0 M aqueous NaOH. The aqueous phase was separated and extracted with ether. First the original organic phase and then the ethereal wash were filtered through diatomaceous earth. The collection flask was changed and the solids remaining atop the diatomaceous earth were washed through with EtOAc. The ethereal wash was concentrated and refiltered as before. The combined EtOAc rinses were combined and concentrated to provide the title compound as a yellow powder (92% yield). $^1$HNMR (300 MHz, $d_6$-DMSO) δ 3.82

(s, 3 H), 7.07 (d, 2 H), 7.72 (dd, 1 H), 7.79 (d, 2 H), 7.85 (dd, 1 H), 7.95 (dd, 1 H).

Example 111B 3-fluoro-4'-hydroxy-1,1'-biphenyl-4-carbonitrile

The product from Example 111A was processed as described in Example 106B, except that the extraction was conducted with EtOAc, to provide the title compound as a tan powder (100% yield). MS (ESI APCI negative ion detection) m/z 212 (M–H)$^-$; $^1$HNMR (300 MHz, CDCl$_3$) δ 3.82 (bs, 1 H), 6.94 (d, 2 H), 7.37 (dd, 1 H), 7.41–7.49 (m, 3 H), 7.63 (dd, 1H).

Example 111C 3-fluoro-4'-hydroxy-3'-iodo-1,1'-biphenyl-4-carbonitrile

The product from Example 111B was processed as described for Example 106C, except that the solids collected after cold-filtering were rinsed consecutively with 50% aqueous methanol and water, and dried under reduced pressure to provide the title compound as an off-white powder (86% yield). MS (ESI negative ion detection) m/z 338 (M–H)$^-$; $^1$HNMR (300 MHz, CDCl$_3$/CD$_3$OD) δ 3.53 (bs, 1 H), 6.96 (d, 1H), 7.34–7.49 (m, 3 H), 7.65 (dd, 1 H), 7.94 (d, 1 H).

Example 111D 2-fluoro-4-(2-{2-[(2R)-2-methyl-1-pyrrolidinyl]ethyl}-1-benzofuran-5-yl)benzonitrile The product from Example 111C was processed as described for Example 106D, except that the solution was heated at 50° C. overnight and then at 80° C. for eight hours. The reaction mixture was cooled to room temperature and chromatographed through a short column of silica with a 0 to 2% gradient of MeOH/CH$_2$Cl$_2$. The appropriate fractions were concentrated and then rechromatographed through a short column of silica with 1% AcOH/CH$_2$Cl$_2$, followed by a 0 to 2% gradient of MeOH/CH$_2$Cl$_2$ to provide the acetic acid salt of the title compound as a brown foamy powder (28% yield). MS (ESI APCI) m/z 349 (M+H)$^+$; $^1$HNMR(300 MHz, CD$_3$OD) □ 1.40 (d, 3 H), 1.60–1.77 (m, 1 H), [1.97 (s)], 1.97–2.11 (m, 2H), 2.20–2.36 (m, 1 H), 2.99–3.10 (m, 1 H), 3.16–3.76 (m, 6 H), 6.79 (s, 1 H), 7.58 (d, 1 H), 7.62 (dd, 1 H), 7.64–7.70 (m, 2 H), 7.81 (dd, 1 H), 7.90 (d, 1 H).

Example 112

3-(2-{2-[(2R)-2-methyl-1-pyrrolidinyl]ethyl}-1-benzofuran-5-yl)benzonitrile

Example 112A 4-bromo-2-iodophenol

4-Bromophenol was processed as described in Example 106C, except that after neutralization the mixture was partitioned between 20% EtOAc/hexanes (250 mL) and brine (50 mL) and the aqueous phase was separated and reextracted until nearly all the product was removed (TLC). The combined organic phases were washed with brine, dried (Na$_2$SO$_4$), and concentrated to provide the (90% pure) title compound (100% yield). A portion was purified by chromatography on silica using a 25 to 80% gradient of CH$_2$Cl$_2$/hexanes. $^1$HNMR (300 MHz, d$_6$-DMSO) □ 6.83 (d, 1 H), 7.36 (dd, 1 H), 7.79 (d, 1 H), 10.59 (s, 1 H).

Example 112B 2-(5-bromo-1-benzofuran-2-yl)ethanol

The product from Example 112A (26.9 g, 90% pure, 80 mmol), 3-butyn-1-ol (6.05 mL, 79.9 mmol), and copper (I) oxide (7.15 g, 50.0 mmol) were suspended in a mixture of pyridine (40 mL) and 1-methyl-2-pyrrolidinone (160 mL) and heated at 70° C. overnight, then at 100° C. for 3.5 hours. The mixture was cooled towards room temperature, diluted with ether and filtered. The filtrate was diluted with additional ether and washed consecutively with 5% aqueous ammonia, 0.5 M aqueous NaOH, and brine. It was dried (Na$_2$SO$_4$), concentrated, and reconcentrated from EtOAc. 2:1 Hexanes/CH$_2$Cl$_2$ was added to the resulting syrup and the mixture was cooled to –78° C. Upon warming towards room temperature, the pure title compound crystallized as an off-white microcrystalline solid. It was collected by filtration and washed with 4:1 hexanes/CH$_2$Cl$_2$, then hexanes (8% yield). $^1$HNMR (300 MHz, d$_6$-DMSO) δ 2.92 (t, 2 H), 3.75 (dt, 2 H), 4.82 (t, 1 H), 6.63 (s, 1 H), 7.35 (dd, 1 H), 7.48 (d, 1 H), 7.75 (d, 1 H).

Example 112C

3-[2-(2-hydroxyethyl)-1-benzofuran-5-yl]benzonitrile

The product from Example 112B (193 mg, 0.80 mmol), 3-cyanophenylboronic acid (147 mg, 1.00 mmol), and tetrakis(triphenylphosphine)palladium (35 mg, 0.030 mmol) were suspended into dioxane (3 mL) and then treated with 1.0 M aqueous Na$_2$CO$_3$ (2.1 mL, 2.1 mmol). The mixture was heated at 90° C. for 3.5 hours, then cooled to room temperature, partitioned between EtOAc and water, worked up as usual, dried (Na$_2$SO$_4$), and concentrated. The residue was chromatographed through a short column of silica with a 0 to 2% gradient of EtOAc/CH$_2$Cl$_2$ to provide the title compound as a tea-colored syrup (82% yield). $^1$HNMR (300 MHz, d$_6$-DMSO) δ 2.95 (t, 2 H), 3.78 (dt, 2 H), 4.83 (t, 1H), 6.70 (s, 1 H), 7.59–7.61 (m, 2 H), 7.66 (dd, 1 H), 7.80 (ddd, 1 H), 7.91 (dd, 1 H), 8.04 (ddd, 1 H), 8.15 (dd, 1 H).

Example 112D

2-[5-(3-cyanophenyl)-1-benzofuran-2-yl]ethyl methanesulfonate

The product from Example 112C (170 mg, 0.65 mmol) and triethylamine (100 µL, 0.72 mmol) were dissolved into CH$_2$Cl$_2$ (3 mL) and cooled to 0° C. The solution was treated with methanesulfonyl chloride (55 µL, 0.71 mmol), and after 10 minutes it was permitted to slowly warm to room temperature. More methanesulfonyl chloride (10 µL, 0.13 mmol) and triethylamine (10 µL, 0.072 mmol) were added. The mixture was stirred until the reaction was nearly complete and then washed consecutively with water and brine, dried (Na$_2$SO$_4$), concentrated, and used without further purification in the next step.

Example 112E 3-(2-{2-[(2R)-2-methyl-1-pyrrolidinyl]ethyl}-1-benzofuran-5-yl)benzonitrile The crude product from Example 112D, the mono-(L)-tartaric acid salt of (2R)-2-methylpyrrolidine (306 mg, 1.3 mmol), and Cs$_2$CO$_3$ (652 mg, 2.0 mmol) were stirred in an approximately 0.2 M MeCN solution of (2R)-2-methylpyrrolidine (1.6 mL, 0.3 mmol). The mixture was heated at 40° C. overnight. More Cs₂CO₃ (326 mg, 1.0 mmol) and acetonitrile (0.5 mL) were added and the reaction was stirred at 40° C. for four days. The mixture was cooled to room temperature, diluted with CH₂Cl₂, filtered, and concentrated. The residue was chromatographed twice through a short column of silica with a 0 to 5% gradient of MeOH/CH₂Cl₂ to provide the title compound as an orange-tan gum (28% yield). ¹HNMR (300 MHz, CD₃OD) δ 1.18 (d, 3 H), 1.39–1.54 (m, 1 H), 1.75–1.87 (m, 2H), 1.96–2.09 (m, 1H), 2.27–2.39 (m, 1 H), 2.46–2.63 (m, 2 H), 2.95–3.15 (m, 2 H), 3.20–3.35 (m, 2 H), 6.63 (s, 1H), 7.49–7.52 (m, 2 H), 7.62 (dd, 1 H), 7.67 (ddd, 1 H), 7.78 (dd, 1 H), 7.90 (ddd, 1 H), 7.98 (dd, 1 H).

Example 113

(2R)-1-{2-[5-(4-fluorophenyl)-1-benzofuran-2-yl]ethyl}-2-methylpyrrolidine

Example 113A

2-[5-(4-fluorophenyl)-benzofuran-2-yl]-ethanol

4-Fluorophenylboronic acid was processed as described in Example 112C to provide the title compound as a white microcrystalline solid (79% yield). ¹HNMR (300 MHz, d₆-DMSO) δ 2.94 (t, 2 H), 3.77 (dt, 2 H), 4.84 (t, 1 H), 6.67 (s, 1 H), 7.28 (dd, 2 H), 7.48 (dd, 1H), 7.56 (d, 1 H), 7.70 (dd, 2 H), 7.78 (d, 1 H).

Example 113B (2R)-1-{2-[5-(4-fluorophenyl)-1-benzofuran-2-yl]ethyl}-2-methylpyrrolidine The product from Example 113A was processed as described in Example 112D and Example 112E to provide tile title compound as an orange-tan syrup (60% yield). ¹HNMR (300 MHz, CD₃OD) δ 1.17 (d, 3 H), 1.38–1.52 (m, 1 H), 1.72–1.86 (m, 2 H), 1.94–2.08 (m, 1H), 2.23–2.34 (m, 1 H), 2.41–2.59 (m, 2 H), 2.92–3.13 (m, 2 H), 3.19–3.3 (m, 2 H), 6.59 (s, 1H), 7.15 (m, 2 H, 7.43 (dd, 1 H), 7.46 (d, 1 H), 7.61 (dd, 2 H), 7.68 (d, 1 H).

Example 114

(2R)-1-{2-[5-(3,4-dichlorophenyl)-1-benzofuran-2-yl]ethyl}-2-methylpyrrolidine 3,4-Dichlorophenylboronic acid was processed as described Examples 112C, 112D, and 112E except that in the procedure in Example 112E the reaction was conducted at 60° C. overnight, and after the ethereal extracts were filtered through diatomaceous earth the filtrate was concentrated and semi-purified by HPLC [Waters Nova-Pak HR C18 column (40 mm×100 mm, 6 μm particle size) using a gradient of 10% to 1100% MeCN/0.1% aqueous TFA over 12 min (115 min run time) at a flow rate of 70 mL/min.] to provide the title compound (62% yield) as a TFA salt. MS (ESI APCI) m/z 374/376/378 (M+H)⁺; ¹HNMR (300 MHz, CD₃OD) δ 1.49 (d, 3 H), 1.68–1.82 (m, 1 H), 1.99–2.23 (m, 2 H), 2.30–2.43 (m, 1 H), 3.20–3.63 (m, 5 H), 3.70–3.90 (m, 2 H), 6.80 (s, 1 H), 7.53–7.59 (m, 4 H), 7.78–7.82 (m, 2 H).

Example 115

(2R)-2-methyl-1-{2-[5-(2-methylphenyl)-1-benzofuran-2-yl]ethyl}pyrrolidine

Example 115A (2R,)-1-[2-(5-bromo-1-benzofuran-2-yl)ethyl]-2-methylpyrrolidine

4-Bromo-2-iodophenol (2.99 g, 90% pure, 9 mmol), palladium (II) acetate (112 mg, 0.50 mmol), triphenylphosphine (262 mg, 1.0 mmol), copper (I) iodide (571 mg, 3.0 mmol), and diisopropylamine (114 mL, 100 mmol) were dissolved into a 0.09 M MeCN solution of (R)-1-but-3-ynyl-2-methylpyrrolidine (120 mL, 10.8 mmol) and stirred at room temperature three days, then at 80° C. overnight. The reaction mixture was cooled to room temperature, concentrated, and chromatographed through a short column of silica with 2:1 hexanes/CH₂Cl₂ followed by a 0 to 1% gradient of MeOH/CH₂Cl₂. The appropriate fractions were concentrated, and the residue extracted with MeOH. The extracts were concentrated and partitioned between CH₂Cl₂ and 1 M aqueous Na₂CO₃, worked up as usual, dried (Na₂SO₄), and concentrated to provide the title compound as a dark red syrup (26% yield).

Example 115B (2R)-2-methyl-1-{2-[5-(2-methylphenyl)-1-benzofuran-2-yl]ethyl}pyrrolidine A portion (~330 μL) of a solution of the product from Example 115A (650 mg, 2.1 mmol) and tetrakis(triphenylphosphine)palladium (125 mg, 0.11 mmol) in benzene (6.2 mL) was added to a mixture of (2-methylphenyl)boronic acid (~24 mg, ~0.18 mmol) in ethanol (150 μL). The mixture was treated with 2.0 M aqueous Na₂CO₃ (200 μL, 0.4 mmol), and the reaction vial was sealed, placed on a heater-stirrer apparatus, and heated at 75° C. for four days. The mixture was cooled to room temperature, diluted with 1:1 MeOH/DMSO (1 mL), filtered, and purified by HPLC [Waters Nova-Pak HR C18 column (25 mm×100 mm, 6 μm particle size) using a gradient of 10% to 100% MeCN/0.1% aqueous TFA over 8 min (10 min run time) at a flow rate of 40 mL/min.] to provide the title compound. MS (APCI) m/z 320 (M+H)⁺.

Example 116

(2R)-2-methyl-1-{2-[5-(3-methylphenyl)-1-benzofuran-2-yl]ethyl}pyrrolidine (3-Methylphenyl)boronic acid was processed as described in Example 115B to provide the title compound. MS (APCI) m/z 320 (M+H)⁺.

Example 117

(2R)-2-methyl-1-{2-[5-(4-methylphenyl)-1-benzofuran-2-yl]ethyl}pyrrolidine (4-Methylphenyl)boronic acid was processed as described in Example 115B to provide the title compound. MS (APCI) m/z 320 (M+H)⁺.

Example 118 methyl 4-(2-{2-[(2R)-2-methyl-1-pyrrolidinyl]ethyl}-1-benzofuran-5-yl)benzoate (4-Methoxycarbonylphenyl)boronic acid was processed as described in Example 115B to provide the title compound. MS (APCI) m/z 364 (M+H)⁺.

Example 119

(2R)-1-{2-[5-(2-methoxyphenyl)-1-benzofuran-2-yl]ethyl}-2-methylpyrrolidine (2-Methoxyphenyl)boronic acid was processed as described in Example 115B to provide the title compound. MS (ESI) m/z 336 (M+H)⁺.

Example 120

(2R)-1-{2-[5-(3-methoxyphenyl)-1-benzofuran-2-yl]ethyl}-2-methylpyrrolidine (3-Methoxyphenyl)boronic acid was processed as described in Example 115B to provide the title compound. MS (APCI) m/z 336 (M+H)$^+$.

Example 121

(2R)-1-{2-[5-(4-methoxyphenyl)-1-benzofuran-2-yl]ethyl}-2-methylpyrrolidine (4-Methoxyphenyl)boronic acid was processed as described in Example 115B to provide the title compound. MS (ESI) m/z 364 (M+H)$^+$.

Example 122

(2R)-1-{2-[5-(3-fluorophenyl)-1-benzofuran-2-yl]ethyl}-2-methylpyrrolidine (3-Fluorophenyl)boronic acid was processed as described in Example 115B to provide the title compound. MS (ESI) in/z 324 (M+H)$^+$.

Example 123

(2R)-1-{2-[5-(2-chlorophenyl)-1-benzofuran-2-yl]ethyl}-2-methylpyrrolidine (2-Chlorophenyl)boronic acid was processed as described in Example 115B to provide the title compound. MS (APCI) m/z 340 (M+H)$^+$.

Example 124

(2R)-1-{2-[5-(3-chlorophenyl)-1-benzofuran-2-yl]ethyl}-2-methylpyrrolidine (3-Chlorophenyl)boronic acid was processed as described in Example 115B to provide the title compound. MS (APCI) m/z 340/342 (M+H)$^+$.

Example 125

1-{2-[5-(4-chlorophenyl)-benzofuran-2-yl]-ethyl}-2-methylpyrrolidine (4-Chlorophenyl)boronic acid was processed as described in Example 115B to provide the title compound. MS (ESI) m/z 340/342 (M+H)$^+$.

Example 126

(2R)-2-methyl-1-(2-{5-[3-(trifluoromethyl)phenyl]-1-benzofuran-2-yl}ethyl)pyrrolidine (3-Trifluoromethylphenyl)boronic acid was processed as described in Example 115B to provide the title compound. MS (APCI) m/z 374 (M+H)$^+$.

Example 127

(2R)-2-methyl-1-(2-{5-[4-(trifluoromethyl)phenyl]-1-benzofuran-2-yl}ethyl)pyrrolidine (4-Trifluoromethylphenyl)boronic acid was processed as described in Example 115B to provide the title compound. MS (APCI) m/z 374 (M+H)$^+$.

Example 128

(2R)-2-methyl-1-(2-{5-[3-(trifluoromethoxy)phenyl]-1-benzofuran-2-yl}ethyl)pyrrolidine (3-Trifluoromethoxyphenyl)boronic acid was processed as described in Example 115B to provide the title compound. MS (APCI) m/z 390 (M+H)$^+$.

Example 129

(2R)-2-methyl-1-(2-{5-[4-(trifluoromethoxy)phenyl]-1-benzofuran-2-yl}ethyl)pyrrolidine (4-Trifluoromethoxyphenyl)boronic acid was processed as described in Example 115B to provide the title compound. MS (APCI) m/z 390 (M+H)$^+$.

Example 130

(2R)-1-{2-[5-(3,4-dimethylphenyl)-1-benzofuran-2-yl]ethyl}-2-methylpyrrolidine (3,4-Dimethylphenyl)boronic acid was processed as described in Example 115B to provide the title compound. MS (ESI) m/z 334 (M+H)$^+$.

Example 131

(2R)-1-{2-[5-(3,5-dichlorophenyl)-1-benzofuran-2-yl]ethyl}-2-methylpyrrolidine (3,5-Dichlorophenyl)boronic acid was processed as described in Example 115B to provide the title compound; MS (APCI) m/z 374/376 (M+H)$^+$.

Example 132

(2R)-1-{2-[5-(3,5-dimethylphenyl)-1-benzofuran-2-yl]ethyl}-2-methylpyrrolidine (3,5-Dimethylphenyl)boronic acid was processed as described in Example 115B to provide the title compound. MS (APCI) m/z 334 (M+H)$^+$.

Example 133

[4-(2-{2-[(2R)-2-methyl-1-pyrrolidinyl]ethyl}-1-benzofuran-5-yl)phenyl]methanol

A solution (1.2 mL) of the product from Example 115A (350 mg, 1.1 mmol) in benzene (3.6 mL) was added to a mixture of palladium (II) acetate (11 mg, 0.05 mmol), and biphen-2-yl-dicyclohexylphosphine (28 mg, 0.08 mmol). The reaction mixture was then treated with 4-(hydroxymethyl)phenylboronic acid (87 mg, 0.57 mmol) in ethanol (500 µL) followed by 2M aqueous Na$_2$CO$_3$ (500 µL). The mixture was stirred thoroughly overnight. Additional ethanol (500 µL) was added and the mixture was stirred for four days, diluted with EtOAc, filtered, chromatographed through a short column of silica with a gradient of 0 to 2% MeOH/EtOAc, purified by HPLC [Waters Nova-Pak HR C18 column (25 mm×100 mm, 6 µm particle size) using a gradient of 10% to 100% MeCN/0.1% aqueous TFA over 8 min (10 min run time) at a flow rate of 40 mL/min.], and then rechromatographed through a short column of silica with MeOH/CH$_2$Cl$_2$ to provide the title compound (12% yield). MS (ESI APCI) m/z 336 (M+H)$^+$; $^1$HNMR (300 MHz, CD$_3$OD) δ 1.21 (d, 3 H), 1.42–1.58 (m, 1H), 1.77–1.91 (m, 2 H), 1.99–2.13 (m, 1 H), 2.35–2.77 (m, 3 H), 2.97–3.18 (m, 2 H), 3.2–3.4 (m, 2 H), 4.64 (s, 2 H), 6.61 (s, 1 H), 7.42 (d, 2 H), 7.45–7.48 (m, 2 H), 7.60 (d, 2 H), 7.72 (dd, 1 H).

Example 134

3-(2-{2-[(2R)-2-methyl-1-pyrrolidinyl]ethyl}-1-benzofuran-5-yl)pyridine 3-(1,3,2-Dioxaborinan-2-yl)pyridine was processed as described in Example 133 to provide the title compound (1% yield). MS (ESI APCI) m/z 307 (M+H)⁺; ¹HNMR (300 MHz, CD₃OD) δ 1.20 (d, 3 H), 1.41–1.56 (m, 1 H), 1.76–1.89 (m, 2 H), 1.97–2.12 (m, 1 H), 2.32–2.70 (m, 3 H), 2.98–3.19 (m, 2 H), 3.2–3.4 (m, 2 H), 6.66 (d, 1 H), 7.47–7.57 (m, 3 H), 7.80 (dd, 1 H), 8.10 (ddd, 1 H), 8.49 (m, 1 H), 8.81 (m, 1 H).

Example 135

(2R)-1-(2-{5-[2-(4-fluorophenyl)vinyl]-1-benzofuran-2-yl}ethyl)-2-methylpyrrolidine trans-2-(4-Fluorophenyl)vinylboronic acid was processed as described in Example 133 to provide the title compound (4% yield). MS (ESI APCI) m/z 350 (M+H)⁺.

Example 136

1-[3-(2-{2-[(2R)-2-methyl-1-pyrrolidinyl]ethyl}-1-benzofuran-5-yl)phenyl]ethanone

Example 136A 1-(4'-hydroxy-1,1'-biphenyl-3-yl)ethanone

4-Iodophenol (5.39 g, 24.5 mmol) and 3-acetylphenylboronic acid (4.42 g, 26.95 mmol) were mixed in N,N-dimethylformamide (15 mL) and treated with 1.0 M aqueous Na₂CO₃ (75 mL) and palladium (II) acetate (110 mg, 0.49 mmol). The suspension was heated at 55° C. for one hour and then brought to room temperature. CH₂Cl₂ (100 mL) was added to the mixture which was then filtered. The aqueous layer of the filtrate was extracted with CH₂Cl₂ and the combined organic phases were washed consecutively with pH 6 potassium phosphate buffer and brine, then dried (Na₂SO₄), concentrated, and chromatographed through silica with a 33 to 100% gradient of hexanes/CH₂Cl₂ followed by a gradient of 0 to 3% EtOAc/CH₂Cl₂. Impure fractions were combined, concentrated, and rechromatographed as before, twice, to provide the title compound as an oil which slowly crystallized to a white solid upon standing (~95% yield). MS (ESI APCI negative ion detection) m/z 211 (M–H)⁻; ¹HNMR (300 MHz, CDCl₃) δ 2.65 (s, 3 H), 6.97 (d, 2 H), 7.47–7.53 (m, 3 H), 7.74 (ddd, 1 H), 7.88 (ddd), 8.13 (dd, 1 H).

Example 136B 1-(4'-hydroxy-3'-iodo-1,1'-biphenyl-3-yl)ethanone

The product from Example 136A (5.76 g, 27 mmol) was suspended in concentrated aqueous ammonia (400 mL) and treated with a solution of potassium iodide (23.3 g, 140 mmol) and iodine (7.24 g, 28.5 mmol) in water (100 mL). As the reaction did not go to completion, the mixture was treated with a second solution of potassium iodide (15.8 g, 95 mmol) and iodine (4.83 g, 19 mmol) in water (50 mL). After an hour the ammonia was removed under reduced pressure on a rotary evaporator. The mixture was extracted with EtOAc, and the combined organic phases were washed consecutively with pH 6 potassium phosphate buffer and brine, then dried (Na₂SO₄), concentrated, and chromatographed through silica with 1% acetic acid in a gradient of 0 to 5% EtOAc/CH₂Cl₂ to provide the title compound as a beige powder (21% yield). MS (ESI APCI negative ion detection) m/z 337 (M–H)⁻; ¹HNMR (300 MHz, CDCl₃) δ 2.65 (s, 3 H), 5.37 (bs, 1 H), 7.08 (d, 1 H), 7.48–7.55 (m, 2 H), 7.71 (ddd, 1 H), 7.88–7.93 (m, 2 H), 8.09 (dd, 1 H).

Example 136C

1-[3-(2-{2-[(2R)-2-methyl-1-pyrrolidinyl]ethyl}-1-benzofuran-5-yl)phenyl]ethanone The product from Example 136B (1.15 g, 3.40 mmol), palladium (II) acetate (38 mg, 0.17 mmol), biphen-2-yl-dicyclohexylphosphine (119 mg, 0.34 mmol), diisopropylamine (4.8 mL, 34 mmol), and copper (I) iodide (76 mg, 0.40 mmol) were suspended in a 0.09 M MeCN solution of (R)-1-but-3-ynyl-2-methylpyrrolidine (45 mL, 4.0 mmol). N,N-dimethylformamide (10 mL) was added, and the mixture was heated at 45° C. overnight, cooled to room temperature, partitioned between CH₂Cl₂ (100 mL) and 5% aqueous ammonia (100 mL), worked up as usual but with 5% aqueous ammonia, filtered, and concentrated. The residue was dissolved into CH₂Cl₂ and washed consecutively with water and brine, dried (Na₂SO₄), concentrated, and chromatographed through silica with a gradient of 0 to 4% MeOH/CH₂Cl₂. The appropriate fractions were combined and rechromatographed with 50% CH₂Cl₂/hexanes followed by a gradient of 0 to 4% MeOH/CH₂Cl₂ to provide the title compound as a dark brown gum (30% yield). MS (APCI) m/z 348 (M+H)⁺; ¹HNMR (300 MHz, CD₃OD) δ 1.17 (d, 3 H), 1.38–1.52 (m, 1 H), 1.73–1.86 (m, 2 H), 1.94–2.07 (m, 1 H), 2.23–2.34 (m, 1 H), 2.40–2.58 (m, 2 H), 2.67 (s, 3 H), 2.95–3.14 (m, 2H), 3.19–3.32 (m, 2 H), 6.62 (s, 1 H), 7.49–7.52 (m, 2 H), 7.57 (dd, 1 H), 7.78 (dd, 1 H), 7.88 (ddd, 1 H), 7.96 (ddd, 1H), 8.22 (dd, 1 H).

Example 137

1-[3-(2-{2-[(2R)-2-methyl-1-pyrrolidinyl]ethyl}-1-benzofuran-5-yl)phenyl]ethanol The product from Example 136C (46 mg, 0.12 mmol) in ethanol (2 mL) and tetrahydrofuran (0.5 mL) was treated with sodium borohydride. The mixture was concentrated and passed through a short column of silica with a gradient of 2 to 10% MeOH/CH₂Cl₂. The resulting residue rinsed with ether, dissolved into methanol (1 mL), treated with 0.1 M aqueous hydrochloric acid (0.2 mL) heated at 60□ C for three hours, treated with more 0.1 M aqueous hydrochloric acid (0.05 mL), heated at 60□ C for one hour, concentrated, and chromatographed through a short column of silica with a gradient of 2 to 10% 2 M NH₃ in MeOH/CH₂Cl₂ to provide the title compound as a white powder (11% yield). ¹HNMR (300 MHz, CD₃OD) δ 1.17 (d, 3 H), 1.4–1.54 (m, 1 H), 1.49 (d, 3 H), 1.73–1.86 (m, 2 H), 1.95–2.08 (m, 1 H), 2.24–2.36 (m, 1 H), 2.43–2.60 (m, 2 H), 2.93–3.14 (m, 2 H), 3.19–3.33 (m, 2H), 4.89 (q, 1 H), 6.59 (s, 1 H), 7.32 (ddd, 1 H), 7.39 (dd, 1 H), 7.45–7.47 (m, 2 H), 7.49 (ddd, 1 H), 7.62 (m, 1 H), 7.71 (dd, 1 H).

Example 138

2-[3-(2-{2-[(2R)-2-methyl-1-pyrrolidinyl]ethyl}-1-benzofuran-5-yl)phenyl]-2-propanol The product from Example 136C (87 mg, 0.25 mmol) was dissolved into tetrahydrofuran (5 mL), treated with 3 M methylmagnesium bromide in ether (0.3 mL, 0.9 mmol), stirred overnight, quenched with 0.5 M aqueous dipotassium hydrogen phosphate, and diluted with EtOAc and a little CH₂Cl₂. The resulting emulsion was sonicated, and the aqueous phase was separated and extracted with EtOAc. The combined organic phases were washed consecutively with 0.5 M aqueous dipotassium hydrogen phosphate and brine, dried (Na₂SO₄), concentrated, and chromatographed on silica with a gradient of 2 to 10% MeOH/20% MeCN/CH₂Cl₂ followed by 10% MeOH/CH₂Cl₂ to provide the title compound as an orange resin (~33% yield). ¹HNMR (300 MHz, CD₃OD) δ 1.20 (d, 3 H), 1.42–1.58 (m, 1 H), 1.58 (s, 6 H), 1.76–1.90 (m, 2 H), 1.96–2.12 (m, 1 H), 2.3–2.7 (m, 3 H), 2.97–3.13 (m, 2 H), 3.22–3.4 (m, 2 H), 6.62 (s, 1 H), 7.38 (dd, 1 H), 7.40–7.46 (m, 2 H), 7.46–7.48 (m, 2 H), 7.72 (dd, 1 H), 7.76 (dd, 1 H).

Example 139

1-[3-(2-{2-[(2R)-2-methyl-1-pyrrolidinyl]ethyl}-1-benzofuran-5-yl)phenyl]ethanone oxime The product from Example 136C (240 mg, 0.5 mmol) and hydroxylamine hydrochloride (139 mg, 2.00 mmol) were dissolved into methanol (2 mL) and treated with $Na_2CO_3$ (318 mg, 3.0 mmol). The suspension was stirred at room temperature overnight and then heated at 70° C. three days. The mixture was cooled to room temperature and filtered, the solids being rinsed with 50% $MeOH/CH_2Cl_2$. The filtrate was concentrated, then partitioned between water and $MeOH/CH_2Cl_2$; some clean product remained undissolved and was separated. The organic phase was concentrated, dissolved in a little methanol, and seeded with the previously collected product. After this material had crystallized, both crops of product were rinsed with methanol and permitted to dry to provide the title compound as a white microcrystalline solid (49% yield). $^1$HNMR (300 MHz, $CDCl_3$) δ 1.18 (d, 3 H), 1.4–2.1 (m, 4 H), 2.2–2.6 (m, 3 H), 2.34 (s, 3 H), 3.00–3.12 (m, 2 H), 3.20–3.34 (m, 2 H), 6.49 (s, 1H), 7.41–7.48 (m, 3 H), 7.56–7.63 (m, 2 H), 7.68 (dd, 1 H), 7.70 (bs, 1 H), 7.88 (dd, 1 H).

Example 140

1-[3-(2-{2-[(2R)-2-methyl-1-pyrrolidinyl]ethyl}-1-benzofuran-5-yl)phenyl]ethanone O-methyloxime O-Methylhydroxylamine was processed as described in Example 139, except that after the reaction was complete it was diluted with $CH_2Cl_2$, filtered, concentrated, and chromatographed through a short column of silica with a gradient of 1 to 4% $MeOH/CH_2Cl_2$ to provide the title compound as an orange gum (53% yield). MS (ESI APCI) m/z 377 (M+H)$^+$; $^1$HNMR (300 MHz, $CD_3OD$) δ 1.17 (d, 3 H), 1.41–1.51 (m, 1 H), 1.75–1.84 (m, 2H), 1.96–2.05 (m, 1 H), 2.26 (s, 3 H), 2.27–2.33 (m, 1 H), 2.44–2.59 (m, 2 H), 2.96–3.11 (m, 2H), 3.20–3.3 (m, 2 H), 3.98 (s, 3 H), 6.60 (s, 1 H), 7.45 (dd, 1 H), 7.52–7.54 (m, 2 H), 7.58–7.65 (m, 2 H), 7.74 (s, 1 H), 7.89 (dd, 1 H).

Example 141

1-[3-(2-{2-[(2R)-2-methyl-1-pyrrolidinyl]ethyl}-1-benzofuran-5-yl)phenyl]ethanone O-ethyloxime O-Ethylhydroxylamine was processed as described in Example 139 to provide the title compound as an orange gum (56% yield). MS (ESI APCI) m/z 391 (M+H)$^+$; $^1$HNMR (300 MHz, $CD_3OD$) δ 1.17 (d, 3 H), 1.33 (t, 3 H), 1.41–1.51 (m, 1 H), 1.75–1.85 (m, 2 H), 1.97–2.06 (m, 1 H), 2.27 (s, 3 H), 2.27–2.34 (m, 1 H), 2.45–2.60 (m, 2 H), 2.96–3.12 (m, 2 H), 3.20–3.3 (m, 2 H), 4.23 (q, 2 H), 6.60 (s, 1 H), 7.44 (dd, 1 H), 7.48 (s, 2 H), 7.58–7.64 (m, 2H), 7.73 (s, 1 H), 7.89 (dd, 1 H).

Example 142

1-[3-(2-{2-[(2R)-2-methyl-1-pyrrolidinyl]ethyl}-1-benzofuran-5-yl)phenyl]ethanone O-(tert-butyl) oxime O-tert-Butylhydroxylamine was processed as described in Example 139 to provide the title compound as an orange gum (56% yield). MS (ESI APCI) m/z 419 (M+H)$^+$; $^1$HNMR (300 MHz, $CD_3OD$) δ 1.17 (d, 3 H), 1.37 (s, 9 H), 1.41–1.51 (m, 1 H), 1.75–1.84 (m, 2 H), 1.97–2.06 (m, 1 H), 2.24 (s, 3 H), 2.27–2.34 (m, 1 H), 2.45–2.59 (m, 2 H), 2.96–3.11 (m, 2 H), 3.20–3.3 (m, 2 H), 6.61 (s, 1 H), 7.43 (dd, 1 H), 7.47 (s, 2 H), 7.57–7.64 (m, 2 H), 7.72 (s, 1H), 7.89 (dd, 1 H).

Example 143 ethyl 3-(2-{2-[(2R)-2-methyl-1-pyrrolidinyl]ethyl}-1-benzofuran-5-yl)benzoate

Example 143A ethyl 4'-hydroxy-1,1'-biphenyl-3-carboxylate

4-Iodophenol and 3-ethoxycarbonylphenylboronic acid were processed as described in Example 136A, except that the reaction was done overnight at room temperature and the chromatography was conducted twice with 50% $CH_2Cl_2$/hexanes followed by a gradient of 0 to 1% $MeOH/CH_2Cl_2$ to provide the title compound as a white powder (71% yield). $^1$HNMR (300 MHz, $d_6$-DMSO) δ 1.34 (t, 3 H), 4.34 (q, 2 H), 6.89 (d, 2 H), 7.50–7.59 (m, 3H), 7.83–7.89 (m, 2 H), 8.11 (dd, 1 H), 9.62 (s, 1 H).

Example 143B ethyl 4'-hydroxy-3'-iodo-1,1'-biphenyl-3-carboxylate

The product from Example 143A (7.71 g, 31.8 mmol) was dissolved into N,N-dimethylformamide (30 mL), diluted with concentrated aqueous ammonia (320 mL), and treated with a solution of potassium iodide (27.72 g, 167 mmol) and iodine (8.48 g, 33.4 mmol) in water (100 mL) all at once. After the mixture was stirred for one hour, the ammonia was removed under reduced pressure on a rotary evaporator. The remaining solution was neutralized to pH 7 with aqueous hydrochloric acid, diluted with EtOAc (200 mL), worked up as usual, dried ($Na_2SO_4$), concentrated, and chromatographed on silica with a 33 to 100% gradient of $CH_2Cl_2$/hexanes to provide the title compound as a white microcrystalline solid (37% yield). $^1$HNMR (300 MHz, $d_6$-DMSO) δ 1.35 (t, 3 H), 4.35 (q, 2H), 7.00 (d, 1 H), 7.53–7.60 (m, 2 H), 7.84–7.91 (m, 2 H), 7.97 (d, 1 H), 8.08 (dd, 1 H), 10.55 (bs, 1 H).

Example 143C ethyl 3-(2-{2-[(2R)-2-methyl-1-pyrrolidinyl]ethyl}-1-benzofuran-5-yl)benzoate The product from Example 143B was treated as described for Example 136C, except that the reaction was conducted at 65□ C to provide the title compound as a viscous dark brown oil (52% yield). MS (ESI APCI) m/z 378 (M+H)$^+$.

Example 144

3-(2-{2-[(2R)-2-methyl-1-pyrrolidinyl]ethyl}-1-benzofuran-5-yl)benzoic acid

The product from Example 143C (755 mg, 2 mmol) was dissolved into ethanol (20 mL) and treated with 2 M aqueous NaOH (2 mL). The mixture was heated at 55° C. for 40 minutes, cooled to room temperature, concentrated, and partitioned between isopropanol and a mixture of 1 M aqueous potassium dihydrogen phosphate and brine. The aqueous phase was separated and extracted with isopropanol, and the combined organic phases were washed with a mixture of pH 6 potassium phosphate buffer and brine. The aqueous phase was separated and extracted with isopropanol, and the combined organic phases were washed with brine. Again, the aqueous phase was separated and extracted with isopropanol, and the combined organic phases were diluted with EtOAc, and filtered. The filtrate was dried ($Na_2SO_4$) and concentrated. The residue was chromatographed on silica with 50% EtOAc/$CH_2Cl_2$, followed by 10% MeOH/45% EtOAc/$CH_2Cl_2$, followed by 30% MeOH/$CH_2Cl_2$. The appropriate fractions were concentrated and the residue dissolved into EtOAc/$CH_2Cl_2$, and the solids which precipitated were washed with additional EtOAc/$CH_2Cl_2$ to provide the title compound as a white powder. MS (ESI APCI) m/z 350 (M+H)$^+$; $^1$HNMR (300 MHz, $CD_3OD$) δ 1.39 (s, 3 H), 1.58–1.76 (m, 1 H), 1.91–2.10 (m, 2 H), 2.16–2.31 (m, 1 H), 2.89–3.04 (m, 1 H), 3.08–3.3 (m, 4 H), 3.50–3.71 (m, 2 H), 6.70 (s, 1 H), 7.39–7.59 (m, 3 H), 7.69 (d, 1 H), 7.79 (s, 1 H), 7.92 (d, 1 H), 8.23 (s, 1 H).]

Example 145

N-methoxy-N-methyl-3-(2-{2-[(2R)-2-methyl-1-pyrrolidinyl]ethyl}-1-benzofuran-5-yl)benzamide The product from Example 144 was suspended in $CH_2Cl_2$ (25 mL) and treated with 2 M oxalyl chloride in $CH_2Cl_2$ (3.0 mL, 6.0 mmol). After the bubbling had subsided, N,N-dimethylformamide (300 μL) was added slowly over 15 minutes. After an additional hour, more N,N-dimethylformamide (100 μL) was added. After another 30 minutes, the mixture was concentrated and dissolved into $CH_2Cl_2$ (5 mL). N,O-Dimethylhydroxylamine hydrochloride (488 mg, 5.0 mmol) and pyridine (1 mL) were added, the reaction flask was placed in a water bath, and the mixture was stirred overnight, concentrated, diluted with 1,2-dichloroethane (5 mL), heated at 85□C for four hours, concentrated, and partitioned between $CH_2Cl_2$ and water. Saturated aqueous $NaHCO_3$ was added until the pH of the aqueous phase exceeded seven. Then the aqueous phase was separated and extracted with $CH_2Cl_2$. The combined organic phases were washed consecutively with water and brine, dried ($Na_2SO_4$), and chromatographed on silica with a gradient of 0 to 4% MeOH/$CH_2Cl_2$ to provide the title compound as a viscous brown syrup (60% yield from ester). $^1$HNMR (300 MHz, $CD_3OD$) δ 1.19 (s, 3 H), 1.37–1.54 (m, 1 H), 1.73–1.88 (m, 2 H), 1.95–2.09 (m, 1 H), 2.27–2.39 (m, 1 H), 2.45–2.64 (m, 2 H), 2.95–3.17 (m, 2 H), 3.20–3.3 (m, 2 H), 3.39 (s, 3 H), 3.63 (s, 3 H), 6.62 (s, 1 H), 7.46–7.83 (m, 4 H), 7.73–7.81 (m, 2 H), 7.86 (s, 1 H).

Example 146

1-[3-(2-{2-[(2R)-2-methyl-1-pyrrolidinyl]ethyl}-1-benzofuran-5-yl)phenyl]-1-propanone The product from Example 145 (20 mg, 0.05 mmol) was dissolved into tetrahydrofuran (900 μL), cooled to 0° C., and treated with 1.0 M ethylmagnesium bromide in tetrahydrofuran (150 μL, 150 μmol). The reaction mixture was then stirred at room temperature overnight, quenched by the addition of saturated aqueous $NH_4Cl$, and diluted with EtOAc. The aqueous phase was separated and extracted with EtOAc, and the combined organic phases were washed consecutively with 0.5 M aqueous dipotassium hydrogen phosphate and brine, concentrated, and purified by HPLC [Waters Nova-Pak HR C18 column (25 mm×100 mm, 6 μm particle size) using a gradient of 10% to 100% MeCN/0.1% aqueous TFA over 8 min (10 min run time) at a flow rate of 40 mL/min.] to provide the title compound (44% yield). MS (ESI APCI) m/z 362 (M+H)$^+$; HNMR (300 MHz, $CD_3OD$) δ 1.18 (d, 3 H), 1.21 (t, 3 H), 1.39–1.53 (m, 1 H), 1.74–1.87 (m, 2 H), 1.95–2.09 (m, 1 H), 2.24–2.37 (m, 1 H), 2.42–2.61 (m, 2 H), 2.94–3.18 (m, 4 H), 3.20–3.35 (m, 2 H), 6.63 (s, 1 H), 7.50–7.52 (m, 2 H), 7.58 (dd, 1 H), 7.77–7.79 (m, 1 H), 7.87 (ddd, 1 H), 7.96 (ddd, 1 H), 8.22 (dd, 1 H).

Example 147 cyclopropyl[3-(2-{2-[(2R)-2-methyl-1-pyrrolidinyl]ethyl}-1-benzofuran-5-yl)phenyl]methanone The product from Example 145 and cyclopropylmagnesium bromide were processed as described in Example 146 to provide the title compound (48% yield). MS (ESI APCI) m/z 374 (M+H)$^+$; $^1$HNMR (300 MHz, $CD_3OD$) δ 1.08–1.22 (m, 7 H), 1.39–1.53 (m, 1 H), 1.73–1.86 (m, 2 H), 1.95–2.08 (m, 1 H), 2.23–2.35 (m, 1 H), 2.41–2.60 (m, 2 H), 2.87–3.15 (m, 3H), 3.19–3.35 (m, 2 H), 6.63 (s, 1 H), 7.48–7.55 (m, 2 H), 7.60,(dd, 1 H), 7.78–7.81 (m, 1 H), 7.89 (ddd, 1 H), 8.02 (ddd, 1 H), 8.25 (dd, 1 H).

Example 148

3-methyl-1-[3-(2-{2-[(2R)-2-methyl-1-pyrrolidinyl]ethyl}-1-benzofuran-5-yl)phenyl]-1-butanone The product from Example 145 and isobutylmagnesium chloride were processed as described in Example 146, except that after reacting overnight additional isobutylmagnesium chloride (400 mol %) was added and the reaction mixture was stirred for four more hours, to provide the title compound (19% yield). MS (ESI APCI) m/z 390 (M+H)$^+$; $^1$HNMR (300 MHz, $CD_3OD$) δ 1.01 (d, 6 H), 1.17 (d, 3 H), 1.37–1.53 (m, 1 H), 1.73–1.86 (m, 2 H), 1.94–2.07 (m, 1 H), 2.20–2.35 (m, 2 H), 2.41–2.59 (m, 2 H), 2.95 (d, 2 H), 2.95–3.14 (m, 2 H), 3.19–3.34 (m, 2 H), 6.62 (s, 1 H), 7.49–7.52 (m, 2 H), 7.57 (dd, 1 H), 7.77 (dd, 1 H), 7.86 (ddd, 1 H), 7.93 (ddd, 1 H), 8.19 (dd, 1 H).

Example 149

3-(2-{2-[(2R)-2-methyl-1-pyrrolidinyl]ethyl}-1-benzofuran-5-yl)benzaldehyde

The product from Example 145 and cyclopentylmagnesium bromide were processed as described in Example 146, except that additional cyclopentylmagnesium bromide was added after the reaction had stirred overnight (400 mol %) and after another four hours (600 mol %). The reaction mixture was allowed to stir for three additional days (16% yield). MS (ESI APCI) m/z 334 (M+H)$^+$; $^1$HNMR (300 MHz, $CD_3OD$) δ 1.17 (d, 3 H), 1.38–1.53 (m, 1 H), 1.77–1.86 (m, 2 H), 1.94–2.08 (m, 1 H), 2.23–2.34 (m, 1 H), 2.40–2.59 (m, 2 H), 2.94–3.15 (m, 2 H), 3.19–3.34 (m, 2 H), 6.63 (d, 1 H), 7.51–7.54 (m, 2 H), 7.65 (dd, 1 H), 7.80 (dd, 1 H), 7.87 (ddd, 1 H), 7.96 (ddd, 1 H), 8.16 (dd, 1 H), 10.07 (s, 1 H).

Example 150

[3-(2-{2-[(2R)-2-methyl-1-pyrrolidinyl]ethyl}-1-benzofuran-5-yl)phenyl](2-thienyl)methanone The product from Example 145 and 2-thienyllithium were processed as described in Example 146 to provide the title compound (53% yield). MS (ESI APCI) m/z 416 (M+H)$^+$; $^1$HNMR (300 MHz, $CD_3OD$) δ 1.18 (d, 3 H), 1.38–1.53 (m, 1 H), 1.73–1.86 (m, 2 H), 1.95–2.08 (m, 1 H), 2.24–2.36 (m, 1 H), 2.42–2.61 (m, 2 H), 2.95–3.15 (m, 2 H), 3.19–3.34 (m, 2 H), 6.63 (d, 1 H), 7.27 (d, 1 H), 7.48–7.57 (m, 2 H), 7.63 (dd, 1 H), 7.76–7.84 (m, 3 H), 7.90–7.98 (m, 2 H), 8.07 (dd, 1 H).

Example 151

(3-fluorophenyl)[3-(2-{2-[(2R)-2-methyl-1-pyrrolidinyl]ethyl}-1-benzofuran-5-yl)phenyl]methanone The product from Example 145 and 3-fluorophenylmagnesium bromide were processed as described in Example 146 to provide the title compound (46% yield). MS (ESI APCI) m/z 428 (M+H)$^+$; $^1$HNMR (300 MHz, CD$_3$OD) δ 1.17 (d, 3 H), 1.36–1.53 (m, 1 H), 1.72–1.86 (m, 2 H), 1.94–2.07 (m, 1 H), 2.22–2.33 (m, 1 H), 2.39–2.58 (m, 2 H), 2.93–3.14 (m, 2 H), 3.18–3.3 (m, 2 H), 6.62 (s, 1 H), 7.37–7.45 (m, 1 H), 7.49–7.52 (m, 2 H), 7.52–7.66 (m, 4 H), 7.72 (ddd, 1 H), 7.77 (dd, 1 H), 7.94 (ddd, 1 H), 8.02 (dd, 1 H).

Example 152

[3-(2-{2-[(2R)-2-methyl-1-pyrrolidinyl]ethyl}-1-benzofuran-5-yl)phenyl]methanol

The product from Example 144 (167 mg, 0.48 mmol) was dissolved into 1 M BH$_3$ in tetrahydrofuran (2 mL, 2 mmol), stirred at room temperature overnight, quenched with 0.5 M aqueous dipotassium hydrogen phosphate, and diluted with EtOAc. The organic phase was separated and washed consecutively with 0.5 M aqueous dipotassium hydrogen phosphate and brine, dried (Na$_2$SO$_4$), concentrated, and chromatographed through a short column of silica with a gradient of 0 to 5% MeOH/CH$_2$Cl$_2$, and through a second short column of silica with a gradient of 0 to 5% MeCN/CH$_2$Cl$_2$, collecting and concentrating the material with a mass ion corresponding to a borane complex. This residue was dissolved in methanol (1.5 mL), treated with 0.1 M aqueous hydrochloric acid (0.3 mL), heated at 60° C. for three hours, treated with more 0.1 M aqueous hydrochloric acid (0.1 mL), heated at 60° C. for one hour, concentrated, and chromatographed through a short column of silica with a gradient of 2 to 10% 2 M NH$_3$ in MeOH/CH$_2$Cl$_2$ to provide the title compound as a white powder (13% yield). MS (ESI APCI) m/z 336 (M+H)$^+$; $^1$HNMR (300 MHz, CD$_3$OD) δ 1.18 (s, 3 H), 1.38–1.53 (m, 1 H), 1.73–1.87 (m, 2 H), 1.94–2.08 (m, 1 H), 2.24–2.36 (m, 1H), 2.41–2.60 (m, 2 H), 2.94–3.14 (m, 2 H), 3.19–3.34 (m, 2 H), 4.68 (s, 2 H), 6.60 (s, 1 H), 7.28–7.34 (m, 1 H), 7.40 (dd, 1 H), 7.46–7.49 (m, 2 H), 7.52 (ddd, 1 H), 7.62 (s, 1 H), 7.73 (dd, 1 H).

Example 153

(2R)-1-[2-(5-benzyl-1-benzofuran-2-yl)ethyl]-2-methylpyrrolidine

Example 153A 4-benzyl-2-iodophenol

4-Benzylphenol was processed as described in Example 143B, except that neutralization after the reaction was complete was not conducted and the chromatography was conducted with a gradient of 25 to 33% CH$_2$Cl$_2$/hexanes to provide the title compound (42% yield). $^1$HNMR (300 MHz, CDCl$_3$) δ 3.88 (s, 2 H), 5.13 (s, 1 H), 6.90 (d, 1 H), 7.05 (dd, 1 H), 7.13–7.33 (m, 5 H), 7.47 (d, 1 H).

Example 153B (2R)-1-[2-(5-benzyl-1-benzofuran-2-yl)ethyl]-2-methylpyrrolidine The product from Example 153A was treated as described in Example 136C, except that the reaction was conducted at room temperature for one day, then at 65° C. overnight, and worked up as follows: The reaction mixture was brought to room temperature, concentrated, suspended in CH$_2$Cl$_2$ and mixed with 10% aqueous ammonia, and filtered through diatomaceous earth. The filtrate was diluted with water and the aqueous phase was separated and extracted with CH$_2$Cl$_2$. The combined organic phases were washed with 5% aqueous ammonia and then worked up as usual, dried (Na$_2$SO$_4$), concentrated, and chromatographed three times on silica with MeOH/CH$_2$Cl$_2$. The appropriate fractions were concentrated and the resulting residue dissolved in methanol and filtered. The filtrate was concentrated to provide the title compound as a brown gum (3% yield). MS (ESI APCI) m/z 320 (M+H)$^+$; $^1$HNMR (300 MHz, CD$_3$OD) δ 1.18 (d, 3 H), 1.38–1.53 (m, 1 H), 1.73–1.87 (m, 2 H), 1.95–2.09 (m, 1 H), 2.26–2.39 (m, 1 H), 2.45–2.61 (m, 2 H), 2.90–3.11 (m, 2 H), 3.18–3.3 (m, 2 H), 4.01 (s, 2 H), 6.47 (d, 1 H), 7.05 (dd, 1 H), 7.11–7.33 (m, 7 H).

Example 154

1-(2-{2-[(2R)-2-methyl-1-pyrrolidinyl]ethyl}-1-benzofuran-5-yl)-1H-imidazole

Example 154A 4-(1H-imidazol-1-yl)-2-iodophenol

4-Imidazol-1-ylphenol was processed as described in Example 143B, except that after removal of the ammonia under reduced pressure, the mixture was diluted with brine and extracted with 33% isopropanol/EtOAc. The organic extracts were combined and partially concentrated before being washed with brine. The brine phase was separated and extracted as before. The combined organic phases were then concentrated until only some unseparated N,N-dimethylformamide and water remained, and set aside overnight. The crystals which formed were collected by filtration and washed with 2:1 EtOAc/ether. The filtrate was concentrated and diluted with brine. After a microcrystalline solid had finished precipitating, it too was collected and washed as before, then mostly dissolved in MeOH/CH$_2$Cl$_2$, filtered, and concentrated. The resulting second batch was combined with the first to provide the title compound as an off-white powder (64% yield). $^1$HNMR (300 MHz, CD$_3$OD) δ 6.93 (d, 1 H), 7.10 (d, 1 H), 7.37 (dd, 1 H), 7.43 (dd, 1 H), 7.86 (d, 1 H), 7.97 (d, 1 H).

Example 154B 1-(2-{2-[(2R)-2-methyl-1-pyrrolidinyl]ethyl}-1-benzofuran-5-yl)-1H-imidazole The product from Example 154A was processed as described in Example 136C except that the reaction was carried out at 80° C. for six hours, additional alkyne solution (10 mol %) was added, and after an additional 2.3 hours the reaction was brought to room temperature, concentrated, and chromatographed through a short column of silica covered with a layer of diatomaceous earth with a gradient of 0 to 10% 2 M NH$_3$ in MeOH/CH$_2$Cl$_2$. The appropriate fractions were twice combined, concentrated, and chromatographed through silica with 67% CH$_2$Cl$_2$/hexanes followed by a gradient of 0 to 10% MeOH/CH$_2$Cl$_2$. The appropriate fractions were combined, dissolved into CH$_2$Cl$_2$, washed with 10% aqueous NaOH, dried (Na$_2$SO$_4$), concentrated, rechromatographed again through a short column of silica with a gradient of 0 to 20% MeOH/CH$_2$Cl$_2$, and concentrated to provide the title compound (58% yield). MS (ESI APCI) m/z 296 (M+H)$^+$; $^1$HNMR (300 MHz, CD$_3$OD) δ 1.17 (d, 3 H), 1.37–1.52 (m, 1 H), 1.72–1.86 (m, 2 H), 1.92–2.08 (m, 1 H), 2.22–2.34 (m, 1 H), 2.40–2.59 (m, 2 H), 2.95–3.16 (m, 2 H), 3.18–3.34 (m, 2 H), 6.65 (s, 1 H), 7.14 (s, 1 H), 7.39 (dd, 1 H), 7.51–7.58 (m, 2 H), 7.68 (d, 1 H), 8.06 (s, 1 H).

Example 155

4-(3-bromo-2-{2-[(2R)-2-methyl-1-pyrrolidinyl]ethyl}-1-benzofuran-5-yl)-2-methylbenzonitrile The product of Example 106D was processed as described in Example 101 to provide the title compound as a brownish-orange gum (18% yield). MS (ESI) m/z 423/425 (M+H)$^+$; $^1$HNMR (300 MHz, CD$_3$OD) δ 1.39 (d, 3 H), 1.60–1.77 (m, 1 H), 1.96–2.12 (m, 2 H), 2.20–2.33 (m, 1 H), 2.61 (s, 3 H), 2.9–3.5 (m, 5 H), 3.52–3.76 (m, 2 H), 7.60–7.77 (m, 6 H).

Example 156A 4-(3-chloro-2-{2-[(2R)-2-methyl-1-pyrrolidinyl]ethyl}-1-benzofuran-5-yl)benzonitrile and Example 156B 4-(3,6-dichloro-2-{2-[(2R)-2-methyl-1-pyrrolidinyl]ethyl}-1-benzofuran-5-yl)benzonitrile The mono-(L)-tartaric acid salt of the product of Example 1D (120 mg, 0.25 mmol) was suspended in trifluoroacetic acid and treated with N-chlorosuccinimide (53 mg, 0.40 mmol) and stirred for two days. The reaction mixture was poured into aqueous Na$_2$SO$_3$, made alkaline with aqueous Na$_2$CO$_3$, and extracted with CH$_2$Cl$_2$. The combined organic phases were washed with brine, dried (Na$_2$SO$_4$), concentrated, and purified by HPLC [Waters Nova-Pak HR C18 column (40 mm×100 mm, 6 μm particle size) using a gradient of 10% to 100% MeCN/0.1% aqueous TFA over 12 min (15 min run time) at a flow rate of 70 mL/min.] to provide the title chloro (57% yield) and dichloro (12% yield) compounds as brown gums. 156A MS (ESI) m/z 365/367 (M+H)$^+$; $^1$HNMR (300 MHz, CD$_3$OD) □ 1.48 (d, 3 H), 1.67–1.83 (m, 1 H), 1.99–2.24 (m, 2 H), 2.30–2.44 (m, 1 H), 3.21–3.63 (m, 5 H), 3.72–3.92 (m, 2 H), 7.65 (d, 1 H), 7.73 (dd, 1 H), 7.80–7.89 (m, 5 H). 156B MS (ESI) m/z 399/401/403 (M+H)$^+$; $^1$HNMR (300 MHz, CD$_3$OD) δ 1.48 (d, 3 H), 1.67–1.83 (m, 1 H), 2.00–2.25 (m, 2H), 2.27–2.45 (m, 1 H), 3.21–3.64 (m, 5 H), 3.72–3.92 (m, 2 H), 7.57 (s, 1 H), 7.63 (d, 2 H), 7.80 (s, 1 H), 7.84 (d, 2 H).

Example 157

4-(3-iodo-2-{2-[(2R)-2-methyl-1-pyrrolidinyl]ethyl}-1-benzofuran-5-yl)benzonitrile The mono-(L)-tartaric acid salt of the product of Example 1D and N-iodosuccinimide were processed as in Example 156, except that a large excess of N-iodosuccinimide (2.4 molar equivalents) was utilized, to provide the title compound as a tan gum (18% yield). MS (ESI) m/z 457 (M+H)$^+$; $^1$HNMR (300 MHz, CD$_3$OD) δ 1.49 (d, 3 H), 1.67–1.84 (m, 1 H), 2.00–2.25 (m, 2 H), 2.29–2.44 (m, 1 H), 3.22–3.63 (m, 5 H), 3.72–3.91 (m, 2 H), 7.59–7.64 (m, 2 H), 7.72 (dd, 1 H), 7.80–7.89 (m, 4 H).

Example 158

4-(2-{2-[(2R)-2-methyl-5-oxo-1-pyrrolidinyl]ethyl}-1-benzofuran-5-yl)benzonitrile The mono-(L)-tartaric acid salt of the product of Example 1D (96 mg, 0.20 mmol) was suspended in acetone (10 mL) and treated with a solution of KMnO$_4$ (158 mg, 1.0 mmol) and MgSO$_4$ (120 mg, 1.0 mmol) in water (5 mL) over 30 minutes. After the purple color had disappeared, the solids were filtered off. The filtrate was diluted with EtOAc, washed with aqueous potassium dihydrogen phosphate, concentrated, and purified by HPLC [Waters Nova-Pak HR C18 column (25 mm×100 mm, 6 μm particle size) using a gradient of 10% to 100% MeCN/0.1% aqueous TFA over 8 min (10 min run time) at a flow rate of 40 mL/min.] to provide the title compound (2% yield). MS (ESI APCI) m/z 345 (M+H)$^+$; $^1$HNMR (300 MHz, CD$_3$OD) δ 1.22 (d, 3 H), 1.55–1.64 (m, 1 H), 2.15–2.32 (m, 2 H), 2.34–2.42 (m, 1 H), 2.99–3.13 (m, 2 H), 3.39–3.46 (m, 1 H), 3.68–3.76 (m, 1 H), 3.89–3.97 (m, 1 H), 6.65 (s, 1 H), 7.51–7.56 (m, 2 H), 7.76–7.84 (m, 5 H).

Example 159

4-(3-acetyl-2-{2-[(2R)-2-methyl-1-pyrrolidinyl]ethyl}-1-benzofuran-5-yl)benzonitrile The product of Example 1D (330 mg, 1.0 mmol) was dissolved into CH$_2$Cl$_2$ (500 μL) and cooled to 0° C. Acetyl chloride (140 μL, 2.0 mmol) and 1 M SnCl$_4$ in CH$_2$Cl$_2$ (1.5 mL, 1.5 mmol) were added, the reaction was permitted to warm to room temperature and it was stirred overnight. The mixture was partitioned between 20% EtOAc/CH$_2$Cl$_2$ and 0.5 M aqueous dipotassium hydrogen phosphate. The aqueous phase and solids were separated and extracted with CH$_2$Cl$_2$, and the organic phases were combined and worked up as usual but with an aqueous dipotassium hydrogen phosphate wash, dried (Na$_2$SO$_4$), and concentrated. The residue was then resubjected to the same reaction conditions used previously except with additional CH$_2$Cl$_2$ (7 mL), stirred for five days, and worked up as before. The concentrated residue was chromatographed through silica (MeOH/EtOAc/CH$_2$Cl$_2$) to afford an inseparable mixture of product and starting material.

The mixture (260 mg) and (4-tert-butylphenyl)-hydrazine hydrochloride (201 mg, 1.0 mmol) were dissolved into methanol (2 mL) and treated with 88% aqueous formic acid. The mixture was stirred overnight, concentrated, partitioned between 0.5 M dipotassium hydrogen phosphate and CH$_2$Cl$_2$, worked up as usual, dried (Na$_2$SO$_4$), concentrated, and chromatographed through silica with a gradient of 0.5 to 4% MeOH in 20% MECN/CH$_2$Cl$_2$. The appropriate fractions were concentrated, and after a few days appeared to have decomposed, partially to the desired ketone. The residue was rechromatographed through a short column of silica with a gradient of 0 to 4% MeOH/CH$_2$Cl$_2$, and then purified by HPLC [Waters Nova-Pak HR C18 column (40 mm×100 mm, 6 μm particle size) using a gradient of 10% to 100% MeCN/0.1% aqueous TFA over 12 min (15 min run time) at a flow rate of 70 mL/min.] to provide the title compound (4% yield). MS (ESI APCI) m/z 373 (M+H)$^+$; $^1$HNMR (300 MHz, CD$_3$OD) δ 1.49 (d, 3 H), 1.68–1.84 (m, 1 H), 2.01–2.25 (m, 2 H), 2.31–2.46 (m, 1 H), 2.80 (s, 3 H), 3.3–3.71 (m, 5 H), 3.76–3.92 (m, 2 H), 7.69–7.76 (m, 2 H), 7.84 (d, 2 H), 7.89 (d, 2 H), 8.20–8.22 (m, 1 H).

Example 160 cyclopropyl[4-(2-{2-[(2R)-2-methyl-1-pyrrolidinyl]ethyl}-1-benzofuran-5-yl)phenyl]methanone The product from Example 1D (330 mg, 1.0 mmol) was dissolved into tetrahydrofuran (1 mL), treated with ~0.7 M cyclopropylmagnesium bromide in tetrahydrofuran (2 mL, ~1.4 mmol) and copper (I) iodide (a few milligrams), and heated at 45° C. for one day and at 60° C. for two days. The reaction was brought to room temperature, quenched with 0.4 M aqueous hydrochloric acid (5 mL), and extracted with EtOAc. The organic phase was washed consecutively with 0.5 M aqueous dipotassium hydrogen phosphate and brine, dried ($Na_2SO_4$), concentrated, and purified by HPLC [Waters Nova-Pak HR C18 column (40 mm×100 mm, 6 μm particle size) using a gradient of 10% to 100% MeCN/0.1% aqueous TFA over 12 min (15 min run time) at a flow rate of 70 mL/min.] to provide the title compound as a powder (44% yield). MS (ESI APCI) m/z 374 (M+H)$^+$; $^1$HNMR (300 MHz, $CD_3OD$) δ 1.06–1.21 (m, 7 H), 1.38–1.53 (m, 1 H), 1.73–1.86 (m, 2 H), 1.94–2.08 (m, 1 H), 2.23–2.34 (m, 1 H), 2.40–2.59 (m, 2 H), 2.83–3.15 (m, 3 H), 3.19–3.34 (m, 2 H), 6.62 (s, 1 H), 7.51 (d, 1 H), 7.56 (dd, 1 H), 7.76–7.85 (m, 3 H), 8.12 (d, 2 H).

Example 161

3,5-dimethyl-4-(2-{2-[(2R)-2-methyl-1-pyrrolidinyl]ethyl}-1-benzofuran-5-yl)isoxazole Example 161A 2-[5-(3,5-Dimethyl-isoxazol-4-yl)-benzofuran-2-yl]-ethanol To a well stirred suspension of the product from Example 112B (1.446 g, 6.00 mmol), 3,5-dimethylisoxazole-4-boronic acid (2.09 g, 6.6 mmol) (Frontier Scientific, chemical abstracts number 16114-47-9), palladium (II) acetate (0.07 g, 0.3 mmol), and biphen-2-yl-dicyclohexylphosphine (0.15 g, 0.6 mmol) in toluene (20 mL) was added 10 mL of isopropanol and 10 mL of water. The reaction was heated at 60° C. for 36 hours, then cooled, poured into ethyl acetate (50 mL), and washed with water (100 mL). After drying over sodium sulfate, the organic layer was concentrated in vacuo and purified by flash chromatography, eluting with 1:1:4 of ethyl acetate/hexane/dichloromethane to provide the title compound as a tan oil, (97% yield). MS (DCI) m/z 258.2 (M+H)$^+$; $^1$HNMR (300 MHz, $CDCl_3$) δ 1.74 (s, 1H), 2.24 (s, 3H), 2.40 (s, 3H), 3.05 (t, 2H, J=6.0 Hz), 4.02 (t, 2H, J=6.0 Hz), 7.08 (dd, 1H, J=9.0,2.1 Hz), 7.34 (d, 1H, J=2.1 Hz), 6.54 (s, 1H), 7.46 (d, 1H, 9.0 Hz).

Example 161B

2-[5-(3,5-dimethyl-4-isoxazolyl)-1-benzofuran-2-yl]ethyl methanesulfonate

To a well stirred solution of the product from Example 161A (643 mg, 2.5 mmol) and methanesulfonic anhydride (522 mg, 3 mmol), in 3 mL of dichloromethane at 0° C. was added 0.53 mL (3.75 mmol) of triethylamine slowly. The reaction was allowed to warm to 23° C. and poured into dichloromethane, then washed with aqueous sodium phosphate (buffered to pH 8), dried over sodium sulfate, then concentrated in vacuo to provide the title compound as an oil.

Example 161C 3,5-dimethyl-4-(2-{2-[(2R)-2-methyl-1-pyrrolidinyl]ethyl}-1-benzofuran-5-yl)isoxazole A 3.3 mL (1 mmol) aliquot of the product from Example 161B in 8.33 mL of acetonitrile was transferred to a separate flask. Mono-(L)-tartaric acid salt of (R)-2-methylpyrrolidine (0.82 g, 3.5 mmol) was converted to the free base by shaking with 1 mL of toluene, 0.5 mL of 50% wt/vol sodium hydroxide, and 2 mL of brine. After separating, the toluene layer was decanted by pipette and added to the 3.3 mL aliquot of the product from Example 161B. After stirring for one week at room temperature, the reaction was poured into dichloromethane and washed with aqueous ammonia, dried over sodium sulfate, and purified by flash chromatography, eluting with 97:3 dichloromethane/methanol/0.1% $NH_3$, to give 225 mg (69%) of the title compound as a clear oil. MS (DCI) m/z 325.2 (M+H)$^+$; $^1$HNMR (300 MHz, $CDCl_3$) δ 1.18 (d, 1H, J=6.3 Hz), 2.24 (s, 3H), 2.40 (s, 3H), 1.5–2.0 (m, 6H), 2.5 (m, 1H), 3.02 (t, 2H, J=7.5 Hz), 3.23 (m, 2H), 6.48 (s, 1H), 7.08 (dd, 1H, J=9.0, 2.1 Hz), 7.34 (d, 1H, J=2.1 Hz), 7.44 (d, 1H, 9.0 Hz).

Example 162

4-[2-(2-aminoethyl)-1-benzofuran-5-yl]benzonitrile

Example 162A

4-[2-(2-azidoethyl)-1-benzofuran-5-yl]benzonitrile

Methanesulfonic acid (109 mg, 0.32 mmol), the product from Example 1C and sodium azide (83 mg, 1.28 mmol) was stirred in DMF for 4 days, then poured into dichloromethane and washed with water. The crude product was purified by flash chromatography, eluting with 2:1 dichloromethane/hexane to provide the title compound as a clear syrup (65 mg, 71%).

Example 162B

4-[2-(2-aminoethyl)-1-benzofuran-5-yl]benzonitrile

The product from Example 162A was dissolved in 3 mL of tetrahydrofuran, and treated with triphenylphosphine (262 mg, 1 mmol) was added, along with 0.5 mL water. After 3 days, the reaction was poured into dichloromethane and washed with aqueous ammonia. The organic layer was purified by flash chromatography, eluting with 10–20% methanol/dichloromethane, (0.1% $NH_3$) to give the title compound as a white powder. mp 118–120° C.; MS (DCI) m/z 263.0 (M+H)$^+$; $^1$HNMR (300 MHz, $CD_3OD$) δ 3.00 (m, 2H), 3.08 (m, 2H), 6.64 (s, 1H), 7.56 (m, 2H), 7.82 (m, 5H).

Example 163

4-(2-{2-[(2R)-2-ethyl-1-pyrrolidinyl]ethyl}-1-benzofuran-5-yl)benzonitrile

The product from Example 1C and (2R)-ethylpyrrolidine (Andres, Jose M.; Herraiz-Sierra, Ignacio; Pedrosa, Rafael; Perez-Encabo, Alfonso; Eur. J. Org. Chem.; vol. 9; 2000; pp1719–1726; chemical abstracts number 123168-37-6 hydrochloride salt)were processed as described in Example 1D to provide the titled compound, except that potassium carbonate was substituted for sodium carbonate, and the reaction was run at 60° C., then worked up by pouring into toluene. The organic phase was extracted with 7:2:1 of water/N-methylpyrrolidinone/10% aqueous methanesulfonic acid, and the aqueous phase then covered with isopropyl acetate and adjusted to pH 11 with 50% aqueous NaOH. After shaking and separation of the layers, the isopropanol extract was saved, then combined with a second isopropanol extract of the aqueous layer. The combined isopropanol extract was washed three times with 5% aqueous $NaHCO_3$, water, dried over magnesium sulfate, filtered, and concentrated in vacuo to provide a brown oil. The free base was converted to the mono-L-tartrate salt by addition of 1 equivalent of L-tartaric acid to the free base in ethanol. The mixture was heated to 70° C., and on allowing to cool, deposited an off-white solid. This was slurried with isopropyl acetate, and the solid collected by filtrate as the tartrate salt of the title compound. mp 147° C.; MS m/z (M+H)$^+$345.

Example 164

4-(2-{2-[(2S)-2-(fluoromethyl)-1-pyrrolidinyl]ethyl}-1-benzofuran-5-yl)benzonitrile Example 164A tert-butyl (2S)-2-{[(methylsulfonyl)oxy]methyl}-1-pyrrolidinecarboxylate N-Boc-(2S)-prolinol (6.04 g) in 100 mL of dichloromethane was treated with 4.04 g of triethylamine, cooled to 0° C., and treated with methanesulfonyl chloride (4.0 g) slowly. After stirring at 0° C. for 30 minutes, the reaction was allowed to warm to room temperature, washed with 5% aqueous NaHCO3 solution, dried over sodium sulfate, and concentrated to dryness to give the title compound as an off-white oil (8.47 g).

Example 164B tert-butyl (2S)-2-(fluoromethyl)-1-pyrrolidinecarboxylate

The product from Example 164A (7 g) in 100 mL of THF and tetrabutylammonium fluoride (42 mL of a 1M solution in THF) was heated at reflux for 17 hours, cooled, concentrated to dryness, diluted with 125 mL of ethyl acetate, washed with 5% aqueous NaHCO$_3$, brine, dried over MgSO$_4$, filtered, and the filtrate was concentrated under reduced pressure to provide an oil. The oil was distilled in vacuo (50° C., 1.2 torr) to give 4.9 g of the title compound as a colorless oil.

Example 164C (2S)-2-(fluoromethyl)pyrrolidine

The product of Example 164B (4.4 g) in 100 mL of ethyl acetate was treated with 10 mL of 4N HCl in 1,4-dioxane. The solution was stirred overnight, an additional 5 mL 4N HCl in 1,4-dioxane was added, and the slurry was stirred for another 24 hours. The off-white solid was collected by filtration, washed with acetonitrile, and dried at 50° C. under vacuum to give the title compound as a sticky solid (1.40 g). $^{13}$C NMR (DMSO) δ 81.6 (J$_{CF}$=167 Hz), 58.1 (J$_{CF}$=18 Hz), 45.0, 25.2 (J$_{CF}$=6 Hz), 23.3.

Example 164D 4-(2-{2-[(2S)-2-(fluoromethyl)-1-pyrrolidinyl]ethyl}-1-benzofuran-5-yl)benzonitrile The product from Example 1C and the product from Example 164C were processed as described in Example 1D to provide the titled compound, except that potassium carbonate was substituted for sodium carbonate, and the reaction was run at 60° C. for 3 days, then worked up by pouring into toluene. The organic phase was extracted with 7:2:1 of water/N-methylpyrrolidinone/10% aqueous methanesulfonic acid, and the aqueous phase then covered with isopropyl acetate and adjusted to pH 11 with 50% aqueous NaOH. After shaking and separation of the layers, the isopropanol extract was saved, then combined with a second isopropanol extract of the aqueous layer. The combined isopropanol extract was washed three times with 5% aqueous NaHCO$_3$, water, dried over magnesium sulfate, filtered, and concentrated in vacuo to a brown oil. The free base was converted to the mono-L-tartrate salt by addition of 1 equivalent of L-tartaric acid to the free base in ethanol. Two hours after removal of some of the ethanol under vacuum, the mixture deposited an off-white solid. The solid was collected by filtrate and dried in vacuo overnight to give the title product as the tartrate salt of 4-{2-[2-(2(R)-fluoromethyl-pyrrolidin-1-yl)-ethyl]-benzofuran-5-yl}-benzonitrile, mp 156.3° C., MS m/z (M+H)$^+$349; $^{13}$C NMR (DMSO) δ 158.6, 154.2, 145.2, 133.2, 132,7, 129.4, 127.7, 122.8, 119.2, 118.9, 111.2, 109.4, 103.0, 85.6 and 84.3, 72.1, 62.8, 53.5, 52.3, 27.2, 26.4, 22.7.

Example 165

4-(2-{2-[(2R)-2-methyl-1-pyrrolidinyl]ethyl}-1-benzothien-5-yl)benzonitrile

Example 165A

1-Bromo-4-[(2,2-diethoxyethyl)thio]benzene

1-Bromo-4-[(2,2-diethoxyethyl)thio]benzene (Chemical Abstracts number 96804-05-6) was prepared as described in Banfield et al.; J. Chem. Soc.; 1956; 2603–2607, and in Amin, et al.; J. Chem. Soc. Perkin Trans. 2; 1982; 1489–1492. 4-Bromothiophenol (20 g, 95%) in ethanol (80 mL) was treated with 21 wt % of sodium ethoxide in ethanol (36 g, 1.05 eq). The solution was heated at 55° C. for 30 minutes and bromoacetaldehyde diethylacetal (22.56 g, 1.05 eq) was added. The mixture was heated at reflux for 10 hours, ethanol was removed and the residue was diluted with 80 mL of water. The product was extracted with 2×120 mL of ethyl acetate. The combined ethyl acetate layer was washed with 2×40 mL of 15% NaCl and concentrated under vacuum to a brown oil (32.0 g, 92.5% potency, 96.5% yield). The product can be further purified by column chromatography (silica gel, 5:95 EtOAc:hexane).

Example 165B 5-bromo-1-benzothiophene

5-Bromobenzo[b]thiophene (Chemical Abstracts number 4923-87-9) was prepared as described in Banfield et al.; J. Chem. Soc.; 1956; 2603–2607, and in Seed, Alexander J.; et al. J. Mater. Chem.; vol10; 2000; 2069–2080. A mixture of phosphoric acid (218 g) and chlorobenzene (2 L) was heated at 130° C. and then treated with the product from Example 165A (107.0 g) over 2 hours using a syringe pump. The mixture was heated at 130° C. for 15 hours. Dean-Stark trap was used at the beginning of the reflux to remove water from the mixture. The mixture was allowed to cool to room temperature and quenched with 400 mL of water. The bottom aqueous layer was extracted with 200 mL of methylene chloride. The combined organic layer was washed with 200 mL of 10% Na$_2$CO$_3$, and concentrated to brown oil (129.4 g). The crude oil was dissolved in 1L of 10:90 EtOAC:hexane, filtered through a short pad of silica gel and concentrated to a yellow oil (85.54 g, 95.8% yield). Further purification was done by column chromatography (silica gel, 5:95 EtOAc:hexane).

Example 165C 2-(5-bromo-1-benzothien-2-yl)ethanol

The product from Example 165B (0.93 g) in THF (10 mL) at −55° C. was treated with lithium diisopropylamide (2.4 mL, 2M, 1.1 eq) precooled to −50 to −55° C. forming a red brown solution. The mixture was warmed to −25° C. and treated with a solution of ethylene oxide (0.96 g, 5 eq) in THF (13 mL) keeping the temperature at −20 to −25° C. The mixture was warmed to −15° C. and stirred for 3 hours. The mixture was acidified with 2N HCl, washed with 2×20 mL water and concentrated to crude solid (1.16 g). The crude product was purified by column chromatography (silica gel, 1:1 EtOAc:hexane) to give the title compound (0.62 g). $^1$H NMR(CDCl$_3$, δ) 1.6 (broad s, 1H), 3.17 (t, 2H), 3.93 (m, 2H),7.02 (s, 1H), 7.35 (d of d, 1H), 7.61 (d, 1H), 7.80 (s, 1H). MS (m/z): 274, 276 (M+NH$_4$).

Example 165D 2-(5-bromo-1-benzothien-2-yl)ethyl 4-methylbenzenesulfonate

The product from Example 165C (0.5 g) in methylene chloride (10 mL) was added triethylamine (0.3 g, 1.5 eq) followed by tosyl chloride (0.37 g, 1.0 ea). The solution was stirred at RT overnight and washed with 3×20 mL of water. The methylene chloride layer was concentrated to viscous oil (0.98 g, 68.1% potency, 83.5% yield). The crude product can be purified by crystallization from 20:80 EtOAc:hexane to give crystalline solid (0.48 g). $^1$H NMR(CDCl$_3$, δ) 2.38 (s, 3H), 3.21 (t, 2H), 4.30 (t, 2H), 6.87 (s, 1H), 7.18 (d, 2H), 7.36 (d of d, 1H), 7.55 (d, 1H), 7.63 (d, 2H), 7.75 (d, 1H). MS(m/z): 428, 430 (M+NH$_4$).

Example 165E (2R)-1-[2-(5-bromo-1-benzothien-2-yl)ethyl]-2-methylpyrrolidine

Toluene-4-sulfonic acid, the product from Example 165D (0.45 g), and K$_2$CO$_3$ (0.23 g, 1.5 eq) was treated with a solution of (2R)-2-methylpyrrolidine solution in acetonitrile (11.1 g, 12.6 mg/g of solution, 1.5 eq). The mixture was heated at 55° C. for 24 hours, allowed to cool to room temperature, and concentrated under reduced pressure. The residue was dissolved in 30 mL EtOAc, washed with 2×10 mL water, concentrated, and the residue was purified by column chromatography (silica gel, 10:90 MeOH:CHCl$_3$) to provide the title compound as an oil (0.26 g, 73.3%). $^1$H NMR(CDCl$_3$, δ) 1.10 (d, 3H), 1.4–2.0 (m, 4H), 2.20 (q, 1H), 2.30–2.50 (m, 2H), 3.00–3.23(m, 4H), 6.97 (s, 1H), 7.33 (d of d, 1H), 7.60 (d, 1H), 7.78 (d, 1H). MS (m/z): 324, 326 (M+H)$^+$.

Example 165F 4-(2-{2-[(2R)-2-methyl-1-pyrrolidinyl]ethyl}-1-benzothien-5-yl)benzonitrile The product from Example 165E (0.4 g), 4-cyanophenylboronic acid(0.45 g, 2.5 eq), triphenylphosphine (65 mg, 0.2 eq), and bistriphenylphosphine palladium dichloride (87 mg, 0.1 eq) in isopropanol (8 mL) was treated with potassium phosphate (0.52 g, 2 eq) in 8 mL of water. The mixture was heated at 65° C. under nitrogen for 25 hours, allowed to cool to room temperature, and treated with H$_2$O:NMP:MeSO$_3$H (70:20:10, 10 mL). The mixture was extracted with toluene (2×10 mL) and the acidic aqueous phase was basified to pH 10 using 50% NaOH. The basified solution was extracted with methylene chloride (10 mL), washed with water (2×10 mL), and concentrated to a brown oil. The brown oil was dissolved in EtOAc (20 mL), washed with water (2×10 mL), and concentrated. The residue was purified by column chromatography (silica gel, 10:90 MeOH:CHCl$_3$) to provide the title compound (0.37 g). MS m/z 347(M+H)$^+$. The free base was dissolved in 5 mL of MeOH and added to L-tartaric acid (0.16 g, 1 eq) in 5 mL of MeOH. The mixture was concentrated to dryness, and crystallized from EtOAc/EtOH to give the tartrate salt (0.33 g). $^1$H NMR(DMSO-d$_6$) δ 1.17 (doublet), 1.41–1.49 (multiplet), 1.74–1.82(multiplet), 1.97–2.03(multiplet), 2.55–2.59(multiplet), 2.80 (multiplet), 3.12–3.37(multiplet), 4.11(singlet), 7.33 (singlet), 7.66 (doublet), 7.93(singlet), 8.02(doublet), 8.13(doublet).

Example 166

4-(2-{2-[(2S)-2-methylpyrrolidinyl]ethyl}-1-benzofuran-5-yl)benzonitrile

Example 166A (2S)-2-methylpyrrolidine (2S)-2-methylpyrrolidine hydrobromide can be prepared using the procedure described in Nijhuis, Walter H. N., et al., J. Org. Chem.; vol. 54; 1; (1989) pp. 209–216; or Kim, Mahn-Joo, et al., Bioorg. Med. Chem. Lett.; vol. 6; 1; (1996) pp. 71–76).

Example 166B 4-(2-{2-[(2S)-2-methylpyrrolidinyl]ethyl}-1-benzofuran-5-yl)benzonitrile (2S)-2-Methylpyrrolidine hydrobromide and the product from Example 1C can be processed as described in Example 1D to provide the title compound.

Example 167

(2R)-2-methylpyrrolidine (2R)-2-Methyl pyrrolidine tartrate was prepared using the procedure described in Elworthy, Todd R.; Meyers, A. I., Tetrahedron, vol. 50, 20, (1994) pp 6089–6096, or (2R)-2-methyl pyrrolidine hydrobromide was prepared using the procedure described in Karrer, Ehrhardt, Helv. Chim. Acta, vol. 34, (1951) pp. 2202,2208; Gaffield, William, Lundin, Robert E., Keefer, Larry K., Tetrahedron, 37; 1981; 1861–1869; Yamada et al., Tetrahedron Lett. (1973) p. 381; or Andres, Jose M., Herraiz-Sierra, Ignacio, Pedrosa, Rafael, Perez-Encabo, Alfonso, Eur. J. Org. Chem., 9; (2000) pp 1719–1726.

Example 168

(2R)-2-methyl-1-[2-(5-phenoxy-1-benzofuran-2-yl)ethyl]pyrrolidine

2-Iodo-4-phenoxy-phenol

The title compound is prepared by treating 4-phenoxy phenol (Aldrich, CA no. 831-82-3) as described in Example 143A.

(2R)-2-methyl-1-[2-(5-phenoxy-1-benzofuran-2-yl)ethyl]pyrrolidine

The product from Example 168A and (R)-1-but-3-ynyl-2-methylpyrrolidine is treated as described in Example 136C to provide the title compound.

Example 169

(2R)-1-(2-{5-[(3-fluorophenyl)thiol]-1-benzofuran-2-yl}ethyl)-2-methylpyrrolidine (2R)-1-[2-(5-Bromo-1-benzofuran-2-yl)ethyl]-2-methylpyrrolidine is treated with 2 molar equivalents of tert-butyl lithium and bis(3-fluorophenyl)disulfide (Lancaster synthesis Ltd., Chemical Abstracts number 63930-17-6) in tetrahydrofuran at −78° C. to provide the title compound.

Example 170

3-(2-{3-[(2R)-2-methyl-1-pyrrolidinyl]propyl}-1-benzofuran-5-yl)benzonitrile

Example 170A 3-(5-bromo-1-benzofuran-2-yl)-1-propanol

The product from Example 112A and 4-pentyn-1-ol is processed as described in Example 112B to provide the title compound.

Example 170B

3-[2-(3-hydroxypropyl)-1-benzofuran-5-yl]benzonitrile

The product from Example 170A (193 mg, 0.80 mmol) and 3-cyanophenylboronic acid is processed as described in Example 112C to provide the title compound.

Example 170C

3-[5-(3-cyanophenyl)-1-benzofuran-2-yl]propyl methanesulfonate

The product from Example 170B and methanesulfonyl chloride is processed as described in Example 112D to provide the title compound.

Example 170D 3-(2-{3-[(2R)-2-methyl-1-pyrrolidinyl]propyl}-1-benzofuran-5-yl)benzonitrile The product from Example 170 and (2R)-2-methylpyrrolidine is processed as described in Example 112E to provide the title compound.

Example 171

3-(2-{[(2R)-2-methyl-1-pyrrolidinyl]methyl}-1-benzofuran-5-yl)benzonitrile

2-Propyn-1-ol and the product from Example 112A is processed as described in Examples 112B-E to provide the title compound.

Example 172

3-(2-{4-[(2R)-2-methyl-1-pyrrolidinyl]butyl}-1-benzofuran-5-yl)benzonitrile

5-Hexyn-1-ol and the product from Example 112A are processed as described in Examples 112B-E to provide the title compound.

Example 173

4-(4-{2-[2-(2S)-methyl-1-pyrrolidinyl)ethyl]-1-benzofuran-5-yl}benzoyl)morpholine (2S)-2-Methylpyrrolidine hydrobromide and the product from Example 23D (2-{5-[4-(4-morpholinylcarbonyl)phenyl]-1-benzofuran-2-yl}ethyl methanesulfonate) are processed as described in Example 1D to provide the titled compound.

Example 174

4-{4-methyl-2-oxo-3-[2-(2S)-methyl-1-pyrrolidinyl ethyl]-2H-chromen-6-yl}benzonitrile (2S)-2-Methylpyrrolidine hydrobromide and the product from Example 41C (2-{5-[4-(4-morpholinylcarbonyl)phenyl]-1-benzofuran-2-yl}ethyl methanesulfonate) are processed as described in Example 1D to provide the titled compound.

Example 175

4-{4-methyl-2-oxo-3-[2-(2R)-methyl-1-pyrrolidinyl ethyl]-2H-chromen-6-yl}benzonitrile (2R)-2-Methylpyrrolidine hydrobromide and the product from Example 41C (2-{5-[4-(4-morpholinylcarbonyl)phenyl]-1-benzofuran-2-yl}ethyl methanesulfonate) are processed as described in Example 1D to provide the titled compound.

Example 176

4-{[6-(2-{2-[(2S)-methylpyrrolidinyl]ethyl}-1-benzofuran-5-yl)-3-pyridinyl]carbonyl}morpholine (2S)-2-Methylpyrrolidine hydrobromide and the product from Example 44E (2-{5-[4-(4-morpholinylcarbonyl)phenyl]-1-benzofuran-2-yl}ethyl methanesulfonate) are processed as described in Example 1D to provide the titled compound.

Example 177

4-(2-{2-[(2R)-2-methylpyrrolidinyl]ethyl}-2,3-dihydro-1-benzofuran-5-yl)benzonitrile (2S)-2-Methylpyrrolidine hydrobromide and the product from Example 67D are processed as described in Example 1D to provide the titled compound.

Example 178

4-(2-{2-[(2S)-2-methyl-1-pyrrolidinyl]ethyl}-1-benzofuran-4-yl)benzonitrile (2S)-2-Methylpyrrolidine hydrobromide and the product from Example 85E are processed as described in Example 1D to provide the titled compound.

Example 179

4-{2-[2-(2S)-methyl-pyrrolidin-1-yl)-ethyl]-benzofuran-6-yl}-benzonitrile (2S)-Methylpyrrolidine hydrobromide and the product from Example 86E are processed as described in Example 1D to provide the titled compound.

Example 180

3-(2-{2-[(2S)-2-methyl-1-pyrrolidinyl]ethyl}-1-benzofuran-5-yl)benzonitrile (2S)-2-Methylpyrrolidine hydrobromide and the product from Example 112D are processed as described in Example 1D to provide the titled compound.

Examples 181–202

Compounds of Formula (50)

Examples 181–202 are compounds of formula (50), wherein $R_6$ is aryl or heterocycle. Such compounds can be prepared according to the procedures shown in Schemes 13 and 14 below:

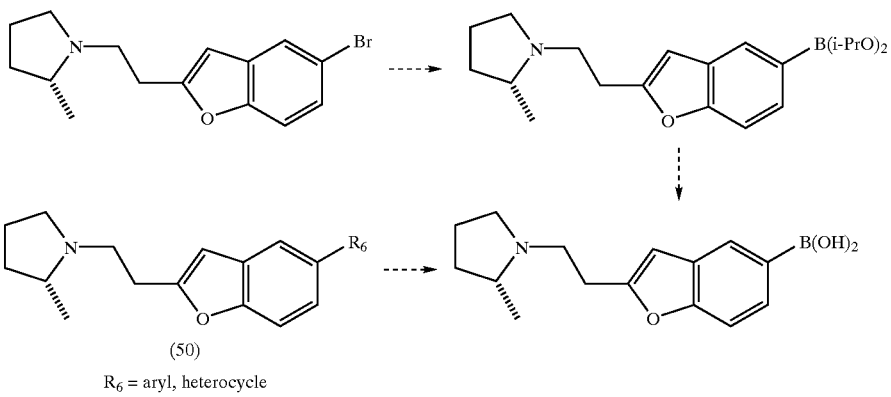

Scheme 14

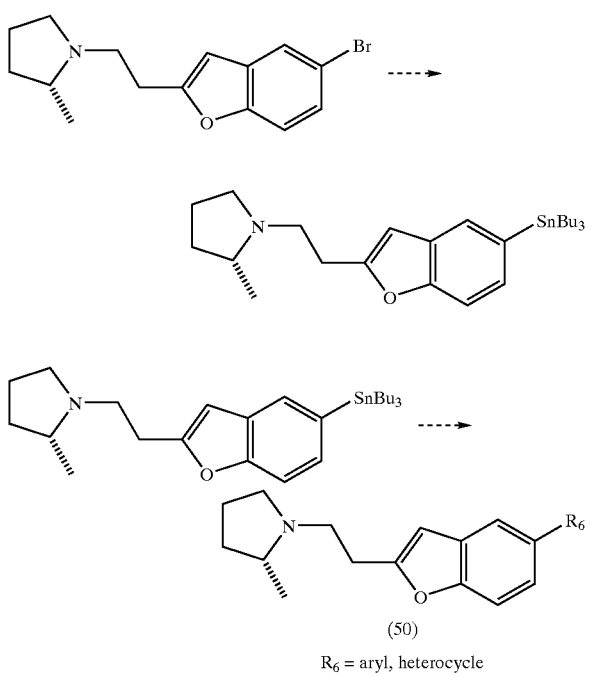

Scheme 13

$R_6$ = aryl, heterocycle

As shown in Scheme 13, (2R)-1-[2-(5-bromo-1-benzofuran-2-yl)ethyl]-2-methylpyrrolidine is treated with tert-butyl lithium and tributylstannyl chloride at −78° C. to provide (2R)-2-methyl-1-{2-[5-(tributylstannyl)-1-benzofuran-2-yl]ethyl}pyrrolidine. (2R)-2-Methyl-1-{2-[5-(tributylstannyl)-1-benzofuran-2-yl]ethyl}pyrrolidine is treated with a suitable starting material, for example, aryl halides, aryl triflates, or heterocyclic halides in the presence of a palladium catalyst, like palladium (II) acetate, and a trivalent phosphine, like tri(2-furyl)phosphine, in an organic solvent such as dimethylformamide at 25° C. to 120° C. to provide compounds of formula (50). Compounds of formula (50) can be isolated and purified by methods known to those skilled in the art. For example, compounds of formula (50) can be partitioned between dichloromethane and water, the organic phase concentrated, and the residue purified by chromatography on silica gel.

As shown in Scheme 14, (2R)-1-[2-(5-bromo-1-benzofuran-2-yl)ethyl]-2-methylpyrrolidine is treated with tert-butyl lithium and a borate ester, such as tri-isopropoxyborane, in tetrahydrofuran at −78° C. to provide diisopropyl 2-{2-[(2R)-2-methyl-1-pyrrolidinyl]ethyl}-1-benzofuran-5-ylboronate. Diisopropyl 2-{2-[(2R)-2-methyl-1-pyrrolidinyl]ethyl}-1-benzofuran-5-ylboronate is treated with water to provide the boronic acid or the boronate ester is used directly in the Suzuki coupling reaction. The boronic acid or the boronate ester is treated with a suitable starting material, for example, aryl halides, aryl triflates, or heterocyclic halides, a palladium catalyst such as palladium (II) acetate, a trivalent phosphine such as biphen-2-yl-dicyclohexylphosphine, and aqueous sodium carbonate or potassium phosphate in an organic solvent, such as ethanol or tetrahydrofuran, at 25° C. to 120° C. to provide compounds of formula (50). Compounds of formula (50) can be isolated and purified by methods known to those skilled in the art. For example, compounds of formula (50) can be partitioned between dichloromethane and water, the organic phase concentrated, and the residue purified by chromatography on silica gel.

Examples of compounds that can be prepared according to procedures described in Schemes 13 and 14 and starting materials suitable for preparing such compounds are provided below in Table 2.

TABLE 2

| Example Number | Compound | Starting Material | Chemical Abstracts number |
|---|---|---|---|
| 181 | 3,5-Dimethyl-4-{2-[2-(2R)-methyl-pyrrolidin-1-yl-ethyl]-benzofuran-5-yl}-isoxazole | 4-Iodo-3,5-di-methyl-isoxazole | 10557-85-4 |
| 182 | 5-{2-[2-(2R)-Methyl-pyrrolidin-1-yl-ethyl]- | 5-Bromo-2-phenyl-oxazole | 92629-11-3 |

TABLE 2-continued

| Example Number | Compound | Starting Material | Chemical Abstracts number |
|---|---|---|---|
| | benzofuran-5-yl}-2-phenyl-oxazole | | |
| 183 | 2-{2-[2-(2R)-Methyl-pyrrolidin-1-yl-ethyl]-benzofuran-5-yl}-thiazole | 2-Bromo-thiazole | 3034-53-5 |
| 184 | 4-{2-[2-(2R)-Methyl-pyrrolidin-1-yl-ethyl]-benzofuran-5-yl}-1H-pyrazole | 4-Iodo-1H-pyrazole | 3469-69-0 |
| 185 | 4-{2-[2-(2R)-Methyl-pyrrolidin-1-yl-ethyl]-benzofuran-5-yl}-1-phenyl-1H-pyrazole | 4-Iodo-1-phenyl-1H-pyrazole | 23889-85-0 |
| 186 | 1-Methyl-4-{2-[(2R)-(2-methyl-pyrrolidin-1-yl)-ethyl]-benzofuran-5-yl}-1H-imidazole | 4-Bromo-1-methyl-1H-imidazole | 25676-75-9 |
| 187 | 4-{2-[2-(2R)-Methyl-pyrrolidin-1-yl-ethyl]-benzofuran-5-yl}-thiazole | 4-Bromo-thiazole | 34259-99-9 |
| 188 | 2-{2-[2-(2R)-Methyl-pyrrolidin-1-yl-ethyl]-benzofuran-5-yl}-1H-imidazole | 2-Iodo-1H-imidazole | 3034-62-6 |
| 189 | 4-{2-[2-(2R)-Methyl-pyrrolidin-1-yl-ethyl]-benzofuran-5-yl}-1H-benzoimidazole | 4-Bromo-1H-benzoimidazole | 83741-35-9 |
| 190 | 3-Methyl-6-{(2R)-[2-(2-methyl-pyrrolidin-1-yl)-ethyl]-benzofuran-5-yl}-pyridazine | 3-Chloro-6-methyl-pyridazine | 1121-79-5 |
| 191 | 2-{2-[2-(2R)-Methyl-pyrrolidin-1-yl-ethyl]-benzofuran-5-yl}-pyrazine | 2-Iodo-pyrazine | 32111-21-0 |
| 192 | 5-{2-[2-(2R)-Methyl-pyrrolidin-1-yl)-ethyl]-benzofuran-5-yl}-pyrimidine | 5-Bromo-pyrimidine | 4595-59-9 |
| 193 | 5-{2-[2-(2R)-Methyl-pyrrolidin-1-yl)-ethyl]-benzofuran-5-yl}-pyridazin-4-ylamine | 5-Bromo-pyridazin-4-ylamine | 55928-90-0 |
| 194 | 5-{2-[2-(2R)-Methyl-pyrrolidin-1-yl)-ethyl]-benzofuran-5-yl}-nicotinonitrile | 5-Bromo-nicotinonitrile | 35590-37-5 |
| 195 | 4-{2-[2-(2R)-Methyl-pyrrolidin-1-yl)-ethyl]-benzofuran-5-yl}-1H-indole | 4-Bromo-1H-indole | 52488-36-5 |
| 196 | 4-{2-[2-(2R)-Methyl-pyrrolidin-1-yl)-ethyl]-benzofuran-5-yl}-phthalonitrile | 4-Iodo-phthalonitrile | 69518-17-8 |
| 197 | 5-{2-[2-(2R)-Methyl-pyrrolidin-1-yl)-ethyl]-benzofuran-5-yl}-indan-1-one | 5-Bromo-indan-1-one | 34598-49-7 |
| 198 | 1-{2-[5-(5,6-Dihydro-2H-pyran-3-yl)-benzofuran-2-yl]-ethyl}-(2R)-methyl-pyrrolidine | 5-Bromo-3,6-dihydro-2H-pyran | 100130-39-0 |
| 199 | 1-[2-(5-Cyclohept-1-enyl-benzofuran-2-yl)-ethyl]-2R)-methyl-pyrrolidine | 1-Iodo-cycloheptene | 49565-03-9 |
| 200 | (2R)-Methyl-1-(2-{5-[2-(11H-10-thia-dibenzo[a,d]cyclohepten-5-ylidene)-ethyl]-benzofuran-2-yl}-ethyl)-pyrrolidine | 5-(2-Bromo-ethylidene)-5,11-dihydro-10-thia-dibenzo[a,d]cycloheptene | 112930-54-8 |
| 201 | 4-{2-[2-(2R)-Methyl-pyrrolidin-1-yl)-ethyl]-benzofuran-5-yl}-pyridine | 4-Bromopyridine hydrochloride | 19524-06-2 |
| 202 | 4-{2-[2-(2R)-Methyl-pyrrolidin-1-yl)-ethyl]-benzofuran-5-yl}-pyridine | 2-Bromopyridine | 109-04-6 |

Examples 203–224

Compounds of Formula (51)

Examples 203–224 are compounds of formula (51), wherein $R_4$ is aryl or heterocycle. Such compounds can be prepared according to the procedure shown in Scheme 15 below:

Scheme 15

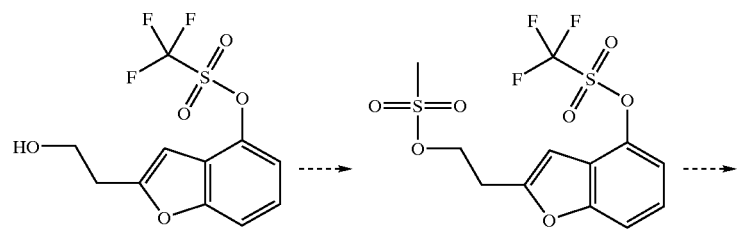

-continued

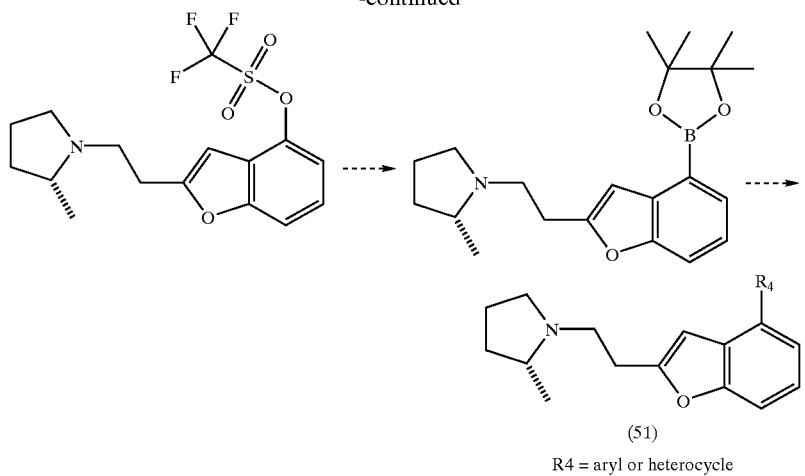

R4 = aryl or heterocycle

As shown in Scheme 15, 2-(2-Hydroxyethyl)-1-benzofuran-4-yl trifluoromethanesulfonate, prepared as described in Examples 85A–85C herein, is treated with methanesulfonyl chloride and triethylamine in CH₂Cl₂ at 0° C. to provide 2-{2-[(methylsulfonyl)oxy]ethyl}-1-benzofuran-4-yl trifluoromethanesulfonate. 2-{2-[(Methylsulfonyl)oxy]ethyl}-1-benzofuran-4-yl trifluoromethanesulfonate is treated with (2R)-methylpyrrolidine mono-(L)-tartaric acid salt and Cs₂CO₃ in MeCN at approximately 35° C. for 1 to 4 days to provide 2-{2-[(2R)-2-methyl-1-pyrrolidinyl]ethyl}-1-benzofuran-4-yl trifluoromethanesulfonate. 2-{2-[(2R)-2-Methyl-1-pyrrolidinyl]ethyl}-1-benzofuran-4-yl trifluoromethanesulfonate is processed as described in Murata, et al., Journal of Organic Chemistry (2000) 65, 164–168 to provide (2R)-2-methyl-1-{2-[4-(4,4,5,5-tetramethyl-1,3,2-dioxaborolan-2-yl)-1-benzofuran-2-yl]ethyl}pyrrolidine. For example, one equivalent of 2-{2-[(2R)-2-methyl-1-pyrrolidinyl]ethyl}-1-benzofuran-4-yl trifluoromethanesulfonate is treated with palladium acetate or [1,1'-bis(diphenylphosphino)ferrocene] dichloropalladium (PdCl₂dppf), 3 equivalents of triethylamine, and 1.5 equivalents of pinacolborane in 1,4-dioxane at 25° C. for several hours or until the reaction is complete as judged by TLC. (2R)-2-Methyl-1-{2-[4-(4,4,5,5-tetramethyl-1,3,2-dioxaborolan-2-yl)-1-benzofuran-2-yl]ethyl}pyrrolidine is treated with a suitable starting material, for example, aryl halides, aryl triflates, or heterocyclic halides, a palladium catalyst, such as palladium (II) acetate, a trivalent phosphine such as biphen-2-yl-dicyclohexylphosphine, and aqueous sodium carbonate or potassium phosphate in an organic solvent such as ethanol or tetrahydrofuran at 25° C. to 120° C. to provide compounds of formula (51). Compounds of formula (51) can be isolated and purified by methods known to those skilled in the art. For example, compounds of formula (51) is partitioned between dichloromethane and water, the organic phase concentrated, and the residue purified by chromatography on silica gel.

Examples of compounds that can be prepared according to procedures described in Scheme 15 starting materials suitable for preparing such compounds are provided below in Table 3.

TABLE 3

| Example Number | Compound | Starting Material | Chemical Abstracts number |
|---|---|---|---|
| 203 | 3,5-Dimethyl-4-{2-[2-(2R)-methyl-pyrrolidin-1-yl-ethyl]-benzofuran-4-yl}-isoxazole | 4-Iodo-3,5-di-methyl-isoxazole | 10557-85-4 |
| 204 | 5-{2-[2-(2R)-Methyl-pyrrolidin-1-yl-ethyl]-benzofuran-4-yl}-2-phenyl-oxazole | 5-Bromo-2-phenyl-oxazole | 92629-11-3 |
| 205 | 2-{2-[2-(2R)-Methyl-pyrrolidin-1-yl-ethyl]-benzofuran-4-yl}-thiazole | 2-Bromo-thiazole | 3034-53-5 |
| 206 | 4-{2-[2-(2R)-Methyl-pyrrolidin-1-yl-ethyl]-benzofuran-4-yl}-1H-pyrazole | 4-Iodo-1H-pyrazole | 3469-69-0 |
| 207 | 4-{2-[2-(2R)-Methyl-pyrrolidin-1-yl-ethyl]-benzofuran-4-yl}-1-phenyl-1H-pyrazole | 4-Iodo-1-phenyl-1H-pyrazole | 23889-85-0 |
| 208 | 1-Methyl-4-{2-[(2R)-(2-methyl-pyrrolidin-1-yl)-ethyl]-benzofuran-4-yl}-1H-imidazole | 4-Bromo-1-methyl-1H-imidazole | 25676-75-9 |
| 209 | 4-{2-[2-(2R)-Methyl-pyrrolidin-1-yl-ethyl]-benzofuran-4-yl}-thiazole | 4-Bromo-thiazole | 34259-99-9 |
| 210 | 2-{2-[2-(2R)-Methyl-pyrrolidin-1-yl-ethyl]-benzofuran-4-yl}-1H-imidazole | 2-Iodo-1H-imidazole | 3034-62-6 |
| 211 | 4-{2-[2-(2R)-Methyl-pyrrolidin-1-yl-ethyl]-benzofuran-4-yl}-1H-benzoimidazole | 4-Bromo-1H-benzoimidazole | 83741-35-9 |
| 212 | 3-Methyl-6-{(2R)-[2-(2-methyl-pyrrolidin-1-yl)-ethyl]-benzofuran-4-yl}-pyridazine | 3-Chloro-6-methyl-pyridazine | 1121-79-5 |
| 213 | 2-{2-[2-(2R)-Methyl-pyrrolidin-1-yl-ethyl]-benzofuran-4-yl}-pyrazine | 2-Iodo-pyrazine | 32111-21-0 |
| 214 | 5-{2-[2-(2R)-Methyl-pyrrolidin-1-yl-ethyl]-benzofuran-4-yl}-pyrimidine | 5-Bromo-pyrimidine | 4595-59-9 |

TABLE 3-continued

| Example Number | Compound | Starting Material | Chemical Abstracts number |
|---|---|---|---|
| 215 | 5-{2-[2-(2R)-Methyl-pyrrolidin-1-yl-ethyl]-benzofuran-4-yl}-pyridazin-4-ylamine | 5-Bromo-pyridazin-4-ylamine | 55928-90-0 |
| 216 | 5-{2-[2-(2R)-Methyl-pyrrolidin-1-yl-ethyl]-benzofuran-4-yl}-nicotinonitrile | 5-Bromo-nicotinonitrile | 35590-37-5 |
| 217 | 4-{2-[2-(2R)-Methyl-pyrrolidin-1-yl-ethyl]-benzofuran-4-yl}-1H-indole | 4-Bromo-1H-indole | 52488-36-5 |
| 218 | 4-{2-[2-(2R)-Methyl-pyrrolidin-1-yl-ethyl]-benzofuran-4-yl}-phthalonitrile | 4-Iodo-phthalonitrile | 69518-17-8 |
| 219 | 5-{2-[2-(2R)-Methyl-pyrrolidin-1-yl-ethyl]-benzofuran-4-yl}-indan-1-one | 5-Bromo-indan-1-one | 34598-49-7 |
| 220 | 1-{2-[4-(5,6-Dihydro-2H-pyran-3-yl)-benzofuran-2-yl]-ethyl}-(2R)-methyl-pyrrolidine | 5-Bromo-3,6-di-hydro-2H-pyran | 100130-39-0 |
| 221 | 1-[2-(4-Cyclohept-1-enyl-benzofuran-2-yl)-ethyl]-(2R)-methyl-pyrrolidine | 1-Iodo-cycloheptene | 49565-03-9 |
| 222 | (2R)-Methyl-1-(2-{4-[2-(11H-10-thia-dibenzo[a,d]cyclohepten-5-ylidene)-ethyl]-benzofuran-2-yl}-ethyl)-pyrrolidine | 5-(2-Bromo-ethyl-idene)-5,11-dihydro-10-thia-dibenzo[a,d]cycloheptene | 112930-54-8 |
| 223 | 4-{2-[2-(2R)-Methyl-pyrrolidin-1-yl-ethyl]-benzofuran-4-yl}-pyridine | 4-Bromopyridine hydrochloride | 19524-06-2 |
| 224 | 4-{2-[2-(2R)-Methyl-pyrrolidin-1-yl-ethyl]-benzofuran-4-yl}-pyridine | 2-Bromopyridine | 109-04-6 |

Examples 225–246

Compounds of Formula (52)

Examples 225–246 are compounds of formula (52), wherein $R_4$ is aryl or heterocycle. Such compounds can be prepared according to the procedure shown in Scheme 16 below:

Scheme 16

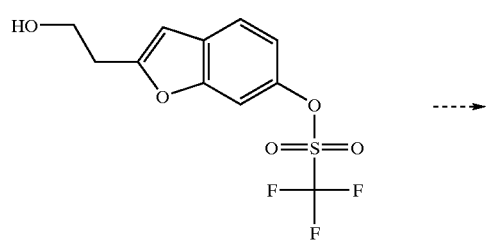

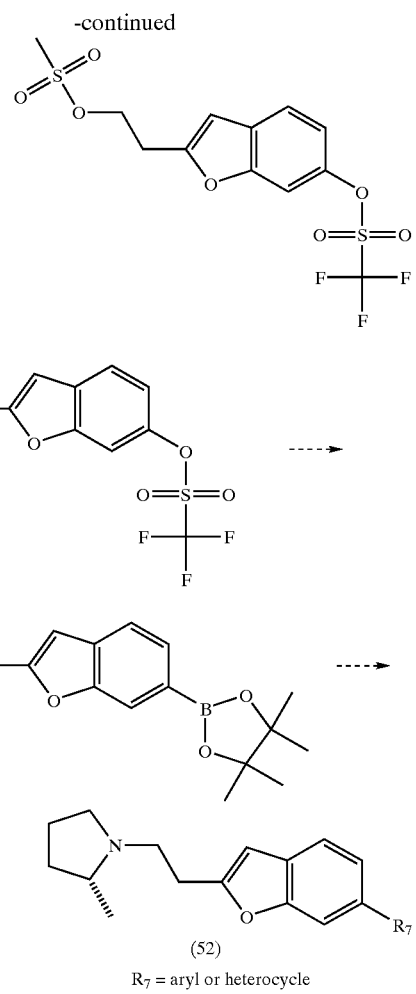

(52)

$R_7$ = aryl or heterocycle

As shown in Scheme 16, 2-(2-hydroxyethyl)-1-benzofuran-6-yl trifluoromethanesulfonate, prepared as described in Examples 86A to 86C, is processed according to procedures described for Examples 203–224 as shown in Scheme 15 to provide compounds of formula (52). Compounds of formula (52) can be isolated and purified by methods known to those skilled in the art. For example, compounds of formula (52) can be partitioned between dichloromethane and water, the organic phase concentrated, and the residue purified by chromatography on silica gel.

Examples of compounds that can be prepared according to procedures described in Scheme 16 and starting materials suitable for preparing such compounds are provided below in Table 4.

TABLE 4

| Example Number | Compound | Starting Material | Chemical Abstracts number |
|---|---|---|---|
| 225 | 3,5-Dimethyl-4-{2-[2-(2(R)-methyl-pyrrolidin-1-yl)-ethyl]-benzofuran-6-yl}-isoxazole | 4-Iodo-3,5-di-methyl-isoxazole | 10557-85-4 |
| 226 | 5-{2-[2-(2(R)-Methyl-pyrrolidin-1-yl)-ethyl]-benzofuran-6-yl}-2-phenyl-oxazole | 5-Bromo-2-phenyl-oxazole | 92629-11-3 |

TABLE 4-continued

| Example Number | Compound | Starting Material | Chemical Abstracts number |
|---|---|---|---|
| 227 | 2-{2-[2-(2(R)-Methyl-pyrrolidin-1-yl)-ethyl]-benzofuran-6-yl}-thiazole | 2-Bromo-thiazole | 3034-53-5 |
| 228 | 4-{2-[2-(2(R)-Methyl-pyrrolidin-1-yl)-ethyl]-benzofuran-6-yl}-1H-pyrazole | 4-Iodo-1H-pyrazole | 3469-69-0 |
| 229 | 4-{2-[2-(2(R)-Methyl-pyrrolidin-1-yl)-ethyl]-benzofuran-6-yl}-1-phenyl-1H-pyrazole | 4-Iodo-1-phenyl-1H-pyrazole | 23889-85-0 |
| 230 | 1-Methyl-4-{2-[2(R)-(2-methyl-pyrrolidin-1-yl)-ethyl]-benzofuran-6-yl}-1H-imidazole | 4-Bromo-1-methyl-1H-imidazole | 25676-75-9 |
| 231 | 4-{2-[2-(2(R)-Methyl-pyrrolidin-1-yl)-ethyl]-benzofuran-6-yl}-thiazole | 4-Bromo-thiazole | 34259-99-9 |
| 232 | 2-{2-[2-(2(R)-Methyl-pyrrolidin-1-yl)-ethyl]-benzofuran-6-yl}-1H-imidazole | 2-Iodo-1H-imidazole | 3034-62-6 |
| 233 | 4-{2-[2-(2(R)-Methyl-pyrrolidin-1-yl)-ethyl]-benzofuran-6-yl}-1H-benzoimidazole | 4-Bromo-1H-benzoimidazole | 83741-35-9 |
| 234 | 3-Methyl-6-{2(R)-[2-(2-methyl-pyrrolidin-1-yl)-ethyl]-benzofuran-6-yl}-pyridazine | 3-Chloro-6-methyl-pyridazine | 1121-79-5 |
| 235 | 2-{2-[2-(2(R)-Methyl-pyrrolidin-1-yl)-ethyl]-benzofuran-6-yl}-pyrazine | 2-Iodo-pyrazine | 32111-21-0 |
| 236 | 5-{2-[2-(2(R)-Methyl-pyrrolidin-1-yl)-ethyl]-benzofuran-6-yl}-pyrimidine | 5-Bromo-pyrimidine | 4595-59-9 |
| 237 | 5-{2-[2-(2(R)-Methyl-pyrrolidin-1-yl)-ethyl]-benzofuran-6-yl}-pyridazin-4-ylamine | 5-Bromo-pyridazin-4-ylamine | 55928-90-0 |
| 238 | 5-{2-[2-(2(R)-Methyl-pyrrolidin-1-yl)-ethyl] benzofuran-6-yl}-nicotinonitrile | 5-Bromo-nicotinonitrile | 35590-37-5 |
| 239 | 4-{2-[2-(2(R)-Methyl-pyrrolidin-1-yl)-ethyl]-benzofuran-6-yl}-1H-indole | 4-Bromo-1H-indole | 52488-36-5 |
| 240 | 4-{2-[2-(2(R)-Methyl-pyrrolidin-1-yl)-ethyl]-benzofuran-6-yl}-phthalonitrile | 4-Iodo-phthalonitrile | 69518-17-8 |
| 241 | 5-{2-[2-(2(R)-Methyl-pyrrolidin-1-yl)-ethyl]-benzofuran-6-yl)-indan-1-one | 5-Bromo-indan-1-one | 34598-49-7 |
| 242 | 1-{2-[6-(5,6-Dihydro-2H-pyran-3-yl)-benzofuran-2-yl]-ethyl}-2(R)-methyl-pyrrolidine | 5-Bromo-3,6-dihydro-2H-pyran | 100130-39-0 |
| 243 | 1-[2-(6-Cyclohept-1-enyl-benzofuran-2-yl)-ethyl]-2(R)-methyl-pyrrolidine | 1-Iodo-cycloheptene | 49565-03-9 |
| 244 | 2(R)-Methyl-1-(2-{6-[2-(11H-10-thia-dibenzo[a,d]cyclohepten-5-ylidene)-ethyl]-benzofuran-2-yl}-ethyl)-pyrrolidine | 5-(2-Bromo-ethylidene)-5,11-dihydro-10-thia-dibenzo[a,d] cycloheptene | 112930-54-8 |
| 245 | 4-{2-[2-(2(R)-Methyl-pyrrolidin-1-yl)-ethyl]-benzofuran-6-yl}-pyridine | 4-Bromopyridine hydrochloride | 19524-06-2 |
| 246 | 4-{2-[2-(2(R)-Methyl-pyrrolidin-1-yl)-ethyl]-benzofuran-6-yl}-pyridine | 2-Bromopyridine | 109-04-6 |

Examples 247–268

Compounds of Formula (53)

Examples 247–268 are compounds of formula (53), wherein $R_5$ is aryl or heterocycle. Such compounds can be prepared according to the procedures shown in Scheme 17 below:

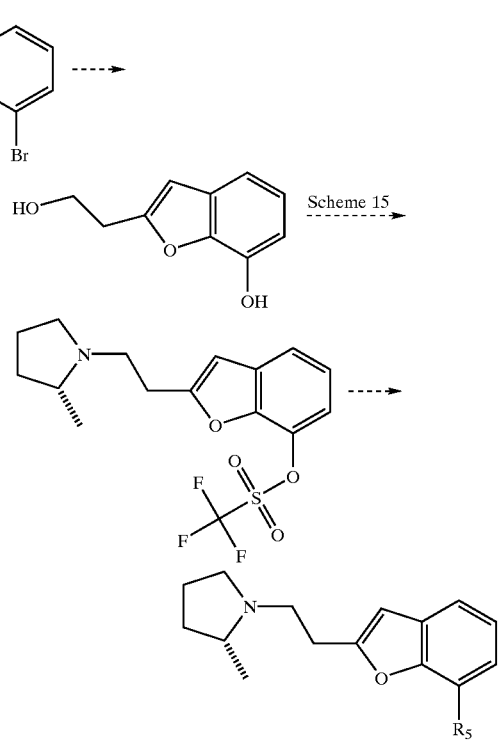

Scheme 17

(53)

$R_5$ = aryl or heterocycle

As shown in Scheme 17, 3-bromo-1,2-benzenediol is treated with bis-triphenylphosphine palladium dichloride, copper iodide, triethylamine, and 3-butyn-1-ol and heated at between 40° C. and 80° C. for several hours or until TLC (thin layer chromatography) indicates the reaction is complete to provide 2-(2-hydroxyethyl)-1-benzofuran-7-ol. 2-(2-Hydroxyethyl)-1-benzofuran-7-ol is then processed according to procedures described for Examples 203–224 as shown as in Scheme 15 to provide 2-{2-[(2R)-2-methyl-1-pyrrolidinyl]ethyl}-1-benzofuran-7-yl trifluoromethanesulfonate, which is processed as described in Murata, et al., Journal of Organic Chemistry (2000) 65, 164–168 and followed by treatment with a suitable starting material, for example, aryl halides, aryl triflates, or heterocyclic halides, a palladium catalyst, such as palladium (II) acetate, a trivalent phosphine such as biphen-2-yl-dicyclohexylphosphine, and aqueous sodium carbonate or potassium phosphate in an organic solvent such as ethanol or tetrahydrofuran at 25° C. to 120° C. to provide compounds formula (53). Compounds of formula (53) can be isolated and purified by methods known to those skilled in the art. For example, compounds of formula (53) can be partitioned between dichloromethane and water, the organic phase concentrated, and the residue purified by chromatography on silica gel.

Examples of compounds that can be prepared according to procedures described in Scheme 17 and starting materials suitable for preparing such compounds are provided below in Table 5.

TABLE 5

| Example Number | Compound | Starting Material | Chemical Abstracts number |
|---|---|---|---|
| 247 | 3,5-Dimethyl-4-{2-[2-(2(R)-methyl-pyrrolidin-1-yl)-ethyl]-benzofuran-7-yl}-isoxazole | 4-Iodo-3,5-di-methyl-isoxazole | 10557-85-4 |
| 248 | 5-{2-[2-(2(R)-Methyl-pyrrolidin-1-yl)-ethyl]-benzofuran-7-yl}-2-phenyl-oxazole | 5-Bromo-2-phenyl-oxazole | 92629-11-3 |
| 249 | 2-{2-[2-(2(R)-Methyl-pyrrolidin-1-yl)-ethyl]-benzofuran-7-yl}-thiazole | 2-Bromo-thiazole | 3034-53-5 |
| 250 | 4-{2-[2-(2(R)-Methyl-pyrrolidin-1-yl)-ethyl]-benzofuran-7-yl}-1H-pyrazole | 4-Iodo-1H-pyrazole | 3469-69-0 |
| 251 | 4-{2-[2-(2(R)-Methyl-pyrrolidin-1-yl)-ethyl]-benzofuran-7-yl}-1-phenyl-1H-pyrazole | 4-Iodo-1-phenyl-1H-pyrazole | 23889-85-0 |
| 252 | 1-Methyl-4-{2-[2(R)-(2-methyl-pyrrolidin-1-yl)-ethyl]-benzofuran-7-yl}-1H-imidazole | 4-Bromo-1-methyl-1H-imidazole | 25676-75-9 |
| 253 | 4-{2-[2-(2(R)-Methyl-pyrrolidin-1-yl)-ethyl]-benzofuran-7-yl}-thiazole | 4-Bromo-thiazole | 34259-99-9 |
| 254 | 2-{2-[2-(2(R)-Methyl-pyrrolidin-1-yl)-ethyl]-benzofuran-7-yl}-1H-imidazole | 2-Iodo-1H-imidazole | 3034-62-6 |
| 255 | 4-{2-[2-(2(R)-Methyl-pyrrolidin-1-yl)-ethyl]-benzofuran-7-yl}-1H-benzoimidazole | 4-Bromo-1H-benzoimidazole | 83741-35-9 |
| 256 | 3-Methyl-6-{2(R)-[2-(2-methyl-pyrrolidin-1-yl)-ethyl]-benzofuran-7-yl}-pyridazine | 3-Chloro-6-methyl-pyridazine | 1121-79-5 |
| 257 | 2-{2-[2-(2(R)-Methyl-pyrrolidin-1-yl)-ethyl]-benzofuran-7-yl}-pyrazine | 2-Iodo-pyrazine | 32111-21-0 |
| 258 | 5-{2-[2-(2(R)-Methyl-pyrrolidin-1-yl)-ethyl]-benzofuran-7-yl}-pyrimidine | 5-Bromo-pyrimidine | 4595-59-9 |
| 259 | 5-{2-[2-(2(R)-Methyl-pyrrolidin-1-yl)-ethyl]-benzofuran-7-yl}-pyridazin-4-ylamine | 5-Bromo-pyridazin-4-ylamine | 55928-90-0 |

TABLE 5-continued

| Example Number | Compound | Starting Material | Chemical Abstracts number |
|---|---|---|---|
| 260 | 5-{2-[2-(2(R)-Methyl-pyrrolidin-1-yl)-ethyl]-benzofuran-7-yl}-nicotinonitrile | 5-Bromo-nicotinonitrile | 35590-37-5 |
| 261 | 4-{2-[2-(2(R)-Methyl-pyrrolidin-1-yl)-ethyl]-benzofuran-7-yl}-1H-indole | 4-Bromo-1H-indole | 52488-36-5 |
| 262 | 4-{2-[2-(2(R)-Methyl-pyrrolidin-1-yl)-ethyl]-benzofuran-7-yl}-phthalonitrile | 4-Iodo-phthalonitrile | 69518-17-8 |
| 263 | 5-{2-[2-(2(R)-Methyl-pyrrolidin-1-yl)-ethyl]-benzofuran-7-yl}-indan-1-one | 5-Bromo-indan-1-one | 34598-49-7 |
| 264 | 1-{2-[7-(5,6-Dihydro-2H-pyran-3-yl)-benzofuran-2-yl]-ethyl}-2(R)-methyl-pyrrolidine | 5-Bromo-3,6-di-hydro-2H-pyran | 100130-39-0 |
| 265 | 1-[2-(7-Cyclohept-1-enyl-benzofuran-2-yl)-ethyl]-2(R)-methyl-pyrrolidine | 1-Iodo-cycloheptene | 49565-03-9 |
| 266 | 2(R)-Methyl-1-(2-{7-[2-(11H-10-thia-dibenzo[a,d]cyclohepten-5-ylidene)-ethyl]-benzofuran-2-yl}-ethyl)-pyrrolidine | 5-(2-Bromo-ethylidene)-5,11-dihydro-10-thia-dibenzo[a,d]cycloheptene | 112930-54-8 |
| 267 | 4-{2-[2-(2(R)-Methyl-pyrrolidin-1-yl)-ethyl]-benzofuran-7-yl}-pyridine | 4-Bromopyridine hydrochloride | 19524-06-2 |
| 268 | 4-{2-[2-(2(R)-Methyl-pyrrolidin-1-yl)-ethyl]-benzofuran-7-yl}-pyridine | 2-Bromopyridine | 109-04-6 |

Examples 269–283

Compounds of Formula (54)

Examples 269–283 are compounds of formula (54), wherein $R_6$ is a heterocycle selected from imidazolyl, benzimidazolyl, 3H-imidazo[4,5-c]pyridinyl, pyrrolyl, and pyrazolyl, and wherein the heterocycle can be substituted with 1, 2, or 3 substituents selected from alkenyl, alkoxy, alkoxyalkyl, alkoxycarbonyl, alkyl, alkylcarbonyl, alkylcarbonyloxy, alkylsulfinyl, alkylsulfonyl, alkylthio, arylalkyl, carboxy, carboxyalkyl, cyano, cyanoalkyl, formyl, halogen, haloalkoxy, haloalkyl, haloalkylcarbonyl, hydroxy, hydroxyalkyl, mercapto, nitro, oxo, —$NR_AR_B$, $(NR_AR_B)$ alkyl, $(NR_AR_B)$carbonyl and $(NR_AR_B)$sulfonyl; and $R_A$ and $R_B$ are as defined in formula (I). Such compounds can be prepared according to the procedures shown in Scheme 18 below:

Scheme 18

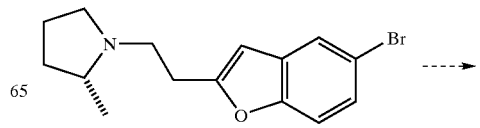

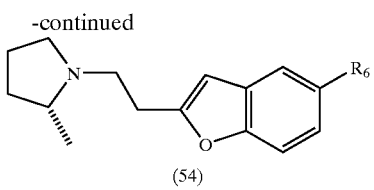

(54)

As shown in Scheme 18, (2R)-1-[2-(5-bromo-1-benzofuran-2-yl)ethyl]-2-methylpyrrolidine is treated with a palladium source such as palladium (II) acetate, a trivalent phosphine such as 1,1'-bis(diphenylphosphino)ferrocene, a base such as $Cs_2CO_3$, a metal alkoxide such as sodium tert-butoxide, and a suitable starting material such as imidazolyl, benzimidazolyl, 3H-imidazo[4,5-c]pyridinyl, pyrrolyl, and pyrazolyl in an organic solvent such as toluene at 60° C. to 140° C. to provide compounds of formula (54). Compounds of formula (54) can be isolated and purified by methods known to those skilled in the art. For example, compounds of formula (54) can be partitioned between dichloromethane and water, the organic phase concentrated, and the residue purified by chromatography on silica gel.

Compounds of formula (54) also are prepared by treating (2R)-1-[2-(5-bromo-1-benzofuran-2-yl)ethyl]-2-methylpyrrolidine with a copper source such as the benzene complex of copper (I) trifluoromethanesulfonate, a ligand such as 1,10-phenanthroline, trans, trans-dibenzylideneacetone, a base such as $Cs_2CO_3$ and a suitable starting material such as imidazolyl, benzimidazolyl, 3H-imidazo[4,5-c]pyridinyl, pyrrolyl, and pyrazolyl in an organic solvent such as xylenes at 100° C. to 150° C. to provide compounds of formula (54).

Examples of compounds that can be prepared according to procedures described in Scheme 18 and starting materials suitable for preparing such compounds are provided below in Table 6.

TABLE 6

| Example Number | Compound | Starting Material | Chemical Abstracts number |
|---|---|---|---|
| 269 | 1-{2-[2-(2(R)-methylpyrrolidin-1-yl)-ethyl]-benzofuran-5-yl}-1H-imidazole-4,5-dicarbonitrile | 1H-imidazole-4,5-di-carbonitrile | 1122-28-7 |
| 270 | 4,5-dichloro-1-{2-[2-(2(R)-methyl-pyrrolidin-1-yl)-ethyl]-benzofuran-5-yl}-1H-imidazole | 4,5-dichloro-1H-imidazole | 15965-30-7 |
| 271 | 1-{2-[2-(2(R)-methylpyrrolidin-1-yl)-ethyl]-benzofuran-5-yl}-1H-benzoimidazoLe | 1H-benzoimidazole | 51-17-2 |
| 272 | 3-{2-[2-(2(R)-methylpyrrolidin-1-yl)-ethyl]-benzofuran-5-yl}-3H-imidazo[4,5-c]pyridine | 3H-imidazo[4,5-c]pyridine | 272-97-9 |
| 273 | (5-hydroxymethyl-3-{2-[2-(2(R)-methylpyrrolidin-1-yl)-ethyl]-benzofuran-5-yl}-3H-imidazol-4-yl)-methanol | (5-hydroxymethyl-3H-imidazol-4-yl)methanol | 33457-48-6 |
| 274 | 1-{2-[2-(2(R)-methylpyrrolidin-1-yl)-ethyl]-benzofuran-5-yl}-1H-pyrrole | 1H-pyrrole | 109-97-9 |
| 275 | 1-(1-{2-[2-(2(R)-methylpyrrolidin-1-yl)-ethyl]-benzofuran-5-yl}-1H-pyrrol-3-yl)-ethanone | 1-(1H-pyrrol-3-yl)-ethanone | 1072-82-8 |
| 276 | 3-methyl-1-{2-[2-(2(R)-methylpyrrolidin-1-yl)-ethyl]-benzofuran-5-yl}-1H-pyrrole | 3-methyl-1H-pyrrole | 616-43-3 |
| 277 | 1-{2-[2-(2(R)-methylpyrrolidin-1-yl)-ethyl]-benzofuran-5-yl}-3,4-bis-trifluoromethyl-1H-pyrrole | 3,4-bis-trifluoromethyl-1H-pyrrole | 82912-41-2 |
| 278 | 1-{2-[2-(2(R)-methylpyrrolidin-1-yl)-ethyl]-benzofuran-5-yl}-1H-pyrazole | 1H-pyrazole | 288-13-1 |
| 279 | 4-methyl-1-{2-[2-(2(R)-methylpyrrolidin-1-yl)-ethyl]-benzofuran-5-yl}-1H-pyrazole | 4-methyl-1H-pyrazole | 7554-65-6 |
| 280 | 1-{2-[2-(2(R)-methylpyrrolidin-1-yl)-ethyl]-benzofuran-5-yl}-1H-pyrazole-4-carboxylic acid ethyl ester | 1H-pyrazole-4-carboxylic acid ethyl ester | 37622-90-5 |
| 281 | 1-{2-[2-(2(R)-methylpyrrolidin-1-yl)-ethyl]-benzofuran-5-yl}-1H-pyrazole-4-carbonitrile | 1H-pyrazole-4-carbonitrile | 31108-57-3 |
| 282 | 4-chloro-1-{2-[2-(2(R)-methylpyrrolidin-1-yl)-ethyl]-benzofuran-5-yl}-1H-pyrazole | 4-chloro-1H-pyrazole | 15878-00-9 |
| 283 | 3,5-dimethyl-1-{2-[2-(2(R)-methylpyrrolidin-1-yl)-ethyl]-benzofuran-5-yl}-1H-pyrazole | 3,5-dimethyl-1H-pyrazole | 67-51-6 |

Examples 284–287

Compounds of Formula (55)

Examples 284–287 are compounds of formula (55) wherein $R_A$ and $R_{20}$ are as defined in formula (I). Such compounds can be prepared according to procedures shown in Scheme 19.

Scheme 19

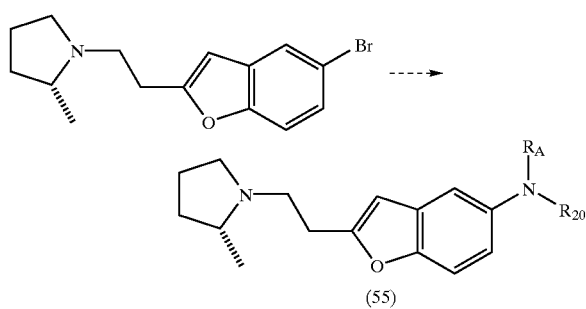

(55)

As shown in Scheme 19, (2R)-1-[2-(5-bromo-1-benzofuran-2-yl)ethyl]-2-methylpyrrolidine is treated with a palladium source such as palladium (II) acetate, a palladium activating ligand such as 1,1'-bis(diphenylphosphino) ferrocene, tri-tertbutylphosphine, BINAP, or 2-(di-tert-butylphosphino)-o-biphenyl, or 1,3-bis(2,6-diisopropylphenyl)-4,5-dihydroimidazol-2-ylidene, a base such as $Cs_2CO_3$, a metal alkoxide such as sodium tert-butoxide, and a suitable starting material, for example, a heterocycle, or an aryl group, or a cycloalkyl group, wherein the heterocycle, aryl or cycloalkyl group has a —$NHR_A$ substituent in an organic solvent such as toluene at 60° C. to 140° C. to provide compounds of formula (55). Compounds of formula (55) can be isolated and purified by methods known to those skilled in the art. For example, compounds of formula (55) can be partitioned between dichloromethane and water, the organic phase concentrated, and the residue purified by chromatography on silica gel.

Examples of compounds that can be prepared according to procedures described in Scheme 19 and starting materials suitable for preparing such compounds are provided below in Table 7.

TABLE 7

| Example Number | Compound | Starting Material | Chemical Abstracts number |
|---|---|---|---|
| 284 | (4-Methoxy-phenyl)-methyl-{2-[2-(2(R)-methyl-pyrrolidin-1-yl)-ethyl]-benzofuran-5-yl}-amine | N-methyl para-anisidine | 5961-59-1 |
| 285 | Benzo[1,3]dioxol-5-yl-methyl-{2-[2-(2-methyl-pyrrolidin-1-yl)-ethyl]-benzofuran-5-yl}-amine | Benzo[1,3]dioxol-5-yl-ethyl-amine | 32953-14-3 |
| 286 | Cyclohexyl-methyl-{2-[2-(2(R)-methyl-pyrrolidin-1-yl)-ethyl]-benzofuran-5-yl}-amine | N-methyl cyclohexylamine | 100-60-7 |
| 287 | {2-[2-(2(R)-Methyl-pyrrolidin-1-yl)-ethyl]-benzofuran-5-yl}-(tetrahydro-pyran-4-yl)-amine | Tetrahydro-pyran-4-ylamine | 38041-19-9 |

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13–30. The present invention contemplates various stereoisomers and mixtures thereof and are specifically included within the scope of this invention. Stereoisomers include enantiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The present invention provides pharmaceutical compositions which comprise compounds of the present invention formulated together with one or more non-toxic pharmaceutically acceptable carriers. The pharmaceutical compositions can be formulated for oral administration in solid or liquid form, for parenteral injection or for rectal administration.

Further included within the scope of the present invention are pharmaceutical compositions comprising one or more of the compounds of formula I–VII prepared and formulated in combination with one or more non-toxic pharmaceutically acceptable compositions. The pharmaceutical compositions can be formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous, intraarticular injection and infusion.

Pharmaceutical compositions of this invention for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the such as), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the such as. It may also be desirable to include isotonic agents, for example, sugars, sodium chloride and the such as. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the present invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

The active compounds can also be in micro-encapsulated form, if appropriate, with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose, or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of such composition that they release the active ingredient(s) only, or preferentially, in a certain part of the intestinal tract in a delayed manner. Examples of embedding compositions which can be used include polymeric substances and waxes.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the such as.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of embedding compositions which can be used include polymeric substances and waxes.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, excipients, and the such as. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

The terms "pharmaceutically acceptable salts, esters and amides," as used herein, refer to carboxylate salts, amino acid addition salts, zwitterions, esters and amides of compounds of formula I–VII which are, within the scope of sound medical judgement, suitable for use in contact with the tissues of humans and lower animals without undue toxicity, irritation, allergic response, and the such as, are commensurate with a reasonable benefit/risk ratio, and are effective for their intended use.

The compounds of the present invention can be used in the form of pharmaceutically acceptable salts derived from inorganic or organic acids. By "pharmaceutically acceptable salt" is meant those salts which are, within the scope of sound medical judgement, suitable for use in contact with the tissues of humans and lower animals without undue toxicity, irritation, allergic response and the such as and are commensurate with a reasonable benefit/risk ratio. Pharmaceutically acceptable salts are well-known in the art. For example, S. M. Berge et al. describe pharmaceutically acceptable salts in detail in J. Pharmaceutical Sciences, 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the such as and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, piperazine and the such as. Preferred salts of the compounds of the invention include phosphate, tris and acetate.

The term "pharmaceutically acceptable ester," as used herein, refers to esters of compounds of the present invention which hydrolyze in vivo and include those that break down readily in the human body to leave the parent compound or a salt thereof. Examples of pharmaceutically acceptable, non-toxic esters of the present invention include $C_1$-to-$C_6$ alkyl esters and $C_5$-to-$C_7$ cycloalkyl esters, although $C_1$-to-$C_4$ alkyl esters are preferred. Esters of the compounds of formula I–VII may be prepared according to conventional methods.

The term "pharmaceutically acceptable amide," as used herein, refers to non-toxic amides of the present invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula I–VII may be prepared according to conventional methods.

The term "pharmaceutically acceptable prodrug" or "prodrug," as used herein, represents those prodrugs of the compounds of the present invention which are, within the scope of sound medical judgement, suitable for use in contact with the tissues of humans and lower animals without undue toxicity, irritation, allergic response, and the such as, commensurate with a reasonable benefit/risk ratio, and effective for their intended use. Prodrugs of the present invention may be rapidly transformed in vivo to a parent compound of formula I–VII, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

The present invention contemplates pharmaceutically active compounds either chemically synthesized or formed by in vivo biotransformation to compounds of formula I–VII.

The compounds of the present invention, including but not limited to those specified in the examples, possess an affinity for the histamine-3 receptors. As histamine-3 receptor ligands, the compounds of the present invention may be useful for the treatment and prevention of diseases or conditions such as acute myocardial infarction, Alzheimer's disease, attention-deficit hyperactivity disorder, bipolar disorder, cognitive enhancement, cognitive deficits in psychiatric disorder, drug abuse, deficits of memory and learning, jet lag, Parkinson's disease, epilepsy, schizophrenia, dementia, depression, cutaneous carcinoma, mild cognitive impairment, medullary thyroid carcinoma, melanoma, allergic rhinitis, asthma, narcolepsy, mood and attention alteration, Meniere's disease, gastrointestinal disorders, inflammation, migraine, motion sickness, neurogenic inflammation, obsessive compulsive disorder, Tourette's syndrome, obesity, pain, seizures, septic shock, vertigo, and wakefulness.

The ability of the compounds of the present invention, including but not limited to those specified in the examples, to treat septic shock and cardiovascular disorders, in particular, acute myocardial infarction may be demonstrated by Imamura et al., Circ. Res., (1996) 78, 475–481; Imamura et. al., Circ. Res., (1996) 78, 863–869; R. Levi and N. C. E. Smith, "Histamine $H_3$-receptors: A new frontier in myocardial ischemia", J. Pharm. Exp. Ther., 292: 825–830, (2000); and Hatta, E., K Yasuda and R. Levi, "Activation of histamine $H_3$ receptors inhibits carrier-mediated norepinephrine release in a human model of protracted myocradial ischemia", J. Pharm. Exp. Ther., 283: 494–500, (1997).

The ability of the compounds of the invention, including but not limited to those specified in the examples, to treat sleep disorders, in particular, narcolepsy may be demonstrated by Lin et al., Brain Res. (1990) 523, 325–330; Monti et al., Neuropsychopharmacology (1996) 15, 31–35; Sakai, et al., Life Sci. (1991) 48, 2397–2404; Mazurkiewicz-Kwilecki and Nsonwah, Can. J. Physiol. Pharmacol. (1989) 67, 75–78; Panula, P. et al., Neuroscience (1998) 44, 465–481); Wada et al., Trends in Neuroscience (1991) 14, 415; and Monti et al., Eur. J. Pharmacol. (1991) 205, 283.

The ability of the compounds of the invention, including but not limited to those specified in the examples, to treat cognition and memory process disorders may be demonstrated by Mazurkiewicz-Kwilecki and Nsonwah, Can. J. Physiol. Pharmacol. (1989) 67, 75–78; Panula, P. et al., Neuroscience (1997) vol. 82, 993–997; Haas et al., Behav. Brain Res. (1995) 66, 41–44; De Almeida and Izquierdo, Arch. Int. Pharmacodyn. (1986) 283, 193–198; Kamei et al., Psychopharmacology (1990) 102, 312–318; and Kamei and Sakata, Jpn. J. Pharmacol. (1991) 57, 437–482; Schwartz et al., Psychopharmacology; The fourth Generation of Progress. Bloom and Kupfer (eds). Raven Press, New York, (1995) 397; and Wada et al., Trends in Neurosci., (1991) 14, 415.

The ability of the compounds of the invention, including but not limited to those specified in the examples, to treat attention-deficit hyperactivity disorder (ADHD) may be demonstrated by Shaywitz et al., Psychopharmacology (1984) 82, 73–77; Dumery and Blozovski, Exp. Brain Res. (1987) 67, 61–69; Tedford et al., J. Pharmacol. Exp. Ther. (1995) 275, 598–604; and Tedford et al., Soc. Neurosci. Abstr. (1996) 22, 22.

The ability of the compounds of the invention, including but not limited to those specified in the examples, to treat seizures, in particular, epilepsy may be demonstrated by Yokoyama et al., Eur. J. Pharmacol. (1993) 234, 129; Yokoyama and Iinuma, CNS Drugs (1996) 5, 321; Onodera et al., Prog. Neurobiol. (1994) 42, 685; R. Leurs, R. C. Vollinga and H. Timmerman, "The medicinal chemistry and therapeutic potentials of ligand of the histamine $H_3$ receptor", Progress in Drug Research 45: 170–165, (1995); Leurs and Timmerman, Prog. Drug Res. (1992) 39, 127; The Histamine $H_3$ Receptor, Leurs and Timmerman (eds), Elsevier Science, Amsterdam, The Netherlands (1998); H. Yokoyama and K. linuma, "Histamine and Seizures: Implications for the treatment of epilepsy", CNS Drugs, 5(5); 321–330, (1995); and K. Hurukami, H. Yokoyama, K. Onodera, K. Iinuma and T. Watanabe, AQ-0145, "A newly developed histamine $H_3$ antagonist, decreased seizure susceptibility of electrically induced convulsions in mice", Meth. Find. Exp. Clin. Pharmacol., 17(C): 70–73, (1995).

The ability of the compounds of the invention, including but not limited to those specified in the examples, to treat motion sickness, Alzheimer's disease, and Parkinson's disease may be demonstrated by Onodera et al., Prog. Neurobiol. (1994) 42, 685; Leurs and Timmerman, Prog. Drug Res. (1992) 39, 127; and The Histamine $H_3$ Receptor, Leurs and Timmerman (eds), Elsevier Science, Amsterdam, The Netherlands (1998).

The ability of the compounds of the invention, including but not limited to those specified in the examples, to treat narcolepsy, schizophrenia, depression, and dementia may be demonstrated by R. Leurs, R. C. Vollinga and H. Timmerman, "The medicinal chemistry and therapeutic potentials of ligand of the histamine $H_3$ receptor", Progress in Drug Research 45: 170–165, (1995); The Histamine $H_3$ Receptor, Leurs and Timmerman (eds), Elsevier Science, Amsterdam, The Netherlands (1998); and Perez-Garcia C, et. al., Laboratory of Pharmacology, University of San Pablo CEU, Madrid, Spain, Psychopharmacology (Berl) (1999) February, 142(2): 215–20).

The ability of the compounds of the invention, including but not limited to those specified in the examples, to treat wakefulness, cognitive enhancement, mood and attention alteration, vertigo and motion sickness, and treatment of cognitive deficits in psychiatric disorder may be demonstrated by (Schwartz, Physiol. Review (1991) 71, p. 1–51).

The ability of the compounds of the present invention, including but not limited to those specified in the examples, to treat mild cognitive impairment, deficits of memory, deficits of learning and dementia may be demonstrated by (C. E. Tedford, in "The Histamine $H_3$ Receptor: a target for new drugs", the Pharmacochemistry Library, vol. 30 (1998) edited by R. Leurs and H. Timmerman, Elsevier (N.Y.). p. 269 and references also contained therein.)

The ability of the compounds of the invention, including but not limited to those specified in the examples, to treat obesity may be demonstrated by Leurs et al., Trends in Pharm. Sci. (1998) 19, 177–183; Itoh. E., Fujimiay, M., and Inui, A., Thioperamide, A histamine $H_3$ receptor antagonist, powerfully suppresses peptide YY-induced fodd intake in rats, Biol. Psych. 45(4): 475–481, (1999); Yates S. I., Pawlowski, G. P., Antal, J. M., Ali, S. M., Jiang, J., and Brunden, K. R., Effects of a novel histamine $H_3$ receptor antagonist, GT-2394, on food intake and weight gain in Sprague-Dawley rats, Abstracts, Society for Neuroscience, 102.10, p. 219, November, (2000); and Bjenning, C., Johannesson, U., Juul, A-G., Lange, K. Z., and Rimvall, K., Peripherally administered ciproxifan elevates hypothalamic histamine levels and potently reduces food intake in the Sprague Dawley rat., Abstracts, International Sendai Histamine Symposium, Sendai, Japan, November, 2000, #P 39.

The ability of the compounds of the invention, including but not limited to those specified in the examples, to treat inflammation and pain may be demonstrated by Phillips et al., Annual Reports in Medicinal Chemistry (1998) 33, 31–40.

The ability of the compounds of the invention, including but not limited to those specified in the examples, to treat migraine may be demonstrated by R. Leurs, R. C. Vollinga and H. Timmerman, "The medicinal chemistry and therapeutic potentials of ligands of the histamine $H_3$ receptor", Progress in Drug Research 45: 170–165, (1995); and Matsubara et al., Eur. J. Pharmacol. (1992) 224, 145; and Rouleau et al., J. Pharmacol. Exp. Ther. (1997) 281, 1085.

The ability of the compounds of the invention, including but not limited to those specified in the examples, to treat cancer, in particular, melanoma, cutaneous carcinoma and medullary thyroid carcinoma may be demonstrated by Polish Med. Sci. Mon., (1998) vol. 4, issue 5, 747; Adam Szelag, "Role of histamine $H_3$-receptors in the proliferation of neoplastic cells in vitro", Med. Sci. Monit., 4(5): 747–755, (1998); and Fitzsimons, C., H. Duran, F. Labombarda, B. Molinari and E. Rivera, "Histamine receptors signalling in epidermal tumor cell lines with H-ras gene alterations", Inflammation Res., 47 (Suppl 1): S50-S51, (1998).

The ability of the compounds of the invention, including but not limited to those specified in the examples, to treat vestibular dysfunctions, in particular, Meniere's disease may be demonstrated by R. Leurs, R. C. Vollinga and H. Timmerman, "The medicinal chemistry and therapeutic potentials of ligands of the histamine $H^3$ receptor", Progress in Drug Research 45: 170–165, (1995).

The ability of the compounds of the present invention, including but not limited to those specified in the examples, to treat asthma may be demonstrated by Delaunois A., Gustin P., Garbarg M., and Ansay M., "Modulation of acetylcholine, capsaicin and substance P effects by histamine $H_3$ receptors in isolated perfused rabbit lungs", European Journal of Pharmacology 277(2–3):243–50, (1995); and Dimitriadou, et al., "Functional relationship between mast cells and C-sensitive nerve fibres evidenced by histamine $H_3$-receptor modulation in rat lung and spleen", Clinical Science. 87(2):151–63, (1994).

The ability of the compounds of the present invention, including but not limited to those specified in the examples, to allergic rhinitis may be demonstrated by McLeod et al., Progress in Resp. Research 31, 133 (2001).

Aqueous liquid compositions of the present invention are particularly useful for the treatment and prevention of asthma, epilepsy, Raynaud's syndrome, male sexual dysfunction, female sexual dysfunction, migraine, pain, eating disorders, urinary incontinence, functional bowel disorders, neurodegeneration and stroke.

When used in the above or other treatments, a therapeutically effective amount of one of the compounds of the present invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and such as factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.003 to about 30 mg/kg/day. For purposes of oral administration, more preferable doses can be in the range of from about 0.1 to about 15 mg/kg/day. If desired, the effective daily dose can be divided into multiple doses for purposes of administration; consequently, single dose compositions may contain such amounts or submultiples thereof to make up the daily dose.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. All references cited herein are incorporated by referance. In the case of inconsistencies, the instant disclosure, including definitions, will prevail.

What is claimed is:

1. A compound of formula (I)

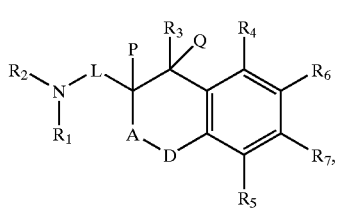

(I)

or a pharmaceutically acceptable salt, ester, or amide thereof, wherein

A is a covalent bond;

D is O;

L is selected from the group consisting of lower alkylene, fluoroalkylene, and hydroxyalkylene;

P and Q taken together form a covalent bond or are both hydrogen;

$R_1$ and $R_2$ are each independently selected from the group consisting of alkyl, aryl, arylalkyl, cycloalkyl, cycloalkylalkyl, heterocycle, heterocyclealkyl, hydroxyalkyl, alkenyl, and alkynyl; or $R_1$ and $R_2$ taken together with the nitrogen atom to which they are attached, together form a heterocycle;

$R_3$ is selected from the group consisting of hydrogen, alkoxy, alkoxycarbonyl, alkyl, alkylcarbonyl, alkylcarbonyloxy, alkylsulfinyl, alkylsulfonyl, alkylthio, aryl, carboxy, carboxyalkyl, cyano, cyanoalkyl, formyl, halogen, haloalkoxy, haloalkyl, heterocycle, hydroxy, hydroxyalkyl, mercapto, nitro, —$NR_AR_B$, $(NR_AR_B)$alkyl, $(NR_AR_B)$carbonyl, and $(NR_AR_B)$sulfonyl;

$R_4$, $R_5$, $R_6$ and $R_7$ are each independently selected from the group consisting of hydrogen, alkoxy, alkoxycarbonyl, alkyl, alkylcarbonyl, alkylcarbonyloxy, alkylsulfinyl, alkylsulfonyl, alkylthio, aryl, carboxy, carboxyalkyl, cyano, cyanoalkyl, cycloalkyl, formyl, halogen, haloalkoxy, haloalkyl, hydroxy, hydroxyalkyl, mercapto, nitro, —$NR_AR_B$, $(NR_AR_B)$alkyl, $(NR_AR_B)$carbonyl, $(NR_AR_B)$sulfonyl, —$L_2R_{20}$, and —$R_{20}L_3R_{22}$;

$L_2$ is selected from the group consisting of alkylene, alkenylene, O, S, S(O), S(O)$_2$, C(=O), C=(NOR$_{21}$), and N(R$_A$);

$L_3$ is selected from the group consisting of a covalent bond, alkylene, alkenylene, O, S, C(=O), N(=OR$_{21}$), and N(R$_A$)

$R_{20}$ is selected from the group consisting of aryl, heterocycle, and cycloalkyl;

$R_{21}$ is selected from the group consisting of hydrogen and alkyl;

$R_{22}$ is selected from the group consisting of aryl, heterocycle, and cycloalkyl;

$R_A$ and $R_B$ are each independently selected from the group consisting of hydrogen, alkyl, alkylcarbonyl and formyl;

provided that at least one of $R_4$, $R_5$, $R_6$, or $R_7$ is aryl, cycloalkyl, —$L_2R_{20}$ or —$R_{20}L_3R_{22}$.

2. A compound according to claim 1 wherein

A is a covalent bond;

D is O;

L is —$CH_2CH_2$—;

P and Q taken together form a covalent bond;

$R_1$ and $R_2$ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl;

$R_3$, $R_4$, $R_5$ and $R_7$ are hydrogen;

$R_6$ is $L_2R_{20}$;

$L_2$ is C(=O); and $R_{20}$ is aryl.

3. A compound according to claim 1 wherein

A is a covalent bond;

D is O;

L is —$CH_2CH_2$—;

P and Q taken together form a covalent bond;

$R_1$ and $R_2$ taken together with the nitrogen atom to which they are attached, together form a heterocycle selected from the group consisting of 1-azepanyl, (3S)-3-(dimethylamino)pyrrolidinyl, (3R)-3-(dimethylamino) pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl) pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo [2.2.1]hept-5-yl, and 1,4-dioxa-8-azaspiro[4.5]dec-8-yl;

$R_3$, $R_4$, $R_5$ and $R_7$ are hydrogen;

$R_6$ is $L_2R_{20}$;

$L_2$ is C(=O); and $R_{20}$ is aryl.

4. A compound according to claim 1 wherein

A is a covalent bond;

D is O;

L is —CH$_2$CH$_2$—;

P and Q taken together form a covalent bond;

R$_1$ and R$_2$ taken together with the nitrogen atom to which they are attached, together form a heterocycle (2R)-2-methyl-1-pyrrolidinyl;

R$_3$, R$_4$, R$_5$ and R$_7$ are hydrogen;

R$_6$ is L$_2$R$_{20}$;

L$_2$ is C(=O); and

R$_{20}$ is phenyl substituted with 0, 1, 2 or 3 substitutents selected from the group consisting of hydrogen, alkoxy, alkyl, alkoxycarbonyl, alkylcarbonyl, alkylthio, carboxy, cyano, formyl, haloalkoxy, haloalkyl, halogen, hydroxyalkyl, oximyl, (NR$_A$R$_B$)carbonyl, and —NR$_A$R$_B$.

5. A compound according to claim 4 selected from the group consisting of (4-fluorophenyl)(2-{2-[(2R)-2-methyl-1-pyrrolidinyl]ethyl}-1-benzofuran-5-yl)methanone;

(3-fluorophenyl)(2-{2-[(2R)-2-methyl-1-pyrrolidinyl]ethyl}-1-benzofuran-5-yl)methanone;

(2-fluorophenyl)(2-{2-[(2R)-2-methyl-1-pyrrolidinyl]ethyl}-1-benzofuran-5-yl)methanone;

(3-chlorophenyl)(2-{2-[(2R)-2-methyl-1-pyrrolidinyl]ethyl}-1-benzofuran-5-yl)methanone;

(4-chlorophenyl)(2-{2-[(2R)-2-methyl-1-pyrrolidinyl]ethyl}-1-benzofuran-5-yl)methanone;

(4-methoxyphenyl)(2-{2-[(2R)-2-methyl-1-pyrrolidinyl]ethyl}-1-benzofuran-5-yl)methanone;

(4-fluoro-3-methylphenyl)(2-{2-[(2R)-2-methyl-1-pyrrolidinyl]ethyl}-1-benzofuran-5-yl)methanone;

(4-chloro-3-methylphenyl)(2-{2-[(2R)-2-methyl-1-pyrrolidinyl]ethyl}-1-benzofuran-5-yl)methanone;

(2-{2-[(2R)-2-methyl-1-pyrrolidinyl]ethyl}-1-benzofuran-5-yl)[4-(methylthio)phenyl]methanone;

[4-(dimethylamino)phenyl](2-{2-[(2R)-2-methyl-1-pyrrolidinyl]ethyl}-1-benzofuran-5-yl)methanone;

(4-methylphenyl)(2-{2-[(2R)-2-methyl-1-pyrrolidinyl]ethyl}-1-benzofuran-5-yl)methanone;

(3,5-difluorophenyl)(2-{2-[(2R)-2-methyl-1-pyrrolidinyl]ethyl}-1-benzofuran-5-yl)methanone;

(2-methoxyphenyl)(2-{2-[(2R)-2-methyl-1-pyrrolidinyl]ethyl}-1-benzofuran-5-yl)methanone;

(3-methoxyphenyl)(2-{2-[(2R)-2-methyl-1-pyrrolidinyl]ethyl}-1-benzofuran-5-yl)methanone; and (2-{2-[(2R)-2-methyl-1-pyrrolidinyl]ethyl}-1-benzofuran-5-yl)(phenyl)methanone.

6. A compound according to claim 1 wherein

A is a covalent bond;

D is O;

L is —CH$_2$CH$_2$—;

P and Q taken together form a covalent bond;

R$_1$ and R$_2$ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl;

R$_3$, R$_4$, R$_5$ and R$_7$ are hydrogen;

R$_6$ is L$_2$R$_{20}$;

L$_2$ is C(=O); and

R$_{20}$ is cycloalkyl.

7. A compound according to claim 1 wherein

A is a covalent bond;

D is O;

L is —CH$_2$CH$_2$—;

P and Q taken together form a covalent bond;

R$_1$ and R$_2$ taken together with the nitrogen atom to which they are attached, together form a heterocycle selected from the group consisting of 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, and 1,4-dioxa-8-azaspiro[4.5]dec-8-yl;

R$_3$, R$_4$, R$_5$ and R$_7$ are hydrogen;

R$_6$ is L$_2$R$_{20}$;

L$_2$ is C(=O); and

R$_{20}$ is cycloalkyl.

8. A compound according to claim 1 wherein

A is a covalent bond;

D is O;

L is —CH$_2$CH$_2$—;

P and Q taken together form a covalent bond;

R$_1$ and R$_2$ taken together with the nitrogen atom to which they are attached, together form a heterocycle (2R)-2-methyl-1-pyrrolidinyl;

R$_3$, R$_4$, R$_5$ and R$_7$ are hydrogen;

R$_6$ is L$_2$R$_{20}$;

L$_2$ is C(=O); and

R$_{20}$ is cycloalkyl.

9. A compound according to claim 8 that is cyclopropyl (2-{2-[(2R)-2-methyl-1-pyrrolidinyl]ethyl}-1-benzofuran-5-yl)methanone.

10. A compound according to claim 1 wherein

A is a covalent bond;

D is O;

L is —CH$_2$CH$_2$—;

P and Q taken together form a covalent bond;

R$_1$ and R$_2$ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl;

R₃, R₄, R₅ and R₇ are hydrogen;

R₆ is L₂R₂₀;

L₂ is selected from the group consisting of alkylene and alkenylene; and

R₂₀ is aryl.

11. A compound according to claim 1 wherein

A is a covalent bond;

D is O;

L is —CH₂CH₂—;

P and Q taken together form a covalent bond;

R₁ and R₂ taken together with the nitrogen atom to which they are attached, together form a heterocycle selected from the group consisting of 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, and 1,4-dioxa-8-azaspiro[4.5]dec-8-yl;

R₃, R₄, R₅ and R₇ are hydrogen;

R₆ is L₂R₂₀;

L₂ is selected from the group consisting of alkylene and alkenylene; and

R₂₀ is aryl.

12. A compound according to claim 1 wherein

A is a covalent bond;

D is O;

L is —CH₂CH₂—;

P and Q taken together form a covalent bond;

R₁ and R₂ taken together with the nitrogen atom to which they are attached, together form a heterocycle (2R)-2-methyl-1-pyrrolidinyl;

R₃, R₄, R₅ and R₇ are hydrogen; and

R₆ is L₂R₂₀;

L₂ is selected from the group consisting of alkylene and alkenylene; and

R₂₀ is phenyl substituted with 0, 1, 2, or 3 substituents selected from the group consisting of hydrogen, alkoxy, alkyl, alkoxycarbonyl, alkylcarbonyl, alkylthio, carboxy, cyano, formyl, haloalkoxy, haloalkyl, halogen, hydroxyalkyl, oximyl, (NR_AR_B)carbonyl, and —NR_AR_B.

13. A compound according to claim 12 selected from the group consisting of (2R)-1-(2-{5-[2-(4-fluorophenyl)vinyl]-1-benzofuran-2-yl}ethyl)-2-methylpyrrolidine; and (2R)-1-[2-(5-benzyl-1-benzofuran-2-yl)ethyl]-2-methylpyrrolidine.

14. A compound according to claim 1 wherein

A is a covalent bond;

D is O;

L is —CH₂CH₂—;

P and Q taken together form a covalent bond;

R₁ and R₂ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl;

R₃, R₄, R₅ and R₇ are hydrogen; and

R₆ is alkylcarbonyl.

15. A compound according to claim 1 wherein

A is a covalent bond;

D is O;

L is —CH₂CH₂—;

P and Q taken together form a covalent bond;

R₁ and R₂ taken together with the nitrogen atom to which they are attached, together form a heterocycle selected from the group consisting of 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, and 1,4-dioxa-8-azaspiro[4.5]dec-8-yl;

R₃, R₄, R₅ and R₇ are hydrogen; and

R₆ is alkylcarbonyl.

16. A compound according to claim 1 wherein

A is a covalent bond;

D is O;

L is —CH₂CH₂—;

P and Q taken together form a covalent bond;

R₁ and R₂ taken together with the nitrogen atom to which they are attached, together form a heterocycle (2R)-2-methyl-1-pyrrolidinyl;

R₃, R₄, R₅ and R₇ are hydrogen; and

R₆ is alkylcarbonyl.

17. A compound according to claim 16 that is 3-ethyl-1-(2-{2-[(2R)-2-methyl-1-pyrrolidinyl]ethyl}-1-benzofuran-5-yl)-1-pentanone.

18. A compound according to claim 1 wherein

A is a covalent bond;

D is O;

L is —CH₂CH₂—;

P and Q taken together form a covalent bond;

R₁ and R₂ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl;

$R_3$, $R_4$, $R_5$ and $R_7$ are hydrogen;

$R_6$ is —$R_{20}L_3R_{22}$;

$R_{20}$ is heterocycle;

$L_3$ is selected from the group consisting of a covalent bond and alkylene; and $R_{22}$ is aryl.

19. A compound according to claim 1 wherein

A is a covalent bond;

D is O;

L is —CH₂CH₂—;

P and Q taken together form a covalent bond;

R₁ and R₂ taken together with the nitrogen atom to which they are attached, together form a heterocycle selected from the group consisting of 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, and 1,4-dioxa-8-azaspiro[4.5]dec-8-yl;

$R_3$, $R_4$, $R_5$ and $R_7$ are hydrogen;

$R_6$ is —$R_{20}L_3R_{22}$;

$R_{20}$ is heterocycle;

$L_3$ is selected from the group consisting of a covalent bond and alkylene; and $R_{22}$ is aryl.

20. A compound according to claim 1 wherein

A is a covalent bond;

D is O;

L is —CH₂CH₂—;

P and Q taken together form a covalent bond;

R₁ and R₂ taken together with the nitrogen atom to which they are attached, together form a heterocycle (2R)-2-methyl-1-pyrrolidinyl;

$R_3$, $R_4$, $R_5$ and $R_7$ are hydrogen;

$R_6$ is —$R_{20}L_3R_{22}$;

$R_{20}$ is 1,2,4-oxadiazol-3-yl;

$L_3$ is selected from the group consisting of a covalent bond and alkylene; and $R_{22}$ is phenyl substituted with 0, 1, 2, or 3 substitutents selected from the group consisting of hydrogen, alkoxy, alkyl, alkoxycarbonyl, alkylcarbonyl, alkylthio, carboxy, cyano, formyl, haloalkoxy, haloalkyl, halogen, hydroxyalkyl, oximyl, (NR$_A$R$_B$)carbonyl, and —NR$_A$R$_B$.

21. A compound according to claim 1 wherein

A is a covalent bond;

D is O;

L is —CH₂CH₂—;

P and Q taken together form a covalent bond;

R₁ and R₂ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl;

$R_3$, $R_4$, $R_5$ and $R_7$ are hydrogen;

$R_6$ is —$R_{20}L_3R_{22}$;

$R_{20}$ is 1,2,4-oxadiazol-3-yl;

$L_3$ is selected from the group consisting of a covalent bond and alkylene; and $R_{22}$ is heterocycle.

22. A compound according to claim 1 wherein

A is a covalent bond;

D is O;

L is —CH₂CH₂—;

P and Q taken together form a covalent bond;

R₁ and R₂ taken together with the nitrogen atom to which they are attached, together form a heterocycle selected from the group consisting of 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, and 1,4-dioxa-8-azaspiro[4.5]dec-8-yl;

$R_3$, $R_4$, $R_5$ and $R_7$ are hydrogen;

$R_6$ is —$R_{20}L_3R_{22}$;

$R_{20}$ is 1,2,4-oxadiazol-3-yl;

$L_3$ is selected from the group consisting of a covalent bond and alkylene; and $R_{22}$ is heterocycle.

23. A compound according to claim 1 wherein

A is a covalent bond;

D is O,

L is —CH₂CH₂—;

P and Q taken together form a covalent bond;

R₁ and R₂ taken together with the nitrogen atom to which they are attached, together form a heterocycle (2R)-2-methyl-1-pyrrolidinyl;

$R_3$, $R_4$, $R_5$ and $R_7$ are hydrogen;

$R_6$ is —$R_{20}L_3R_{22}$;

$R_{20}$ is 1,2,4-oxadiazol-3-yl;

$L_3$ is selected from the group consisting of a covalent bond and alkylene; and $R_{22}$ is 2-thienyl.

24. A compound according to claim 23 that is 3-(2-{2-[(2R)-2-methylpyrrolidin-1-yl]ethyl}-1-benzofuran-5-yl)-5-(thien-2-ylmethyl)-1,2,4-oxadiazole.

25. A compound according to claim 1 wherein

A is a covalent bond;

D is O;

L is —$CH_2CH_2$—;

P and Q taken together form a covalent bond;

$R_1$ and $R_2$ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl;

$R_3$, $R_4$, $R_5$ and $R_7$ are hydrogen;

$R_6$ is —$R_{20}L_3R_{22}$;

$R_{20}$ is aryl;

$L_3$ is C(=O); and $R_{22}$ is cycloalkyl.

26. A compound according to claim 1 wherein

A is a covalent bond;

D is O;

L is —$CH_2CH_2$—;

P and Q taken together form a covalent bond;

$R_1$ and $R_2$ taken together with the nitrogen atom to which they are attached, together form a heterocycle selected from the group consisting of 1-azepanyl, (3S)-3-(dimethylamino)pyrrolidinyl, (3R)-3-(dimethylamino) pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, and 1,4-dioxa-8-azaspiro[4.5]dec-8-yl;

$R_3$, $R_4$, $R_5$ and $R_7$ are hydrogen;

$R_6$ is —$R_{20}L_3R_{22}$;

$R_{20}$ is aryl;

$L_3$ is C(=O); and $R_{22}$ is cycloalkyl.

27. A compound according to claim 1 wherein

A is a covalent bond;

D is O;

L is —$CH_2CH_2$—;

P and Q taken together form a covalent bond;

$R_1$ and $R_2$ taken together with the nitrogen atom to which they are attached, together form a heterocycle (2R)-2-methyl-1-pyrrolidinyl;

$R_3$, $R_4$, $R_5$ and $R_7$ are hydrogen;

$R_6$ is —$R_{20}L_3R_{22}$;

$R_{20}$ is phenyl;

$L_3$ is C(=O); and $R_{22}$ is cycloalkyl.

28. A compound according to claim 27 selected from the group consisting of cyclopropyl[3-(2-{2-[(2R)-2-methyl-1-pyrrolidinyl]ethyl}-1-benzofuran-5-yl)phenyl]methanone; and cyclopropyl[4-(2-{2-[(2R)-2-methyl-1-pyrrolidinyl]ethyl}-1-benzofuran-5-yl)phenyl]methanone.

29. A compound according to claim 1 wherein

A is a covalent bond;

D is O;

L is —$CH_2CH_2$—;

P and Q taken together form a covalent bond;

$R_1$ and $R_2$ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl;

$R_3$, $R_4$, $R_5$ and $R_7$ are hydrogen;

$R_6$ is —$R_{20}L_3R_{22}$;

$R_{20}$ is aryl;

$L_3$ is C(=O); and $R_{22}$ is aryl.

30. A compound according to claim 1 wherein

A is a covalent bond;

D is O;

L is —$CH_2CH_2$—;

P and Q taken together form a covalent bond;

$R_1$ and $R_2$ taken together with the nitrogen atom to which they are attached, together form a heterocycle selected from the group consisting of 1-azepanyl, (3S)-3-(dimethylamino)pyrrolidinyl, (3R)-3-(dimethylamino) pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, and 1,4-dioxa-8-azaspiro[4.5]dec-8-yl;

$R_3$, $R_4$, $R_5$ and $R_7$ are hydrogen;

$R_6$ is —$R_{20}L_3R_{22}$;

$R_{20}$ is aryl;

$L_3$ is C(=O); and $R_{22}$ is aryl.

31. A compound according to claim 1 wherein

A is a covalent bond;

D is O;

L is —$CH_2CH_2$—;

P and Q taken together form a covalent bond;

$R_1$ and $R_2$ taken together with the nitrogen atom to which they are attached, together form a heterocycle (2R)-2-methyl-1-pyrrolidinyl;

$R_3$, $R_4$, $R_5$ and $R_7$ are hydrogen;

$R_6$ is —$R_{20}L_3R_{22}$;

$R_{20}$ is phenyl;

$L_3$ is C(=O); and $R_{22}$ is phenyl substituted with 0, 1, 2, or 3 substituents selected from the group consisting of hydrogen, alkoxy, alkyl, alkoxycarbonyl, alkylcarbonyl, alkylthio, carboxy, cyano, formyl, haloalkoxy, haloalkyl, halogen, hydroxyalkyl, oximyl, ($NR_AR_B$)carbonyl, and —$NR_AR_B$.

32. A compound according to claim 31 that is (3-fluorophenyl)[3-(2-{2-[(2R)-2-methyl-1-pyrrolidinyl]ethyl}-1-benzofuran-5-yl)phenyl]methanone.

33. A compound according to claim 1 wherein

A is a covalent bond;

D is O;

L is —$CH_2CH_2$—;

P and Q taken together form a covalent bond;

$R_1$ and $R_2$ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl;

$R_3$, $R_4$, $R_5$ and $R_7$ are hydrogen;

$R_6$ is —$R_{20}L_3R_{22}$;

$R_{20}$ is aryl;

$L_3$ is C(=O); and $R_{22}$ is heterocycle.

34. A compound according to claim 1 wherein

A is a covalent bond;

D is O;

L is —$CH_2CH_2$—;

P and Q taken together form a covalent bond;

$R_1$ and $R_2$ taken together with the nitrogen atom to which they are attached, together form a heterocycle selected from the group consisting of 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, and 1,4-dioxa-8-azaspiro[4.5]dec-8-yl;

$R_3$, $R_4$, $R_5$ and $R_7$ are hydrogen;

$R_6$ is —$R_{20}L_3R_{22}$;

$R_{20}$ is aryl;

$L_3$ is C(=O); and $R_{22}$ is heterocycle.

35. A compound according to claim 1 wherein

A is a covalent bond;

D is O;

L is —$CH_2CH_2$—;

P and Q taken together form a covalent bond;

$R_1$ and $R_2$ taken together with the nitrogen atom to which they are attached, together form a heterocycle (2R)-2-methyl-1-pyrrolidinyl;

$R_3$, $R_4$, $R_5$ and $R_7$ are hydrogen;

$R_6$ is —$R_{20}L_3R_{22}$;

$R_{20}$ is phenyl;

$L_3$ is C(=O); and $R_{22}$ is 2-thienyl.

36. A compound according to claim 35 that is [3-(2-{2-[(2R)-2-methyl-1-pyrrolidinyl]ethyl}-1-benzofuran-5-yl)phenyl](2-thienyl)methanone.

37. A compound according to claim 1 of formula (II)

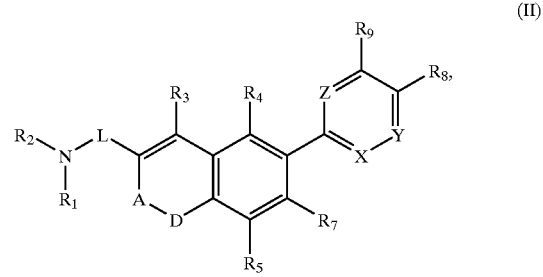

(II)

or a pharmaceutically acceptable salt, ester, or amide thereof, wherein $R_7$ is selected from the group consisting of hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —$NR_AR_B$, ($NR_AR_B$)alkyl, ($NR_AR_B$)carbonyl and ($NR_AR_B$)sulfonyl;

$R_8$ is selected from the group consisting of hydrogen, alkylcarbonyl, arylcarbonyl, cyano, cycloalkylcarbonyl, heterocyclecarbonyl and ($NR_AR_B$)carbonyl;

$R_9$ is selected from the group consisting of hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —$NR_AR_B$, ($NR_AR_B$)alkyl, ($NR_AR_B$)carbonyl and ($NR_AR_B$)sulfonyl;

X is selected from the group consisting of CH and $CR_X$;

Y is selected from the group consisting of CH and $CR_Y$;

Z is selected from the group consisting of CH and $CR_Z$; and $R_X$, $R_Y$ and $R_Z$ are each independently selected from the group consisting of alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —$NR_AR_B$, ($NR_AR_B$)alkyl, ($NR_AR_B$)carbonyl and ($NR_AR_B$)sulfonyl.

38. A compound according to claim 37 wherein

A is a covalent bond;

$R_1$ and $R_2$ are each independently selected from the group consisting of alkyl, hydroxyalkyl, alkenyl and alkynyl; and $R_8$ is cyano.

39. A compound according to claim 37 wherein

A is a covalent bond;

L is —$CH_2CH_2$—;

$R_1$ and $R_2$ are each independently selected from the group consisting of alkyl, hydroxyalkyl, alkenyl and alkynyl;

$R_3$, $R_4$, $R_5$, $R_7$ and $R_9$ are hydrogen;

$R_8$ is cyano;

X is CH;

Y is CH; and

Z is CH.

40. A compound according to claim 39 selected from the group consisting of:

4-{2-[2-(diethylamino)ethyl]-1-benzofuran-5-yl}benzonitrile;

4-(2-{2-[tert-butyl(methyl)amino]ethyl}-1-benzofuran-5-yl)benzonitrile;

4-(2-{2-[isopropyl(methyl)amino]ethyl}-1-benzofuran-5-yl)benzonitrile;

4-(2-{2-[isobutyl(methyl)amino]ethyl}-1-benzofuran-5-yl)benzonitrile;

4-(2-{2-[ethyl(isopropyl)amino]ethyl}-1-benzofuran-5-yl)benzonitrile;

4-(2-{2-[ethyl(propyl)amino]ethyl}-1-benzofuran-5-yl)benzonitrile; and

4-[2-(2-aminoethyl)-1-benzofuran-5-yl]benzonitrile.

41. A compound according to claim 37 wherein

A is a covalent bond;

$R_1$ and $R_2$ are each independently selected from the group consisting of alkyl, hydroxyalkyl, alkenyl and alkynyl; and $R_8$ is heterocyclecarbonyl.

42. A compound according to claim 37 wherein

A is a covalent bond;

$R_1$ and $R_2$ are each independently selected from the group consisting of alkyl, hydroxyalkyl, alkenyl and alkynyl; and $R_8$ is heterocyclecarbonyl wherein the heterocycle is selected from the group consisting of azetidinyl, morpholinyl, piperazinyl, piperidinyl, pyridinyl, pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl.

43. A compound according to claim 37 wherein

A is a covalent bond;

$R_1$ and $R_2$ are each independently selected from the group consisting of alkyl, hydroxyalkyl, alkenyl and alkynyl; and $R_8$ is heterocyclecarbonyl wherein the heterocycle is selected from the group consisting of 1-azetidinyl, 4-morpholinyl, 1-piperazinyl, 1-piperidinyl, 3-pyridinyl, 1-pyrrolidinyl, 2,5-dihydro-1-H-pyrrolyl, 1-pyrrolyl, 3,6-dihydro-1(2H)-pyridinyl, 4-thiomorpholinyl, and 1,1-dioxidothiomorpholin-4-yl.

44. A compound according to claim 37 wherein

A is a covalent bond;

$R_1$ and $R_2$ are each independently selected from the group consisting of alkyl, hydroxyalkyl, alkenyl and alkynyl; and $R_8$ is heterocyclecarbonyl wherein the heterocycle of heterocarbonyl is 4-morpholinyl.

45. A compound according to claim 37 wherein

L is —$CH_2CH_2$—;

A is a covalent bond;

$R_1$ and $R_2$ are each independently selected from the group consisting of alkyl, hydroxyalkyl, alkenyl and alkynyl;

$R_3$, $R_4$, $R_5$, $R_7$ and $R_9$ are hydrogen;

$R_8$ is heterocyclecarbonyl wherein the heterocycle of heterocarbonyl is 4-morpholinyl;

X is CH;

Y is CH; and

Z is CH.

46. A compound according to claim 45 selected from the group consisting of:

N,N-diethyl-N-(2-{5-[4-(4-morpholinylcarbonyl)phenyl]-1-benzofuran-2-yl}ethyl)amine;

N-(tert-butyl)-N-methyl-N-(2-{5-[4-(4-morpholinylcarbonyl)phenyl]-1-benzofuran-2-yl}ethyl)amine;

N-isopropyl-N-methyl-N-(2-{5-[4-(4-morpholinylcarbonyl)phenyl]-1-benzofuran-2-yl}ethyl)amine;

N-isobutyl-N-methyl-N-(2-{5-[4-(4-morpholinylcarbonyl)phenyl]-1-benzofuran-2-yl}ethyl)amine;

N-ethyl-N-isopropyl-N-(2-{5-[4-(4-morpholinylcarbonyl)phenyl]-1-benzofuran-2-yl}ethyl)amine;

N,N-dimethyl-N-(2-{5-[4-(4-morpholinylcarbonyl)phenyl]-1-benzofuran-2-yl}ethyl)amine; and N-ethyl-N-(2-{5-[4-(4-morpholinylcarbonyl)phenyl]-1-benzofuran-2-yl}ethyl)-N-propylamine.

47. A compound according to claim 37 wherein

A is a covalent bond; and $R_1$ and $R_2$ taken together with the nitrogen atom to which they are attached, together form a heterocycle.

48. A compound according to claim 37 wherein

A is a covalent bond;

$R_1$ and $R_2$ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; and $R_8$ is cyano.

49. A compound according to claim 37 wherein

A is a covalent bond;

$R_1$ and $R_2$ taken together with the nitrogen atom to which they are attached, together form a heterocycle selected from the group consisting of 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, and 1,4-dioxa-8-azaspiro[4.5]dec-8-yl; and $R_8$ is cyano.

50. A compound according to claim 37 wherein

L is alkyl;

A is a covalent bond;

$R_1$ and $R_2$ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl;

$R_3$, $R_4$, $R_5$, and $R_7$ are independently selected from the group consisting of hydrogen, alkyl, alkylcarbonyl, and halogen;

$R_8$ and $R_9$ are independently selected from the group consisting of hydrogen, alkoxy, alkyl, alkoxycarbonyl, alkylcarbonyl, carboxy, cyano, formyl, halogen, haloalkyl, haloalkoxy, hydroxyalkyl, and oximyl;

X is selected from the group consisting of CH and $CR_X$;

Y is selected from the group consisting of CH and $CR_Y$;

Z is selected from the group consisting of CH and $CR_Z$; and $R_X$, $R_Y$, and $R_Z$ are independently selected from the group consisting of alkoxy, alkyl, alkoxycarbonyl, alkylcarbonyl, carboxy, cyano, formyl, halogen, haloalkyl, haloalkoxy, hydroxyalkyl, and oximyl.

51. A compound according to claim 37 wherein

L is alkyl;

A is a covalent bond;

$R_1$ and $R_2$ taken together with the nitrogen atom to which they are attached, together form a heterocycle selected from the group consisting of 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, and 1,4-dioxa-8-azaspiro[4.5]dec-8-yl;

$R_3$, $R_4$, $R_5$, and $R_7$ are independently selected from the group consisting of hydrogen, alkyl, alkylcarbonyl, and halogen;

$R_8$ and $R_9$ are independently selected from the group consisting of hydrogen, alkoxy, alkyl, alkoxycarbonyl, alkylcarbonyl, carboxy, cyano, formyl, halogen, haloalkyl, haloalkoxy, hydroxyalkyl, and oximyl;

X is selected from the group consisting of CH and $CR_X$;

Y is selected from the group consisting of CH and $CR_Y$;

Z is selected from the group consisting of CH and $CR_Z$; and $R_X$, $R_Y$, and $R_Z$ are independently selected from the group consisting of alkoxy, alkyl, alkoxycarbonyl, alkylcarbonyl, carboxy, cyano, formyl, halogen, haloalkyl, haloalkoxy, hydroxyalkyl, and oximyl.

52. A compound according to claim 51 selected from the group consisting of:

4-{2-[2-(1-pyrrolidinyl)ethyl]-1-benzofuran-5-yl}benzonitrile;

4-{2-[2-(1-piperidinyl)ethyl]-1-benzofuran-5-yl}benzonitrile;

4-{2-[2-(2-methyl-1-piperidinyl)ethyl]-1-benzofuran-5-yl}benzonitrile;

4-(2-{2-[(3R)-3-hydroxypyrrolidinyl]ethyl}-1-benzofuran-5-yl)benzonitrile;

4-{2-[2-(1H-imidazol-1-yl)ethyl]-1-benzofuran-5-yl}benzonitrile;

4-(2-{2-[(3S)-3-(dimethylamino)pyrrolidinyl]ethyl}-1-benzofuran-5-yl)benzonitrile;

4-(2-{2-[(2S)-2-(hydroxymethyl)pyrrolidinyl]ethyl}-1-benzofuran-5-yl)benzonitrile;

4-(2-{2-[(cis)-2,6-dimethylpiperidinyl]ethyl}-1-benzofuran-5-yl)benzonitrile;

4-{2-[2-(1-azepanyl)ethyl]-1-benzofuran-5-yl}benzonitrile;

4-{2-[2-(4-methyl-1-piperidinyl)ethyl]-1-benzofuran-5-yl}benzonitrile;

4-(2-{2-[2-pyrrolidine methyl carboxylate]ethyl}-1-benzofuran-5-yl)benzonitrile;

4-{2-[2-(3,6-dihydro-1(2H)-pyridinyl)ethyl]-1-benzofuran-5-yl}benzonitrile;

4-(2-{2-[(2R)-2-(hydroxymethyl)pyrrolidinyl]ethyl}-1-benzofuran-5-yl)benzonitrile;

4-(2-{2-[(3R)-(dimethylamino)pyrrolidinyl]ethyl}-1-benzofuran-5-yl)benzonitrile;

4-(2-{2-[1-(2S)-2-methylpyrrolidinyl]ethyl}-1-benzofuran-5-yl)benzonitrile;

4-(2-{2-[1-(2-methylpyrrolidinyl]ethyl}-1-benzofuran-5-yl)benzonitrile;

4-(3-bromo-2-{2-[(2R)-2-methylpyrrolidin-1-yl]ethyl}-1-benzofuran-5-yl)benzonitrile;

2-methyl-4-(2-{2-[(2R)-2-methyl-1-pyrrolidinyl]ethyl}-1-benzofuran-5-yl)benzonitrile;
3-methyl-4-(2-{2-[(2R)-2-methyl-1-pyrrolidinyl]ethyl}-1-benzofuran-5-yl)benzonitrile;
4-(6-methyl-2-{2-[(2R)-2-methyl-1-pyrrolidinyl]ethyl}-1-benzofuran-5-yl)benzonitrile;
4-(4-methyl-2-{2-[(2R)-2-methyl-1-pyrrolidinyl]ethyl}-1-benzofuran-5-yl)benzonitrile;
4-(7-methyl-2-{2-[(2R)-2-methyl-1-pyrrolidinyl]ethyl}-1-benzofuran-5-yl)benzonitrile;
4-(7-fluoro-2-{2-[(2R)-2-methyl-1-pyrrolidinyl]ethyl}-1-benzofuran-5-yl)benzonitrile;
2-fluoro-4-(2-{2-[(2R)-2-methyl-1-pyrrolidinyl]ethyl}-1-benzofuran-5-yl)benzonitrile;
3-(2-{2-[(2R)-2-methyl-1-pyrrolidinyl]ethyl}-1-benzofuran-5-yl)benzonitrile;
(2R)-1-{2-[5-(4-fluorophenyl)-1-benzofuran-2-yl]ethyl}-2-methylpyrrolidine;
(2R)-1-{2-[5-(3,4-dichlorophenyl)-1-benzofuran-2-yl]ethyl}-2-methylpyrrolidine;
(2R)-2-methyl-1-{2-[5-(2-methylphenyl)-1-benzofuran-2-yl]ethyl}pyrrolidine;
(2R)-2-methyl-1-{2-[5-(3-methylphenyl)-1-benzofuran-2-yl]ethyl}pyrrolidine;
(2R)-2-methyl-1-{2-[5-(4-methylphenyl)-1-benzofuran-2-yl]ethyl}pyrrolidine;
4-{2-[2-(2-methylpyrrolidin-1-yl)-ethyl]-benzofuran-5-yl}-benzoic acid methyl ester;
(2R)-1-{2-[5-(2-methoxyphenyl)-1-benzofuran-2-yl]ethyl}-2-methylpyrrolidine;
(2R)-1-{2-[5-(3-methoxyphenyl)-1-benzofuran-2-yl]ethyl}-2-methylpyrrolidine;
(2R)-1-{2-[5-(4-methoxyphenyl)-1-benzofuran-2-yl]ethyl}-2-methylpyrrolidine;
(2R)-1-{2-[5-(3-fluorophenyl)-1-benzofuran-2-yl]ethyl}-2-methylpyrrolidine;
(2R)-1-{2-[5-(2-chlorophenyl)-1-benzofuran-2-yl]ethyl}-2-methylpyrrolidine;
(2R)-1-{2-[5-(3-chlorophenyl)-1-benzofuran-2-yl]ethyl}-2-methylpyrrolidine;
1-{2-[5-(4-chlorophenyl)-benzofuran-2-yl]-ethyl}-2-methylpyrrolidine;
(2R)-2-methyl-1-(2-{5-[3-(trifluoromethyl)phenyl]-1-benzofuran-2-yl}ethyl)pyrrolidine;
(2R)-2-methyl-1-(2-{5-[4-(trifluoromethyl)phenyl]-1-benzofuran-2-yl}ethyl)pyrrolidine;
(2R)-2-methyl-1-(2-{5-[3-(trifluoromethoxy)phenyl]-1-benzofuran-2-yl}ethyl)pyrrolidine;
(2R)-2-methyl-1-(2-{5-[4-(trifluoromethoxy)phenyl]-1-benzofuran-2-yl}ethyl)pyrrolidine;
(2R)-1-{2-[5-(3,4-dimethylphenyl)-1-benzofuran-2-yl]ethyl}-2-methylpyrrolidine;
(2R)-1-{2-[5-(3,5-dichlorophenyl)-1-benzofuran-2-yl]ethyl}-2-methylpyrrolidine;
(2R)-1-{2-[5-(3,5-dimethylphenyl)-1-benzofuran-2-yl]ethyl}-2-methylpyrrolidine;
[4-(2-{2-[(2R)-2-methyl-1-pyrrolidinyl]ethyl}-1-benzofuran-5-yl)phenyl]methanol;
1-[3-(2-{2-[(2R)-2-methyl-1-pyrrolidinyl]ethyl}-1-benzofuran-5-yl)phenyl]ethanone;
1-[3-(2-{2-[(2R)-2-methyl-1-pyrrolidinyl]ethyl}-1-benzofuran-5-yl)phenyl]ethanol;
2-[3-(2-{2-[(2R)-2-methyl-1-pyrrolidinyl]ethyl}-1-benzofuran-5-yl)phenyl]-2-propanol;
1-[3-(2-{2-[(2R)-2-methyl-1-pyrrolidinyl]ethyl}-1-benzofuran-5-yl)phenyl]ethanone oxime;
1-[3-(2-{2-[(2R)-2-methyl-1-pyrrolidinyl]ethyl}-1-benzofuran-5-yl)phenyl]ethanone O-methyloxime;
1-[3-(2-{2-[(2R)-2-methyl-1-pyrrolidinyl]ethyl}-1-benzofuran-5-yl)phenyl]ethanone O-ethyloxime;
1-[3-(2-{2-[(2R)-2-methyl-1-pyrrolidinyl]ethyl}-1-benzofuran-5-yl)phenyl]ethanone O-(tert-butyl)oxime;
ethyl 3-(2-{2-[(2R)-2-methyl-1-pyrrolidinyl]ethyl}-1-benzofuran-5-yl)benzoate;
3-(2-{2-[(2R)-2-methyl-1-pyrrolidinyl]ethyl}-1-benzofuran-5-yl)benzoic acid;
N-methoxy-N-methyl-3-(2-{2-[(2R)-2-methyl-1-pyrrolidinyl]ethyl}-1-benzofuran-5-yl)benzamide;
1-[3-(2-{2-[(2R)-2-methyl-1-pyrrolidinyl]ethyl}-1-benzofuran-5-yl)phenyl]-1-propanone;
3-methyl-1-[3-(2-{2-[(2R)-2-methyl-1-pyrrolidinyl]ethyl}-1-benzofuran-5-yl)phenyl]-1-butanone;
3-(2-{2-[(2R)-2-methyl-1-pyrrolidinyl]ethyl}-1-benzofuran-5-yl)benzaldehyde;
[3-(2-{2-[(2R)-2-methyl-1-pyrrolidinyl]ethyl}-1-benzofuran-5-yl)phenyl]methanol;
4-(3-bromo-2-{2-[(2R)-2-methyl-1-pyrrolidinyl]ethyl}-1-benzofuran-5-yl)-2-methylbenzonitrile;
4-(3-chloro-2-{2-[(2R)-2-methyl-1-pyrrolidinyl]ethyl}-1-benzofuran-5-yl)benzonitrile;
4-(3,6-dichloro-2-{2-[(2R)-2-methyl-1-pyrrolidinyl]ethyl}-1-benzofuran-5-yl)benzonitrile;
4-(3-iodo-2-{2-[(2R)-2-methyl-1-pyrrolidinyl]ethyl}-1-benzofuran-5-yl)benzonitrile;
4-(2-{2-[(2R)-2-methyl-5-oxo-1-pyrrolidinyl]ethyl}-1-benzofuran-5-yl)benzonitrile;
4-(3-acetyl-2-{2-[(2R)-2-methyl-1-pyrrolidinyl]ethyl}-1-benzofuran-5-yl)benzonitrile;
4-(2-{2-[(2R)-2-ethyl-1-pyrrolidinyl]ethyl}-1-benzofuran-5-yl)benzonitrile;
4-(2-{2-[(2S)-2-(fluoromethyl)-1-pyrrolidinyl]ethyl}-1-benzofuran-5-yl)benzonitrile;
4-(2-{2-[(2R)-2-methyl-1-pyrrolidinyl]ethyl}-1-benzothien-5-yl)benzonitrile;
3-(2-{3-[(2R)-2-methyl-1-pyrrolidinyl]propyl}-1-benzofuran-5-yl)benzonitrile;
3-(2-{[(2R)-2-methyl-1-pyrrolidinyl]methyl}-1-benzofuran-5-yl)benzonitrile; and
3-(2-{4-[(2R)-2-methyl-1-pyrrolidinyl]butyl}-1-benzofuran-5-yl)benzonitrile.

53. A compound according to claim 37 wherein
A is a covalent bond;
L is —CH$_2$CH$_2$—;
R$_1$ and R$_2$ taken together with the nitrogen atom to which they are attached, together form a heterocycle substituted with 0, 1 or 2 substituents selected from alkyl;
R$_3$, R$_4$, R$_5$, R$_7$, and R$_9$ are hydrogen;
R$_8$ is cyano;
X is CH;
Y is CH; and
Z is CH.

54. A compound according to claim 53 selected from the group consisting of 4-(2-{2-[(2S)-2-methyl-1-pyrrolidinyl]ethyl}-1-benzofuran-5-yl)benzonitrile;
4-(2-{2-[2-methyl-1-pyrrolidinyl]ethyl}-1-benzofuran-5-yl)benzonitrile;
4-(2-{2-[(2S)-2-ethyl-1-pyrrolidinyl]ethyl}-1-benzofuran-5-yl)benzonitrile;
4-(2-{2-[(2R)-2-ethyl-1-pyrrolidinyl]ethyl}-1-benzofuran-5-yl)benzonitrile;
4-(2-{2-[2-ethyl-1-pyrrolidinyl]ethyl}-1-benzofuran-5-yl)benzonitrile;
4-(2-{2-[(2R,5R)-2,5-dimethylpyrrolidinyl]ethyl}-1-benzofuran-5-yl)benzonitrile;
4-(2-{2-[(2S,5S)-2,5-dimethylpyrrolidinyl]ethyl}-1-benzofuran-5-yl)benzonitrile;
4-(2-{2-[(trans)-2,5-dimethylpyrrolidinyl]ethyl}-1-benzofuran-5-yl)benzonitrile; and
3-(2-{2-[(2S)-2-methyl-1-pyrrolidinyl]ethyl}-1-benzofuran-5-yl)benzonitrile.

55. A compound according to claim 53 that is 4-(2-{2-[(2R)-2-methyl-1-pyrrolidinyl]ethyl}-1-benzofuran-5-yl)benzonitrile.

56. A compound according to claim 37 wherein
L is —CH$_2$CH$_2$—;
A is a covalent bond;
R$_1$ and R$_2$ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl;
R$_3$ is heterocycle;
R$_4$, R$_5$, R$_7$ and R$_9$ are hydrogen;
R$_8$ is cyano;
X is CH;
Y is CH; and
Z is CH.

57. A compound according to claim 37 wherein
L is —CH$_2$CH$_2$—;
A is a covalent bond;
R$_1$ and R$_2$ taken together with the nitrogen atom to which they are attached, together form a heterocycle selected from the group consisting of 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, and 1,4-dioxa-8-azaspiro[4.5]dec-8-yl;
R$_3$ is heterocycle;
R$_4$, R$_5$, R$_7$ and R$_9$ are hydrogen;
R$_8$ is cyano;
X is CH;
Y is CH; and
Z is CH.

58. A compound according to claim 37 wherein
L is —CH$_2$CH$_2$—;
A is a covalent bond;
R$_1$ and R$_2$ taken together with the nitrogen atom to which they are attached, together form a heterocycle (2R)-2-methyl-1-pyrrolidinyl;
R$_3$ is a heterocycle selected from the group consisting of 2-furyl, 3-pyridinyl, and 2-thienyl wherein the heterocycle is substituted with 0, 1, or 2 substituents selected from the group consisting of hydrogen, alkoxy, alkyl, alkoxycarbonyl, alkylcarbonyl, carboxy, cyano, formyl, halogen, haloalkyl, haloalkoxy, hydroxyalkyl, and oximyl;
R$_4$, R$_5$, R$_7$ and R$_9$ are hydrogen;
R$_8$ is cyano;
X is CH;
Y is CH; and
Z is CH.

59. A compound according to claim 58 selected from the group consisting of 4-(3-(2-furyl)-2-{2-[(2R)-2-methylpyrrolidin-1-yl]ethyl}-1-benzofuran-5-yl)benzonitrile;
4-[2-{2-[(2R)-2-methyl-1-pyrrolidinyl]ethyl}-3-(3-pyridinyl)-1-benzofuran-5-yl]benzonitrile;
4-[2-{2-[(2R)-2-methyl-1-pyrrolidinyl]ethyl}-3-(3-thienyl)-1-benzofuran-5-yl]benzonitrile; and
4-(3-(2-formyl-3-thienyl)-2-{2-[(2R)-2-methyl-1-pyrrolidinyl]ethyl}-1-benzofuran-5-yl)benzonitrile.

60. A compound according to claim 37 wherein
A is a covalent bond;
R$_1$ and R$_2$ taken together with the nitrogen atom to which they are attached, together form a heterocycle; and
R$_8$ is heterocyclecarbonyl.

61. A compound according to claim 37 wherein
A is a covalent bond;
R$_1$ and R$_2$ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; and
R$_8$ is heterocyclecarbonyl wherein the heterocycle of heterocyclecarbonyl is selected from the group consisting of azetidinyl, morpholinyl, piperazinyl, piperidinyl, pyridinyl, pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl.

62. A compound according to claim 37 wherein
A is a covalent bond;
R$_1$ and R$_2$ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; and R$_8$ is heterocyclecarbonyl wherein the heterocycle of heterocyclecarbonyl is selected from the group consisting of 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl.

63. A compound according to claim 37 wherein

A is a covalent bond;

R$_1$ and R$_2$ taken together with the nitrogen atom to which they are attached, together form a heterocycle selected from the group consisting of 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, and 1,4-dioxa-8-azaspiro[4.5]dec-8-yl; and R$_8$ is heterocyclecarbonyl wherein the heterocycle of heterocyclecarbonyl is selected from the group consisting of azetidinyl, morpholinyl, piperazinyl, piperidinyl, pyridinyl, pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl.

64. A compound according to claim 37 wherein

A is a covalent bond;

R$_1$ and R$_2$ taken together with the nitrogen atom to which they are attached, together form a heterocycle selected from the group consisting of 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, and 1,4-dioxa-8-azaspiro[4.5]dec-8-yl; and R$_8$ is heterocyclecarbonyl wherein the heterocycle of heterocyclecarbonyl is selected from the group consisting of 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl.

65. A compound according to claim 37 wherein

A is a covalent bond;

R$_1$ and R$_2$ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; and R$_8$ is heterocyclecarbonyl wherein the heterocycle of heterocyclecarbonyl is 4-morpholinyl.

66. A compound according to claim 37 wherein

A is a covalent bond;

R$_1$ and R$_2$ taken together with the nitrogen atom to which they are attached, together form a heterocycle selected from the group consisting of 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, and 1,4-dioxa-8-azaspiro[4.5]dec-8-yl; and R$_8$ is heterocyclecarbonyl wherein the heterocycle of heterocyclecarbonyl is 4-morpholinyl.

67. A compound according to claim 37 wherein

L is —CH$_2$CH$_2$—;

A is a covalent bond;

R$_1$ and R$_2$ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl;

R$_3$, R$_4$, R$_5$, R$_7$ and R$_9$ are hydrogen;

R$_8$ is heterocyclecarbonyl wherein the heterocycle of heterocyclecarbonyl is 4-morpholinyl;

X is CH;

Y is CH; and

Z is CH.

68. A compound according to claim 37 wherein

L is —CH$_2$CH$_2$—;

A is a covalent bond;

R$_1$ and R$_2$ taken together with the nitrogen atom to which they are attached, together form a heterocycle selected from the group consisting of 1-azepanyl, (3S)-3-

(dimethylamino)pyrrolidinyl, (3R)-3-(dimethylamino)
pyrrolidinyl, 1H-imidazol-1-yl, 3R)-3-hydroxy-1-
pyrrolidinyl, (3S)-3-hydroxy-1-pyrrolidinyl, (2S)-2-
(hydroxymethyl)pyrrolidinyl, (2R)-2-(hydroxymethyl)
pyrrolidinyl, (cis)-2,6-dimethylpiperidinyl, 4-methyl-
1-piperidinyl, 2-methyl-1-piperidinyl, 1-piperidinyl,
(2R,5R)-2,5-dimethylpyrrolidinyl, (cis)-2,5-
dimethylpyrrolidinyl, 1-pyrrolidinyl, 2-methyl-1-
pyrrolidinyl, (2R)-2-methyl-1-pyrrolidinyl, (2S)-2-
methyl-1-pyrrolidinyl, (2R)-2-methyl-5-oxo-1-
pyrrolidinyl, (2S)-2-methyl-5-oxo-1-pyrrolidinyl, 3,6-
dihydro-1(2H)-pyridinyl, (2S)-2-(methoxycarbonyl)-1-
pyrrolidinyl, (2R)-2-(methoxycarbonyl)-1-
pyrrolidinyl, (2S)-2-(fluoromethyl)-1-pyrrolidinyl,
(2R)-2-(fluoromethyl)-1-pyrrolidinyl, (2R)-2-ethyl-1-
pyrrolidinyl, 2,2-dimethyl-1-pyrrolidinyl, (2S)-2-ethyl-
1-pyrrolidinyl 4-morpholinyl, 2-oxa-5-azabicyclo
[2.2.1]hept-5-yl, and 1,4-dioxa-8-azaspiro[4.5]dec-8-
yl;

$R_3$, $R_4$, $R_5$, $R_7$ and $R_9$ are hydrogen;

$R_8$ is heterocyclecarbonyl wherein the heterocycle of heterocyclecarbonyl is 4-morpholinyl;

X is CH;

Y is CH; and

Z is CH.

69. A compound according to claim 68 selected from the group consisting of:
4-(4-{2-[2-(2-methyl-1-pyrrolidinyl)ethyl]-1-benzofuran-5-yl}benzoyl)morpholine;
4-(4-{2-[2-(1-piperidinyl)ethyl]-1-benzofuran-5-yl}benzoyl)morpholine;
4-(4-{2-[2-(2-methyl-1-piperidinyl)ethyl]-1-benzofuran-5-yl}benzoyl)morpholine;
(3R)-1-(2-{5-[4-(4-morpholinylcarbonyl)phenyl]-1-benzofuran-2-yl}ethyl)-3-pyrrolidinol;
4-[4-(2-{2-[(2R,5R)-2,5-dimethylpyrrolidinyl]ethyl}-1-benzofuran-5-yl)benzoyl]morpholine;
4-[4-(2-{2-[(cis)-2,6-dimethylpiperidinyl]ethyl}-1-benzofuran-5-yl)benzoyl]morpholine;
4-(4-{2-[2-(azepinyl)ethyl]-1-benzofuran-5-yl}benzoyl)morpholine;
4-(4-{2-[2-(4-methyl-1-piperidinyl)ethyl]-1-benzofuran-5-yl}benzoyl)morpholine;
4-(4-{2-[2-(4-morpholine)ethyl]-1-benzofuran-5-yl}benzoyl)morpholine;
4-(4-{2-[2-(3,6-dihydro-1(2H)-pyridinyl)ethyl]-1-benzofuran-5-yl}benzoyl)morpholine; and
4-(4-{2-[2-(2S)-pyrrolidinylmethanol)ethyl]-1-benzofuran-5-yl}benzoyl)morpholine.

70. A compound according to claim 1 of formula (III)

(III)

or a pharmaceutically acceptable salt, ester, or amide thereof, wherein $R_6$ is selected from the group consisting of hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —$NR_AR_B$, ($NR_AR_B$) alkyl, ($NR_AR_B$)carbonyl and ($NR_AR_B$)sulfonyl;

$R_8$ is selected from the group consisting of hydrogen, alkylcarbonyl, arylcarbonyl, cyano, cycloalkylcarbonyl, heterocyclecarbonyl and ($NR_AR_B$) carbonyl;

$R_9$ is selected from the group consisting of hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —$NR_AR_B$, ($NR_AR_B$) alkyl, ($NR_AR_B$)carbonyl and ($NR_AR_B$)sulfonyl;

X is selected from the group consisting of CH and $CR_X$;

Y is selected from the group consisting of CH and $CR_Y$;

Z is selected from the group consisting of CH and $CR_Z$; and $R_X$, $R_Y$ and $R_Z$ are each independently selected from the group consisting of alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —$NR_AR_B$, ($NR_AR_B$)alkyl, ($NR_AR_B$)carbonyl and ($NR_AR_B$) sulfonyl.

71. A compound according to claim 70 wherein

A is a covalent bond;

$R_1$ and $R_2$ are each independently selected from the group consisting of hydrogen, alkyl, hydroxyalkyl, alkenyl and alkynyl; and $R_8$ is selected from the group consisting of cyano and heterocyclecarbonyl.

72. A compound according to claim 70 wherein

A is a covalent bond;

$R_1$ and $R_2$ are each independently selected from the group consisting of alkyl, hydroxyalkyl, alkenyl and alkynyl; and $R_8$ is selected from the group consisting of cyano and heterocyclecarbonyl wherein the heterocycle of heterocyclecarbonyl is selected from the group consisting of azetidinyl, morpholinyl, piperazinyl, piperidinyl, pyridinyl, pyrrolidinyl, 2,5-dihydro-1H-pyrrolyl, 1-pyrrolyl, 3,6-dihydro-1(2H)-pyridinyl, thiomorpholinyl, and 1,1-dioxidothiomorpholinyl.

73. A compound according to claim 70 wherein

A is a covalent bond;

$R_1$ and $R_2$ are each independently selected from the group consisting of alkyl, hydroxyalkyl, alkenyl and alkynyl; and $R_8$ is selected from the group consisting of cyano and heterocyclecarbonyl wherein the heterocycle of heterocyclecarbonyl is selected from the group consisting of 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl.

74. A compound according to claim 70 wherein

A is a covalent bond;

$R_1$ and $R_2$ taken together with the nitrogen atom to which they are attached, together form a heterocycle; and $R_8$ is selected from the group consisting of cyano and heterocyclecarbonyl.

75. A compound according to claim 70 wherein

A is a covalent bond;

R₁ and R₂ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; and R₈ is selected from the group consisting of cyano and heterocyclecarbonyl wherein the heterocycle of heterocyclecarbonyl is selected from the group consisting of 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl.

76. A compound according to claim 70 wherein

A is a covalent bond;

R₁ and R₂ taken together with the nitrogen atom to which they are attached, together form a heterocycle selected from the group consisting of 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, and 1,4-dioxa-8-azaspiro[4.5]dec-8-yl; and R₈ is selected from the group consisting of cyano and heterocyclecarbonyl wherein the heterocycle of heterocyclecarbonyl is selected from the group consisting of 1-azetidinyl, 4-morpholinyl, 1-piperazinyl, 1-piperidinyl, 3-pyridinyl, 1-pyrrolidinyl, 2,5-dihydro-1H-pyrrolyl, 1-pyrrolyl, 3,6-dihydro-1(2H)-pyridinyl, 4-thiomorpholinyl, and 1,1-dioxidothiomorpholin-4-yl.

77. A compound according to claim 76 that is 4-(2-{2-[(2R)-2-methyl-1-pyrrolidinyl]ethyl}-1-benzofuran-6-yl)benzonitrile.

78. A compound according to claim 1 of formula (IV)

(IV)

or a pharmaceutically acceptable salt, ester, or amide thereof, wherein

R₇ is selected from the group consisting of hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —NR_AR_B, (NR_AR_B)alkyl, (NR_AR_B)carbonyl and (NR_AR_B)sulfonyl;

R₈ is selected from the group consisting of hydrogen, alkylcarbonyl, arylcarbonyl, cyano, cycloalkylcarbonyl, heterocyclecarbonyl and (NR_AR_B)carbonyl;

R₉ is selected from the group consisting of hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —NR_AR_B, (NR_AR_B)alkyl, (NR_AR_B)carbonyl and (NR_AR_B)sulfonyl;

X is selected from the group consisting of CH and CR_X;
Y is selected from the group consisting of CH and CR_Y;
Z is selected from the group consisting of CH and CR_Z; and R_X, R_Y and R_Z are each independently selected from the group consisting of alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —NR_AR_B, (NR_AR_B)alkyl, (NR_AR_B)carbonyl and (NR_AR_B)sulfonyl.

79. A compound according to claim 78 wherein

A is a covalent bond;

R₁ and R₂ are each independently selected from the group consisting of alkyl, hydroxyalkyl, alkenyl and alkynyl; and R₈ is cyano.

80. A compound according to claim 78 wherein

L is —CH₂CH₂—;

A is a covalent bond;

R₁ and R₂ are each independently selected from the group consisting of alkyl, hydroxyalkyl, alkenyl and alkynyl;

R₃, R₄, R₅, R₇ and R₉ are hydrogen;

R₈ is cyano;

X is CH;

Y is CH; and

Z is CH.

81. A compound according to claim 80 that is 4-(2-{2-[(2R)-2-methylpyrrolidinyl]ethyl}-2,3-dihydro-1-benzofuran-5-yl)benzonitrile.

82. A compound according to claim 1 of formula (V)

(V)

or a pharmaceutically acceptable salt, ester, or amide thereof, wherein

R₆ is selected from the group consisting of hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —NR$_A$R$_B$, (NR$_A$R$_B$)alkyl, (NR$_A$R$_B$)carbonyl and (NR$_A$R$_B$)sulfonyl;

R$_8$ is selected from the group consisting of hydrogen, alkylcarbonyl, arylcarbonyl, cyano, cycloalkylcarbonyl, heterocyclecarbonyl and (NR$_A$R$_B$)carbonyl;

R$_9$ is selected from the group consisting of hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —NR$_A$R$_B$, (NR$_A$R$_B$)alkyl, (NR$_A$R$_B$)carbonyl and (NR$_A$R$_B$)sulfonyl, X is selected from the group consisting of CH and CR$_X$;

Y is selected from the group consisting of CH and CR$_Y$;

Z is selected from the group consisting of CH and CR$_Z$; and

R$_X$, R$_Y$ and R$_Z$ are each independently selected from the group consisting of alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —NR$_A$R$_B$, (NR$_A$R$_B$)alkyl, (NR$_A$R$_B$)carbonyl and (NR$_A$R$_B$)sulfonyl.

83. A compound according to claim 82 wherein
A is a covalent bond;
R$_1$ and R$_2$ are each independently selected from the group consisting of alkyl, hydroxyalkyl, alkenyl and alkynyl; and
R$_8$ is cyano.

84. A compound according to claim 82 wherein
L is —CH$_2$CH$_2$—;
A is a covalent bond;
R$_1$ and R$_2$ are each independently selected from the group consisting of alkyl, hydroxyalkyl, alkenyl and alkynyl;
R$_3$, R$_4$, R$_5$, R$_6$ and R$_9$ are hydrogen;
R$_8$ is cyano;
X is CH;
Y is CH; and
Z is CH.

85. A compound according to claim 1 of formula (VI)

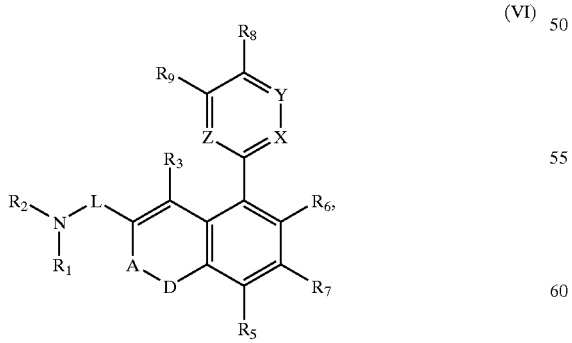

(VI)

or a pharmaceutically acceptable salt, ester, or amide thereof, wherein
R$_5$, R$_6$, and R$_7$ are independently selected from the group consisting of hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —NR$_A$R$_B$, (NR$_A$R$_B$)alkyl, (NR$_A$R$_B$)carbonyl and (NR$_A$R$_B$)sulfonyl;

R$_8$ is selected from the group consisting of hydrogen, alkylcarbonyl, arylcarbonyl, cyano, cycloalkylcarbonyl, heterocyclecarbonyl and (NR$_A$R$_B$)carbonyl;

R$_9$ is selected from the group consisting of hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —NR$_A$R$_B$, (NR$_A$R$_B$)alkyl, (NR$_A$R$_B$)carbonyl and (NR$_A$R$_B$)sulfonyl;

X is selected from the group consisting of CH and CR$_X$;

Y is selected from the group consisting of CH and CR$_Y$;

Z is selected from the group consisting of CH and CR$_Z$; and

R$_X$, R$_Y$ and R$_Z$ are each independently selected from the group consisting of alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —NR$_A$R$_B$, (NR$_A$R$_B$)alkyl, (NR$_A$R$_B$)carbonyl and (NR$_A$R$_B$)sulfonyl.

86. A compound according to claim 85 wherein
A is a covalent bond; and
R$_1$ and R$_2$ taken together with the nitrogen atom to which they are attached, together form a heterocycle.

87. A compound according to claim 85 wherein
A is a covalent bond;
R$_1$ and R$_2$ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; and
R$_8$ is cyano.

88. A compound according to claim 85 wherein
A is a covalent bond;
R$_1$ and R$_2$ taken together with the nitrogen atom to which they are attached, together form a heterocycle selected from the group consisting of 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, and 1,4-dioxa-8-azaspiro[4.5]dec-8-yl; and $R_8$ is cyano.

89. A compound according to claim 85 wherein

L is —CH₂CH₂—;

A is a covalent bond;

$R_1$ and $R_2$ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl;

$R_3$, $R_5$, $R_6$, $R_7$ and $R_9$ are hydrogen;

$R_8$ is cyano;

X is CH;

Y is CH; and

Z is CH.

90. A compound according to claim 85 wherein

L is —CH₂CH₂—;

A is a covalent bond;

$R_1$ and $R_2$ taken together with the nitrogen atom to which they are attached, together form a heterocycle selected from the group consisting of 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, and 1,4-dioxa-8-azaspiro[4.5]dec-8-yl;

$R_3$, $R_5$, $R_6$, $R_7$ and $R_9$ are hydrogen;

$R_8$ is cyano;

X is CH;

Y is CH; and

Z is CH.

91. A compound according to claim 90 that is 4-(2-{2-[(2R)-2-methyl-1-pyrrolidinyl]ethyl}-1-benzofuran-4-yl)benzonitrile.

92. A compound according to claim 1 of formula (VII)

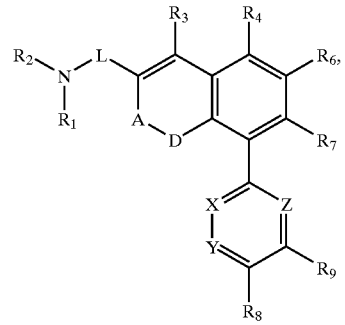

(VII)

or a pharmaceutically acceptable salt, ester, or amide thereof, wherein $R_4$, $R_6$, and $R_7$ are independently selected from the group consisting of hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —$NR_AR_B$, ($NR_AR_B$)alkyl, ($NR_AR_B$)carbonyl and ($NR_AR_B$)sulfonyl;

$R_8$ is selected from the group consisting of hydrogen, alkylcarbonyl, arylcarbonyl, cyano, cycloalkylcarbonyl, heterocyclecarbonyl and ($NR_AR_B$)carbonyl;

$R_9$ is selected from the group consisting of hydrogen, alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —$NR_AR_B$, ($NR_AR_B$)alkyl, ($NR_AR_B$)carbonyl and ($NR_AR_B$)sulfonyl;

X is selected from the group consisting of CH and $CR_X$;

Y is selected from the group consisting of CH and $CR_Y$;

Z is selected from the group consisting of CH and $CR_Z$; and $R_X$, $R_Y$ and $R_Z$ are each independently selected from the group consisting of alkoxy, alkoxycarbonyl, alkyl, alkylcarbonyl, alkylcarbonyloxy, alkylsulfinyl, alkylsulfonyl, alkylthio, carboxy, carboxyalkyl, cyano, cyanoalkyl, formyl, halogen, haloalkoxy, haloalkyl, hydroxy, hydroxyalkyl, mercapto, nitro, —$NR_AR_B$, ($NR_AR_B$)alkyl, ($NR_AR_B$)carbonyl and ($NR_AR_B$)sulfonyl.

93. A compound according to claim 92 wherein

A is a covalent bond; and $R_1$ and $R_2$ taken together with the nitrogen atom to which they are attached, together form a heterocycle.

94. A compound according to claim 92 wherein

A is a covalent bond;

$R_1$ and $R_2$ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl; and $R_8$ is cyano.

95. A compound according to claim 92 wherein

A is a covalent bond;

$R_1$ and $R_2$ taken together with the nitrogen atom to which they are attached, together form a heterocycle selected from the group consisting of 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, and 1,4-dioxa-8-azaspiro[4.5]dec-8-yl; and $R_8$ is cyano.

96. A compound according to claim 92 wherein

L is —$CH_2CH_2$—;

A is a covalent bond;

$R_1$ and $R_2$ taken together with the nitrogen atom to which they are attached, together form a heterocycle selected from the group consisting of azepanyl, azetidinyl, imadazolyl, morpholinyl, piperazinyl, piperidinyl, pyridinyl, pyrrolidinyl, (2R)-2-methyl-1-pyrrolidinyl, 2,5-dihydro-1H-pyrrolyl, pyrrolyl, 3,6-dihydro-1(2H)-pyridinyl, thiomorpholinyl, and 1,1-dioxidothiomorpholinyl;

$R_3$, $R_4$, $R_6$, $R_7$ and $R_9$ are hydrogen;

$R_8$ is cyano;

X is CH;

Y is CH; and

Z is CH.

97. A compound according to claim 92 wherein

L is —$CH_2CH_2$—;

A is a covalent bond;

$R_1$ and $R_2$ taken together with the nitrogen atom to which they are attached, together form a heterocycle selected from the group consisting of 1-azepanyl, (3S)-3-(dimethylamino)pyrrolidinyl, (3R)-3-(dimethylamino)pyrrolidinyl, 1H-imidazol-1-yl, (3R)-3-hydroxy-1-pyrrolidinyl, (3S)-3-hydroxy-1-pyrrolidinyl, (2S)-2-(hydroxymethyl)pyrrolidinyl, (2R)-2-(hydroxymethyl)pyrrolidinyl, (cis)-2,6-dimethylpiperidinyl, 4-methyl-1-piperidinyl, 2-methyl-1-piperidinyl, 1-piperidinyl, (2R,5R)-2,5-dimethylpyrrolidinyl, (cis)-2,5-dimethylpyrrolidinyl, 1-pyrrolidinyl, 2-methyl-1-pyrrolidinyl, (2R)-2-methyl-1-pyrrolidinyl, (2S)-2-methyl-1-pyrrolidinyl, (2R)-2-methyl-5-oxo-1-pyrrolidinyl, (2S)-2-methyl-5-oxo-1-pyrrolidinyl, 3,6-dihydro-1(2H)-pyridinyl, (2S)-2-(methoxycarbonyl)-1-pyrrolidinyl, (2R)-2-(methoxycarbonyl)-1-pyrrolidinyl, (2S)-2-(fluoromethyl)-1-pyrrolidinyl, (2R)-2-(fluoromethyl)-1-pyrrolidinyl, (2R)-2-ethyl-1-pyrrolidinyl, 2,2-dimethyl-1-pyrrolidinyl, (2S)-2-ethyl-1-pyrrolidinyl 4-morpholinyl, 2-oxa-5-azabicyclo[2.2.1]hept-5-yl, and 1,4-dioxa-8-azaspiro[4.5]dec-8-yl;

$R_3$, $R_4$, $R_6$, $R_7$ and $R_9$ are hydrogen;

$R_8$ is cyano;

X is CH;

Y is CH; and

Z is CH.

98. A compound according to claim 1 wherein one substituent of $R_4$, $R_5$, $R_6$ and $R_7$ is selected from the group consisting of hydrogen, alkoxy, alkoxycarbonyl, alkyl, alkylcarbonyl, alkylcarbonyloxy, alkylsulfinyl, alkylsulfonyl, alkylthio, aryl, carboxy, carboxyalkyl, cyano, cyanoalkyl, cycloalkyl, formyl, halogen, haloalkoxy, haloalkyl, hydroxy, hydroxyalkyl, mercapto, nitro, —$NR_AR_B$, ($NR_AR_B$)alkyl, ($NR_AR_B$)carbonyl, ($NR_AR_B$)sulfonyl, —$L_2R_{20}$, and —$R_{20}L_3R_{25}$; and the other substituents of $R_4$, $R_5$, $R_6$ and $R_7$ are each independently selected from the group consisting of hydrogen and alkyl.

99. A compound according to claim 98 wherein $R_4$, $R_5$, $R_6$ and $R_7$ are each independently selected from the group consisting of hydrogen, alkyl, —$L_2R_{20}$, and —$R_{20}L_3R_{22}$.

100. A compound according to claim 98 selected from the group consisting of 1-[2-(4--cyclohept-1-enyl-benzofuran-2-yl)-ethyl]-(2R)-methyl-pyrrolidine;

5-{2-[2-(2(R)-methyl-pyrrolidin-1-yl)-ethyl]-benzofuran-6-yl}-2-phenyl-oxazole;

4-{2-[2-(2(R)-methyl-pyrrolidin-1-yl)-ethyl]-benzofuran-6-yl}-1-phenyl-1H-pyrazole;

1-[2-(6-cyclohept-1-enyl-benzofuran-2-yl)-ethyl]-2(R)-methyl-pyrrolidine;

5-{2-[2-(2(R)-methyl-pyrrolidin-1-yl)-ethyl]-benzofuran-7-yl}-2-phenyl-oxazole;

4-{2-[2-(2(R)-methyl-pyrrolidin-1-yl)-ethyl]-benzofuran-7-yl}-1-phenyl-1H-pyrazole; and 1-[2-(7-cyclohept-1-enyl-benzofuran-2-yl)-ethyl]-2(R)-methyl-pyrrolidine.

101. A compound according to claim 1 selected from the group consisting of (3-fluorophenyl)[3-(2-{2-[(2R)-2-methyl-1-pyrrolidinyl]ethyl}-1-benzofuran-5-yl)phenyl]methanone;

(2R)-2-methyl-1-[2-(5-phenoxy-1-benzofuran-2-yl)ethyl]pyrrolidine;

(2R)-1-(2-{5-[(3-fluorophenyl)thio]-1-benzofuran-2-yl}ethyl)-2-methylpyrrolidine;

4-(4-{2-[2-(2S)-methyl-1-pyrrolidinyl)ethyl]-1-benzofuran-5-yl}benzoyl)morpholine, 4-{[6-(2-{2-[(2S)-methylpyrrolidinyl]ethyl}-1-benzofuran-5-yl)-3-pyridinyl]carbonyl}morpholine;

4-(2-{2-[(2R)-2-methylpyrrolidinyl]ethyl}-2,3-dihydro-1-benzofuran-5-yl)benzonitrile;

4-(2-{2-[(2S)-2-methyl-1-pyrrolidinyl]ethyl}-1-benzofuran-4-yl)benzonitrile;

4-{2-[2-(2(S)-methyl-pyrrolidin-1-yl)-ethyl]-benzofuran-6-yl}-benzonitrile;

3-(2-{2-[(2S)-2-methyl-1-pyrrolidinyl]ethyl}-1-benzofuran-5-yl)benzonitrile;

(4-methoxy-phenyl)-methyl-{2-[2-(2(R)-methyl-pyrrolidin-1-yl)-ethyl]-benzofuran-5-yl}-amine;

benzo[1,3]dioxol-5-yl-methyl-{2-[2-(2-methyl-pyrrolidin-1-yl)-ethyl]-benzofuran-5-yl}-amine;

cyclohexyl-methyl-{2-[2-(2(R)-methyl-pyrrolidin-1-yl)-ethyl]-benzofuran-5-yl}-amine; and {2-[2-(2(R)-methyl-pyrrolidin-1-yl)-ethyl]-benzofuran-5-yl}-(tetrahydro-pyran-4-yl)-amine.

102. A pharmaceutical composition comprising a therapeutically effective amount of a compound of claim 1 in combination with a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 6,969,730 B2 | Page 1 of 1 |
| APPLICATION NO. | : 10/081207 | |
| DATED | : November 29, 2005 | |
| INVENTOR(S) | : Marlon D. Cowart et al. | |

It is certified that error appears in the above-identified patent and that said Letters Patent is hereby corrected as shown below:

Column 70, line 32, "(1.83 g, 75%/)" to read as --(1.83 g, 75%)--

Column 100, line 33, "heated at 60☐C" to read as --heated at 60°C--

Column 100, line 35, "heated at 60☐C" to read as --heated at 60°C--

Column 127, line 8, "25°C . to 120°C." to read as --25°C to 120°C--

Signed and Sealed this
Thirtieth Day of October, 2012

David J. Kappos
*Director of the United States Patent and Trademark Office*